US012594327B2

(12) United States Patent
Wilson et al.

(10) Patent No.: US 12,594,327 B2
(45) Date of Patent: Apr. 7, 2026

(54) COMPOSITIONS USEFUL FOR TREATING GM1 GANGLIOSIDOSIS

(71) Applicant: The Trustees of the University of Pennsylvania, Philadelphia, PA (US)

(72) Inventors: James M. Wilson, Philadelphia, PA (US); Christian Hinderer, New Orleans, LA (US); Nathan Katz, Stamford, CT (US)

(73) Assignee: The Trustees of the University of Pennylvania, Philadelphia, PA (US)

(*) Notice: Subject to any disclaimer, the term of this patent is extended or adjusted under 35 U.S.C. 154(b) by 1267 days.

(21) Appl. No.: 17/281,378

(22) PCT Filed: Sep. 30, 2019

(86) PCT No.: PCT/US2019/053797
§ 371 (c)(1),
(2) Date: Mar. 30, 2021

(87) PCT Pub. No.: WO2020/072354
PCT Pub. Date: Apr. 9, 2020

(65) Prior Publication Data

US 2023/0040603 A1 Feb. 9, 2023

Related U.S. Application Data

(60) Provisional application No. 62/835,178, filed on Apr. 17, 2019, provisional application No. 62/739,811, filed on Oct. 1, 2018.

(51) Int. Cl.

| | |
|---|---|
| ***C12N 15/86*** | (2006.01) |
| ***A61K 38/47*** | (2006.01) |
| ***C12N 9/38*** | (2006.01) |

(52) U.S. Cl.
CPC ............ *A61K 38/47* (2013.01); *C12N 9/2471* (2013.01); *C12N 15/86* (2013.01); *C12N 2750/14143* (2013.01); *C12Y 302/01023* (2013.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,439,065 | B2 | 10/2008 | Ferrari et al. |
| 7,588,772 | B2 | 9/2009 | Kay et al. |
| 7,906,111 | B2 | 3/2011 | Wilson et al. |
| 8,734,809 | B2 | 5/2014 | Gao et al. |
| 8,927,514 | B2 | 1/2015 | Chatterjee et al. |
| 2006/0136184 | A1 | 6/2006 | Gustafsson et al. |
| 2010/0173979 | A1* | 7/2010 | Dodge .................. C12N 15/86 514/44 R |
| 2013/0045186 | A1 | 2/2013 | Gao et al. |
| 2014/0032186 | A1 | 1/2014 | Gustafsson et al. |
| 2015/0344911 | A1 | 12/2015 | Chatterjee et al. |
| 2018/0311290 | A1 | 11/2018 | Sena-esteves et al. |
| 2019/0038777 | A1 | 2/2019 | Donsante et al. |
| 2019/0055578 | A1 | 2/2019 | Sah et al. |
| 2019/0060359 | A1 | 2/2019 | Norviel et al. |
| 2019/0192693 | A1 | 6/2019 | High et al. |
| 2021/0228739 | A1 | 7/2021 | Esteves |
| 2022/0090129 | A1 | 3/2022 | Miller et al. |
| 2022/0096659 | A1 | 3/2022 | Laoharawee et al. |

FOREIGN PATENT DOCUMENTS

| | | |
|---|---|---|
| WO | WO 2003/042397 | 5/2003 |
| WO | WO 2005/033321 | 4/2005 |
| WO | WO 2006/110689 | 10/2006 |
| WO | WO 2011/126808 | 10/2011 |

(Continued)

OTHER PUBLICATIONS

Pediatrics Nationwide Spring/Summer 2018 , 19 pages, retrieved from the internet: https://pediatricsnationwide.org/wp-content/uploads/2021/02/15459_MKTG_PedsNW_SprSmmr-2018-FINAL.pdf (Year: 2018).*

Morreau et al., The Journal of Biological Chemistry, vol. 264, No. 34, pp. 20655-20663, Dec. 1989 (Year: 1989).*

Oskar Laur, Addgene plasmid #128045; retrieved from the internet at: https://www.addgene.org/128045/sequences/ (Year: 2025).*

ClinicalTrials.gov: NCT04713475—"Study of Safety, Tolerability and Efficacy of PBGM01 in Pediatric Subjects with GM1 Gangliosidosis (Imagine-1)", available at https://clinicaltrials.gov/ct2/show/NCT04713475 (First Posted: Jan. 19, 2021).

Passage Bio, Press Release—"Passage Bio Presents New Interim Clinical and Biomarker Data for Patients with GM1 Gangliosidosis in Imagine-1 Study At ASGCT 25th Annual Meeting", May 18, 2022.

(Continued)

*Primary Examiner* — Evelyn Y Pyla
(74) *Attorney, Agent, or Firm* — Howson & Howson LLP; Cathy A. Kodroff

(57) ABSTRACT

A recombinant adeno-associated virus (rAAV) comprising an AAVhu68 capsid and a vector genome comprising a lysosomal beta-galactosidase gene (for example, galactosidase beta 1 gene, GBL1) is provided (i.e., rAAVhu68.GBL1). Also provided a composition containing an effective amount of rAAVhu68.GBL1 to ameliorate symptoms of GM1 gangliosidosis, including, e.g., increased average life span, decreased need for feeding tube, reduction in seizure incidence and frequency, reduction in progression towards neurocognitive decline and/or improvement in neurocognitive development.

17 Claims, 22 Drawing Sheets

Specification includes a Sequence Listing.

(56) References Cited

FOREIGN PATENT DOCUMENTS

| | | | |
|---|---|---|---|
| WO | WO 2013/049493 | | 4/2013 |
| WO | WO-2014/186579 | | 11/2014 |
| WO | WO 2015/012924 | | 1/2015 |
| WO | WO 2016/049230 | | 3/2016 |
| WO | WO-2017/136202 | | 8/2017 |
| WO | WO 2017/136500 | | 8/2017 |
| WO | WO 2017/160360 | | 9/2017 |
| WO | WO-2018/093925 | | 5/2018 |
| WO | WO 2018/160582 | | 9/2018 |
| WO | WO 2016/172155 | | 11/2018 |
| WO | WO 2020/072354 | | 4/2020 |
| WO | WO 2020/072873 | | 4/2020 |
| WO | WO-2020/117898 | | 6/2020 |
| WO | WO 2021/155337 | A1 | 8/2021 |

OTHER PUBLICATIONS

Passage Bio, Press Release—"Passage Bio Presents New Interim Clinical Data for Patients with GM1 Gangliosidosis in Imagine-1 Study At 2022 WORLDSymposium", Feb. 11, 2022.
Passage Bio, Press Release—"Passage Bio Announces Positive Interim Safety and Biomarker Data and Advances Phase 1/2 Trial of PBGM01 In GM1 Gangliosidosis", Dec. 17, 2021.
Passage Bio, Press Release—"Passage Bio Announces First Patient Dosed in Imagine-1 Study of PBGM01 Gene Therapy for Infantile GM1 Gangliosidosis", Apr. 1, 2021.
Passage Bio, Press Release—"Passage Bio Announces Publication of Preclinical Data That Show Single Injection of Optimized AAV Vector into Cerebral Spinal Fluid Corrects Neurological Disease, Supporting Advancement of PBGM01 into Clinic", Oct. 13, 2020.
Weinstein et al., "Interim Safety, Biomarker, and Efficacy Data from Imagine-1: A Phase 1/2 Open-label, Multicenter Study to Assess the Safety, Tolerability, and Efficacy of a Single Dose, ICM Administration of PBGM01 in Subjects with Type I (Early Onset) and Type IIa (Late Onset) Infantile GM1 Gangliosidosis (GM1)," Abstract Presented at ASGCT $25^{th}$ Annual Meeting, May 2022.
International Search Report and Written Opinion issued for International Patent Application No. PCT/US2019/053797, dated Feb. 2, 2020.
Substantive Report issued in Chilean Patent Application No. 202100798, dated Jun. 29, 2022, with machine translation.
Absoud et al., Pediatric UK demyelinating disease longitudinal study (PUDDLS), BMC Pediatrics, vol. 11(68):1-10, Jul. 2011.
Arthur et al., Filipin recognizes both GM1 and cholesterol in GM1 gangliosidosis mouse brain, Journal of Lipid Research, vol. 52(7)1345-1351, Jul. 2011.
Audentes Therapeutics, Audentes Announces Continuing Positive Data from First Dose of ASPIRO, a Phase 1/2 Clinical Trial of AT132 in Patients with X-Linked Myotubular Myopathy, Press Release, May 2018.
Baek et al., AAV-Mediated Gene Delivery in Adult GM1-Gangliosidosis Mice Corrects Lysosomal Storage in CNS and Improves Survival, PLOS One, vol. 5(10):1-16, Oct. 2010.
Bartus et al., Parkinson's disease gene therapy: success by design meets failure by efficacy, Molecular Therapy, vol. 22(3):487-497, Mar. 2014.
Batka et al., The need for speed in rodent locomotion analyses, Anatomical Record (Hoboken), vol. 297(10):1839-1864, Oct. 2014.
Bayley, N., Bayley Scales of Infant and Toddler Development—Third Edition, San Antonio, TX: Harcourt Assessment, Journal of Psychoeducational Assessment, vol. 25(2):180-190, Jun. 2007.
Bell et al., Analysis of tumors arising in male B6C3F1 mice with and without AAV vector delivery to liver, Molecular Therapy, vol. 14(1):34-44, Jul. 2006.
Bell et al., Motor Neuron Transduction After Intracisternal Delivery of AAV9 in a Cynomolgus Macaque. Human Gene Therapy Methods, vol. 26(2):43-44, Apr. 2015.
Bell et al., No Evidence for Tumorigenesis of AAV Vectors in a Large-Scale Study in Mice. Molecular Therapy, vol. 12(2):299-306, Aug. 2005.
Bell et al., The AAV9 receptor and its modification to improve in vivo lung gene transfer in mice, The Journal of Clinical Investigation, vol. 121(6):2427-2435, Jun. 2011.
Bevan et al., Systemic Gene Delivery in Large Species for Targeting Spinal Cord, Brain, and Peripheral Tissues for Pediatric Disorders, Molecular Therapy, vol. 19(11):1971-1980, Nov. 2011.
Broekman et al., Complete correction of enzymatic deficiency and neurochemistry in the GM1-gangliosidosis mouse brain by neonatal adeno-associated virus-mediated gene delivery, Molecular Therapy, vol. 15(1):30-7, Jan. 2007.
Brunetti-Pierri et al., GM1 gangliosidosis: Review of clinical, molecular, and therapeutic aspects, Molecular Genetics and Metabolism, vol. 94:391-396, Feb. 2008.
Bryant et al., Lessons learned from the clinical development and market authorization of Glybera, Human Gene Therapy Clinical Development, vol. 24(2):55-64, Jun. 2013.
Buning et al., Recent developments in adeno-associated virus vector technology, The Journal of Gene Medicine, vol. 10(7):717-733, Jul. 2008.
Caciotti et al., GM1 gangliosidosis and Morquio B disease: An update on genetic alterations and clinical findings, Biochimica et Biophysica Acta (BBA)—Molecular Basis of Disease, vol. 1812(7):782-790, Apr. 2011.
Calcedo et al., Worldwide Epidemiology of Neutralizing Antibodies to Adeno-Associated Viruses, Journal of Infectious Diseases, vol. 199(3):381-390, Feb. 2009.
Castle al., Long-distance Axonal Transport of AAV9 Is Driven by Dynein and Kinesin-2 and Is Trafficked in a Highly Motile Rab7-positive Compartment, Molecular Therapy, vol. 22(3):554-566, Mar. 2014.
Chandler et al., Vector design influences hepatic genotoxicity after adeno-associated virus gene therapy, The Journal of Clinical Investigation, vol. 125(2):870-880, Jan. 2015.
Ciesielska et al., Cerebral Infusion of AAV9 Vector-encoding Non-self Proteins Can Elicit Cell-mediated Immune Responses, Molecular Therapy, vol. 21(1):158-166, Jan. 2013.
Colle et al., Efficient intracerebral delivery of AAV5 vector encoding human ARSA in non-human primate, Human Molecular Genetics, vol. 19(1):147-58, Jan. 2010.
Consolaro, A., and Ravelli, A., Assessment Tools in Juvenile Idiopathic Arthritis. Handbook of Systemic Autoimmune Diseases, Dec. 2016.
Couto et al., Direct Exposure of Mouse Spermatozoa to Very High Concentrations of a Serotype-2 Adeno-Associated Virus Gene Therapy Vector Fails to Lead to Germ Cell Transduction, Human Gene Therapy, vol. 15(3):287-291, Mar. 2004.
D'Azzo et al., Molecular defect in combined beta-galactosidase and neuraminidase deficiency in man, Proceedings of the National Academy of Sciences, vol. 79(15):4535-4539, Aug. 1982.
Donsante et al., Observed incidence of tumorigenesis in long-term rodent studies of rAAV vectors, Gene Therapy, vol. 8(17):1343-6, Sep. 2001.
Ellinwood et al., Safe, Efficient, and Reproducible Gene Therapy of the Brain in the Dog Models of Sanfilippo and Hurler Syndromes, Molecular Therapy, vol. 19(2):251-259, Feb. 2011.
Ferla et al., Non-clinical Safety and Efficacy of an AAV2/8 Vector Administered Intravenously for Treatment of Mucopolysaccharidosis Type VI, Molecular Therapy—Methods & Clinical Development, vol. 6:143-158, Jul. 2017.
Folkerth, R., Abnormalities of Developing White Matter in Lysosomal Storage Diseases, Journal of Neuropathology and Experimental Neurology, vol. 58(9):887-902, Sep. 1999.
Foust et al., Intravascular AAV9 preferentially targets neonatal neurons and adult astrocytes, Nature Biotechnology, vol. 27(1):59-65, Jan. 2009.
Gao et al., Adeno-associated viruses undergo substantial evolution in primates during natural infections, Proc. Natl. Acad. Sci. U.S.A., vol. 100(10):6081-6086, May 2003.

(56) References Cited

OTHER PUBLICATIONS

Gao et al., Clades of Adeno-Associated Viruses Are Widely Disseminated in Human Tissues, Journal of Virology, vol. 78(12):6381-6388, Jun. 2004.
GenBank Accession No. AAA51819.1, Oct. 1994.
GenBank Accession No. AY530629,.
GenBank Accession No. D63791.1, Jul. 2016.
GenBank Accession No. KP659662.1, Dec. 2018.
GenBank Accession No. NC001401, Aug. 2018.
GenBank Accession No. AY530553, Jun. 2004.
Gil-Farina et al., Recombinant AAV Integration Is Not Associated with Hepatic Genotoxicity in Nonhuman Primates and Patients, Molecular Therapy, vol. 24(6):1100-1105, Jun. 2016.
Godel et al., Human dorsal-root-ganglion perfusion measured in-vivo by MRI, NeuroImage, vol. 141:81-87, Nov. 2016.
Gombash et al., Systemic gene delivery transduces the enteric nervous system of guinea pigs and cynomolgus macaques, Gene Therapy, vol. 24:640-648, Oct. 2017.
Graham et al., Characteristics of a human cell line transformed by DNA from human adenovirus type 5, The Journal of General Virology, vol. 36(1):59-74, Jul. 1977.
Gray et al., Global CNS gene delivery and evasion of anti-AAV-neutralizing antibodies by intrathecal AAV administration in non-human primates, Gene Therapy, vol. 20(4):450-9, Apr. 2013.
Gray et al., Preclinical differences of intravascular AAV9 delivery to neurons and glia: a comparative study of adult mice and nonhuman primates, Molecular Therapy, vol. 19(6):1058-69, Jun. 2011.
Gray-Edwards et al., Lipidomic Evaluation of Feline Neurologic Disease after AAV Gene Therapy, Molecular Therapy, vol. 6:135-142, Sep. 20017.
Greig et al., Non-Clinical Study Examining AAV8.TBG.hLDLR Vector-Associated Toxicity in Chow-Fed Wild-Type and LDLR (+/−) Rhesus Macaques, Human Gene Therapy—Clinical Development, vol. 28(1):39-50, Mar. 2017.
Grieger, J., and Samulski, R., Adeno-associated virus as a gene therapy vector: Vector development, production and clinical applications, Gene Therapy and Gene Delivery Systems, vol. 99:119-145, Oct. 2005.
Grimm et al., Titration of AAV-2 particles via a novel capsid ELISA: packaging of genomes can limit production of recombinant AAV-2, Gene Therapy, vol. 6(7):1322-1330, Jul. 1999.
Gross et al., Cerebrospinal Fluid for Delivery of AAV Gene Therapy in GM1 Gangliosidosis, Molecular Therapy, vol. 24(1):S240, May 2016.
Gurda et al., Evaluation of AAV-mediated Gene Therapy for Central Nervous System Disease in Canine Mucopolysaccharidosis VII, Molecular Therapy, vol. 24(2):206-216, Feb. 2016.
Gururaj et al., Magnetic Resonance Imaging Findings and Novel Mutations in GM1 Gangliosidosis, Journal of Child Neurology, vol. 20(1):57-60, Jan. 2005.
Hahn et al. Generalized CNS disease and massive GM1-ganglioside accumulation in mice defective in lysosomal acid beta-galactosidase, Human Molecular Genetics, vol. 6(2):205-211, Feb. 1997.
Haurigot et al., Whole body correction of mucopolysaccharidosis IIIA by intracerebrospinal fluid gene therapy, The Journal of Clinical Investigation, vol. 123(8):3254-3271, Aug. 2013.
Hinderer et al., A Single Injection of an Optimized Adeno-Associated Viral Vector into Cerebrospinal Fluid Corrects Neurological Disease in a Murine Model of GM1 Gangliosidosis, Human Gene Therapy, vol. 31(21-22):1169-1177, Nov. 2020.
Hinderer et al., Severe Toxicity in Nonhuman Primates and Piglets Following High-Dose Intravenous Administration of an Adeno-Associated Virus Vector Expressing Human SMN, Human Gene Therapy, vol. 29(3):285-298, Mar. 2018.
Hinderer et al., Delivery of an Adeno-Associated Virus Vector into Cerebrospinal Fluid Attenuates Central Nervous System Disease in Mucopolysaccharidosis Type II Mice, Human Gene Therapy, vol. 27(11):906-915, Nov. 2016.
Hinderer et al., Evaluation of Intrathecal Routes of Administration for Adeno-Associated Viral Vectors in Large Animals, Human Gene Therapy, vol. 29(1):15-24, Jan. 2018.
Hinderer et al., Intrathecal gene therapy corrects CNS pathology in a feline model of mucopolysaccharidosis I, Molecular Therapy, vol. 22(12):2018-27, Dec. 2014.
Hinderer et al., Neonatal Systemic AAV Induces Tolerance to CNS Gene Therapy in Mps I Dogs and Nonhuman Primates, Molecular Therapy, vol. 23(8):1298-307, Aug. 2015.
Hinderer et al., Widespread gene transfer in the central nervous system of cynomolgus macaques following delivery of AAV9 into the cisterna magna, Molecular Therapy—Methods & Clinical Development, vol. 1:14051, Dec. 2014.
Hofer et a., Phenotype determining alleles in GM1 gangliosidosis patients bearing novel GLB1 mutations, Clinical Genetics, vol. 78(3):236-246, Sep. 2010.
Hordeaux et al., Safe and Sustained Expression of Human Iduronidase After Intrathecal Administration of Adeno-Associated Virus Serotype 9 in Infant Rhesus Monkeys, Human Gene Therapy, vol. 30(8):957-966, Aug. 2019.
Hordeaux et al., Toxicology Study of Intra-Cisterna Magna Adeno-Associated Virus 9 Expressing Human Alpha-L-Iduronidase in Rhesus Macaques, Molecular Therapy, Methods & Clinical Development, vol. 10:79-88, Jul. 2018.
Iannaccone et al., The PedsQL in pediatric patients with Spinal Muscular Atrophy: feasibility, reliability, and validity of the Pediatric Quality of Life Inventory Generic Core Scales and Neuromuscular Module, Neuromuscular disorders (NMD), vol. 19(12):805-812, Dec. 2009.
Janson et al., Clinical protocol. Gene therapy of Canavan disease: AAV-2 vector for neurosurgical delivery of aspartoacylase gene (ASPA) to the human brain, Human Gene Therapy, vol. 13(11):1391-412, Jul. 2002.
Utz et al., Infantile gangliosidoses: Mapping a timeline of clinical changes. Molecular Genetics and Metabolism, 121(2):170-179, Jun. 2017.
Jeyakumar et al., Central nervous system inflammation is a hallmark of pathogenesis in mouse models of GM1 and GM2 gangliosidosis, Brain, vol. 126(4):974-987, Apr. 2003.
Fisher et al., Transduction with recombinant adeno-associated virus for gene therapy is limited by leading-strand synthesis, Journal Virology, vol. 70(1):520-532, Jan. 1996.
Kaplitt et al., Safety and tolerability of gene therapy with an adeno-associated virus (AAV) borne GAD gene for Parkinson's disease: an open label, phase I trial, Lancet, vol. 369(9579):2097-105, Jun. 2007.
Kay et al., Evidence for gene transfer and expression of factor IX in hemophilia B patients treated with an AAV vector, Nature Genetics, vol. 24(3):257-61, Mar. 2000.
Kaye et al., Dysmyelinogenesis in animal model of GM1 gangliosidosis, Pediatric Neurology, vol. 8(4):255-261, Jul.-Aug. 1992.
Kobayashi, O. et al., Thalamic hyperdensity on CT in infantile GM1-gangliosidosis, Brain and Development, vol. 16(6):472-474, Nov.-Dec. 1994.
Li et al., Adeno-associated virus capsid antigen presentation is dependent on endosomal escape, The Journal of Clinical Investigation, vol. 123(3):1390-1401, Mar. 2013.
Li et al., Assessing the potential for AAV vector genotoxicity in a murine model, Blood, vol. 117(12):3311-3319, Mar. 2011.
Lock et al. Rapid, Simple, and Versatile Manufacturing of Recombinant Adeno-Associated Viral Vectors at Scale, Human Gene Therapy, vol. 21(10):1259-1271, Oct. 2010.
Lock et al., Absolute Determination of Single-Stranded and Self-Complementary Adeno-Associated Viral Vector Genome Titers by Droplet Digital PCR, Human Gene Therapy Methods, vol. 25(2):115-125, Apr. 2014.
Zanta-Boussif et al., Validation of a mutated PRE sequence allowing high and sustained transgene expression while abrogating WHV-X protein synthesis: application to the gene therapy of WAS, Gene Therapy, vol. 16(5):605-619, May 2009.
Mandel et al., Clinical trials in neurological disorders using AAV vectors: promises and challenges, Current Opinion in Molecular Therapeutics, Abstract, vol. 6(5):482-490, Oct. 2004.

(56) References Cited

OTHER PUBLICATIONS

Matsuda et al., Beta-galactosidase-deficient mouse as an animal model for GM1-gangliosidosis. Glycoconjugate Journal, Abstract, vol. 14(6):729-736, Sep. 1997.
McCarty et al., Integration of adeno-associated virus (AAV) and recombinant AAV vectors, Annual Review of Genetics, vol. 38:819-45, Aug. 2004.
McCurdy et al., Sustained Normalization of Neurological Disease after Intracranial Gene Therapy in a Feline Model, Science Translational Medicine, vol. 6(231):231ra48, Apr. 2014.
Melnick et al., Association of 20-Millimicron Particles with Adenoviruses, Journal of Bacteriology, vol. 90(1):271-274, Jul. 1965.
Mendell et al., Single-Dose Gene-Replacement Therapy for Spinal Muscular Atrophy, New England Journal of Medicine, vol. 377(18):1713-1722, Nov. 2017.
Miller, N., Glybera and the future of gene therapy in the European Union, Nature Reviews—Discovery, vol. 11(5):419, May 2012.
Mittermeyer et al., Long-term evaluation of a phase 1 study of AADC gene therapy for Parkinson's disease, Human Gene Therapy, vol. 23(4):377-81, Apr. 2012.
Morreau et al., Alternative splicing of beta-galactosidase mRNA generates the classic lysosomal enzyme and a beta-galactosidase-related protein, Journal of Biological Chemistry, vol. 264(34):20655-20663, Dec. 1989.
Nathawani et al., Adenovirus-Associated Virus Vector-Mediated Gene Transfer in Hemophilia B, New England Journal of Medicine, vol. 365(25):2357-2365, Dec. 2011.
Nestrasil et al. et al., Distinct progression patterns of brain disease in infantile and juvenile gangliosidoses: Volumetric quantitative MRI study. Molecular Genetics and Metabolism. vol. 123(2):97-104, Feb. 2018.
Oehmig et al., Integration of active human beta-galactosidase gene (100kb) into genome using HSV/AAV amplicon vector, Gene Therapy, vol. 14:1078-1091, Apr. 2007.
Oshima et al., Cloning, sequencing, and expression of cDNA for human β-galactosidase, Biochemical and Biophysical Research Communications, vol. 157(1):238-244, Nov. 1988.
Ou et al., SAAMP 2.0: An algorithm to predict genotype-phenotype correlation of lysosomal storage diseases, Clinical Genetics, vol. 93(5):1008-1014, May 2018.
Penaud-Budloo et al., Adeno-Associated Virus Vector Genomes Persist as Episomal Chromatin in Primate Muscle, Journal of Virology, vol. 82(16):7875-7885, Aug. 2008.
Peters, C., and Steward, C., Hematopoietic cell transplantation for inherited metabolic diseases: an overview of outcomes and practice guidelines, Bone Marrow Transplantation, vol. 31:229-39, Feb. 2003.
Kwapiszewski et al., Determination of Acid B-Galactosidase Activity: Methodology and Perspectives, Indian Journal of Clinical Biochemistry, vol. 29(1):57-62, Jan. 2014.
Rangarajan et al., AAV5-Factor VIII Gene Transfer in Severe Hemophilia A, New England Journal of Medicine, vol. 377(26):2519-2530, Dec. 2017.
Regier et al., MRI/MRS as a surrogate marker for clinical progression in GM1 gangliosidosis, American Journal of Medical Genetics Part A, vol. 170(3):634-644, Mar. 2016.
Regier et al., The GM1 and GM2 Gangliosidoses: Natural History and Progress toward Therapy, Pediatric endocrinology reviews : PER, vol. 13(1):663-673, Jun. 2016.
Rosas et al., Patterns of scAAV Vector Insertion Associated With Oncogenic Events in a Mouse Model for Genotoxicity, Molecular Therapy, vol. 20(11):2098-2110, Nov. 2012.
Samaranch et al., Strong cortical and spinal cord transduction after AAV7 and AAV9 delivery into the cerebrospinal fluid of nonhuman primates, Human Gene Therapy, vol. 24(5):526-32, May 2013.
Santamaria et al., Twenty-one novel mutations in the GLB1 gene identified in a large group of GM1-gangliosidosis and Morquio B patients: possible common origin for the prevalent p.R59H mutation among gypsies, Human Mutation, vol. 27(10):1060, Oct. 2006.
Scharf et al., Developmental Milestones, Pediatrics in Review, vol. 37(1):25-37, Jan. 2016.
Schuster et al., Biodistribution of adeno-associated virus serotype 9 (AAV9) vector after intrathecal and intravenous delivery in mouse, Frontiers in Neuroanatomy, vol. 8(42), Jun. 2014.
Severini et al., High frequency of type 1 GM1 gangliosidosis in southern Brazil, Clinical Genetics, vol. 56(2):168-169, Aug. 1999.
Shaprio et al., The integration of mindfulness and psychology, Journal of Clinical Psychology, vol. 65(6), Apr. 2009.
Shield et al., Bone marrow transplantation correcting β-galactosidase activity does not influence neurological outcome in juvenile GM1-gangliosidosis, Journal of Inherited Metabolic Disease, vol. 28(5):797-798, Sep. 2005.
Sommer et al., Quantification of adeno-associated virus particles and empty capsids by optical density measurement, Molecular Therapy, vol. 7(1):122-128, Jan. 2003.
Sperb et al., Genotypic and phenotypic characterization of Brazilian patients with GM1 gangliosidosis, Gene, vol. 512(1):113-116, Jan. 2013.
Suzuki et al., GM1-gangliosidosis: Accumulation of ganglioside GM1 in cultured skin fibroblasts and correlation with clinical types, Human Genetics, Abstract, vol. 43(2):127-131, Aug. 1978.
Tardieu et al., Intracerebral administration of adeno-associated viral vector serotype rh. 10 carrying human SGSH and SUMF1 cDNAs in children with mucopolysaccharidosis type IIIA disease: results of a phase I/II trial, Human Gene Therapy, vol. 25(6):506-16, Jun. 2014.
Tessitore et al., GM1-Ganglioside-Mediated Activation of the Unfolded Protein Response Causes Neuronal Death in a Neurodegenerative Gangliosidosis, Molecular Cell, vol. 15(5):753-766, Sep. 2004.
Thompson et al., A comprehensive comparison of multiple sequence alignments vol. 27(13):2682-2690, Jul. 1999.
Taghian et al., A Safe and Reliable Technique for CNS Delivery of AAV Vectors in the Cisterna Magna, Molecular Therapy, vol. 28(2):411-421, Nov. 2019.
Van Der Voorn et al., The leukoencephalopathy of infantile GM1 gangliosidosis: oligodendrocytic loss and axonal dysfunction, Acta Neuropathologica, vol. 107(6):539-545, Jun. 2004.
Van Hoof, H., and Hers, G., The abnormalities of lysosomal enzymes in mucopolysaccharidoses, European Journal of Biochemistry, vol. 7(1):34-44, Dec. 1968.
Varni et al., 2011, The PedsQL™ Infant Scales: feasibility, internal consistency reliability, and validity in healthy and ill infants, Quality of Life Research, vol. 20(1):45-55, Feb. 2011.
Vite et al., Effective gene therapy for an inherited CNS disease in a large animal model, Annals of Neurology, vol. 57(3):355-64, Mar. 2005.
Weismann et al., Systemic AAV9 gene transfer in adult GM1 gangliosidosis mice reduces lysosomal storage in CNS and extends lifespan, Human Molecular Genetics, vol. 24(15):4353-4364, May 2015.
Wijnhoven et al., Assessment of gross motor development in the WHO Multicentre Growth Reference Study, Food and Nutrition Bulletin, vol. 25(1):S37-45, Mar. 2004.
Wobus et al., Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection, Journal of Virology, vol. 74(19):9281-9293, Oct. 2000.
Worgall et al., Treatment of Late Infantile Neuronal Ceroid Lipofuscinosis by CNS Administration of a Serotype 2 Adeno-Associated Virus Expressing CLN2 cDNA, Human Gene Therapy, vol. 19(5):463-474, May 2008.
Jin et al., Direct Liquid Chromatography/Mass Spectrometry Analysis for Complete Characterization of Recombinant Adeno-Associated Virus Capsid Proteins, Human Gene Therapy Methods, vol. 28(5):255-267, Oct. 2017.
Zhang et al., Adenovirus-adeno- associated virus hybrid for large-scale recombinant adeno-associated virus production, Human Gene Therapy, vol. 20(9):922-9, Sep. 2009.
International Search Report and Written Opinion issued on International Patent Application No. PCT/US2019/053797, dated Feb. 2, 2020.

(56) References Cited

OTHER PUBLICATIONS

Yuan et al., Enhancement of exogenous gene expression in Jurkat cells by efficient promoter. Chinese Medicinal Biotechnology, 7(4)281-285. Aug. 2012. Abstract.
Jarnes et al., Imagine-1 study: Updated interim safety, biomarker, and efficacy data from the phase 1/2 open-label, multicenter study of a single dose, intracisterna magna administration of PBGM01 in type I (early onset) and type IIA (late onset) infantile GM1 gangliosidosis, 19th Annual WORLDSymposium, Orlando, FL., Feb. 22-26, 2023. Poster.
Jarnes et al., Imagine-1 study: Updated interim safety, biomarker, and efficacy data from the phase 1/2 open-label, multicenter study of a single dose, intracisterna magna administration of PBGM01 in type I (early onset) and type IIA (late onset) infantile GM1 gangliosidosis, 19th Annual WORLDSymposium, Orlando, FL., Feb. 22-26, 2023. Abstract.
Ni, Y., Biomarker and Bioanalytical Strategy to Inform AAV Based-Gene Therapy Trials, SAPA Annual Conference, Oct. 1, 2022.
Ni, Y., Rare Disease Patient Diagnostics: the Current Paradigm and Challenges, Philly Cell and Gene Therapy Annual Conference. Jun. 17-18, 2022.
Ni et al., Adeno-Associated Viral (AAV) Vector-Mediated GLB1 Gene Transfer Reduces Substrate Accumulations in a Murine Model of GM1 Gangliosidosis, 26th ASGCT Annual Meeting, Los Angeles, CA. May 16-20, 2023.
Ni et al., Adeno-associated viral (AAV) vector-mediated GLB1 gene transfer reduces substrates accumulation in a murine model of GMI gangliosidosis, 26th ASGCT Annual Meeting, Los Angeles, CA. May 16-20, 2023. Abstract.
Weinstein, D., Safety, Biomarker, and Preliminary Efficacy Results Following ICM Administration of PBGM01 in Children with Late Onset Infantile GM1-Gangliosidosis. 18th Annual WORLDSymposium. Oral Presentation. Feb. 7-11, 2022.
Weinstein, D., Interim Safety, Biomarker, and Efficacy Data from Imagine-1: A Phase 1/2 Open-Label, Multicenter Study to Assess the Safety, Tolerability, and Efficacy of a Single Dose, ICM Administration of PBGM01 in Subjects with Type I (Early Onset) and Type IIa (Late Onset) Infantile GM1 Gangliosidosis (GM1). NTSAD Annual Family Conference, Denver, CO. Jul. 7-10, 2022.
Weinstein et al., Safety, Biomarker, and Preliminary Efficacy Results Following ICM Administration of PBGM01 in Children with Late Onset Infantile GM1 Gangliosidosis: Implications for the Gene Therapy Trial for Krabbe Disease, 2022 Krabbe Translational Research Meeting. Presentation Mar. 17, 2022.
Weinstein et al., The Imagine-1 Trial: Study on Safety, Tolerability, and Efficacy of a PBGM01 in Children with Infantile GM1 Gangliosidosis (GM1), Cure GM1 Conference. Presentation Oct. 12, 2022.
Weinstein, D., Interim Safety, Biomarker, and Efficacy Data from Imagine-1: A Phase 1/2 Open-Label, Multicenter Study to Assess the Safety, Tolerability, and Efficacy of a Single Dose, ICM Administration of PBGM01 in Subjects with Type I (Early Onset) and Type IIa (Late Onset) Infantile GM1 Gangliosidosis (GM1), VII Latin American Course on Lysosomal Storage Diseases. Presentation Oct. 18, 2022.
Weinstein, D., Gene Therapy for Treatment of Neurodegenerative Diseases: Approaches and Challenges, Philly Cell and Gene Therapy Annual Conference. Presentation Jun. 18, 2022.
Jarnes, J., IMAGINE-1. A Phase 1/2 Open-Label, Multicenter Study to Assess the Safety, Tolerability, and Efficacy of a Single Dose of PBGM01 Delivered Into the Cisterna Magna of Subjects with Type 1 (Early Onset) and Type 2a (Late Onset) Infantile GM1-Gangliosidosis. 18th Annual WORLDSymposium, San Diego, CA, Feb. 7-11, 2022. Oral Presentation.
Jarnes et al., Phase 1/2 Open-Label, Multicenter Study to Assess the Safety, Tolerability, and Efficacy of a Single Dose of PBGM01 Delivered Into the Cisterna Magna of Subjects With Type 1 (Early Onset) and Type 2a (Late Onset) Infantile GM1-Gangliosidosis. 18th Annual WORLDSymposium, San Diego, CA, Feb. 7-11, 2022. Poster.
Al-Zaidy, S., Passage Bio Clinical Programs in Pediatric GM1 Gangliosidosis and Early Infantile Krabbe Disease, United Leukodystrophy Foundation (ULF) Two-Part Clinical Trials 101 Live Webinar Series—Industry Panel. Presentation Oct. 13, 2022.
Jarnes, J., Imagine-1 Study: Updated interim safety, biomarker, and efficacy data from the Phase 1/2 open-label, multicenter study of a single dose, intracisterna magna administration of PBGM01 in type I (early onset) and type IIA (late onset) infantile GM1 gangliosidosis, 19th Annual WORLDSymposium, Orlando, FL. Oral Presentation. Feb. 22-26, 2023.
Browne, S., A Preclinical Perspective on Genetic Medicines Development for CNS Disorders, Gene Therapy Forum. Presentation Dec. 2021.
Hinderer et al., A Single Injection of an Optimized AAV Vector into Cerebrospinal Fluid Prevents Neurological Disease in a Murine Model of GM1 Gangliosidosis, Abstract presented at ASGCT 22nd Annual Meeting, Apr. 29-May 2, 2019, Washington, D.C., Published to Public Apr. 15, 2019. Abstract.
Hinderer et al., A single injection of an optimized AAV vector into cerebrospinal fluid corrects neurological disease in a murine model of GM1 gangliosidosis, Poster Presentation presented at ASGCT 22nd Annual Meeting, Apr. 29-May 2, 2019, Washington, D.C. Oral Presentation.
Kodis, E., Natural History Study of Infantile and Juvenile GM1 Gangliosidosis (GM1) Patients, Virtual GM1 Family Meeting, Presentation, Sep. 8, 2020.
Passage Bio Receives FDA Clearance of IND Application for Lead Gene Therapy Candidate PBGM01 for Treatment of Infantile GM1 Gangliosidosis. Press Release. Jan. 4, 2021.
Passage Bio Announces Positive Interim Clinical Data from First Six Patients with GM1 Gangliosidosis in Imagine-1 Study. Press Release. Dec. 14, 2022.
Passage Bio to Showcase GM1 Gangliosidosis and Krabbe Clinical Programs at 2022 WORLDSymposium, February 7 - 11. Press Release. Jan. 31, 2022.
Passage Bio Announces Promising Interim Clinical Data from First Eight Patients with GM1 Gangliosidosis in Imagine-1 Study. Press Release. Aug. 7, 2023.
Passage Bio Presents Additional Interim Data from Imagine-1 Study for GM1 Gangliosidosis at 19th Annual WORLDSymposiumTM 2023. Press Release. Feb. 24, 2023.
Passage Bio to Present Updated Interim Data from Imagine-1 Study for GM1 Gangliosidosis at 19th Annual WORLDSymposium™M 2023. Press Release. Feb. 15, 2023.
Passage Bio Receives MHRA Clinical Trial Authorization for PBGM01 for Treatment of GM1 Gangliosidosis. Press Release. Dec. 2020.
Passage Bio and Invitae Announce Collaboration to Facilitate Genetic Testing to Support Early Diagnosis and Greater Awareness of Clinical Trials for Patients with GM1. Press Release. Nov. 9, 2020.
Passage Bio's PBGM01 Receives Orphan Drug Designation from EMA for Treatment of GM1 Gangliosidosis. Press Release. Oct. 26, 2020.
Passage Bio Receives Rare Pediatric Disease Designation for PBGM01 for Patients with GM1 Gangliosidosis. Press Release. May 21, 2020.
FDA Grants Passage Bio Orphan Drug Designation for PBGM01 for Treatment of Infantile GM1 Gangliosidosis. Press Release. Apr. 21, 2020.
Passage Bio Announces Launch of Natural History Study to Evaluate Patients with GM1 Gangliosidosis. Press Release. Aug. 13, 2019.
Passage Bio, Inc., Form 10-Q—Quarterly Report, United States Securities and Exchange Commission, filed Nov. 10, 2020, pp. 1-94 [online], [PDF], [retrieved on Jul. 1, 2024]. Retrieved from the Internet <https://d18rn0p25nwr6d.cloudfront.net/CIK-0001787297/063f5dbe-df36-40d0-9f99-9f323b674dle.pdf>.
Passage Bio, Inc., Form 10-Q—Quarterly Report, United States Securities and Exchange Commission, filed Aug. 13, 2020, pp.

(56) References Cited

OTHER PUBLICATIONS 1-156 [online], [PDF], [retrieved on Jul. 1, 2024]. Retrieved from the Internet <https://d18rn0p25nwr6d.cloudfront.net/CIK-0001787297/460f002a-57e5-4bbb-b1d2-a9c35d04878b.pdf>.

Passage Bio, Inc., Form 10-Q—Quarterly Report, United States Securities and Exchange Commission, filed May 11, 2020, pp. 1-228 [online], [PDF], [retrieved on Jul. 1, 2024]. Retrieved from the Internet <https://d18rn0p25nwr6d.cloudfront.net/CIK-0001787297/50a1a44d-0fc9-4ab8-a92d-21fddad794fa.pdff>.

Passage Bio, Inc., Form 10-Q—Quarterly Report, United States Securities and Exchange Commission, filed Nov. 4, 2021, pp. 1-122 [online], [PDF], [retrieved on Jul. 1, 2024]. Retrieved from the Internet <https://d18rn0p25nwr6d.cloudfront.net/CIK-0001787297/b923c8ac-1485-4b9b-a39c-06226f77cb69.pdf>.

Passage Bio, Inc., Form 10-Q—Quarterly Report, United States Securities and Exchange Commission, filed Aug. 5, 2021, pp. 1-93 [online], [PDF], [retrieved on Jul. 1, 2024]. Retrieved from the Internet <https://d18rn0p25nwr6d.cloudfront.net/CIK-0001787297/38332eeb-edb6-4d55-9b82-09ef6d9927cc.pdf>.

Passage Bio, Inc., Form 10-Q—Quarterly Report, United States Securities and Exchange Commission, filed May 5, 2021, pp. 1-101 [online], [PDF], [retrieved on Jul. 1, 2024]. Retrieved from the Internet <https://d18rn0p25nwr6d.cloudfront.net/CIK-0001787297/883ff597-a4cd-4ad0-863f-d28f445ace13.pdf>.

Passage Bio, Inc., Form 10-K—Annual Report, United States Securities and Exchange Commission, filed Mar. 3, 2021, pp. 1-196 [online], [PDF], [retrieved on Jul. 1, 2024]. Retrieved from the Internet <https://d18rn0p25nwr6d.cloudfront.net/CIK-0001787297/130127e5-5a35-4bf8-8a7d-edb68c4a852f.pdf>.

Passage Bio, Inc., Form 10-Q—Quarterly Report, United States Securities and Exchange Commission, filed Nov. 10, 2022, pp. 1-116 [online], [PDF], [retrieved on Jul. 1, 2024]. Retrieved from the Internet <https://d18rn0p25nwr6d.cloudfront.net/CIK-0001787297/36fdfdde-9ebf-40ee-b8c3-413086a3dd83.pdf>.

Passage Bio, Inc., Form 10-Q—Quarterly Report, United States Securities and Exchange Commission, filed Aug. 4, 2022, pp. 1-120 [online], [PDF], [retrieved on Jul. 1, 2024]. Retrieved from the Internet <https://d18rn0p25nwr6d.cloudfront.net/CIK-0001787297/7a9fff41-1755-4e09-8dad-0c8ff2928e56.pdf>.

Passage Bio, Inc., Form 10-Q—Quarterly Report, United States Securities and Exchange Commission, filed May 16, 2022, pp. 1-98 [online], [PDF], [retrieved on Jul. 1, 2024]. Retrieved from the Internet <https://d18rn0p25nwr6d.cloudfront.net/CIK-0001787297/7e5f9f7d-a030-475b-8a75-83f38e52692e.pdf>.

Passage Bio, Inc., Form 10-K—Annual Report, United States Securities and Exchange Commission, filed Mar. 3, 2022, pp. 1-198 [online], [PDF], [retrieved on Jul. 1, 2024]. Retrieved from the Internet <https://d18rn0p25nwr6d.cloudfront.net/CIK-0001787297/64747509-d0fd-43e5-95e6-569107e806ce.pdf>.

Passage Bio, Inc., Form 10-Q—Quarterly Report, United States Securities and Exchange Commission, filed Nov. 13, 2023, pp. 1-117 [online], [PDF], [retrieved on Jul. 1, 2024]. Retrieved from the Internet <https://d18rn0p25nwr6d.cloudfront.net/CIK-0001787297/247ca6e3-f51c-4446-9f2c-c489f8389b6f.pdf>.

Passage Bio, Inc., Form 10-Q—Quarterly Report, United States Securities and Exchange Commission, filed Aug. 7, 2023, pp. 1-102 [online], [PDF], [retrieved on Jul. 1, 2024]. Retrieved from the Internet <https://d18rn0p25nwr6d.cloudfront.net/CIK-0001787297/9dd14e3b-bfda-435d-acb5-92c977decfdd.pdf>.

Passage Bio, Inc., Form 10-Q—Quarterly Report, United States Securities and Exchange Commission, filed May 11, 2023, pp. 1-100 [online], [PDF], [retrieved on Jul. 1, 2024]. Retrieved from the Internet <https://d18rn0p25nwr6d.cloudfront.net/CIK-0001787297/0f2d8cd3-ad79-44e6-be7b-c3172c7c8995.pdf>.

Passage Bio, Inc., Form 10-K—Annual Report, United States Securities and Exchange Commission, filed Mar. 6, 2023, pp. 1-170 [online], [PDF], [retrieved on Jul. 1, 2024]. Retrieved from the Internet <https://d18rn0p25nwr6d.cloudfront.net/CIK-0001787297/9b78a9d7-54be-441b-a7c2-cd15c9bc3603.pdf>.

Passage Bio, Inc., Form 10-Q—Quarterly Report, United States Securities and Exchange Commission, filed May 14, 2024, pp. 1-100 [online], [PDF], [retrieved on Jul. 1, 2024]. Retrieved from the Internet <https://d18rn0p25nwr6d.cloudfront.net/CIK-0001787297/8e131a0e-2568-4c41-852f-f5731a6a5bf9.pdf>.

Passage Bio, Inc., Form 10-K—Annual Report, United States Securities and Exchange Commission, filed Mar. 4, 2024, pp. 1-249 [online], [PDF], [retrieved on Jul. 1, 2024]. Retrieved from the Internet <https://d18rn0p25nwr6d.cloudfront.net/CIK-0001787297/8fe8b871-1ac3-44ae-8560-2e4a624b1ca3.pdf>.

Office Action dated Nov. 28, 2023 issued in Canadian Patent Application No. 3114175, and Response filed May 28, 2024.

Office Action dated Jul. 12, 2023 issued in Chinese Patent Application No. 201980079543.8.

Office Action dated Feb. 6, 2024 issued in Chinese Patent Application No. 201980079543.8.

Office Action dated Jul. 24, 2023 issued in Colombian Patent Application No. NC2021/0005443.

Office Action dated Sep. 20, 2023 issued in Japanese Patent Application No. 2021-518190.

Substantive Examination Report dated Dec. 21, 2023 issued in Saudi Arabian Patent Application No. 521421639, and Response filed Apr. 18, 2024.

Latour, et al., Human GLB1 knockout cerebral organoids: A model system for testing AAV9-mediated GLB1 gene therapy for reducing GM1 ganglioside storage in GM1 gangliosidosis (Mol Gen Met Rep, 2019, 100513, pp. 1-8) (Year: 2019), available online Sep. 11, 2019.

* cited by examiner

FIG 3C
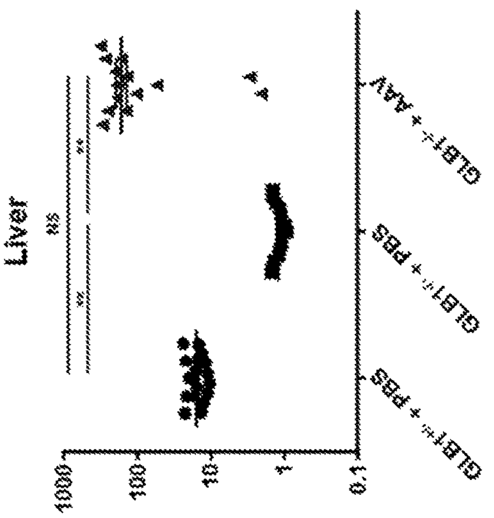
FIG 3B
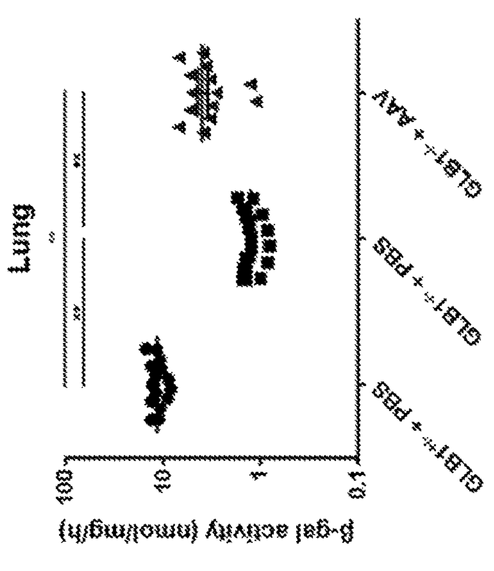
FIIG 3E
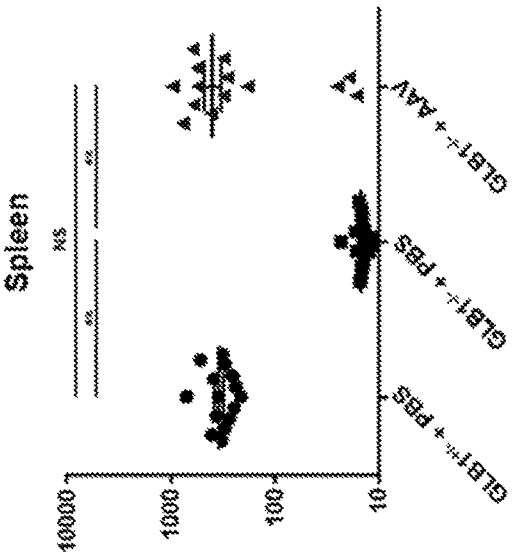
FIG 3D
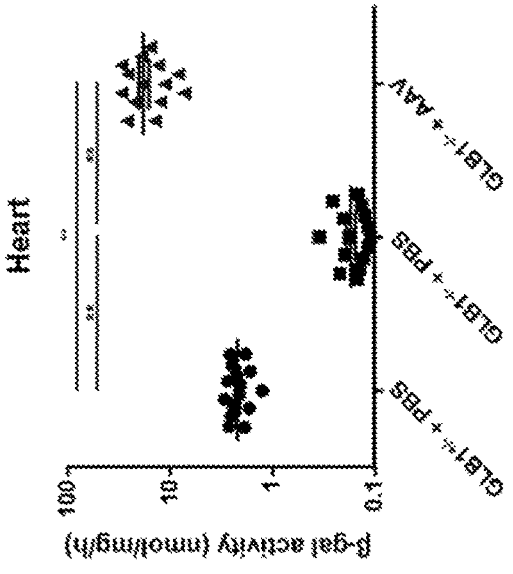

FIG 7A
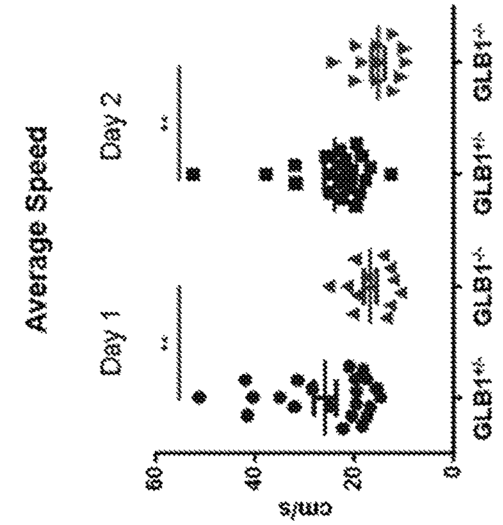
FIG 7B
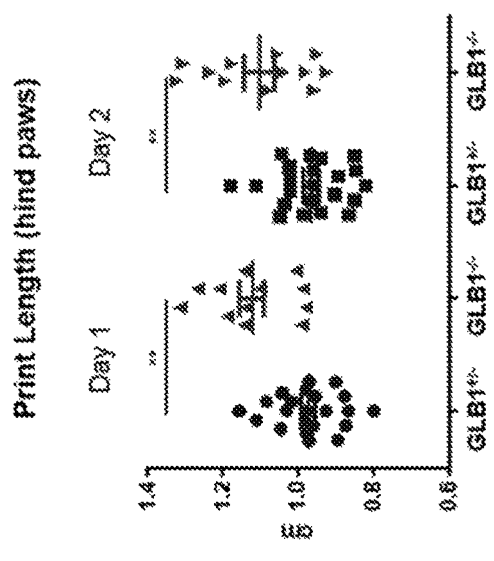
FIG 7C
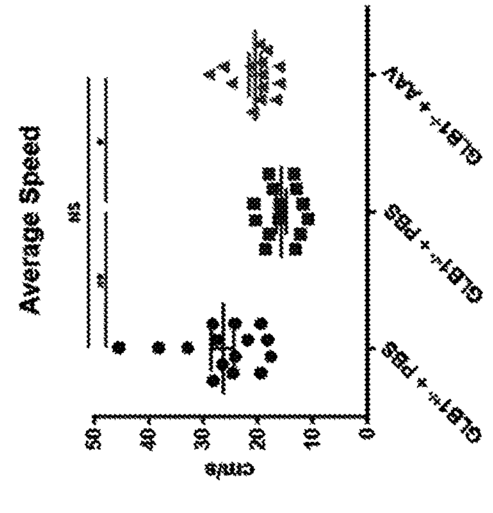
FIIG 7D
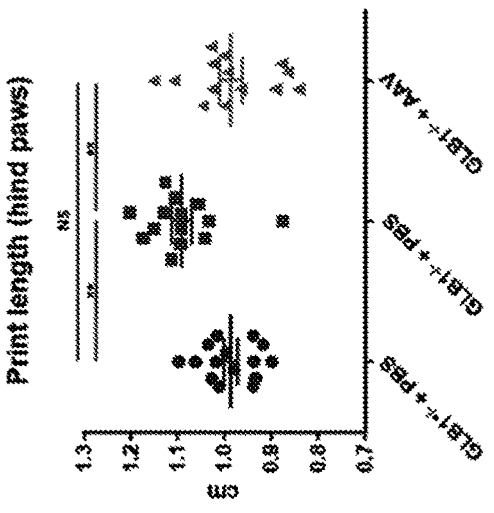

FIG 7E
GLB1$^{+/-}$ + PBS
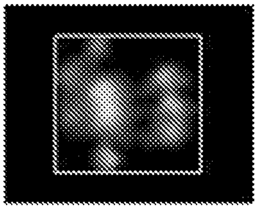
FIG 7F
GLB1$^{-/-}$ + PBS
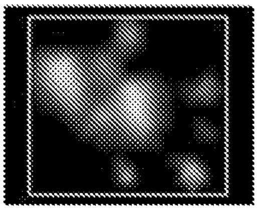
FIG 7G
GLB1$^{-/-}$ + AAV
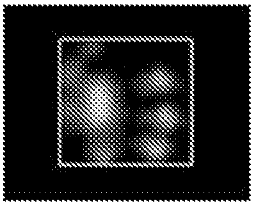
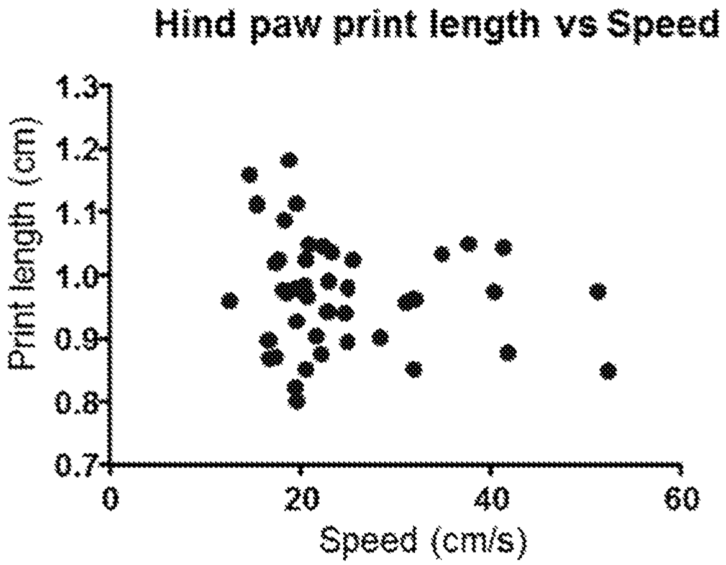
FIG 8B
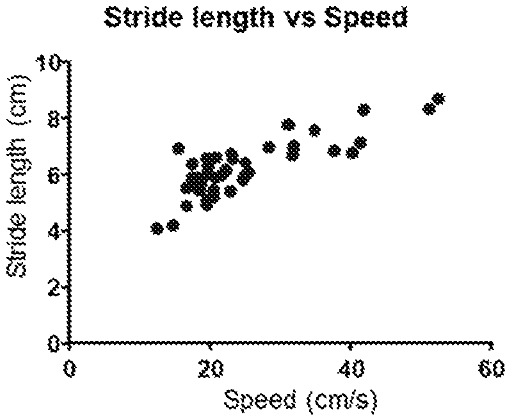
FIG 8A

| | | |
|---|---|---|
| | | 1 100 |
| AAV9 | (1) | MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF |
| hu.68.VP1 | (1) | MAADGYLPDWLEDNLSEGIREWWALKPGAPQPKANQQHQDNARGLVLPGYKYLGPGNGLDKGEPVNEADAAALEHDKAYDQQLKAGDNPYLKYNHADAEF |
| hu.31 | (1) | MAADGYLPDWLEDTLSEGIRBWWKLKPGPPPPKPAERHKDDSRGLVLPGYKYLGPGNGLDKGEPVNAADAAALEHDKAYDQQLKAGDNPYLKYNHADAEF |
| hu.32 | (1) | MAADGYLPDWLEDTLSEGIRBWWKLKPGPPPPKPAERHKDDSRGLVLPGYKYLGPGNGLDKGEPVNAADAAALEHDKAYDQQLKAGDNPYLKYNHADAEF |
| | | 101 200 |
| AAV9 | (101) | QERLKEDTSFGGNLGRAVFQAKKRLLEPLGLVEEAAKTAPGKKRPVEQSPQEPDSSAGIGKSGAQPAKKRLNFGQTGDTESVPDPQPIGEPPAAPSGVGS |
| hu.68.VP1 | (101) | QERLKEDTSFGGNLGRAVFQAKKRLLEPLGLVEEAAKTAPGKKRPVEQSPQEPDSSVGIGKSGAQPAKKRLNFGQTGDTESVPDPQPIGEPPAAPSGVGS |
| hu.31 | (101) | QERLKEDTSFGGNLGRAVFQAKKRLLEPLGLVEEAAKTAPGKKRPVEQSPQEPDSSAGIGKSGSQPAKKKLNFGQTGDTESVPDPQPIGEPPAAPSGVGS |
| hu.32 | (101) | QERLKEDTSFGGNLGRAVFQAKKRLLEPLGLVEEAAKTAPGKKRPVEQSPQEPDSSAGIGKSGSQPAKKKLNFGQTGDTESVPDPQPIGEPPAAPSGVGS |
| | | 201 300 |
| AAV9 | (201) | LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR |
| hu.68.VP1 | (201) | LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR |
| hu.31 | (201) | LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR |
| hu.32 | (201) | LTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQR |
| | | 301 400 |
| AAV9 | (301) | LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF |
| hu.68.VP1 | (301) | LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF |
| hu.31 | (301) | LINNNWGFRPKRLNFKLFNIQVKEVTDNNGVKTIANNLTSTVQVFTDSDYQLPYVLGSAHEGCLPPFPADVFMIPQYGYLTLNDGGQAVGRSSFYCLEYF |
| hu.32 | (301) | LINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEYF |
| | | 401 500 |
| AAV9 | (401) | PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE |
| hu.68.VP1 | (401) | PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE |
| hu.31 | (401) | PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE |
| hu.32 | (401) | PSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNSE |

FIG 10A

```
AAV9       (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG
hu.68.VP1  (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG
hu.31      (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG
hu.32      (501) FAWPGASSWALNGRNSLMNPGPAMASHKEGEDRFFPLSGSLIFGKQGTGRDNVDADKVMITNEEEIKTTNPVATESYGQVATNHQSAQAQAQTGWVQNQG

                 601                                                                                              700
AAV9       (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ
hu.68.VP1  (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ
hu.31      (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ
hu.32      (601) ILPGMVWQDRDVYLQGPIWAKIPHTDGNFHPSPLMGGFMKHPPPQILIKNTPVPADPPTAFNKDKLNSFITQYSTGQVSVEIEWELQKENSKRWNPEIQ

                 701                              736
AAV9       (701) YTSNYYKSNNVEFAVNTEGVYSEPRPIGTRYLTRNL
hu.68.VP1  (701) YTSNYYKSNNVEFAVNTEGVYSEPRPIGTRYLTRNL
hu.31      (701) YTSNYYKSNNVEFAVSTEGVYSEPRPIGTRYLTRNL
hu.32      (701) YTSNYYKSNNVEFAVNTEGVYSEPRPIGTRYLTRNL
```

FIG 10B

| | | |
|---|---|---|
| | | 1 … 100 |
| AAV9 | (1) | ATGGCTGCCGATGGTTATCTTCCAGATTGGCTCGAGGACAACCTTAGTGAAGGAATTCGCGAGTGGTGGGCTTTGAAACCTGGAGCCCCTCAACCCAAGG |
| hu.68.VP1 | (1) | ATGGCTGCCGATGGTTATCTTCCAGATTGGCTCGAGGACAACCTCAGTGAAGGCATTCGCGAGTGGTGGGCTTTGAAACCTGGAGCCCCTCAACCCAAGG |
| hu.31 | (1) | ATGGCTGCCGATGGTTATCTTCCAGATTGGCTCGAGGACACTCTCTCTGAAGGAATAAGACAGTGGTGGAAGCTCAAACCTGGCCCCCCACCACCAAAGC |
| hu.32 | (1) | ATGGCTGCCGATGGTTATCTTCCAGATTGGCTCGAGGACACTCTCTCTGAAGGAATAAGACAGTGGTGGAAGCTCAAACCTGGCCCACCACCACCAAAGC |
| | | 101 … 200 |
| AAV9 | (101) | CAAATCAACAACATCAAGACAACGCTCGAGGTCTTGTGCTTCCGGGTTACAAATACCTTGGACCCGGCAACGGACTCGACAAGGGGGAGCCGGTCAACGC |
| hu.68.VP1 | (101) | CAAATCAACAACATCAAGACAACGCTCGGGGTCTTGTGCTTCCGGGTTACAAATACCTTGGACCCGGCAACGGACTCGACAAGGGGGAGCCGGTCAACGA |
| hu.31 | (101) | CCGCAGAGCGGCATAAGGACGACAGCAGGGGTCTTGTGCTTCCTGGGTACAAGTACCTCGGACCCGGCAACGGACTCGACAAGGGGGAGCCGGTCAACGC |
| hu.32 | (101) | CCGCAGAGCGGCATAAGGACGACAGCAGGGGTCTTGTGCTTCCTGGGTACAAGTACCTCGGACCCGGCAACGGACTCGACAAGGGGGAGCCGGTCAACGC |
| | | 201 … 300 |
| AAV9 | (201) | AGCAGACGCGGCGGCCCTCGAGCACGACAAGGCCTACGACCAGCAGCTCAAGGCCGGAGACAACCCGTACCTCAAGTACAACCACGCCGACGCCGAGTTC |
| hu.68.VP1 | (201) | AGCAGACGCGGCGGCCCTCGAGCACGACAAGGCCTACGACCAGCAGCTCAAGGCCGGAGACAACCCGTACCTCAAGTACAACCACGCCGACGCCGAGTTC |
| hu.31 | (201) | AGCAGACGCGGCGGCCCTCGAGCACGACAAGGCCTACGACCAGCAGCTCAAGGCCGGAGACAACCCGTACCTCAAGTACAACCACGCCGACGCCGAGTTC |
| hu.32 | (201) | AGCAGACGCGGCGGCCCTCGAGCACGACAAGGCCTACGACCAGCAGCTCAAGGCCGGAGACAACCCGTACCTCAAGTACAACCACGCCGACGCCGAGTTC |
| | | 301 … 400 |
| AAV9 | (301) | CAGGAGCGGCTCAAAGAAGATACGTCTTTTGGGGGCAACCTCGGGCGAGCAGTCTTCCAGGCCAAAAAGAGGCTTCTTGAACCTCTTGGTCTGGTTGAGG |
| hu.68.VP1 | (301) | CAGGAGCGGCTCAAAGAAGATACGTCTTTTGGGGGCAACCTCGGGCGAGCAGTCTTCCAGGCCAAAAAGAGGCTTCTTGAACCTCTTGGTCTGGTTGAGG |
| hu.31 | (301) | CAGGAGCGGCTCAAAGAAGATACGTCTTTTGGGGGCAACCTCGGGCGAGCAGTCTTCCAGGCCAAAAAGAGGCTTCTTGAACCTCTTGGTCTGGTTGAGG |
| hu.32 | (301) | CAGGAGCGGCTCAAAGAAGATACGTCTTTTGGGGGCAACCTCGGGCGAGCAGTCTTCCAGGCCAAAAAGAGGCTTCTTGAACCTCTTGGTCTGGTTGAGG |
| | | 401 … 500 |
| AAV9 | (401) | AAGCGGCTAAGACGGCTCCTGGAAAGAAGAGGCTGTAGAGCAGTCTCCTCAGGAACCGGACTCCTCCGCGGGTATTGGCAAATCGGGTGCACAGCCCGC |
| hu.68.VP1 | (401) | AAGCGGCTAAGACGGCTCCTGGAAAGAAGAGGCTGTAGAGCAGTCTCCTCAGGAACCGGACTCCTCCGTGGGTATTGGCAAATCGGGTGCACAGCCCGC |
| hu.31 | (401) | AAGCGGCTAAGACGGCTCCTGGAAAGAAGAGGCTGTAGAGCAGTCTCCTCAGGAACCGGACTCCTCCGCGGGTATTGGCAAATCGGGTTCACAGCCCGC |
| hu.32 | (401) | AAGCGGCTAAGACGGCTCCTGGAAAGAAGAGGCTGTAGAGCAGTCTCCTCAGGAACCGGACTCCTCCGCGGGTATTGGCAAATCGGGTTCACAGCCCGC |

FIG 11A

| | | |
|---|---|---|
| | | 501 600 |
| AAV9 | (501) | TAAAAAGAGACTCAATTTCGGTCAGACTGGCGACACAGAGTCAGTCCCAGACCCTCAACCAATCGGAGAACCTCCCGCAGCCCCCTCAGGTGTGGGATCT |
| hu.68.VP1 | (501) | TAAAAAGAGACTCAATTTCGGTCAGACTGGCGACACAGAGTCAGTCCCCGACCCTCAACCAATCGGAGAACCTCCCGCAGCCCCCTCAGGTGTGGGATCT |
| hu.31 | (501) | TAAAAAGAAACTCAATTTCGGTCAGACTGGCGACACAGAGTCAGTCCCCGACCCTCAACCAATCGGAGAACCTCCCGCAGCCCCCTCAGGTGTGGGATCT |
| hu.32 | (501) | TAAAAAGAAACTCAATTTCGGTCAGACTGGCGACACAGAGTCAGTCCCCGACCCTCAACCAATCGGAGAACCTCCCGCAGCCCCCTCAGGTGTGGGATCT |
| | | 601 700 |
| AAV9 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| hu.68.VP1 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| hu.31 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| hu.32 | (601) | CTTACAATGGCTTCAGGTGGTGGCGCACCAGTGGCAGACAATAACGAAGGTGCCGATGGAGTGGGTAGTTCCTCGGGAAATTGGCATTGCGATTCCCAAT |
| | | 701 800 |
| AAV9 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| hu.68.VP1 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| hu.31 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| hu.32 | (701) | GGCTGGGGGACAGAGTCATCACCACCAGCACCCGAACCTGGGCCCTGCCCACCTACAACAATCACCTCTACAAGCAAATCTCCAACAGCACATCTGGAGG |
| | | 801 900 |
| AAV9 | (801) | ATCTTCAAATGACAACGCCTACTTCGGCTACAGCACCCCCTGGGGGTATTTTGACTTCAACAGATTCCACTGCCACTTCTCACCACGTGACTGGCAGCGA |
| hu.68.VP1 | (801) | ATCTTCAAATGACAACGCCTACTTCGGCTACAGCACCCCCTGGGGGTATTTTGACTTCAACAGATTCCACTGCCACTTCTCACCACGTGACTGGCAAAGA |
| hu.31 | (801) | ATCTTCAAATGACAACGCCTACTTCGGCTACAGCACCCCCTGGGGGTATTTTGACTTCAACAGATTCCACTGCCACTTCTCACCACGTGACTGGCAGCGA |
| hu.32 | (801) | ATCTTCAAATGACAACGCCTACTTCGGCTACAGCACCCCCTGGGGGTATTTTGACTTCAACAGATTCCACTGCCACTTCTCACCACGTGACTGGCAGCGA |
| | | 901 1000 |
| AAV9 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |
| hu.68.VP1 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |
| hu.31 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |
| hu.32 | (901) | CTCATCAACAACAACTGGGGATTCCGGCCTAAGCGACTCAACTTCAAGCTCTTCAACATTCAGGTCAAAGAGGTTACGGACAACAATGGAGTCAAGACCA |

FIG 11B

```
                 901                                                                                            1000
AAV9       (901) CTCATCAACAACAACTGGGGATTCCGGCCTAAGCGACTCAACTTCAAGCTCTTCAACATTCAGGTCAAAGAGGTTACGGACAACAATGGAGTCAAGACCA
hu.68.VP1  (901) CTCATCAACAACAACTGGGGATTCCGGCCTAAGCGACTCAACTTCAAGCTCTTCAACATTCAGGTCAAAGAGGTTACGGACAACAATGGAGTCAAGACCA
hu.31      (901) CTCATCAACAACAACTGGGGATTCCGGCCTAAGCGACTCAACTTCAAGCTCTTCAACATTCAGGTCAAAGAGGTTACGGACAACAATGGAGTCAAGACCA
hu.32      (901) CTCATCAACAACAACTGGGGATTCCGGCCTAAGCGACTCAACTTCAAGCTCTTCAACATTCAGGTCAAAGAGGTTACGGACAACAATGGAGTCAAGACCA

                 1001                                                                                           1100
AAV9      (1001) TCGCCAATAACCTTACCAGCACGGTCCAGGTCTTCACGGACTCAGACTATCAGCTCCCGTACGTGCTCGGGTCGGCTCACGAGGGCTGCCTCCCGCCGTT
hu.68.VP1 (1001) TCGCTAATAACCTTACCAGCACGGTCCAGGTCTTCACGGACTCAGACTATCAGCTCCCGTACGTGCTCGGGTCGGCTCACGAGGGCTGCCTCCCGCCGTT
hu.31     (1001) TCGCCAATAACCTTACCAGCACGGTCCAGGTCTTCACGGACTCAGACTATCAGCTCCCGTACGTGCTCGGGTCGGCTCACGAGGGCTGCCTCCCGCCGTT
hu.32     (1001) TCGCCAATAACCTTACCAGCACGGTCCAGGTCTTCACGGACTCAGACTATCAGCTCCCGTACGTGCTCGGGTCGGCTCACGAGGGCTGCCTCCCGCCGTT

                 1101                                                                                           1200
AAV9      (1101) CCCAGCGGACGTTTTCATGATTCCTCAGTACGGGTATCTGACGCTTAATGATGGAAGCCAGGCCGTGGGTCGTTCGTCCTTTTACTGCCTGGAATATTTC
hu.68.VP1 (1101) CCCAGCGGACGTTTTCATGATTCCTCAGTACGGGTATCTAACGCTTAATGATGGAAGCCAAGCCGTGGGTCGTTCGTCCTTTTACTGCCTGGAATATTTC
hu.31     (1101) CCCAGCGGACGTTTTCATGATTCCTCAGTACGGGTATCTGACGCTTAATGATGGAGGCCAGGCCGTGGGTCGTTCGTCCTTTTACTGCCTGGAATATTTC
hu.32     (1101) CCCAGCGGACGTTTTCATGATTCCTCAGTACGGGTATCTGACGCTTAATGATGGGAGCCAGGCCGTGGGTCGTTCGTCCTTTTACTGCCTGGAATATTTC

                 1201                                                                                           1300
AAV9      (1201) CCGTCGCAAATGCTAAGAACGGGTAACAACTTCCAGTTCAGCTACGAGTTTGAGAACGTACCTTTCCATAGCAGCTACGCTCACAGCCAAAGCCTGGACC
hu.68.VP1 (1201) CCGTCGCAAATGCTAAGAACGGGTAACAACTTCCAGTTCAGCTACGAGTTTGAGAACGTACCTTTCCATAGCAGCTATGCTCACAGCCAAAGCCTGGACC
hu.31     (1201) CCGTCGCAAATGCTAAGAACGGGTAACAACTTCCAGTTCAGCTACGAGTTTGAGAACGTACCTTTCCATAGCAGCTACGCTCACAGCCAAAGCCTGGACC
hu.32     (1201) CCGTCGCAAATGCTAAGAACGGGTAACAACTTCCAGTTCAGCTACGAGTTTGAGAACGTACCTTTCCATAGCAGCTACGCTCACAGCCAAAGCCTGGACC

                 1301                                                                                           1400
AAV9      (1301) GACTAATGAATCCACTCATCGACCAATACTTGTACTATCTCTCAAAGACTATTAACGGTTCTGGACAGAATCAACAAACGCTAAAATTCAGTGTGGCCGG
hu.68.VP1 (1301) GACTCATGAATCCACTCATCGACCAATACTTGTACTATCTCTCAAAGACTATTAACGGTTCTGGACAGAATCAACAAACGCTAAAATTCAGTGTGGCCGG
hu.31     (1301) GACTAATGAATCCACTCATCGACCAATACTTGTACTATCTCTCAAAGACTATTAACGGTTCTGGACAGAATCAACAAACGCTAAAATTCAGTGTGGCCGG
hu.32     (1301) GACTAATGAATCCACTCATCGACCAATACTTGTACTATCTCTCAAAGACTATTAACGGTTCTGGACAGAATCAACAAACGCTAAAATTCAGCGTGGCCGG
```

FIG 11C

```
                1401                                                                                            1500
AAV9     (1401) ACCCAGCAACATGGCTGTCCAGGGAAGAAACTACATACCTGGACCCAGCTACCGACAACAACGTGTCTCAACCACTGTGACTCAAAACAACAACAGCGAA
hu.68.VP1 (1401) ACCCAGCAACATGGCTGTCCAGGGAAGAAACTACATACCTGGACCCAGCTACCGACAACAACGTGTCTCAACCACTGTGACTCAAAACAACAACAGCGAA
hu.31    (1401) ACCCAGCAACATGGCTGTCCAGGGAAGAAACTACATACCTGGACCCAGCTACCGACAACAACGTGTCTCAACCACTGTGACTCAAAACAACAACAGCGAA
hu.32    (1401) ACCCAGCAACATGGCTGTCCAGGGAAGAAACTACATACCTGGACCCAGCTACCGACAACAACGTGTCTCAACCACTGTGACTCAAAACAACAACAGCGAA

                1501                                                                                            1600
AAV9     (1501) TTTGCTTGGCCTGGAGCTTCTTCTTGGGCTCTCAATGGACGTAATAGCTTGATGAATCCTGGACCTGCTATGGCCAGCCACAAAGAAGGAGAGGACCGTT
hu.68.VP1 (1501) TTTGCTTGGCCTGGAGCTTCTTCTTGGGCTCTCAATGGACGTAATAGCTTGATGAATCCTGGACCTGCTATGGCCAGCCACAAAGAAGGAGAGGACCGTT
hu.31    (1501) TTTGCTTGGCCTGGAGCTTCTTCTTGGGCTCTCAATGGACGTAATAGCTTGATGAATCCTGGACCTGCTATGGCCAGCCACAAAGAAGGAGAGGACCGTT
hu.32    (1501) TTTGCTTGGCCTGGAGCTTCTTCTTGGGCTCTCAATGGACGTAATAGCTTGATGAATCCTGGACCTGCTATGGCCAGCCACAAAGAAGGAGAGGACCGTT

                1601                                                                                            1700
AAV9     (1601) TCTTTCCTTTGTCTGGATCTTTAATTTTTGGCAAACAAGGAACTGGAAGAGACAACGTGGATGCGGACAAAGTCATGATAACCAACGAAGAAGAAATTAA
hu.68.VP1 (1601) TCTTTCCTTTGTCTGGATCTTTAATTTTTGGCAAACAAGGAACTGGAAGAGACAACGTGGATGCGGACAAAGTCATGATAACCAACGAAGAAGAAATTAA
hu.31    (1601) TCTTTCCTTTGTCCGGATCTTTAATTTTTGGCAAACAAGGAACTGGAAGAGACAACGTGGATGCGGACAAAGTCATGATAACCAACGAAGAAGAAATTAA
hu.32    (1601) TCTTTCCTTTGTCTGGATCTTTAATTTTTGGCAAACAAGGAACTGGAAGAGACAACGTGGATGCGGACAAAGTCATGATAACCAACGAAGAAGAAATTAA

                1701                                                                                            1800
AAV9     (1701) AACTACTAACCCGGTAGCAACGGAGTCCTATGGACAAGTGGCCACAAACCACCAGAGTGCCCAAGCACAGGCGCAGACCGGCTGGGTTCAAAACCAAGGA
hu.68.VP1 (1701) AACTACCAACCCAGTAGCAACGGAGTCCTATGGACAAGTGGCCACAAACCACCAGAGTGCCCAAGCACAGGCGCAGACCGGCTGGGTTCAAAACCAAGGA
hu.31    (1701) AACTACTAACCCGGTAGCAACGGAGTCCTATGGACAAGTGGCCACAAACCACCAGAGTGCCCAAGCACAGGCGCAGACCGGCTGGGTTCAAAACCAAGGA
hu.32    (1701) AACTACTAACCCGGTAGCAACGGAGTCCTATGGACAAGTGGCCACAAACCACCAGAGTGCCCAAGCACAGGCGCAGACCGGCTGGGTTCAAAACCAAGGA
```

FIG 11D

```
                  1801                                                                                            1900
AAV9     (1801)  ATACTTCCGGGTATGGTTTGGCAGGACAGAGATGTGTACCTGCAAGGACCCATTTGGGCCAAAATTCCTCACACGGACGGCAACTTTCACCCTTCTCCGC
hu.68.VP1 (1801) ATACTTCCGGGTATGGTTTGGCAGGACAGAGATGTGTACCTGCAAGGACCCATTTGGGCCAAAATTCCTCACACGGACGGCAACTTTCACCCTTCTCCGC
hu.31    (1801)  ATACTTCCGGGTATGGTTTGGCAGGACAGAGATGTGTACCTGCAAGGACCCATTTGGGCCAAAATTCCTCACACGGACGGCAACTTTCACCCTTCTCCGC
hu.32    (1801)  ATACTTCCGGGTATGGTTTGGCAGGACAGAGATGTGTACCTGCAAGGACCCATTTGGGCCAAAATTCCTCACACGGACGGCAACTTTCACCCTTCTCCGC

                  1901                                                                                            2000
AAV9     (1901)  TGATGGGAGGGTTTGGAATGAAGCACCCGCCTCCTCAGATCCTCATCAAAAACACACCTGTACCTGCGGATCCTCCAACGGCCTTCAACAAGGACAAGCT
hu.68.VP1 (1901) TGATGGGAGGGTTTGGAATGAAGCACCCGCCTCCTCAGATCCTCATCAAAAACACACCTGTACCTGCGGATCCTCCAACGGCTTTCAACAAGGACAAGCT
hu.31    (1901)  TAATGGGAGGGTTTGGAATGAAGCACCCGCCTCCTCAGATCCTCATCAAAAACACACCTGTACCTGCGGATCCTCCAACGGCTTTCAATAAGGACAAGCT
hu.32    (1901)  TAATGGGAGGGTTTGGAATGAAGCACCCGCCTCCTCAGATCCTCATCAAAAACACACCTGTACCTGCGGATCCTCCAACGGCTTTCAATAAGGACAAGCT

                  2001                                                                                            2100
AAV9     (2001)  GAACTCTTTCATCACCCAGTATTCTACTGGCCAAGTCAGCGTGGAGATCGAGTGGGAGCTGCAGAAGGAAAACAGCAAGCGCTGGAACCCGGAGATCCAG
hu.68.VP1 (2001) GAACTCTTTCATCACCCAGTATTCTACTGGCCAAGTCAGCGTGGAGATTGAGTGGGAGCTGCAGAAGGAAAACAGCAAGCGCTGGAACCCGGAGATCCAG
hu.31    (2001)  GAACTCTTTCATCACCCAGTATTCTACTGGCCAAGTCAGCGTGGAGATTGAGTGGGAGCTGCAGAAGGAAAACAGCAAGCGCTGGAACCCGGAGATCCAG
hu.32    (2001)  GAACTCTTTCATCACCCAGTATTCTACTGGCCAAGTCAGCGTGGAGATTGAGTGGGAGCTGCAGAAGGAAAACAGCAAGCGCTGGAACCCGGAGATCCAG

                  2101                                                                                            2200
AAV9     (2101)  TACACTTCCAACTATTACAAGTCTAATAATGTTGAATTTGCTGTTAATACTGAAGGTGTATATAGTGAACCCCGCCCCATTGGCACCAGATACCTGACTC
hu.68.VP1 (2101) TACACTTCCAACTATTACAAGTCTAATAATGTTGAATTTGCTGTTAATACTGAAGGTGTTTATTCTGAACCCCGCCCCATTGGCACCAGATACCTGACTC
hu.31    (2101)  TACACTTCCAACTATTACAAGTCTAATAATGTTGAATTTGCTGTTAGTACTGAAGGTGTATATAGTGAACCCCGCCCCATTGGCACCAGATACCTGACTC
hu.32    (2101)  TACACTTCCAACTATTACAAGTCTAATAATGTTGAATTTGCTGTTAATACTGAAGGTGTATATAGTGAACCCCGCCCCATTGGCACCAGATACCTGACTC

                  2201 2211
AAV9     (2201)  GTAATCTGTAA
hu.68.VP1 (2201) GTAATCTGTAA
hu.31    (2201)  GTAATCTGTAA
hu.32    (2201)  GTAATCTGTAA
```

FIG 11E

SEQUENCE LISTING

```
<160> NUMBER OF SEQ ID NOS: 26

<210> SEQ ID NO 1
<211> LENGTH: 2211
<212> TYPE: DNA
<213> ORGANISM: Artificial Sequence
<220> FEATURE:
<223> OTHER INFORMATION: AAVhu68 vp1 capsid of Homo Sapiens origin
<220> FEATURE:
<221> NAME/KEY: CDS
<222> LOCATION: (1)..(2211)

<400> SEQUENCE: 1

atg gct gcc gat ggt tat ctt cca gat tgg ctc gag gac aac ctc agt       48
Met Ala Ala Asp Gly Tyr Leu Pro Asp Trp Leu Glu Asp Asn Leu Ser
1               5                   10                  15

gaa ggc att cgc gag tgg tgg gct ttg aaa cct gga gcc cct caa ccc       96
Glu Gly Ile Arg Glu Trp Trp Ala Leu Lys Pro Gly Ala Pro Gln Pro
            20                  25                  30

aag gca aat caa caa cat caa gac aac gct cgg ggt ctt gtg ctt ccg      144
Lys Ala Asn Gln Gln His Gln Asp Asn Ala Arg Gly Leu Val Leu Pro
        35                  40                  45

ggt tac aaa tac ctt gga ccc ggc aac gga ctc gac aag ggg gag ccg      192
Gly Tyr Lys Tyr Leu Gly Pro Gly Asn Gly Leu Asp Lys Gly Glu Pro
    50                  55                  60

gtc aac gaa gca gac gcg gcg gcc ctc gag cac gac aag gcc tac gac      240
Val Asn Glu Ala Asp Ala Ala Ala Leu Glu His Asp Lys Ala Tyr Asp
65                  70                  75                  80

cag cag ctc aag gcc gga gac aac ccg tac ctc aag tac aac cac gcc      288
Gln Gln Leu Lys Ala Gly Asp Asn Pro Tyr Leu Lys Tyr Asn His Ala
                85                  90                  95

gac gcc gag ttc cag gag cgg ctc aaa gaa gat acg tct ttt ggg ggc      336
Asp Ala Glu Phe Gln Glu Arg Leu Lys Glu Asp Thr Ser Phe Gly Gly
            100                 105                 110

aac ctc ggg cga gca gtc ttc cag gcc aaa aag agg ctt ctt gaa cct      384
Asn Leu Gly Arg Ala Val Phe Gln Ala Lys Lys Arg Leu Leu Glu Pro
        115                 120                 125

ctt ggt ctg gtt gag gaa gcg gct aag acg gct cct gga aag aag agg      432
Leu Gly Leu Val Glu Glu Ala Ala Lys Thr Ala Pro Gly Lys Lys Arg
    130                 135                 140

cct gta gag cag tct cct cag gaa ccg gac tcc tcc gtg ggt att ggc      480
Pro Val Glu Gln Ser Pro Gln Glu Pro Asp Ser Ser Val Gly Ile Gly
145                 150                 155                 160

aaa tcg ggt gca cag ccc gct aaa aag aga ctc aat ttc ggt cag act      528
Lys Ser Gly Ala Gln Pro Ala Lys Lys Arg Leu Asn Phe Gly Gln Thr
                165                 170                 175

ggc gac aca gag tca gtc ccc gac cct caa cca atc gga gaa cct ccc      576
Gly Asp Thr Glu Ser Val Pro Asp Pro Gln Pro Ile Gly Glu Pro Pro
            180                 185                 190
```

-continued

```
gca gcc ccc tca ggt gtg gga tct ctt aca atg gct tca ggt ggt ggc      624
Ala Ala Pro Ser Gly Val Gly Ser Leu Thr Met Ala Ser Gly Gly Gly
        195                 200                 205

gca cca gtg gca gac aat aac gaa ggt gcc gat gga gtg ggt agt tcc      672
Ala Pro Val Ala Asp Asn Asn Glu Gly Ala Asp Gly Val Gly Ser Ser
    210                 215                 220

tcg gga aat tgg cat tgc gat tcc caa tgg ctg ggg gac aga gtc atc      720
Ser Gly Asn Trp His Cys Asp Ser Gln Trp Leu Gly Asp Arg Val Ile
225                 230                 235                 240

acc acc agc acc cga acc tgg gcc ctg ccc acc tac aac aat cac ctc      768
Thr Thr Ser Thr Arg Thr Trp Ala Leu Pro Thr Tyr Asn Asn His Leu
                245                 250                 255

tac aag caa atc tcc aac agc aca tct gga gga tct tca aat gac aac      816
Tyr Lys Gln Ile Ser Asn Ser Thr Ser Gly Gly Ser Ser Asn Asp Asn
            260                 265                 270

gcc tac ttc ggc tac agc acc ccc tgg ggg tat ttt gac ttc aac aga      864
Ala Tyr Phe Gly Tyr Ser Thr Pro Trp Gly Tyr Phe Asp Phe Asn Arg
        275                 280                 285

ttc cac tgc cac ttc tca cca cgt gac tgg caa aga ctc atc aac aac      912
Phe His Cys His Phe Ser Pro Arg Asp Trp Gln Arg Leu Ile Asn Asn
    290                 295                 300

aac tgg gga ttc cgg cct aag cga ctc aac ttc aag ctc ttc aac att      960
Asn Trp Gly Phe Arg Pro Lys Arg Leu Asn Phe Lys Leu Phe Asn Ile
305                 310                 315                 320

cag gtc aaa gag gtt acg gac aac aat gga gtc aag acc atc gct aat     1008
Gln Val Lys Glu Val Thr Asp Asn Asn Gly Val Lys Thr Ile Ala Asn
                325                 330                 335

aac ctt acc agc acg gtc cag gtc ttc acg gac tca gac tat cag ctc     1056
Asn Leu Thr Ser Thr Val Gln Val Phe Thr Asp Ser Asp Tyr Gln Leu
            340                 345                 350

ccg tac gtg ctc ggg tcg gct cac gag ggc tgc ctc ccg ccg ttc cca     1104
Pro Tyr Val Leu Gly Ser Ala His Glu Gly Cys Leu Pro Pro Phe Pro
        355                 360                 365

gcg gac gtt ttc atg att cct cag tac ggg tat cta acg ctt aat gat     1152
Ala Asp Val Phe Met Ile Pro Gln Tyr Gly Tyr Leu Thr Leu Asn Asp
    370                 375                 380

gga agc caa gcc gtg ggt cgt tcg tcc ttt tac tgc ctg gaa tat ttc     1200
Gly Ser Gln Ala Val Gly Arg Ser Ser Phe Tyr Cys Leu Glu Tyr Phe
385                 390                 395                 400

ccg tcg caa atg cta aga acg ggt aac aac ttc cag ttc agc tac gag     1248
Pro Ser Gln Met Leu Arg Thr Gly Asn Asn Phe Gln Phe Ser Tyr Glu
                405                 410                 415

ttt gag aac gta cct ttc cat agc agc tat gct cac agc caa agc ctg     1296
Phe Glu Asn Val Pro Phe His Ser Ser Tyr Ala His Ser Gln Ser Leu
            420                 425                 430

gac cga ctc atg aat cca ctc atc gac caa tac ttg tac tat ctc tca     1344
Asp Arg Leu Met Asn Pro Leu Ile Asp Gln Tyr Leu Tyr Tyr Leu Ser
        435                 440                 445

aag act att aac ggt tct gga cag aat caa caa acg cta aaa ttc agt     1392
Lys Thr Ile Asn Gly Ser Gly Gln Asn Gln Gln Thr Leu Lys Phe Ser
    450                 455                 460

gtg gcc gga ccc agc aac atg gct gtc cag gga aga aac tac ata cct     1440
Val Ala Gly Pro Ser Asn Met Ala Val Gln Gly Arg Asn Tyr Ile Pro
465                 470                 475                 480

gga ccc agc tac cga caa caa cgt gtc tca acc act gtg act caa aac     1488
Gly Pro Ser Tyr Arg Gln Gln Arg Val Ser Thr Thr Val Thr Gln Asn
                485                 490                 495

aac aac agc gaa ttt gct tgg cct gga gct tct tct tgg gct ctc aat     1536
Asn Asn Ser Glu Phe Ala Trp Pro Gly Ala Ser Ser Trp Ala Leu Asn
```

-continued

```
            500                 505                 510

gga cgt aat agc ttg atg aat cct gga cct gct atg gcc agc cac aaa      1584
Gly Arg Asn Ser Leu Met Asn Pro Gly Pro Ala Met Ala Ser His Lys
        515                 520                 525

gaa gga gag gac cgt ttc ttt cct ttg tct gga tct tta att ttt ggc      1632
Glu Gly Glu Asp Arg Phe Phe Pro Leu Ser Gly Ser Leu Ile Phe Gly
    530                 535                 540

aaa caa gga act gga aga gac aac gtg gat gcg gac aaa gtc atg ata      1680
Lys Gln Gly Thr Gly Arg Asp Asn Val Asp Ala Asp Lys Val Met Ile
545                 550                 555                 560

acc aac gaa gaa gaa att aaa act acc aac cca gta gca acg gag tcc      1728
Thr Asn Glu Glu Glu Ile Lys Thr Thr Asn Pro Val Ala Thr Glu Ser
                565                 570                 575

tat gga caa gtg gcc aca aac cac cag agt gcc caa gca cag gcg cag      1776
Tyr Gly Gln Val Ala Thr Asn His Gln Ser Ala Gln Ala Gln Ala Gln
            580                 585                 590

acc ggc tgg gtt caa aac caa gga ata ctt ccg ggt atg gtt tgg cag      1824
Thr Gly Trp Val Gln Asn Gln Gly Ile Leu Pro Gly Met Val Trp Gln
        595                 600                 605

gac aga gat gtg tac ctg caa gga ccc att tgg gcc aaa att cct cac      1872
Asp Arg Asp Val Tyr Leu Gln Gly Pro Ile Trp Ala Lys Ile Pro His
    610                 615                 620

acg gac ggc aac ttt cac cct tct ccg ctg atg gga ggg ttt gga atg      1920
Thr Asp Gly Asn Phe His Pro Ser Pro Leu Met Gly Gly Phe Gly Met
625                 630                 635                 640

aag cac ccg cct cct cag atc ctc atc aaa aac aca cct gta cct gcg      1968
Lys His Pro Pro Pro Gln Ile Leu Ile Lys Asn Thr Pro Val Pro Ala
                645                 650                 655

gat cct cca acg gct ttc aac aag gac aag ctg aac tct ttc atc acc      2016
Asp Pro Pro Thr Ala Phe Asn Lys Asp Lys Leu Asn Ser Phe Ile Thr
            660                 665                 670

cag tat tct act ggc caa gtc agc gtg gag att gag tgg gag ctg cag      2064
Gln Tyr Ser Thr Gly Gln Val Ser Val Glu Ile Glu Trp Glu Leu Gln
        675                 680                 685

aag gaa aac agc aag cgc tgg aac ccg gag atc cag tac act tcc aac      2112
Lys Glu Asn Ser Lys Arg Trp Asn Pro Glu Ile Gln Tyr Thr Ser Asn
    690                 695                 700

tat tac aag tct aat aat gtt gaa ttt gct gtt aat act gaa ggt gtt      2160
Tyr Tyr Lys Ser Asn Asn Val Glu Phe Ala Val Asn Thr Glu Gly Val
705                 710                 715                 720

tat tct gaa ccc cgc ccc att ggc acc aga tac ctg act cgt aat ctg      2208
Tyr Ser Glu Pro Arg Pro Ile Gly Thr Arg Tyr Leu Thr Arg Asn Leu
                725                 730                 735

taa                                                                  2211


<210> SEQ ID NO 2
<211> LENGTH: 736
<212> TYPE: PRT
<213> ORGANISM: Artificial Sequence
<220> FEATURE:
<223> OTHER INFORMATION: Synthetic Construct

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

-continued

```
Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
```

```
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 3
<211> LENGTH: 736
<212> TYPE: PRT
<213> ORGANISM: Artificial Sequence
<220> FEATURE:
<223> OTHER INFORMATION: modified hu68vp1
<220> FEATURE:
<221> NAME/KEY: MISC_FEATURE
<222> LOCATION: (23)..(23)
<223> OTHER INFORMATION: Xaa may be W (Trp, tryptophan), or oxidated W.
<220> FEATURE:
<221> NAME/KEY: MISC_FEATURE
<222> LOCATION: (35)..(35)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (57)..(57)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (66)..(66)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (94)..(94)

```
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (97)..(97)
<223> OTHER INFORMATION: Xaa may be D (asp, aspartic acid), or
      isomerized D.
<220> FEATURE:
<221> NAME/KEY: MISC_FEATURE
<222> LOCATION: (107)..(107)
<223> OTHER INFORMATION: Xaa may be D (asp, aspartic acid), or
      isomerized D.
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: MISC_FEATURE
<222> LOCATION: (149)..(149)
<223> OTHER INFORMATION: Xaa may be S (Ser, serine), or Phosphorilated S
<220> FEATURE:
<221> NAME/KEY: MISC_FEATURE
<222> LOCATION: (149)..(149)
<223> OTHER INFORMATION: Xaa may be S (Ser, serine), or Phosphorylated S
<220> FEATURE:
<221> NAME/KEY: MISC_FEATURE
<222> LOCATION: (247)..(247)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (253)..(253)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (259)..(259)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (270)..(270)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (297)..(297)
<223> OTHER INFORMATION: Xaa represents D (Asp, aspartic acid) or
      amindated D to N (Asn, asparagine)
<220> FEATURE:
<221> NAME/KEY: MISC_FEATURE
<222> LOCATION: (304)..(304)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (306)..(306)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (314)..(314)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (319)..(319)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (329)..(329)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (332)..(332)
<223> OTHER INFORMATION: Xaa may be K (lys, lysine), or acetylated K
```

```
<220> FEATURE:
<221> NAME/KEY: MISC_FEATURE
<222> LOCATION: (336)..(336)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (384)..(384)
<223> OTHER INFORMATION: Xaa may be D (asp, aspartic acid), or
      isomerized D.
<220> FEATURE:
<221> NAME/KEY: MISC_FEATURE
<222> LOCATION: (404)..(404)
<223> OTHER INFORMATION: Xaa may be M (Met, Methionine), or oxidated M.
<220> FEATURE:
<221> NAME/KEY: MISC_FEATURE
<222> LOCATION: (409)..(409)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (436)..(436)
<223> OTHER INFORMATION: Xaa may be M (Met, Methionine), or oxidated M.
<220> FEATURE:
<221> NAME/KEY: MISC_FEATURE
<222> LOCATION: (452)..(452)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (477)..(477)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (499)..(499)
<223> OTHER INFORMATION: Xaa may be S (Ser, serine), or Phosphorylated S
<220> FEATURE:
<221> NAME/KEY: MISC_FEATURE
<222> LOCATION: (512)..(512)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (515)..(515)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (518)..(518)
<223> OTHER INFORMATION: Xaa may be M (Met, Methionine), or oxidated M.
<220> FEATURE:
<221> NAME/KEY: MISC_FEATURE
<222> LOCATION: (524)..(524)
<223> OTHER INFORMATION: Xaa may be M (Met, Methionine), or oxidated M.
<220> FEATURE:
<221> NAME/KEY: MISC_FEATURE
<222> LOCATION: (559)..(559)
<223> OTHER INFORMATION: Xaa may be M (Met, Methionine), or oxidated M.
<220> FEATURE:
<221> NAME/KEY: MISC_FEATURE
<222> LOCATION: (569)..(569)
<223> OTHER INFORMATION: Xaa may be T (Thr, threonine), or
      Phosphorylated T
<220> FEATURE:
<221> NAME/KEY: MISC_FEATURE
<222> LOCATION: (586)..(586)
<223> OTHER INFORMATION: Xaa may be S (Ser, serine), or Phosphorylated S
<220> FEATURE:
<221> NAME/KEY: MISC_FEATURE
<222> LOCATION: (599)..(599)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (605)..(605)
<223> OTHER INFORMATION: Xaa may be M (Met, Methionine), or oxidated M.
<220> FEATURE:
```

<221> NAME/KEY: MISC_FEATURE
<222> LOCATION: (619)..(619)
<223> OTHER INFORMATION: Xaa may be W (Trp, tryptophan), or oxidated W (e.g., kynurenine).
<220> FEATURE:
<221> NAME/KEY: MISC_FEATURE
<222> LOCATION: (628)..(628)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (640)..(640)
<223> OTHER INFORMATION: Xaa may be M (Met, Methionine), or oxidated M.
<220> FEATURE:
<221> NAME/KEY: MISC_FEATURE
<222> LOCATION: (651)..(651)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (663)..(663)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (666)..(666)
<223> OTHER INFORMATION: Xaa may be K (lys, lysine), or acetylated K
<220> FEATURE:
<221> NAME/KEY: MISC_FEATURE
<222> LOCATION: (689)..(689)
<223> OTHER INFORMATION: Xaa may be K (lys, lysine), or acetylated K
<220> FEATURE:
<221> NAME/KEY: MISC_FEATURE
<222> LOCATION: (693)..(693)
<223> OTHER INFORMATION: Xaa may be K (lys, lysine), or acetylated K
<220> FEATURE:
<221> NAME/KEY: MISC_FEATURE
<222> LOCATION: (695)..(695)
<223> OTHER INFORMATION: Xaa may be W (Trp, tryptophan), or oxidated W.
<220> FEATURE:
<221> NAME/KEY: MISC_FEATURE
<222> LOCATION: (709)..(709)
<223> OTHER INFORMATION: Xaa may be Asn, or deamidated to Asp, isoAsp, or Asp/isoAsp
<220> FEATURE:
<221> NAME/KEY: MISC_FEATURE
<222> LOCATION: (735)..(735)
<223> OTHER INFORMATION: Xaa may be Asn, or deamidated to Asp, isoAsp, or Asp/isoAsp

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Xaa Ala Leu Lys Pro Gly Ala Pro Gln Pro
            20                  25                  30

Lys Ala Xaa Gln Gln His Gln Asp Asn Ala Arg Gly Leu Val Leu Pro
        35                  40                  45

Gly Tyr Lys Tyr Leu Gly Pro Gly Xaa Gly Leu Asp Lys Gly Glu Pro
    50                  55                  60

Val Xaa Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Xaa His Ala
                85                  90                  95

Xaa Ala Glu Phe Gln Glu Arg Leu Lys Glu Xaa Thr Ser Phe Gly Gly
            100                 105                 110

Xaa Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

```
Pro Val Glu Gln Xaa Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Xaa Ala Leu Pro Thr Tyr Xaa Asn His Leu
                245                 250                 255

Tyr Lys Xaa Ile Ser Asn Ser Thr Ser Gly Gly Ser Ser Xaa Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Xaa Trp Gln Arg Leu Ile Asn Xaa
    290                 295                 300

Asn Xaa Gly Phe Arg Pro Lys Arg Leu Xaa Phe Lys Leu Phe Xaa Ile
305                 310                 315                 320

Gln Val Lys Glu Val Thr Asp Asn Xaa Gly Val Xaa Thr Ile Ala Xaa
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Xaa
    370                 375                 380

Gly Ser Gln Ala Val Gly Arg Ser Ser Phe Tyr Cys Leu Glu Tyr Phe
385                 390                 395                 400

Pro Ser Gln Xaa Leu Arg Thr Gly Xaa Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Xaa Asn Pro Leu Ile Asp Gln Tyr Leu Tyr Tyr Leu Ser
        435                 440                 445

Lys Thr Ile Xaa Gly Ser Gly Gln Asn Gln Gln Thr Leu Lys Phe Ser
    450                 455                 460

Val Ala Gly Pro Ser Asn Met Ala Val Gln Gly Arg Xaa Tyr Ile Pro
465                 470                 475                 480

Gly Pro Ser Tyr Arg Gln Gln Arg Val Ser Thr Thr Val Thr Gln Asn
                485                 490                 495

Asn Asn Xaa Glu Phe Ala Trp Pro Gly Ala Ser Ser Trp Ala Leu Xaa
            500                 505                 510

Gly Arg Xaa Ser Leu Xaa Asn Pro Gly Pro Ala Xaa Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Xaa Ile
545                 550                 555                 560

Thr Asn Glu Glu Glu Ile Lys Thr Xaa Asn Pro Val Ala Thr Glu Ser
```

```
                565                 570                 575

Tyr Gly Gln Val Ala Thr Asn His Gln Xaa Ala Gln Ala Gln Ala Gln
            580                 585                 590

Thr Gly Trp Val Gln Asn Gln Gly Ile Leu Pro Gly Xaa Val Trp Gln
        595                 600                 605

Asp Arg Asp Val Tyr Leu Gln Gly Pro Ile Xaa Ala Lys Ile Pro His
    610                 615                 620

Thr Asp Gly Xaa Phe His Pro Ser Pro Leu Met Gly Gly Phe Gly Xaa
625                 630                 635                 640

Lys His Pro Pro Pro Gln Ile Leu Ile Lys Xaa Thr Pro Val Pro Ala
                645                 650                 655

Asp Pro Pro Thr Ala Phe Xaa Lys Asp Xaa Leu Asn Ser Phe Ile Thr
            660                 665                 670

Gln Tyr Ser Thr Gly Gln Val Ser Val Glu Ile Glu Trp Glu Leu Gln
        675                 680                 685

Xaa Glu Asn Ser Xaa Arg Xaa Asn Pro Glu Ile Gln Tyr Thr Ser Asn
    690                 695                 700

Tyr Tyr Lys Ser Xaa Asn Val Glu Phe Ala Val Asn Thr Glu Gly Val
705                 710                 715                 720

Tyr Ser Glu Pro Arg Pro Ile Gly Thr Arg Tyr Leu Thr Arg Xaa Leu
                725                 730                 735


<210> SEQ ID NO 4
<211> LENGTH: 677
<212> TYPE: PRT
<213> ORGANISM: Homo sapiens
<220> FEATURE:
<221> NAME/KEY: SIGNAL
<222> LOCATION: (1)..(23)
<220> FEATURE:
<221> NAME/KEY: mat_peptide
<222> LOCATION: (24)..(677)

<400> SEQUENCE: 4

Met Pro Gly Phe Leu Val Arg Ile Leu Leu Leu Leu Leu Val Leu Leu
            -20                 -15                 -10

Leu Leu Gly Pro Thr Arg Gly Leu Arg Asn Ala Thr Gln Arg Met Phe
        -5                  -1  1               5

Glu Ile Asp Tyr Ser Arg Asp Ser Phe Leu Lys Asp Gly Gln Pro Phe
10                  15                  20                  25

Arg Tyr Ile Ser Gly Ser Ile His Tyr Ser Arg Val Pro Arg Phe Tyr
                30                  35                  40

Trp Lys Asp Arg Leu Leu Lys Met Lys Met Ala Gly Leu Asn Ala Ile
            45                  50                  55

Gln Thr Tyr Val Pro Trp Asn Phe His Glu Pro Trp Pro Gly Gln Tyr
        60                  65                  70

Gln Phe Ser Glu Asp His Asp Val Glu Tyr Phe Leu Arg Leu Ala His
    75                  80                  85

Glu Leu Gly Leu Leu Val Ile Leu Arg Pro Gly Pro Tyr Ile Cys Ala
90                  95                  100                 105

Glu Trp Glu Met Gly Gly Leu Pro Ala Trp Leu Leu Glu Lys Glu Ser
                110                 115                 120

Ile Leu Leu Arg Ser Ser Asp Pro Asp Tyr Leu Ala Ala Val Asp Lys
            125                 130                 135

Trp Leu Gly Val Leu Leu Pro Lys Met Lys Pro Leu Leu Tyr Gln Asn
        140                 145                 150
```

-continued

```
Gly Gly Pro Val Ile Thr Val Gln Val Glu Asn Glu Tyr Gly Ser Tyr
    155                 160                 165

Phe Ala Cys Asp Phe Asp Tyr Leu Arg Phe Leu Gln Lys Arg Phe Arg
170                 175                 180                 185

His His Leu Gly Asp Asp Val Val Leu Phe Thr Thr Asp Gly Ala His
                190                 195                 200

Lys Thr Phe Leu Lys Cys Gly Ala Leu Gln Gly Leu Tyr Thr Thr Val
            205                 210                 215

Asp Phe Gly Thr Gly Ser Asn Ile Thr Asp Ala Phe Leu Ser Gln Arg
        220                 225                 230

Lys Cys Glu Pro Lys Gly Pro Leu Ile Asn Ser Glu Phe Tyr Thr Gly
    235                 240                 245

Trp Leu Asp His Trp Gly Gln Pro His Ser Thr Ile Lys Thr Glu Ala
250                 255                 260                 265

Val Ala Ser Ser Leu Tyr Asp Ile Leu Ala Arg Gly Ala Ser Val Asn
                270                 275                 280

Leu Tyr Met Phe Ile Gly Gly Thr Asn Phe Ala Tyr Trp Asn Gly Ala
            285                 290                 295

Asn Ser Pro Tyr Ala Ala Gln Pro Thr Ser Tyr Asp Tyr Asp Ala Pro
        300                 305                 310

Leu Ser Glu Ala Gly Asp Leu Thr Glu Lys Tyr Phe Ala Leu Arg Asn
    315                 320                 325

Ile Ile Gln Lys Phe Glu Lys Val Pro Glu Gly Pro Ile Pro Pro Ser
330                 335                 340                 345

Thr Pro Lys Phe Ala Tyr Gly Lys Val Thr Leu Glu Lys Leu Lys Thr
                350                 355                 360

Val Gly Ala Ala Leu Asp Ile Leu Cys Pro Ser Gly Pro Ile Lys Ser
            365                 370                 375

Leu Tyr Pro Leu Thr Phe Ile Gln Val Lys Gln His Tyr Gly Phe Val
        380                 385                 390

Leu Tyr Arg Thr Thr Leu Pro Gln Asp Cys Ser Asn Pro Ala Pro Leu
    395                 400                 405

Ser Ser Pro Leu Asn Gly Val His Asp Arg Ala Tyr Val Ala Val Asp
410                 415                 420                 425

Gly Ile Pro Gln Gly Val Leu Glu Arg Asn Asn Val Ile Thr Leu Asn
                430                 435                 440

Ile Thr Gly Lys Ala Gly Ala Thr Leu Asp Leu Leu Val Glu Asn Met
            445                 450                 455

Gly Arg Val Asn Tyr Gly Ala Tyr Ile Asn Asp Phe Lys Gly Leu Val
        460                 465                 470

Ser Asn Leu Thr Leu Ser Ser Asn Ile Leu Thr Asp Trp Thr Ile Phe
    475                 480                 485

Pro Leu Asp Thr Glu Asp Ala Val Arg Ser His Leu Gly Gly Trp Gly
490                 495                 500                 505

His Arg Asp Ser Gly His His Asp Glu Ala Trp Ala His Asn Ser Ser
                510                 515                 520

Asn Tyr Thr Leu Pro Ala Phe Tyr Met Gly Asn Phe Ser Ile Pro Ser
            525                 530                 535

Gly Ile Pro Asp Leu Pro Gln Asp Thr Phe Ile Gln Phe Pro Gly Trp
        540                 545                 550

Thr Lys Gly Gln Val Trp Ile Asn Gly Phe Asn Leu Gly Arg Tyr Trp
    555                 560                 565

Pro Ala Arg Gly Pro Gln Leu Thr Leu Phe Val Pro Gln His Ile Leu
```

-continued

```
570                 575                 580                 585

Met Thr Ser Ala Pro Asn Thr Ile Thr Val Leu Glu Leu Glu Trp Ala
                590                 595                 600

Pro Cys Ser Ser Asp Asp Pro Glu Leu Cys Ala Val Thr Phe Val Asp
            605                 610                 615

Arg Pro Val Ile Gly Ser Ser Val Thr Tyr Asp His Pro Ser Lys Pro
        620                 625                 630

Val Glu Lys Arg Leu Met Pro Pro Pro Pro Gln Lys Asn Lys Asp Ser
    635                 640                 645

Trp Leu Asp His Val
650


<210> SEQ ID NO 5
<211> LENGTH: 2034
<212> TYPE: DNA
<213> ORGANISM: Homo sapiens

<400> SEQUENCE: 5

atgccggggt tcctggttcg catcctcctt ctgctgctgg ttctgctgct tctgggccct     60

acgcgcggct tgcgcaatgc cacccagagg atgtttgaaa ttgactatag ccgggactcc    120

ttcctcaagg atggccagcc atttcgctac atctcaggaa gcattcacta ctcccgtgtg    180

ccccgcttct actggaagga ccggctgctg aagatgaaga tggctgggct gaacgccatc    240

cagacgtatg tgccctggaa ctttcatgag ccctggccag gacagtacca gttttctgag    300

gaccatgatg tggaatattt tcttcggctg gctcatgagc tgggactgct ggttatcctg    360

aggcccgggc cctacatctg tgcagagtgg gaaatgggag gattacctgc ttggctgcta    420

gagaaagagt ctattcttct ccgctcctcc gacccagatt acctggcagc tgtggacaag    480

tggttgggag tccttctgcc caagatgaag cctctcctct atcagaatgg agggccagtt    540

ataacagtgc aggttgaaaa tgaatatggc agctactttg cctgtgattt tgactacctg    600

cgcttcctgc agaagcgctt tcgccaccat ctgggggatg atgtggttct gtttaccact    660

gatggagcac ataaaacatt cctgaaatgt ggggccctgc agggcctcta caccacggtg    720

gactttggaa caggcagcaa catcacagat gctttcctaa gccagaggaa gtgtgagccc    780

aaaggaccct tgatcaattc tgaattctat actggctggc tagatcactg gggccaacct    840

cactccacaa tcaagaccga agcagtggct tcctccctct atgatatact tgcccgtggg    900

gcgagtgtga acttgtacat gtttataggt gggaccaatt ttgcctattg gaatggggcc    960

aactcaccct atgcagcaca gcccaccagc tacgactatg atgcccccact gagtgaggct   1020

ggggacctca ctgagaagta ttttgctctg cgaaacatca tccagaagtt tgaaaaagta   1080

ccagaaggtc ctatccctcc atctacacca aagtttgcat atggaaaggt cactttggaa   1140

aagttaaaga cagtgggagc agctctggac attctgtgtc cctctgggcc catcaaaagc   1200

ctttatccct tgacatttat ccaggtgaaa cagcattatg ggtttgtgct gtaccggaca   1260

acacttcctc aagattgcag caacccagca cctctctctt cacccctcaa tggagtccac   1320

gatcgagcat atgttgctgt ggatgggatc ccccagggag tccttgagcg aaacaatgtg   1380

atcactctga acataacagg gaaagctgga gccactctgg accttctggt agagaacatg   1440

ggacgtgtga actatggtgc atatatcaac gattttaagg gtttggtttc taacctgact   1500

ctcagttcca atatcctcac ggactggacg atctttccac tggacactga ggatgcagtg   1560

cgcagccacc tgggggctg gggacaccgt gacagtggcc accatgatga agcctgggcc   1620
```

-continued cacaactcat ccaactacac gctcccggcc ttttatatgg ggaacttctc cattcccagt 1680
gggatcccag acttgcccca ggacaccttt atccagtttc ctggatggac caagggccag 1740
gtctggatta atggctttaa ccttggccgc tattggccag cccggggccc tcagttgacc 1800
ttgtttgtgc cccagcacat cctgatgacc tcggccccaa acaccatcac cgtgctggaa 1860
ctggagtggg caccctgcag cagtgatgat ccagaactat gtgctgtgac gttcgtggac 1920
aggccagtta ttggctcatc tgtgacctac gatcatccct ccaaacctgt tgaaaaaaga 1980
ctcatgcccc cacccccgca aaaaaacaaa gattcatggc tggaccatgt atga 2034

<210> SEQ ID NO 6
<211> LENGTH: 2031
<212> TYPE: DNA
<213> ORGANISM: Artificial Sequence
<220> FEATURE:
<223> OTHER INFORMATION: Engineered coding sequence for human GLB1

<400> SEQUENCE: 6
atgccgggct ttctggtgcg cattctgctg ctgctgctgg tgctgctgct gctgggcccg 60
acccgcggcc tgcgcaacgc gacccagcgc atgtttgaaa ttgattatag ccgcgatagc 120
tttctgaaag atggccagcc gtttcgctat attagcggca gcattcatta tagccgcgtg 180
ccgcgctttt attggaaaga tcgcctgctg aaaatgaaaa tggcgggcct gaacgcgatt 240
cagacctatg tgccgtggaa ctttcatgaa ccgtggccgg gccagtatca gtttagcgaa 300
gatcatgatg tggaatattt tctgcgcctg gcgcatgaac tgggcctgct ggtgattctg 360
cgcccgggcc cgtatatttg cgcggaatgg gaaatgggcg gcctgccggc gtggctgctg 420
gaaaaagaaa gcattctgct gcgcagcagc gatccggatt atctggcggc ggtggataaa 480
tggctgggcg tgctgctgcc gaaaatgaaa ccgctgctgt atcagaacgg cggcccggtg 540
attaccgtgc aggtggaaaa cgaatatggc agctattttg cgtgcgattt tgattatctg 600
cgctttctgc agaaacgctt tcgccatcat ctgggcgatg atgtggtgct gtttaccacc 660
gatggcgcgc ataaaacctt tctgaaatgc ggcgcgctgc agggcctgta taccaccgtg 720
gattttggca ccggcagcaa cattaccgat gcgtttctga gccagcgcaa atgcgaaccg 780
aaaggcccgc tgattaacag cgaattttat accggctggc tggatcattg gggccagccg 840
catagcacca ttaaaaccga agcggtggcg agcagcctgt atgatattct ggcgcgcggc 900
gcgagcgtga acctgtatat gtttattggc ggcaccaact ttgcgtattg gaacggcgcg 960
aacagcccgt atgcggcgca gccgaccagc tatgattatg atgcgccgct gagcgaagcg 1020
ggcgatctga ccgaaaaata ttttgcgctg cgcaacatta ttcagaaatt tgaaaaagtg 1080
ccggaaggcc cgattccgcc gagcaccccg aaatttgcgt atggcaaagt gaccctggaa 1140
aaactgaaaa ccgtgggcgc ggcgctggat attctgtgcc cgagcggccc gattaaaagc 1200
ctgtatccgc tgacctttat tcaggtgaaa cagcattatg gctttgtgct gtatcgcacc 1260
accctgccgc aggattgcag caacccggcg ccgctgagca gcccgctgaa cggcgtgcat 1320
gatcgcgcgt atgtggcggt ggatggcatt ccgcagggcg tgctggaacg caacaacgtg 1380
attaccctga acattaccgg caaagcgggc gcgaccctgg atctgctggt ggaaaacatg 1440
ggccgcgtga actatggcgc gtatattaac gattttaaag gcctggtgag caacctgacc 1500
ctgagcagca acattctgac cgattggacc atttttccgc tggataccga agatgcggtg 1560
cgcagccatc tgggcggctg gggccatcgc gatagcggcc atcatgatga agcgtgggcg 1620
cataacagca gcaactatac cctgccggcg ttttatatgg gcaactttag cattccgagc 1680
ggcattccgg atctgccgca ggataccttt attcagtttc cgggctggac caaaggccag 1740
gtgtggatta acggctttaa cctgggccgc tattggccgg cgcgcggccc gcagctgacc 1800
ctgtttgtgc cgcagcatat tctgatgacc agcgcgccga acaccattac cgtgctggaa 1860
ctggaatggg cgccgtgcag cagcgatgat ccggaactgt gcgcggtgac ctttgtggat 1920
cgcccggtga ttggcagcag cgtgacctat gatcatccga gcaaaccggt ggaaaaacgc 1980
ctgatgccgc cgccgccgca gaaaaacaaa gatagctggc tggatcatgt g 2031

<210> SEQ ID NO 7
<211> LENGTH: 2031
<212> TYPE: DNA
<213> ORGANISM: Artificial sequence
<220> FEATURE:
<223> OTHER INFORMATION: Engineered coding sequence for human GLB1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)

<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:

<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)

<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:

<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t -continued
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)

<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1080)..(1080)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:

-continued

<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
<220> FEATURE:
<221> NAME/KEY: misc_feature
<222> LOCATION: (1263)..(1263)
<223> OTHER INFORMATION: n is a, c, g, or t
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1290)..(1290)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1335)..(1335)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1341)..(1341)
<223> OTHER INFORMATION: n is a, c, g, or t
<220> FEATURE:
<221> NAME/KEY: misc_feature
<222> LOCATION: (1347)..(1347)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1359)..(1359)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t
<220> FEATURE:
<221> NAME/KEY: misc_feature
<222> LOCATION: (1365)..(1365)

<223> OTHER INFORMATION: n is a, c, g, or t
<220> FEATURE:
<221> NAME/KEY: misc_feature
<222> LOCATION: (1371)..(1371)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
<220> FEATURE:
<221> NAME/KEY: misc_feature
<222> LOCATION: (1401)..(1401)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1410)..(1410)
<223> OTHER INFORMATION: n is a, c, g, or t
<220> FEATURE:
<221> NAME/KEY: misc_feature
<222> LOCATION: (1413)..(1413)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1425)..(1425)
<223> OTHER INFORMATION: n is a, c, g, or t
<220> FEATURE:
<221> NAME/KEY: misc_feature
<222> LOCATION: (1428)..(1428)
<223> OTHER INFORMATION: n is a, c, g, or t
<220> FEATURE:
<221> NAME/KEY: misc_feature
<222> LOCATION: (1431)..(1431)
<223> OTHER INFORMATION: n is a, c, g, or t
<220> FEATURE:
<221> NAME/KEY: misc_feature
<222> LOCATION: (1443)..(1443)
<223> OTHER INFORMATION: n is a, c, g, or t
<220> FEATURE:
<221> NAME/KEY: misc_feature
<222> LOCATION: (1446)..(1446)
<223> OTHER INFORMATION: n is a, c, g, or t
<220> FEATURE:
<221> NAME/KEY: misc_feature
<222> LOCATION: (1449)..(1449)
<223> OTHER INFORMATION: n is a, c, g, or t
<220> FEATURE:
<221> NAME/KEY: misc_feature
<222> LOCATION: (1458)..(1458)
<223> OTHER INFORMATION: n is a, c, g, or t
<220> FEATURE:
<221> NAME/KEY: misc_feature
<222> LOCATION: (1461)..(1461)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1485)..(1485)
<223> OTHER INFORMATION: n is a, c, g, or t
<220> FEATURE:
<221> NAME/KEY: misc_feature
<222> LOCATION: (1488)..(1488)
<223> OTHER INFORMATION: n is a, c, g, or t
<220> FEATURE:
<221> NAME/KEY: misc_feature
<222> LOCATION: (1491)..(1491)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1500)..(1500)
<223> OTHER INFORMATION: n is a, c, g, or t
<220> FEATURE:
<221> NAME/KEY: misc_feature
<222> LOCATION: (1503)..(1503)
<223> OTHER INFORMATION: n is a, c, g, or t
<220> FEATURE:
<221> NAME/KEY: misc_feature
<222> LOCATION: (1506)..(1506)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
<220> FEATURE:
<221> NAME/KEY: misc_feature
<222> LOCATION: (1518)..(1518)
<223> OTHER INFORMATION: n is a, c, g, or t
<220> FEATURE:
<221> NAME/KEY: misc_feature
<222> LOCATION: (1521)..(1521)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1539)..(1539)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (1548)..(1548)
<223> OTHER INFORMATION: n is a, c, g, or t
<220> FEATURE:
<221> NAME/KEY: misc_feature
<222> LOCATION: (1557)..(1557)
<223> OTHER INFORMATION: n is a, c, g, or t
<220> FEATURE:
<221> NAME/KEY: misc_feature
<222> LOCATION: (1560)..(1560)
<223> OTHER INFORMATION: n is a, c, g, or t
<220> FEATURE:
<221> NAME/KEY: misc_feature
<222> LOCATION: (1563)..(1563)
<223> OTHER INFORMATION: n is a, c, g, or t
<220> FEATURE:
<221> NAME/KEY: misc_feature
<222> LOCATION: (1566)..(1566)
<223> OTHER INFORMATION: n is a, c, g, or t
<220> FEATURE:
<221> NAME/KEY: misc_feature
<222> LOCATION: (1572)..(1572)
<223> OTHER INFORMATION: n is a, c, g, or t
<220> FEATURE:

-continued

<221> NAME/KEY: misc_feature
<222> LOCATION: (1575)..(1575)
<223> OTHER INFORMATION: n is a, c, g, or t
<220> FEATURE:
<221> NAME/KEY: misc_feature
<222> LOCATION: (1578)..(1578)
<223> OTHER INFORMATION: n is a, c, g, or t
<220> FEATURE:
<221> NAME/KEY: misc_feature
<222> LOCATION: (1584)..(1584)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1596)..(1596)
<223> OTHER INFORMATION: n is a, c, g, or t
<220> FEATURE:
<221> NAME/KEY: misc_feature
<222> LOCATION: (1599)..(1599)
<223> OTHER INFORMATION: n is a, c, g, or t
<220> FEATURE:
<221> NAME/KEY: misc_feature
<222> LOCATION: (1614)..(1614)
<223> OTHER INFORMATION: n is a, c, g, or t
<220> FEATURE:
<221> NAME/KEY: misc_feature
<222> LOCATION: (1620)..(1620)
<223> OTHER INFORMATION: n is a, c, g, or t
<220> FEATURE:
<221> NAME/KEY: misc_feature
<222> LOCATION: (1629)..(1629)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t
<220> FEATURE:
<221> NAME/KEY: misc_feature
<222> LOCATION: (1644)..(1644)
<223> OTHER INFORMATION: n is a, c, g, or t
<220> FEATURE:
<221> NAME/KEY: misc_feature
<222> LOCATION: (1647)..(1647)
<223> OTHER INFORMATION: n is a, c, g, or t
<220> FEATURE:
<221> NAME/KEY: misc_feature
<222> LOCATION: (1650)..(1650)
<223> OTHER INFORMATION: n is a, c, g, or t
<220> FEATURE:
<221> NAME/KEY: misc_feature
<222> LOCATION: (1662)..(1662)
<223> OTHER INFORMATION: n is a, c, g, or t
<220> FEATURE:
<221> NAME/KEY: misc_feature
<222> LOCATION: (1671)..(1671)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1680)..(1680)
<223> OTHER INFORMATION: n is a, c, g, or t
<220> FEATURE:
<221> NAME/KEY: misc_feature
<222> LOCATION: (1683)..(1683)
<223> OTHER INFORMATION: n is a, c, g, or t
<220> FEATURE:
<221> NAME/KEY: misc_feature
<222> LOCATION: (1689)..(1689)
<223> OTHER INFORMATION: n is a, c, g, or t
<220> FEATURE:
<221> NAME/KEY: misc_feature
<222> LOCATION: (1695)..(1695)
<223> OTHER INFORMATION: n is a, c, g, or t
<220> FEATURE:
<221> NAME/KEY: misc_feature
<222> LOCATION: (1698)..(1698)
<223> OTHER INFORMATION: n is a, c, g, or t
<220> FEATURE:
<221> NAME/KEY: misc_feature
<222> LOCATION: (1707)..(1707)
<223> OTHER INFORMATION: n is a, c, g, or t
<220> FEATURE:
<221> NAME/KEY: misc_feature
<222> LOCATION: (1722)..(1722)
<223> OTHER INFORMATION: n is a, c, g, or t
<220> FEATURE:
<221> NAME/KEY: misc_feature
<222> LOCATION: (1725)..(1725)
<223> OTHER INFORMATION: n is a, c, g, or t
<220> FEATURE:
<221> NAME/KEY: misc_feature
<222> LOCATION: (1731)..(1731)
<223> OTHER INFORMATION: n is a, c, g, or t
<220> FEATURE:
<221> NAME/KEY: misc_feature
<222> LOCATION: (1737)..(1737)
<223> OTHER INFORMATION: n is a, c, g, or t
<220> FEATURE:
<221> NAME/KEY: misc_feature
<222> LOCATION: (1743)..(1743)
<223> OTHER INFORMATION: n is a, c, g, or t
<220> FEATURE:
<221> NAME/KEY: misc_feature
<222> LOCATION: (1755)..(1755)
<223> OTHER INFORMATION: n is a, c, g, or t
<220> FEATURE:
<221> NAME/KEY: misc_feature
<222> LOCATION: (1764)..(1764)
<223> OTHER INFORMATION: n is a, c, g, or t
<220> FEATURE:
<221> NAME/KEY: misc_feature
<222> LOCATION: (1767)..(1767)
<223> OTHER INFORMATION: n is a, c, g, or t
<220> FEATURE:
<221> NAME/KEY: misc_feature
<222> LOCATION: (1770)..(1770)
<223> OTHER INFORMATION: n is a, c, g, or t
<220> FEATURE:
<221> NAME/KEY: misc_feature
<222> LOCATION: (1779)..(1779)
<223> OTHER INFORMATION: n is a, c, g, or t
<220> FEATURE:
<221> NAME/KEY: misc_feature
<222> LOCATION: (1782)..(1782)
<223> OTHER INFORMATION: n is a, c, g, or t
<220> FEATURE:
<221> NAME/KEY: misc_feature
<222> LOCATION: (1785)..(1785)
<223> OTHER INFORMATION: n is a, c, g, or t
<220> FEATURE:
<221> NAME/KEY: misc_feature
<222> LOCATION: (1788)..(1788)
<223> OTHER INFORMATION: n is a, c, g, or t
<220> FEATURE:
<221> NAME/KEY: misc_feature
<222> LOCATION: (1791)..(1791)
<223> OTHER INFORMATION: n is a, c, g, or t
<220> FEATURE:
<221> NAME/KEY: misc_feature
<222> LOCATION: (1797)..(1797)
<223> OTHER INFORMATION: n is a, c, g, or t
<220> FEATURE:
<221> NAME/KEY: misc_feature
<222> LOCATION: (1800)..(1800)
<223> OTHER INFORMATION: n is a, c, g, or t
<220> FEATURE:
<221> NAME/KEY: misc_feature
<222> LOCATION: (1803)..(1803)

<223> OTHER INFORMATION: n is a, c, g, or t
<220> FEATURE:
<221> NAME/KEY: misc_feature
<222> LOCATION: (1809)..(1809)
<223> OTHER INFORMATION: n is a, c, g, or t
<220> FEATURE:
<221> NAME/KEY: misc_feature
<222> LOCATION: (1812)..(1812)
<223> OTHER INFORMATION: n is a, c, g, or t
<220> FEATURE:
<221> NAME/KEY: misc_feature
<222> LOCATION: (1824)..(1824)
<223> OTHER INFORMATION: n is a, c, g, or t
<220> FEATURE:
<221> NAME/KEY: misc_feature
<222> LOCATION: (1830)..(1830)
<223> OTHER INFORMATION: n is a, c, g, or t
<220> FEATURE:
<221> NAME/KEY: misc_feature
<222> LOCATION: (1833)..(1833)
<223> OTHER INFORMATION: n is a, c, g, or t
<220> FEATURE:
<221> NAME/KEY: misc_feature
<222> LOCATION: (1836)..(1836)
<223> OTHER INFORMATION: n is a, c, g, or t
<220> FEATURE:
<221> NAME/KEY: misc_feature
<222> LOCATION: (1839)..(1839)
<223> OTHER INFORMATION: n is a, c, g, or t
<220> FEATURE:
<221> NAME/KEY: misc_feature
<222> LOCATION: (1845)..(1845)
<223> OTHER INFORMATION: n is a, c, g, or t
<220> FEATURE:
<221> NAME/KEY: misc_feature
<222> LOCATION: (1851)..(1851)
<223> OTHER INFORMATION: n is a, c, g, or t
<220> FEATURE:
<221> NAME/KEY: misc_feature
<222> LOCATION: (1854)..(1854)
<223> OTHER INFORMATION: n is a, c, g, or t
<220> FEATURE:
<221> NAME/KEY: misc_feature
<222> LOCATION: (1857)..(1857)
<223> OTHER INFORMATION: n is a, c, g, or t
<220> FEATURE:
<221> NAME/KEY: misc_feature
<222> LOCATION: (1863)..(1863)
<223> OTHER INFORMATION: n is a, c, g, or t
<220> FEATURE:
<221> NAME/KEY: misc_feature
<222> LOCATION: (1872)..(1872)
<223> OTHER INFORMATION: n is a, c, g, or t
<220> FEATURE:
<221> NAME/KEY: misc_feature
<222> LOCATION: (1875)..(1875)
<223> OTHER INFORMATION: n is a, c, g, or t
<220> FEATURE:
<221> NAME/KEY: misc_feature
<222> LOCATION: (1881)..(1881)
<223> OTHER INFORMATION: n is a, c, g, or t
<220> FEATURE:
<221> NAME/KEY: misc_feature
<222> LOCATION: (1884)..(1884)
<223> OTHER INFORMATION: n is a, c, g, or t
<220> FEATURE:
<221> NAME/KEY: misc_feature
<222> LOCATION: (1893)..(1893)
<223> OTHER INFORMATION: n is a, c, g, or t
<220> FEATURE:
<221> NAME/KEY: misc_feature
<222> LOCATION: (1899)..(1899)
<223> OTHER INFORMATION: n is a, c, g, or t
<220> FEATURE:
<221> NAME/KEY: misc_feature
<222> LOCATION: (1905)..(1905)
<223> OTHER INFORMATION: n is a, c, g, or t
<220> FEATURE:
<221> NAME/KEY: misc_feature
<222> LOCATION: (1908)..(1908)
<223> OTHER INFORMATION: n is a, c, g, or t
<220> FEATURE:
<221> NAME/KEY: misc_feature
<222> LOCATION: (1911)..(1911)
<223> OTHER INFORMATION: n is a, c, g, or t
<220> FEATURE:
<221> NAME/KEY: misc_feature
<222> LOCATION: (1917)..(1917)
<223> OTHER INFORMATION: n is a, c, g, or t
<220> FEATURE:
<221> NAME/KEY: misc_feature
<222> LOCATION: (1923)..(1923)
<223> OTHER INFORMATION: n is a, c, g, or t
<220> FEATURE:
<221> NAME/KEY: misc_feature
<222> LOCATION: (1926)..(1926)
<223> OTHER INFORMATION: n is a, c, g, or t
<220> FEATURE:
<221> NAME/KEY: misc_feature
<222> LOCATION: (1929)..(1929)
<223> OTHER INFORMATION: n is a, c, g, or t
<220> FEATURE:
<221> NAME/KEY: misc_feature
<222> LOCATION: (1935)..(1935)
<223> OTHER INFORMATION: n is a, c, g, or t
<220> FEATURE:
<221> NAME/KEY: misc_feature
<222> LOCATION: (1938)..(1938)
<223> OTHER INFORMATION: n is a, c, g, or t
<220> FEATURE:
<221> NAME/KEY: misc_feature
<222> LOCATION: (1941)..(1941)
<223> OTHER INFORMATION: n is a, c, g, or t
<220> FEATURE:
<221> NAME/KEY: misc_feature
<222> LOCATION: (1944)..(1944)
<223> OTHER INFORMATION: n is a, c, g, or t
<220> FEATURE:
<221> NAME/KEY: misc_feature
<222> LOCATION: (1947)..(1947)
<223> OTHER INFORMATION: n is a, c, g, or t
<220> FEATURE:
<221> NAME/KEY: misc_feature
<222> LOCATION: (1959)..(1959)
<223> OTHER INFORMATION: n is a, c, g, or t
<220> FEATURE:
<221> NAME/KEY: misc_feature
<222> LOCATION: (1962)..(1962)
<223> OTHER INFORMATION: n is a, c, g, or t
<220> FEATURE:
<221> NAME/KEY: misc_feature
<222> LOCATION: (1968)..(1968)
<223> OTHER INFORMATION: n is a, c, g, or t
<220> FEATURE:
<221> NAME/KEY: misc_feature
<222> LOCATION: (1971)..(1971)
<223> OTHER INFORMATION: n is a, c, g, or t
<220> FEATURE:
<221> NAME/KEY: misc_feature
<222> LOCATION: (1980)..(1980)
<223> OTHER INFORMATION: n is a, c, g, or t
<220> FEATURE:
<221> NAME/KEY: misc_feature
<222> LOCATION: (1983)..(1983)
<223> OTHER INFORMATION: n is a, c, g, or t
<220> FEATURE:
<221> NAME/KEY: misc_feature
<222> LOCATION: (1989)..(1989)
<223> OTHER INFORMATION: n is a, c, g, or t
<220> FEATURE:
<221> NAME/KEY: misc_feature
<222> LOCATION: (1992)..(1992)
<223> OTHER INFORMATION: n is a, c, g, or t
<220> FEATURE:
<221> NAME/KEY: misc_feature
<222> LOCATION: (1995)..(1995)
<223> OTHER INFORMATION: n is a, c, g, or t
<220> FEATURE:

<221> NAME/KEY: misc_feature
<222> LOCATION: (1998)..(1998)
<223> OTHER INFORMATION: n is a, c, g, or t
<220> FEATURE:
<221> NAME/KEY: misc_feature
<222> LOCATION: (2016)..(2016)
<223> OTHER INFORMATION: n is a, c, g, or t
<220> FEATURE:
<221> NAME/KEY: misc_feature
<222> LOCATION: (2022)..(2022)
<223> OTHER INFORMATION: n is a, c, g, or t
<220> FEATURE:
<221> NAME/KEY: misc_feature
<222> LOCATION: (2031)..(2031)
<223> OTHER INFORMATION: n is a, c, g, or t

<400> SEQUENCE: 7
atgccnggnt tyytngtnmg nathytnytn ytnytnytng tnytnytnyt nytnggnccn 60
acnmgnggny tnmgnaaygc nacncarmgn atgttygara thgaytayws nmgngaywsn 120
ttyytnaarg ayggncarcc nttymgntay athwsnggnw snathcayta ywsnmgngtn 180
ccnmgnttyt aytggaarga ymgnytnytn aaratgaara tggcnggnyt naaygcnath 240
caracntayg tnccntggaa yttycaygar ccntggccng gncartayca rttywsngar 300
gaycaygayg tngartaytt yytnmgnytn gcncaygary tnggnytnyt ngtnathytn 360
mgnccnggnc cntayathtg ygcngartgg garatgggng gnytnccngc ntggytnytn 420
garaargarw snathytnyt nmgnwsnwsn gayccngayt ayytngcngc ngtngayaar 480
tggytnggng tnytnytncc naaratgaar ccnytnytnt aycaraaygg nggnccngtn 540
athacngtnc argtngaraa ygartayggn wsntayttyg cntgygaytt ygaytayytn 600
mgnttyytnc araarmgntt ymgncaycay ytnggngayg aygtngtnyt nttyacnacn 660
gayggngcnc ayaaracntt yytnaartgy ggngcnytnc arggnytnta yacnacngtn 720
gayttyggna cnggnwsnaa yathacngay gcnttyytnw sncarmgnaa rtgygarccn 780
aarggnccny tnathaayws ngarttytay acnggntggy tngaycaytg gggncarccn 840
caywsnacna thaaracnga rgcngtngcn wsnwsnytnt aygayathyt ngcnmgnggn 900
gcnwsngtna ayytntayat gttyathggn ggnacnaayt tygcntaytg gaayggngcn 960
aaywsnccnt aygcngcnca rccnacnwsn taygaytayg aygcnccnyt nwsngargcn 1020
ggngayytna cngaraarta yttygcnytn mgnaayatha thcaraartt ygaraargtn 1080
ccngarggnc cnathccncc nwsnacnccn aarttygcnt ayggnaargt nacnytngar 1140
aarytnaara cngtnggngc ngcnytngay athytntgyc cnwsnggncc nathaarwsn 1200
ytntayccny tnacnttyat hcargtnaar carcaytayg gnttygtnyt ntaymgnacn 1260
acnytnccnc argaytgyws naayccngcn ccnytnwsnw snccnytnaa yggngtncay 1320
gaymgngcnt aygtngcngt ngayggnath ccncarggng tnytngarmg naayaaygtn 1380
athacnytna ayathacngg naargcnggn gcnacnytng ayytnytngt ngaraayatg 1440
ggnmgngtna aytayggngc ntayathaay gayttyaarg gnytngtnws naayytnacn 1500
ytnwsnwsna ayathytnac ngaytggacn athttyccny tngayacnga rgaygcngtn 1560
mgnwsncayy tnggnggntg gggncaymgn gaywsnggnc aycaygayga rgcntgggcn 1620
cayaaywsnw snaaytayac nytnccngcn ttytayatgg gnaayttyws nathccnwsn 1680
ggnathccng ayytnccnca rgayacntty athcarttyc cnggntggac naarggncar 1740
gtntggatha ayggnttyaa yytnggnmgn taytggccng cnmgnggncc ncarytnacn 1800
ytnttygtnc cncarcayat hytnatgacn wsngcnccna ayacnathac ngtnytngar 1860
ytngartggg cnccntgyws nwsngaygay ccngarytnt gygcngtnac nttygtngay 1920
mgnccngtna thggnwsnws ngtnacntay gaycayccnw snaarccngt ngaraarmgn 1980
ytnatgccnc cnccnccnca raaraayaar gaywsntggy tngaycaygt n 2031

<210> SEQ ID NO 8
<211> LENGTH: 2034
<212> TYPE: DNA
<213> ORGANISM: Artificial sequence
<220> FEATURE:
<223> OTHER INFORMATION: Engineered coding sequence for human GLB1

<400> SEQUENCE: 8
atgcccggct ttctcgtgcg gattctcctg ctgctgctgg tgcttctgct gctgggccct 60
accagaggcc tgagaaacgc cacccagcgg atgttcgaga tcgactacag ccgggacagc 120
ttcctgaagg acggccagcc cttccggtac atcagcggca gcatccacta cagcagagtg 180
ccccggttct actggaagga ccggctgctg aagatgaaga tggccggcct gaacgccatc 240
cagacctacg tgccctggaa cttccacgag ccttggcctg gccagtacca gttcagcgag 300
gaccacgacg tggaatactt tctgcggctg gcccacgagc tgggcctgct cgtgattctg 360
aggcctggcc cttacatctg cgccgagtgg gagatgggag gactgcctgc ttggctgctg 420
gaaaaagaga gcatcctgct gcggagcagc gaccccgatt atctggccgc cgtggataag 480
tggctgggcg tgctgctgcc caagatgaag cccctgctgt accagaacgg cggacccgtg 540
atcaccgtgc aggtggaaaa cgagtacggc agctacttcg cctgcgactt cgactacctg 600
cggttcctgc agaagcggtt cagacaccac ctgggcgacg acgtggtgct gttcacaaca 660
gacggcgccc acaagacctt tctgaagtgt ggcgctctgc agggcctgta caccaccgtg 720
gattttggca ccggcagcaa tatcaccgac gcctttctga gccagcggaa gtgcgagcca 780
aagggccccc tgatcaacag cgagttctac accggctggc tggaccactg gggccagcct 840
cacagcacca tcaagacaga ggccgtggcc agcagcctgt acgacatcct ggctagaggc 900
gccagcgtga acctgtacat gtttatcggc ggcaccaact tcgcctactg gaacggcgcc 960
aacagccctt atgccgccca gcccaccagc tacgactacg atgcccctct gtctgaggcc 1020
ggcgacctga ccgagaagta ctttgccctg cggaacatca tccagaaatt cgagaaggtg 1080
cccgagggcc ccatcccccc tagcacacct aagttcgcct acggcaaagt gaccctggaa 1140
aagctgaaaa ccgtgggagc cgccctggac atcctgtgtc ctagcggccc tatcaagagc 1200
ctgtaccccc tgaccttcat ccaagtgaag cagcactacg gcttcgtgct gtaccggacc 1260
accctgcccc aggactgtag caatcctgcc ccactgagca gcccccctgaa cggcgtgcac 1320 gatagagcct acgtggccgt ggatggcatc ccacaggggg tgctggaacg gaacaatgtg 1380
atcaccctga acatcaccgg caaggctggc gccaccctgg acctgctggt ggaaaacatg 1440
ggcagagtga actacggcgc ctacatcaac gacttcaagg gcctggtgtc caacctgacc 1500
ctgagcagca acatcctgac cgactggacc atcttcccac tggacaccga ggatgccgtg 1560
cggagccatc tgggaggatg gggacacaga gatagcggcc accacgatga agcctgggcc 1620
cacaacagca gcaactacac cctgcctgcc ttctacatgg gcaacttcag catccccagc 1680
ggcatccccg acctgccaca ggacaccttt atccagttcc ccggctggac aaagggacaa 1740
gtgtggatca atggcttcaa cctgggcaga tactggcccg ccagaggccc tcagctgacc 1800
ctgtttgtgc cccagcacat tctgatgacc agcgccccca acaccatcac cgtgctggaa 1860

```
ctggaatggg cccoctgcag cagcgacgac cctgaactgt gtgccgtgac cttcgtggac   1920

aggcccgtga tcggcagcag cgtgacctac gaccacccca gcaagcccgt ggaaaagcgg   1980

ctgatgcctc ccccacccca gaagaacaag gactcctggc tggatcacgt gtga         2034
```

<210> SEQ ID NO 9
<211> LENGTH: 1229
<212> TYPE: DNA
<213> ORGANISM: Homo sapiens

<400> SEQUENCE: 9

```
ggcctccgcg ccgggttttg gcgcctcccg cgggcgcccc cctcctcacg gcgagcgctg     60

ccacgtcaga cgaagggcgc agcgagcgtc ctgatccttc cgcccggacg ctcaggacag    120

cggcccgctg ctcataagac tcggccttag aaccccagta tcagcagaag gacattttag    180

gacgggactt gggtgactct agggcactgg ttttctttcc agagagcgga acaggcgagg    240

aaaagtagtc ccttctcggc gattctgcgg agggatctcc gtggggcggt gaacgccgat    300

gattatataa ggacgcgccg ggtgtggcac agctagttcc gtcgcagccg ggatttgggt    360

cgcggttctt gtttgtggat cgctgtgatc gtcacttggt gagtagcggg ctgctgggct    420

ggccggggct ttcgtggccg ccgggccgct cggtgggacg gaagcgtgtg gagagaccgc    480

caagggctgt agtctgggtc cgcgagcaag gttgccctga actgggggtt gggggggagcg    540

cagcaaaatg gcggctgttc ccgagtcttg aatggaagac gcttgtgagg cgggctgtga    600

ggtcgttgaa acaaggtggg gggcatggtg ggcggcaaga acccaaggtc ttgaggcctt    660

cgctaatgcg ggaaagctct tattcgggtg agatgggctg ggcaccatc tggggaccct    720

gacgtgaagt ttgtcactga ctggagaact cggtttgtcg tctgttgcgg gggcggcagt    780

tatggcggtg ccgttgggca gtgcacccgt acctttggga gcgcgcgccc tcgtcgtgtc    840

gtgacgtcac ccgttctgtt ggcttataat gcagggtggg gccacctgcc ggtaggtgtg    900

cggtaggctt ttctccgtcg caggacgcag ggttcgggcc tagggtaggc tctcctgaat    960

cgacaggcgc cggacctctg gtgaggggag ggataagtga ggcgtcagtt tctttggtcg   1020

gttttatgta cctatcttct taagtagctg aagctccggt tttgaactat gcgctcgggg   1080

ttggcgagtg tgttttgtga agttttttag gcaccttttg aaatgtaatc atttgggtca   1140

atatgtaatt ttcagtgtta gactagtaaa ttgtccgcta aattctggcc gtttttggct   1200

tttttgttag acgaagcttt attgcggta                                    1229
```

<210> SEQ ID NO 10
<211> LENGTH: 666
<212> TYPE: DNA
<213> ORGANISM: Artificial Sequence
<220> FEATURE:
<223> OTHER INFORMATION: chicken beta actin promoter with a
      cytomegalovirus enhancer (CB7)

<400> SEQUENCE: 10

```
ctagtcgaca ttgattattg actagttatt aatagtaatc aattacgggg tcattagttc     60

atagcccata tatggagttc cgcgttacat aacttacggt aaatggcccg cctggctgac    120

cgcccaacga cccccgccca ttgacgtcaa taatgacgta tgttcccata gtaacgccaa    180

tagggacttt ccattgacgt caatgggtgg actatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360
```

acgtattagt catcgctatt accatggtcg aggtgagccc cacgttctgc ttcactctcc 420
ccatctcccc cccctcccca cccccaattt tgtatttatt tatttttaa ttattttgtg 480 cagcgatggg ggcggggggg gggggggggc gcgcgccagg cggggcgggg cggggcgagg 540
ggcggggcgg ggcgaggcgg agaggtgcgg cggcagccaa tcagagcggc gcgctccgaa 600
agtttccttt tatggcgagg cggcggcggc ggcggcccta taaaaagcga agcgcgcggc 660
gggcgg 666

<210> SEQ ID NO 11
<211> LENGTH: 1180
<212> TYPE: DNA
<213> ORGANISM: Artificial sequence
<220> FEATURE:
<223> OTHER INFORMATION: human elongation initiation factor 1 alpha
promoter (EF1a)

<400> SEQUENCE: 11
tggctccggt gcccgtcagt gggcagagcg cacatcgccc acagtccccg agaagttggg 60
gggaggggtc ggcaattgaa ccggtgccta gagaaggtgg cgcggggtaa actgggaaag 120
tgatgtcgtg tactggctcc gcctttttcc cgagggtggg ggagaaccgt atataagtgc 180
agtagtcgcc gtgaacgttc tttttcgcaa cgggtttgcc gccagaacac aggtaagtgc 240
cgtgtgtggt tcccgcgggc ctggcctctt tacgggttat ggcccttgcg tgccttgaat 300
tacttccacc tggctgcagt acgtgattct tgatcccgag cttcgggttg gaagtgggtg 360
ggagagttcg aggccttgcg cttaaggagc cccttcgcct cgtgcttgag ttgaggcctg 420
gcctgggcgc tggggccgcc gcgtgcgaat ctggtggcac cttcgcgcct gtctcgctgc 480
tttcgataag tctctagcca tttaaaattt ttgatgacct gctgcgacgc tttttttctg 540
gcaagatagt cttgtaaatg cgggccaaga tctgcacact ggtatttcgg tttttggggc 600
cgcgggcggc gacggggccc gtgcgtccca gcgcacatgt tcggcgaggc ggggcctgcg 660
agcgcggcca ccgagaatcg gacgggggta gtctcaagct ggccggcctg ctctggtgcc 720
tggcctcgcg ccgccgtgta tcgccccgcc ctgggcggca aggctggccc ggtcggcacc 780
agttgcgtga gcggaaagat ggccgcttcc cggccctgct gcagggagct caaaatggag 840
gacgcggcgc tcgggagagc gggcgggtga gtcacccaca caaaggaaaa gggcctttcc 900
gtcctcagcc gtcgcttcat gtgactccac ggagtaccgg gcgccgtcca ggcacctcga 960
ttagttctcg agcttttgga gtacgtcgtc tttaggttgg ggggaggggt tttatgcgat 1020
ggagtttccc cacactgagt gggtggagac tgaagttagg ccagcttggc acttgatgta 1080
attctccttg gaatttgccc tttttgagtt tggatcttgg ttcattctca agcctcagac 1140
agtggttcaa agtttttttc ttccatttca ggtgtcgtga 1180

<210> SEQ ID NO 12
<211> LENGTH: 4205
<212> TYPE: DNA
<213> ORGANISM: Artificial sequence
<220> FEATURE:
<223> OTHER INFORMATION: UbC.GLB1.SV40 vector genome

<400> SEQUENCE: 12
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180

-continued

```
aggaagatct ggcctccgcg ccgggttttg gcgcctcccg cgggcgcccc cctcctcacg    240
gcgagcgctg ccacgtcaga cgaagggcgc agcgagcgtc ctgatccttc cgcccggacg    300
ctcaggacag cggcccgctg ctcataagac tcggccttag aaccccagta tcagcagaag    360
gacattttag gacgggactt gggtgactct agggcactgg ttttctttcc agagagcgga    420
acaggcgagg aaaagtagtc ccttctcggc gattctgcgg agggatctcc gtggggcggt    480
gaacgccgat gattatataa ggacgcgccg ggtgtggcac agctagttcc gtcgcagccg    540
ggatttgggt cgcggttctt gtttgtggat cgctgtgatc gtcacttggt gagtagcggg    600
ctgctgggct ggccggggct ttcgtggccg ccgggccgct cggtgggacg gaagcgtgtg    660
gagagaccgc caagggctgt agtctgggtc cgcgagcaag gttgccctga actgggggtt    720
ggggggagcg cagcaaaatg gcggctgttc ccgagtcttg aatggaagac gcttgtgagg    780
cgggctgtga ggtcgttgaa acaaggtggg gggcatggtg ggcggcaaga acccaaggtc    840
ttgaggcctt cgctaatgcg ggaaagctct tattcgggtg agatgggctg ggcaccatc     900
tggggaccct gacgtgaagt ttgtcactga ctggagaact cggtttgtcg tctgttgcgg    960
gggcggcagt tatggcggtg ccgttgggca gtgcacccgt acctttggga gcgcgcgccc   1020
tcgtcgtgtc gtgacgtcac ccgttctgtt ggcttataat gcagggtggg gccacctgcc   1080
ggtaggtgtg cggtaggctt ttctccgtcg caggacgcag ggttcgggcc tagggtaggc   1140
tctcctgaat cgacaggcgc cggacctctg gtgaggggag ggataagtga ggcgtcagtt   1200
tctttggtcg gttttatgta cctatcttct taagtagctg aagctccggt tttgaactat   1260
gcgctcgggg ttggcgagtg tgttttgtga agttttttag gcaccttttg aaatgtaatc   1320
atttgggtca atatgtaatt ttcagtgtta gactagtaaa ttgtccgcta aattctggcc   1380
gtttttggct tttttgttag acgaagcttt attgcggtag tttatcacag ttaaattgct   1440
aacgcagtca gtgcttctga cacaacagtc tcgaacttaa gctgcagaag ttggtcgtga   1500
ggcactgggc aggtaagtat caaggttaca agacaggttt aaggagacca atagaaactg   1560
ggcttgtcga gacagagaag actcttgcgt ttctgatagg cacctattgg tcttactgac   1620
atccactttg cctttctctc cacaggtgtc cactcccagt tcaattacag ctcttaaggc   1680
tagagtactt aatacgactc actataggct agaattcacg cgtgccacca tgcccggctt   1740
tctcgtgcgg attctcctgc tgctgctggt gcttctgctg ctgggcccta ccagaggcct   1800
gagaaacgcc acccagcgga tgttcgagat cgactacagc cgggacagct tcctgaagga   1860
cggccagccc ttccggtaca tcagcggcag catccactac agcagagtgc cccggttcta   1920
ctggaaggac cggctgctga agatgaagat ggccggcctg aacgccatcc agacctacgt   1980
gccctggaac ttccacgagc cttggcctgg ccagtaccag ttcagcgagg accacgacgt   2040
ggaatacttt ctgcggctgg cccacgagct gggcctgctc gtgattctga ggcctggccc   2100
ttacatctgc gccgagtggg agatgggagg actgcctgct tggctgctgg aaaaagagag   2160
catcctgctg cggagcagcg accccgatta tctggccgcc gtggataagt ggctgggcgt   2220
gctgctgccc aagatgaagc ccctgctgta ccagaacggc ggacccgtga tcaccgtgca   2280
ggtggaaaac gagtacggca gctacttcgc ctgcgacttc gactacctgc ggttcctgca   2340
gaagcggttc agacaccacc tgggcgacga cgtggtgctg ttcacaacag acggcgccca   2400
caagaccttt ctgaagtgtg gcgctctgca gggcctgtac accaccgtgg attttggcac   2460
cggcagcaat atcaccgacg cctttctgag ccagcggaag tgcgagccaa agggccccct   2520
gatcaacagc gagttctaca ccggctggct ggaccactgg ggccagcctc acagcaccat   2580
```

-continued caagacagag gccgtggcca gcagcctgta cgacatcctg gctagaggcg ccagcgtgaa 2640
cctgtacatg tttatcggcg gcaccaactt cgcctactgg aacggcgcca acagccctta 2700
tgccgcccag cccaccagct acgactacga tgcccctctg tctgaggccg gcgacctgac 2760
cgagaagtac tttgccctgc ggaacatcat ccagaaattc gagaaggtgc ccgagggccc 2820 catccccccct agcacaccta agttcgccta cggcaaagtg accctggaaa agctgaaaac 2880
cgtgggagcc gccctggaca tcctgtgtcc tagcggccct atcaagagcc tgtacccccct 2940 gaccttcatc caagtgaagc agcactacgg cttcgtgctg taccggacca ccctgcccca 3000
ggactgtagc aatcctgccc cactgagcag ccccctgaac ggcgtgcacg atagagccta 3060
cgtggccgtg gatggcatcc cacagggggt gctggaacgg aacaatgtga tcaccctgaa 3120
catcaccggc aaggctggcg ccaccctgga cctgctggtg gaaaacatgg gcagagtgaa 3180
ctacggcgcc tacatcaacg acttcaaggg cctggtgtcc aacctgaccc tgagcagcaa 3240
catcctgacc gactggacca tcttcccact ggacaccgag gatgccgtgc ggagccatct 3300
gggaggatgg ggacacagag atagcggcca ccacgatgaa gcctgggccc acaacagcag 3360
caactacacc ctgcctgcct tctacatggg caacttcagc atccccagcg gcatccccga 3420
cctgccacag gacaccttta tccagttccc cggctggaca aagggacaag tgtggatcaa 3480
tggcttcaac ctgggcagat actggcccgc cagaggccct cagctgaccc tgtttgtgcc 3540
ccagcacatt ctgatgacca gcgcccccaa caccatcacc gtgctggaac tggaatgggc 3600
cccctgcagc agcgacgacc ctgaactgtg tgccgtgacc ttcgtggaca ggcccgtgat 3660
cggcagcagc gtgacctacg accaccccag caagcccgtg gaaaagcggc tgatgcctcc 3720
cccaccccag aagaacaagg actcctggct ggatcacgtg tgatgactcg aggccgcttc 3780
gagcagacat gataagatac attgatgagt ttggacaaac cacaactaga atgcagtgaa 3840
aaaaatgctt tatttgtgaa atttgtgatg ctattgcttt atttgtaacc attataagct 3900
gcaataaaca agttaacaac aacaattgca ttcattttat gtttcaggtt cagggggaga 3960
tgtgggaggt tttttaaagc aagtaaaacc tctacaaatg tggtaaaatc gataaggatc 4020
ttcctagagc atggctacgt agataagtag catggcgggt taatcattaa ctacaaggaa 4080
cccctagtga tggagttggc cactccctct ctgcgcgctc gctcgctcac tgaggccggg 4140
cgaccaaagg tcgcccgacg cccgggcttt gcccgggcgg cctcagtgag cgagcgagcg 4200
cgcag 4205

<210> SEQ ID NO 13
<211> LENGTH: 4081
<212> TYPE: DNA
<213> ORGANISM: Artificial Sequence
<220> FEATURE:
<223> OTHER INFORMATION: EF1a.GLB1.SV40 vector genome

<400> SEQUENCE: 13
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcc gatgtacggg ccagatatac gcgttgacat tgattattga ctaggctttt 240
gcaaaaagct ttgcaaagat ggataaagtt ttaaacagag aggaatcttt gcagctaatg 300
gaccttctag gtcttgaaag gagtgggaat tggctccggt gcccgtcagt gggcagagcg 360

-continued

```
cacatcgccc acagtccccg agaagttggg gggaggggtc ggcaattgaa ccggtgccta    420
gagaaggtgg cgcggggtaa actgggaaag tgatgtcgtg tactggctcc gcctttttcc    480
cgagggtggg ggagaaccgt atataagtgc agtagtcgcc gtgaacgttc tttttcgcaa    540
cgggtttgcc gccagaacac aggtaagtgc cgtgtgtggt tcccgcgggc ctggcctctt    600
tacgggttat ggcccttgcg tgccttgaat tacttccacc tggctgcagt acgtgattct    660
tgatcccgag cttcgggttg gaagtgggtg ggagagttcg aggccttgcg cttaaggagc    720
cccttcgcct cgtgcttgag ttgaggcctg gcctgggcgc tggggccgcc gcgtgcgaat    780
ctggtggcac cttcgcgcct gtctcgctgc tttcgataag tctctagcca tttaaaattt    840
ttgatgacct gctgcgacgc tttttttctg gcaagatagt cttgtaaatg cgggccaaga    900
tctgcacact ggtatttcgg tttttggggc cgcgggcggc gacggggccc gtgcgtccca    960
gcgcacatgt tcggcgaggc ggggcctgcg agcgcggcca ccgagaatcg gacgggggta   1020
gtctcaagct ggccggcctg ctctggtgcc tggcctcgcg ccgccgtgta tcgccccgcc   1080
ctgggcggca aggctggccc ggtcggcacc agttgcgtga gcggaaagat ggccgcttcc   1140
cggccctgct gcagggagct caaaatggag gacgcggcgc tcgggagagc gggcgggtga   1200
gtcacccaca caaaggaaaa gggcctttcc gtcctcagcc gtcgcttcat gtgactccac   1260
ggagtaccgg gcgccgtcca ggcacctcga ttagttctcg agcttttgga gtacgtcgtc   1320
tttaggttgg ggggaggggt tttatgcgat ggagtttccc cacactgagt gggtggagac   1380
tgaagttagg ccagcttggc acttgatgta attctccttg gaatttgccc tttttgagtt   1440
tggatcttgg ttcattctca agcctcagac agtggttcaa agtttttttc ttccatttca   1500
ggtgtcgtga ggaattagct tggtactaat acgactcact atagggagac ccaagctggc   1560
taggtaagct tggtaccgag ctcggatcaa ttcacgcgtg ccaccatgcc cggctttctc   1620
gtgcggattc tcctgctgct gctggtgctt ctgctgctgg gccctaccag aggcctgaga   1680
aacgccaccc agcggatgtt cgagatcgac tacagccggg acagcttcct gaaggacggc   1740
cagcccttcc ggtacatcag cggcagcatc cactacagca gagtgccccg gttctactgg   1800
aaggaccggc tgctgaagat gaagatggcc ggcctgaacg ccatccagac ctacgtgccc   1860
tggaacttcc acgagccttg gcctggccag taccagttca gcgaggacca cgacgtggaa   1920
tactttctgc ggctggccca cgagctgggc ctgctcgtga ttctgaggcc tggcccttac   1980
atctgcgccg agtgggagat gggaggactg cctgcttggc tgctggaaaa agagagcatc   2040
ctgctgcgga gcagcgaccc cgattatctg gccgccgtgg ataagtggct gggcgtgctg   2100
ctgcccaaga tgaagcccct gctgtaccag aacggcggac ccgtgatcac cgtgcaggtg   2160
gaaaacgagt acggcagcta cttcgcctgc gacttcgact acctgcggtt cctgcagaag   2220
cggttcagac accacctggg cgacgacgtg gtgctgttca caacagacgg cgcccacaag   2280
acctttctga agtgtggcgc tctgcagggc ctgtacacca ccgtggattt tggcaccggc   2340
agcaatatca ccgacgcctt tctgagccag cggaagtgcg agccaaaggg cccccctgatc   2400
aacagcgagt tctacaccgg ctggctggac cactggggcc agcctcacag caccatcaag   2460
acagaggccg tggccagcag cctgtacgac atcctggcta gaggcgccag cgtgaacctg   2520
tacatgttta tcggcggcac caacttcgcc tactggaacg gcgccaacag cccttatgcc   2580
gcccagccca ccagctacga ctacgatgcc cctctgtctg aggccggcga cctgaccgag   2640
aagtactttg ccctgcggaa catcatccag aaattcgaga aggtgcccga gggcccccatc   2700
ccccctagca cacctaagtt cgcctacggc aaagtgaccc tggaaaagct gaaaaccgtg   2760
```

```
ggagccgccc tggacatcct gtgtcctagc ggccctatca agagcctgta ccccctgacc   2820
ttcatccaag tgaagcagca ctacggcttc gtgctgtacc ggaccaccct gccccaggac   2880
tgtagcaatc ctgccccact gagcagcccc ctgaacggcg tgcacgatag agcctacgtg   2940
gccgtggatg gcatcccaca gggggtgctg gaacggaaca atgtgatcac cctgaacatc   3000
accggcaagg ctggcgccac cctggacctg ctggtggaaa acatgggcag agtgaactac   3060
ggcgcctaca tcaacgactt caagggcctg gtgtccaacc tgaccctgag cagcaacatc   3120
ctgaccgact ggaccatctt cccactggac accgaggatg ccgtgcggag ccatctggga   3180
ggatggggac acagagatag cggccaccac gatgaagcct gggcccacaa cagcagcaac   3240
tacaccctgc ctgccttcta catgggcaac ttcagcatcc ccagcggcat ccccgacctg   3300
ccacaggaca cctttatcca gttccccggc tggacaaagg gacaagtgtg gatcaatggc   3360
ttcaacctgg gcagatactg gcccgccaga ggccctcagc tgaccctgtt tgtgccccag   3420
cacattctga tgaccagcgc ccccaacacc atcaccgtgc tggaactgga atgggccccc   3480
tgcagcagcg acgaccctga actgtgtgcc gtgaccttcg tggacaggcc cgtgatcggc   3540
agcagcgtga cctacgacca ccccagcaag cccgtggaaa agcggctgat gcctccccca   3600
ccccagaaga acaaggactc ctggctggat cacgtgtgat gactcgaggc cgcttcgagc   3660
agacatgata agatacattg atgagtttgg acaaaccaca actagaatgc agtgaaaaaa   3720
atgctttatt tgtgaaattt gtgatgctat tgctttattt gtaaccatta taagctgcaa   3780
taaacaagtt aacaacaaca attgcattca ttttatgttt caggttcagg gggagatgtg   3840
ggaggttttt taaagcaagt aaaacctcta caaatgtggt aaaatcgata aggatcttcc   3900
tagagcatgg ctacgtagat aagtagcatg gcgggttaat cattaactac aaggaacccc   3960
tagtgatgga gttggccact ccctctctgc gcgctcgctc gctcactgag gccgggcgac   4020
caaaggtcgc ccgacgcccg ggctttgccc gggcggcctc agtgagcgag cgagcgcgca   4080
g                                                                   4081
```

<210> SEQ ID NO 14
<211> LENGTH: 4202
<212> TYPE: DNA
<213> ORGANISM: Artificial Sequence
<220> FEATURE:
<223> OTHER INFORMATION: UbC.GLB1.SV40 - 2

<400> SEQUENCE: 14

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatct ggcctccgcg ccgggttttg gcgcctcccg cgggcgcccc cctcctcacg    240
gcgagcgctg ccacgtcaga cgaagggcgc agcgagcgtc ctgatccttc cgcccggacg    300
ctcaggacag cggcccgctg ctcataagac tcggccttag aaccccagta tcagcagaag    360
gacattttag gacgggactt gggtgactct agggcactgg ttttctttcc agagagcgga    420
acaggcgagg aaaagtagtc ccttctcggc gattctgcgg agggatctcc gtggggcggt    480
gaacgccgat gattatataa ggacgcgccg ggtgtggcac agctagttcc gtcgcagccg    540
ggatttgggt cgcggttctt gtttgtggat cgctgtgatc gtcacttggt gagtagcggg    600
ctgctgggct ggccggggct ttcgtggccg ccgggccgct cggtgggacg gaagcgtgtg    660
```

-continued

```
gagagaccgc caagggctgt agtctgggtc cgcgagcaag gttgccctga actgggggtt    720
ggggggagcg cagcaaaatg gcggctgttc ccgagtcttg aatggaagac gcttgtgagg    780
cgggctgtga ggtcgttgaa acaaggtggg gggcatggtg ggcggcaaga acccaaggtc    840
ttgaggcctt cgctaatgcg ggaaagctct tattcgggtg agatgggctg gggcaccatc    900
tggggaccct gacgtgaagt ttgtcactga ctggagaact cggtttgtcg tctgttgcgg    960
gggcggcagt tatggcggtg ccgttgggca gtgcacccgt acctttggga gcgcgcgccc   1020
tcgtcgtgtc gtgacgtcac ccgttctgtt ggcttataat gcagggtggg gccacctgcc   1080
ggtaggtgtg cggtaggctt ttctccgtcg caggacgcag ggttcgggcc tagggtaggc   1140
tctcctgaat cgacaggcgc cggacctctg gtgaggggag ggataagtga ggcgtcagtt   1200
tctttggtcg gttttatgta cctatcttct taagtagctg aagctccggt tttgaactat   1260
gcgctcgggg ttggcgagtg tgttttgtga agttttttag gcaccttttg aaatgtaatc   1320
atttgggtca atatgtaatt ttcagtgtta gactagtaaa ttgtccgcta aattctggcc   1380
gtttttggct tttttgttag acgaagcttt attgcggtag tttatcacag ttaaattgct   1440
aacgcagtca gtgcttctga cacaacagtc tcgaacttaa gctgcagaag ttggtcgtga   1500
ggcactgggc aggtaagtat caaggttaca agacaggttt aaggagacca atagaaactg   1560
ggcttgtcga gacagagaag actcttgcgt ttctgatagg cacctattgg tcttactgac   1620
atccactttg cctttctctc cacaggtgtc cactcccagt tcaattacag ctcttaaggc   1680
tagagtactt aatacgactc actataggct agaattcacg cgtgccacca tgccgggctt   1740
tctggtgcgc attctgctgc tgctgctggt gctgctgctg ctgggcccga cccgcggcct   1800
gcgcaacgcg acccagcgca tgtttgaaat tgattatagc cgcgatagct ttctgaaaga   1860
tggccagccg tttcgctata ttagcggcag cattcattat agccgcgtgc cgcgctttta   1920
ttggaaagat cgcctgctga aaatgaaaat ggcgggcctg aacgcgattc agacctatgt   1980
gccgtggaac tttcatgaac cgtggccggg ccagtatcag tttagcgaag atcatgatgt   2040
ggaatatttt ctgcgcctgg cgcatgaact gggcctgctg gtgattctgc gcccgggccc   2100
gtatatttgc gcggaatggg aaatgggcgg cctgccggcg tggctgctgg aaaaagaaag   2160
cattctgctg cgcagcagcg atccggatta tctggcggcg gtggataaat ggctgggcgt   2220
gctgctgccg aaaatgaaac cgctgctgta tcagaacggc ggcccggtga ttaccgtgca   2280
ggtggaaaac gaatatggca gctattttgc gtgcgatttt gattatctgc gctttctgca   2340
gaaacgcttt cgccatcatc tgggcgatga tgtggtgctg tttaccaccg atggcgcgca   2400
taaaaccttt ctgaaatgcg gcgcgctgca gggcctgtat accaccgtgg attttggcac   2460
cggcagcaac attaccgatg cgtttctgag ccagcgcaaa tgcgaaccga aaggcccgct   2520
gattaacagc gaattttata ccggctggct ggatcattgg ggccagccgc atagcaccat   2580
taaaaccgaa gcggtggcga gcagcctgta tgatattctg gcgcgcggcg cgagcgtgaa   2640
cctgtatatg tttattggcg gcaccaactt tgcgtattgg aacggcgcga acagcccgta   2700
tgcggcgcag ccgaccagct atgattatga tgcgccgctg agcgaagcgg gcgatctgac   2760
cgaaaaatat tttgcgctgc gcaacattat tcagaaattt gaaaaagtgc cggaaggccc   2820
gattccgccg agcaccccga aatttgcgta tggcaaagtg accctggaaa aactgaaaac   2880
cgtgggcgcg gcgctggata ttctgtgccc gagcggcccg attaaaagcc tgtatccgct   2940
gacctttatt caggtgaaac agcattatgg ctttgtgctg tatcgcacca ccctgccgca   3000
ggattgcagc aacccggcgc cgctgagcag cccgctgaac ggcgtgcatg atcgcgcgta   3060
```

tgtggcggtg gatggcattc cgcagggcgt gctggaacgc aacaacgtga ttaccctgaa 3120
cattaccggc aaagcgggcg cgaccctgga tctgctggtg gaaaacatgg gccgcgtgaa 3180
ctatggcgcg tatattaacg attttaaagg cctggtgagc aacctgaccc tgagcagcaa 3240
cattctgacc gattggacca tttttccgct ggataccgaa gatgcggtgc gcagccatct 3300
gggcggctgg ggccatcgcg atagcggcca tcatgatgaa gcgtgggcgc ataacagcag 3360
caactatacc ctgccggcgt tttatatggg caactttagc attccgagcg gcattccgga 3420
tctgccgcag gatacccttta ttcagtttcc gggctggacc aaaggccagg tgtggattaa 3480
cggctttaac ctgggccgct attggccggc gcgcggcccg cagctgaccc tgtttgtgcc 3540
gcagcatatt ctgatgacca gcgcgccgaa caccattacc gtgctggaac tggaatgggc 3600
gccgtgcagc agcgatgatc cggaactgtg cgcggtgacc tttgtggatc gcccggtgat 3660
tggcagcagc gtgacctatg atcatccgag caaaccggtg gaaaaacgcc tgatgccgcc 3720
gccgccgcag aaaaacaaag atagctggct ggatcatgtg tgactcgagg ccgcttcgag 3780
cagacatgat aagatacatt gatgagtttg gacaaaccac aactagaatg cagtgaaaaa 3840
aatgctttat ttgtgaaatt tgtgatgcta ttgctttatt tgtaaccatt ataagctgca 3900
ataaacaagt taacaacaac aattgcattc attttatgtt tcaggttcag ggggagatgt 3960
gggaggtttt ttaaagcaag taaaacctct acaaatgtgg taaaatcgat aaggatcttc 4020
ctagagcatg gctacgtaga taagtagcat ggcgggttaa tcattaacta caaggaaccc 4080
ctagtgatgg agttggccac tccctctctg cgcgctcgct cgctcactga ggccgggcga 4140
ccaaaggtcg cccgacgccc gggctttgcc cgggcggcct cagtgagcga gcgagcgcgc 4200
ag 4202

<210> SEQ ID NO 15
<211> LENGTH: 4206
<212> TYPE: DNA
<213> ORGANISM: Artificial sequence
<220> FEATURE:
<223> OTHER INFORMATION: UbC.GLB1.SV40 - 3

<400> SEQUENCE: 15
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct ggcctccgcg ccgggttttg gcgcctcccg cgggcgcccc cctcctcacg 240
gcgagcgctg ccacgtcaga cgaagggcgc agcgagcgtc ctgatccttc cgcccggacg 300
ctcaggacag cggcccgctg ctcataagac tcggccttag aaccccagta tcagcagaag 360
gacattttag gacgggactt gggtgactct agggcactgg ttttctttcc agagagcgga 420
acaggcgagg aaaagtagtc ccttctcggc gattctgcgg agggatctcc gtggggcggt 480
gaacgccgat gattatataa ggacgcgccg ggtgtggcac agctagttcc gtcgcagccg 540
ggatttgggt cgcggttctt gtttgtggat cgctgtgatc gtcacttggt gagtagcggg 600
ctgctgggct ggccggggct ttcgtggccg ccgggccgct cggtgggacg gaagcgtgtg 660
gagagaccgc caagggctgt agtctgggtc cgcgagcaag gttgccctga actgggggtt 720
ggggggagcg cagcaaaatg gcggctgttc ccgagtcttg aatggaagac gcttgtgagg 780
cgggctgtga ggtcgttgaa acaaggtggg gggcatggtg ggcggcaaga acccaaggtc 840

-continued

```
ttgaggcctt cgctaatgcg ggaaagctct tattcgggtg agatgggctg gggcaccatc    900
tggggaccct gacgtgaagt ttgtcactga ctggagaact cggtttgtcg tctgttgcgg    960
gggcggcagt tatggcggtg ccgttgggca gtgcacccgt acctttggga gcgcgcgccc   1020
tcgtcgtgtc gtgacgtcac ccgttctgtt ggcttataat gcagggtggg gccacctgcc   1080
ggtaggtgtg cggtaggctt ttctccgtcg caggacgcag ggttcgggcc tagggtaggc   1140
tctcctgaat cgacaggcgc cggacctctg gtgaggggag ggataagtga ggcgtcagtt   1200
tctttggtcg gttttatgta cctatcttct taagtagctg aagctccggt tttgaactat   1260
gcgctcgggg ttggcgagtg tgttttgtga agttttttag gcaccttttg aaatgtaatc   1320
atttgggtca atatgtaatt ttcagtgtta gactagtaaa ttgtccgcta aattctggcc   1380
gtttttggct tttttgttag acgaagcttt attgcggtag tttatcacag ttaaattgct   1440
aacgcagtca gtgcttctga cacaacagtc tcgaacttaa gctgcagaag ttggtcgtga   1500
ggcactgggc aggtaagtat caaggttaca agacaggttt aaggagacca atagaaactg   1560
ggcttgtcga gacagagaag actcttgcgt ttctgatagg cacctattgg tcttactgac   1620
atccactttg cctttctctc cacaggtgtc cactcccagt tcaattacag ctcttaaggc   1680
tagagtactt aatacgactc actataggct agaattcacg cgtgccacca tgccggggtt   1740
cctggttcgc atcctccttc tgctgctggt tctgctgctt ctgggcccta cgcgcggctt   1800
gcgcaatgcc acccagagga tgtttgaaat tgactatagc cgggactcct tcctcaagga   1860
tggccagcca tttcgctaca tctcaggaag cattcactac tcccgtgtgc cccgcttcta   1920
ctggaaggac cggctgctga agatgaagat ggctgggctg aacgccatcc agacgtatgt   1980
gccctggaac tttcatgagc cctggccagg acagtaccag ttttctgagg accatgatgt   2040
ggaatatttt cttcggctgg ctcatgagct gggactgctg gttatcctga ggcccgggcc   2100
ctacatctgt gcagagtggg aaatgggagg attacctgct tggctgctag agaaagagtc   2160
tattcttctc cgctcctccg acccagatta cctggcagct gtggacaagt ggttgggagt   2220
ccttctgccc aagatgaagc ctctcctcta tcagaatgga gggccagtta taacagtgca   2280
ggttgaaaat gaatatggca gctactttgc ctgtgatttt gactacctgc gcttcctgca   2340
gaagcgcttt cgccaccatc tgggggatga tgtggttctg tttaccactg atggagcaca   2400
taaaacattc ctgaaatgtg ggccctgca gggcctctac accacggtgg actttggaac   2460
aggcagcaac atcacagatg ctttcctaag ccagaggaag tgtgagccca aaggacccctt  2520
gatcaattct gaattctata ctggctggct agatcactgg ggccaacctc actccacaat   2580
caagaccgaa gcagtggctt cctccctcta tgatatactt gcccgtgggg cgagtgtgaa   2640
cttgtacatg tttataggtg ggaccaattt tgcctattgg aatggggcca actcacccta   2700
tgcagcacag cccaccagct acgactatga tgccccactg agtgaggctg gggacctcac   2760
tgagaagtat tttgctctgc gaaacatcat ccagaagttt gaaaaagtac cagaaggtcc   2820
tatccctcca tctacaccaa agtttgcata tggaaaggtc actttggaaa agttaaagac   2880
agtgggagca gctctggaca ttctgtgtcc ctctgggccc atcaaaagcc tttatccctt   2940
gacatttatc caggtgaaac agcattatgg gtttgtgctg taccggacaa cacttcctca   3000
agattgcagc aacccagcac ctctctcttc accccctcaat ggagtccacg atcgagcata  3060
tgttgctgtg gatgggatcc cccagggagt ccttgagcga aacaatgtga tcactctgaa   3120
cataacaggg aaagctggag ccactctgga ccttctggta gagaacatgg gacgtgtgaa   3180
ctatggtgca tatatcaacg attttaaggg tttggtttct aacctgactc tcagttccaa   3240
```

```
tatcctcacg gactggacga tctttccact ggacactgag gatgcagtgc gcagccacct   3300

ggggggctgg ggacaccgtg acagtggcca ccatgatgaa gcctgggccc acaactcatc   3360

caactacacg ctcccggcct tttatatggg gaacttctcc attcccagtg ggatcccaga   3420

cttgccccag gacaccttta tccagtttcc tggatggacc aagggccagg tctggattaa   3480

tggctttaac cttggccgct attggccagc ccggggccct cagttgacct tgtttgtgcc   3540

ccagcacatc ctgatgacct cggccccaaa caccatcacc gtgctggaac tggagtgggc   3600

accctgcagc agtgatgatc cagaactatg tgctgtgacg ttcgtggaca ggccagttat   3660

tggctcatct gtgacctacg atcatccctc caaacctgtt gaaaaaagac tcatgccccc   3720

acccccgcaa aaaaacaaag attcatggct ggaccatgta tgaatgactc gaggccgctt   3780

cgagcagaca tgataagata cattgatgag tttggacaaa ccacaactag aatgcagtga   3840

aaaaaatgct ttatttgtga aatttgtgat gctattgctt tatttgtaac cattataagc   3900

tgcaataaac aagttaacaa caacaattgc attcatttta tgtttcaggt tcagggggag   3960

atgtgggagg ttttttaaag caagtaaaac ctctacaaat gtggtaaaat cgataaggat   4020

cttcctagag catggctacg tagataagta gcatggcggg ttaatcatta actacaagga   4080

acccctagtg atggagttgg ccactccctc tctgcgcgct cgctcgctca ctgaggccgg   4140

gcgaccaaag gtcgcccgac gcccgggctt tgcccgggcg gcctcagtga gcgagcgagc   4200

gcgcag                                                              4206
```

<210> SEQ ID NO 16
<211> LENGTH: 4362
<212> TYPE: DNA
<213> ORGANISM: Artificial sequence
<220> FEATURE:
<223> OTHER INFORMATION: Vector genome CB7.CI.GLB1.RBG
<220> FEATURE:
<221> NAME/KEY: repeat_region
<222> LOCATION: (1)..(130)
<223> OTHER INFORMATION: 5" ITR from AAV2
<220> FEATURE:
<221> NAME/KEY: repeat_region
<222> LOCATION: (4232)..(4362)
<223> OTHER INFORMATION: 5" ITR from AAV2

<400> SEQUENCE: 16

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctaccag ggtaatgggg    180

atcctctaga actatagcta gtcgacattg attattgact agttattaat agtaatcaat    240

tacggggtca ttagttcata gcccatatat ggagttccgc gttacataac ttacggtaaa    300

tggcccgcct ggctgaccgc ccaacgaccc ccgcccattg acgtcaataa tgacgtatgt    360

tcccatagta acgccaatag ggactttcca ttgacgtcaa tgggtggact atttacggta    420

aactgcccac ttggcagtac atcaagtgta tcatatgcca agtacgcccc ctattgacgt    480

caatgacggt aaatggcccg cctggcatta tgcccagtac atgaccttat gggactttcc    540

tacttggcag tacatctacg tattagtcat cgctattacc atggtcgagg tgagccccac    600

gttctgcttc actctcccca tctccccccc ctccccaccc ccaattttgt atttatttat    660

tttttaatta ttttgtgcag cgatgggggc gggggggggg ggggggcgcg cgccaggcgg    720

ggcggggcgg ggcgaggggc ggggcggggc gaggcggaga ggtgcggcgg cagccaatca    780
```

-continued

```
gagcggcgcg ctccgaaagt ttccttttat ggcgaggcgg cggcggcggc ggccctataa    840
aaagcgaagc gcgcggcggg cggggagtcg ctgcgacgct gccttcgccc cgtgccccgc    900
tccgccgccg cctcgcgccg cccgccccgg ctctgactga ccgcgttact cccacaggtg    960
agcgggcggg acggcccttc tcctccgggc tgtaattagc gcttggttta atgacggctt   1020
gtttcttttc tgtggctgcg tgaaagcctt gaggggctcc gggagggccc tttgtgcggg   1080
gggagcggct cggggggtgc gtgcgtgtgt gtgtgcgtgg ggagcgccgc gtgcggctcc   1140
gcgctgcccg gcggctgtga gcgctgcggg cgcggcgcgg ggctttgtgc gctccgcagt   1200
gtgcgcgagg ggagcgcggc cgggggcggt gccccgcggt gcgggggggg ctgcgagggg   1260
aacaaaggct gcgtgcgggg tgtgtgcgtg ggggggtgag cagggggtgt gggcgcgtcg   1320
gtcgggctgc aacccccct gcacccccct ccccgagttg ctgagcacgg cccggcttcg   1380
ggtgcggggc tccgtacggg gcgtggcgcg gggctcgccg tgccgggcgg ggggtggcgg   1440
caggtggggg tgccgggcgg ggcggggccg cctcgggccg gggagggctc gggggagggg   1500
cgcggcggcc cccggagcgc cggcggctgt cgaggcgcgg cgagccgcag ccattgcctt   1560
ttatggtaat cgtgcgagag ggcgcaggga cttcctttgt cccaaatctg tgcggagccg   1620
aaatctggga ggcgccgccg cacccccctct agcgggcgcg ggcgaagcg gtgcggcgcc   1680
ggcaggaagg aaatgggcgg ggagggcctt cgtgcgtcgc cgcgccgccg tccccttctc   1740
cctctccagc ctcggggctg tccgcggggg gacggctgcc ttcggggggg acggggcagg   1800
gcggggttcg gcttctggcg tgtgaccggc ggctctagag cctctgctaa ccatgttcat   1860
gccttcttct ttttcctaca gctcctgggc aacgtgctgg ttattgtgct gtctcatcat   1920
tttggcaaag aattcacgcg tgccaccatg cccggctttc tcgtgcggat tctcctgctg   1980
ctgctggtgc ttctgctgct gggccctacc agaggcctga gaaacgccac ccagcggatg   2040
ttcgagatcg actacagccg ggacagcttc ctgaaggacg gccagccctt ccggtacatc   2100
agcggcagca tccactacag cagagtgccc cggttctact ggaaggaccg gctgctgaag   2160
atgaagatgg ccggcctgaa cgccatccag acctacgtgc cctggaactt ccacgagcct   2220
tggcctggcc agtaccagtt cagcgaggac cacgacgtgg aatactttct gcggctggcc   2280
cacgagctgg gcctgctcgt gattctgagg cctggccctt acatctgcgc cgagtgggag   2340
atgggaggac tgcctgcttg gctgctggaa aaagagagca tcctgctgcg gagcagcgac   2400
cccgattatc tggccgccgt ggataagtgg ctgggcgtgc tgctgcccaa gatgaagccc   2460
ctgctgtacc agaacggcgg acccgtgatc accgtgcagg tggaaaacga gtacggcagc   2520
tacttcgcct gcgacttcga ctacctgcgg ttcctgcaga agcggttcag acaccacctg   2580
ggcgacgacg tggtgctgtt cacaacagac ggcgcccaca agacctttct gaagtgtggc   2640
gctctgcagg gcctgtacac caccgtggat tttggcaccg gcagcaatat caccgacgcc   2700
tttctgagcc agcggaagtg cgagccaaag ggccccctga tcaacagcga gttctacacc   2760
ggctggctgg accactgggg ccagcctcac agcaccatca agacagaggc cgtggccagc   2820
agcctgtacg acatcctggc tagaggcgcc agcgtgaacc tgtacatgtt tatcggcggc   2880
accaacttcg cctactggaa cggcgccaac agcccttatg ccgcccagcc caccagctac   2940
gactacgatg cccctctgtc tgaggccggc gacctgaccg agaagtactt tgccctgcgg   3000
aacatcatcc agaaattcga gaaggtgccc gagggcccca tccccccctag cacacctaag   3060
ttcgcctacg gcaaagtgac cctggaaaag ctgaaaaccg tgggagccgc cctggacatc   3120
ctgtgtccta gcggccctat caagagcctg tacccccctga ccttcatcca agtgaagcag   3180
```

-continued

```
cactacggct tcgtgctgta ccggaccacc ctgccccagg actgtagcaa tcctgcccca   3240

ctgagcagcc ccctgaacgg cgtgcacgat agagcctacg tggccgtgga tggcatccca   3300

caggggtgc tggaacggaa caatgtgatc accctgaaca tcaccggcaa ggctggcgcc   3360

accctggacc tgctggtgga aaacatgggc agagtgaact acggcgccta catcaacgac   3420

ttcaagggcc tggtgtccaa cctgaccctg agcagcaaca tcctgaccga ctggaccatc   3480

ttcccactgg acaccgagga tgccgtgcgg agccatctgg gaggatgggg acacagagat   3540

agcggccacc acgatgaagc ctgggcccac aacagcagca actacaccct gcctgccttc   3600

tacatgggca acttcagcat ccccagcggc atccccgacc tgccacagga cacctttatc   3660

cagttccccg gctggacaaa gggacaagtg tggatcaatg gcttcaacct gggcagatac   3720

tggcccgcca gaggccctca gctgaccctg tttgtgcccc agcacattct gatgaccagc   3780

gcccccaaca ccatcaccgt gctggaactg gaatgggccc cctgcagcag cgacgaccct   3840

gaactgtgtg ccgtgacctt cgtggacagg cccgtgatcg gcagcagcgt gacctacgac   3900

caccccagca agcccgtgga aaagcggctg atgcctcccc caccccagaa gaacaaggac   3960

tcctggctgg atcacgtgtg atgactcgag gacggggtga actacgcctg aggatccgat   4020

ctttttccct ctgccaaaaa ttatggggac atcatgaagc cccttgagca tctgacttct   4080

ggctaataaa ggaaatttat tttcattgca atagtgtgtt ggaatttttt gtgtctctca   4140

ctcggaagca attcgttgat ctgaatttcg accacccata atacccatta ccctggtaga   4200

taagtagcat ggcgggttaa tcattaacta caaggaaccc ctagtgatgg agttggccac   4260

tccctctctg cgcgctcgct cgctcactga ggccgggcga ccaaaggtcg cccgacgccc   4320

gggctttgcc cgggcggcct cagtgagcga gcgagcgcgc ag                       4362
```

<210> SEQ ID NO 17
<211> LENGTH: 973
<212> TYPE: DNA
<213> ORGANISM: Artificial sequence
<220> FEATURE:
<223> OTHER INFORMATION: chicken beta-actin intron

<400> SEQUENCE: 17

```
gtgagcgggc gggacggccc ttctcctccg ggctgtaatt agcgcttggt ttaatgacgg     60

cttgtttctt ttctgtggct gcgtgaaagc cttgaggggc tccgggaggg ccctttgtgc    120

gggggagcg gctcgggggg tgcgtgcgtg tgtgtgtgcg tggggagcgc cgcgtgcggc    180

tccgcgctgc ccggcggctg tgagcgctgc gggcgcggcg cggggctttg tgcgctccgc    240

agtgtgcgcg aggggagcgc ggccgggggc ggtgccccgc ggtgcggggg gggctgcgag    300

gggaacaaag gctgcgtgcg gggtgtgtgc gtgggggggt gagcaggggg tgtgggcgcg    360

tcggtcgggc tgcaaccccc cctgcacccc cctccccgag ttgctgagca cggcccggct    420

tcgggtgcgg ggctccgtac ggggcgtggc gcggggctcg ccgtgccggg cgggggggtgg    480

cggcaggtgg gggtgccggg cggggcgggg ccgcctcggg ccggggaggg ctcgggggag    540

ggcgcggcg gcccccggag cgccggcggc tgtcgaggcg cggcgagccg cagccattgc    600

cttttatggt aatcgtgcga gagggcgcag ggacttcctt tgtcccaaat ctgtgcggag    660

ccgaaatctg ggaggcgccg ccgcaccccc tctagcgggc gcggggcgaa gcggtgcggc    720

gccggcagga aggaaatggg cggggagggc cttcgtgcgt cgccgcgccg ccgtcccctt    780

ctccctctcc agcctcgggg ctgtccgcgg ggggacggct gccttcgggg gggacggggc    840
```

```
agggcggggt tcggcttctg gcgtgtgacc ggcggctcta gagcctctgc taaccatgtt    900

catgccttct tctttttcct acagctcctg ggcaacgtgc tggttattgt gctgtctcat    960

cattttggca aag                                                       973


<210> SEQ ID NO 18
<211> LENGTH: 282
<212> TYPE: DNA
<213> ORGANISM: Artificial sequence
<220> FEATURE:
<223> OTHER INFORMATION: CB promoter

<400> SEQUENCE: 18

tggtcgaggt gagccccacg ttctgcttca ctctccccat ctcccccccc tccccacccc     60

caattttgta tttatttatt ttttaattat tttgtgcagc gatgggggcg gggggggggg    120

gggggcgcgc gccaggcggg gcggggcggg gcgaggggcg gggcggggcg aggcggagag    180

gtgcggcggc agccaatcag agcggcgcgc tccgaaagtt tccttttatg gcgaggcggc    240

ggcggcggcg gccctataaa aagcgaagcg cgcggcgggc gg                       282


<210> SEQ ID NO 19
<211> LENGTH: 382
<212> TYPE: DNA
<213> ORGANISM: Artificial sequence
<220> FEATURE:
<223> OTHER INFORMATION: CMV Immediate early Promoter

<400> SEQUENCE: 19

ctagtcgaca ttgattattg actagttatt aatagtaatc aattacgggg tcattagttc     60

atagcccata tatggagttc cgcgttacat aacttacggt aaatggcccg cctggctgac    120

cgcccaacga cccccgccca ttgacgtcaa taatgacgta tgttcccata gtaacgccaa    180

tagggacttt ccattgacgt caatgggtgg actatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360

acgtattagt catcgctatt ac                                             382


<210> SEQ ID NO 20
<211> LENGTH: 736
<212> TYPE: PRT
<213> ORGANISM: Artificial Sequence
<220> FEATURE:
<223> OTHER INFORMATION: Encoded AAV9 vp1 amino acid sequence

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
```

-continued

```
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525
```

-continued

```
Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 21
<211> LENGTH: 736
<212> TYPE: PRT
<213> ORGANISM: Artificial Sequence
<220> FEATURE:
<223> OTHER INFORMATION: Encoded AAVhu31 vp1 amino acid sequence

<400> SEQUENCE: 21

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160
```

-continued

```
Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Gly Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575
```

-continued

```
Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Ser Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 22
<211> LENGTH: 736
<212> TYPE: PRT
<213> ORGANISM: Artificial Sequence
<220> FEATURE:
<223> OTHER INFORMATION: Encoded AAVhu32 vp1 amino acid sequence

<400> SEQUENCE: 22

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205
```

-continued

```
Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
```

-continued

```
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 23
<211> LENGTH: 2211
<212> TYPE: DNA
<213> ORGANISM: Artificial Sequence
<220> FEATURE:
<223> OTHER INFORMATION: AAV9 vp1 coding sequence

<400> SEQUENCE: 23

```
atggctgccg atggttatct tccagattgg ctcgaggaca accttagtga aggaattcgc     60

gagtggtggg ctttgaaacc tggagcccct caacccaagg caaatcaaca acatcaagac    120

aacgctcgag gtcttgtgct tccgggttac aaataccttg gacccggcaa cggactcgac    180

aagggggagc cggtcaacgc agcagacgcg gcggccctcg agcacgacaa ggcctacgac    240

cagcagctca aggccggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcagtctcct caggaaccgg actcctccgc gggtattggc    480

aaatcgggtg cacagcccgc taaaaagaga ctcaatttcg gtcagactgg cgacacagag    540

tcagtcccag accctcaacc aatcggagaa cctcccgcag ccccctcagg tgtgggatct    600

cttacaatgg cttcaggtgg tggcgcacca gtggcagaca ataacgaagg tgccgatgga    660

gtgggtagtt cctcgggaaa ttggcattgc gattcccaat ggctggggga cagagtcatc    720

accaccagca cccgaacctg ggccctgccc acctacaaca atcacctcta caagcaaatc    780

tccaacagca catctggagg atcttcaaat gacaacgcct acttcggcta cagcaccccc    840

tgggggtatt ttgacttcaa cagattccac tgccacttct caccacgtga ctggcagcga    900

ctcatcaaca acaactgggg attccggcct aagcgactca acttcaagct cttcaacatt    960

caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atggaagcca ggccgtgggt cgttcgtcct tttactgcct ggaatatttc   1200

ccgtcgcaaa tgctaagaac gggtaacaac ttccagttca gctacgagtt tgagaacgta   1260

cctttccata gcagctacgc tcacagccaa agcctggacc gactaatgaa tccactcatc   1320

gaccaatact tgtactatct ctcaaagact attaacggtt ctggacagaa tcaacaaacg   1380

ctaaaattca gtgtggccgg acccagcaac atggctgtcc agggaagaaa ctacatacct   1440

ggacccagct accgacaaca acgtgtctca accactgtga ctcaaaacaa caacagcgaa   1500
```

```
tttgcttggc ctggagcttc ttcttgggct ctcaatggac gtaatagctt gatgaatcct   1560

ggacctgcta tggccagcca caaagaagga gaggaccgtt tctttccttt gtctggatct   1620

ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaagcacag gcgcagaccg gctgggttca aaaccaagga   1800

atacttccgg gtatggtttg gcaggacaga gatgtgtacc tgcaaggacc catttgggcc   1860

aaaattcctc acacggacgg caactttcac ccttctccgc tgatgggagg gtttggaatg   1920

aagcacccgc ctcctcagat cctcatcaaa aacacacctg tacctgcgga tcctccaacg   1980

gccttcaaca aggacaagct gaactctttc atcacccagt attctactgg ccaagtcagc   2040

gtggagatcg agtgggagct gcagaaggaa aacagcaagc gctggaaccc ggagatccag   2100

tacacttcca actattacaa gtctaataat gttgaatttg ctgttaatac tgaaggtgta   2160

tatagtgaac cccgccccat tggcaccaga tacctgactc gtaatctgta a            2211
```

<210> SEQ ID NO 24
<211> LENGTH: 2211
<212> TYPE: DNA
<213> ORGANISM: Artificial Sequence
<220> FEATURE:
<223> OTHER INFORMATION: AAVhu31 vp1 coding sequence

<400> SEQUENCE: 24

```
atggctgccg atggttatct tccagattgg ctcgaggaca accttagtga aggaattcgc     60

gagtggtggg ctttgaaacc tggagcccct caacccaagg caaatcaaca acatcaagac    120

aacgctcgag gtcttgtgct tccgggttac aaataccttg gacccggcaa cggactcgac    180

aagggggagc cggtcaacgc agcagacgcg gcggccctcg agcacgacaa ggcctacgac    240

cagcagctca aggccggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcagtctcct caggaaccgg actcctccgc gggtattggc    480

aaatcgggtg cacagcccgc taaaaagaga ctcaatttcg gtcagactgg cgacacagag    540

tcagtcccag accctcaacc aatcggagaa cctcccgcag ccccctcagg tgtgggatct    600

cttacaatgg cttcaggtgg tggcgcacca gtggcagaca ataacgaagg tgccgatgga    660

gtgggtagtt cctcgggaaa ttggcattgc gattcccaat ggctgggga cagagtcatc    720

accaccagca cccgaacctg ggccctgccc acctacaaca atcacctcta caagcaaatc    780

tccaacagca catctggagg atcttcaaat gacaacgcct acttcggcta cagcaccccc    840

tgggggtatt ttgacttcaa cagattccac tgccacttct caccacgtga ctggcagcga    900

ctcatcaaca acaactgggg attccggcct aagcgactca acttcaagct cttcaacatt    960

caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atggaagcca ggccgtgggt cgttcgtcct tttactgcct ggaatatttc   1200

ccgtcgcaaa tgctaagaac gggtaacaac ttccagttca gctacgagtt tgagaacgta   1260

cctttccata gcagctacgc tcacagccaa agcctggacc gactaatgaa tccactcatc   1320
```

-continued

```
gaccaatact tgtactatct ctcaaagact attaacggtt ctggacagaa tcaacaaacg   1380

ctaaaattca gtgtggccgg acccagcaac atggctgtcc agggaagaaa ctacatacct   1440

ggacccagct accgacaaca acgtgtctca accactgtga ctcaaaacaa caacagcgaa   1500

tttgcttggc ctggagcttc ttcttgggct ctcaatggac gtaatagctt gatgaatcct   1560

ggacctgcta tggccagcca caaagaagga gaggaccgtt tctttccttt gtctggatct   1620

ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaagcacag gcgcagaccg gctgggttca aaaccaagga   1800

atacttccgg gtatggtttg gcaggacaga gatgtgtacc tgcaaggacc catttgggcc   1860

aaaattcctc acacggacgg caactttcac ccttctccgc tgatgggagg gtttggaatg   1920

aagcacccgc ctcctcagat cctcatcaaa aacacacctg tacctgcgga tcctccaacg   1980

gccttcaaca aggacaagct gaactctttc atcacccagt attctactgg ccaagtcagc   2040

gtggagatcg agtgggagct gcagaaggaa aacagcaagc gctggaaccc ggagatccag   2100

tacacttcca actattacaa gtctaataat gttgaatttg ctgttaatac tgaaggtgta   2160

tatagtgaac cccgccccat tggcaccaga tacctgactc gtaatctgta a            2211
```

<210> SEQ ID NO 25
<211> LENGTH: 2211
<212> TYPE: DNA
<213> ORGANISM: Artificial Sequence
<220> FEATURE:
<223> OTHER INFORMATION: AAVhu32 vp1 coding sequence

<400> SEQUENCE: 25

```
atggctgccg atggttatct tccagattgg ctcgaggaca ctctctctga aggaataaga     60

cagtggtgga agctcaaacc tggcccacca ccaccaaagc ccgcagagcg gcataaggac    120

gacagcaggg gtcttgtgct tcctgggtac aagtacctcg gacccggcaa cggactcgac    180

aagggggagc cggtcaacgc agcagacgcg gcggccctcg agcacgacaa ggcctacgac    240

cagcagctca aggccggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcagtctcct caggaaccgg actcctccgc gggtattggc    480

aaatcgggtt cacagcccgc taaaaagaaa ctcaatttcg gtcagactgg cgacacagag    540

tcagtccccg accctcaacc aatcggagaa cctcccgcag ccccctcagg tgtgggatct    600

cttacaatgg cttcaggtgg tggcgcacca gtggcagaca ataacgaagg tgccgatgga    660

gtgggtagtt cctcgggaaa ttggcattgc gattcccaat ggctggggga cagagtcatc    720

accaccagca cccgaacctg ggccctgccc acctacaaca atcacctcta caagcaaatc    780

tccaacagca catctggagg atcttcaaat gacaacgcct acttcggcta cagcaccccc    840

tgggggtatt ttgacttcaa cagattccac tgccacttct caccacgtga ctggcagcga    900

ctcatcaaca acaactgggg attccggcct aagcgactca acttcaagct cttcaacatt    960

caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atgggagcca ggccgtgggt cgttcgtcct tttactgcct ggaatatttc   1200
```

-continued

```
ccgtcgcaaa tgctaagaac gggtaacaac ttccagttca gctacgagtt tgagaacgta   1260

cctttccata gcagctacgc tcacagccaa agcctggacc gactaatgaa tccactcatc   1320

gaccaatact tgtactatct ctcaaagact attaacggtt ctggacagaa tcaacaaacg   1380

ctaaaattca gcgtggccgg acccagcaac atggctgtcc agggaagaaa ctacatacct   1440

ggacccagct accgacaaca acgtgtctca accactgtga ctcaaaacaa caacagcgaa   1500

tttgcttggc ctggagcttc ttcttgggct ctcaatggac gtaatagctt gatgaatcct   1560

ggacctgcta tggccagcca caaagaagga gaggaccgtt tctttccttt gtctggatct   1620

ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaagcacag gcgcagaccg gctgggttca aaaccaagga   1800

atacttccgg gtatggtttg gcaggacaga gatgtgtacc tgcaaggacc catttgggcc   1860

aaaattcctc acacggacgg caactttcac ccttctccgc taatgggagg gtttggaatg   1920

aagcacccgc ctcctcagat cctcatcaaa aacacacctg tacctgcgga tcctccaacg   1980

gctttcaata aggacaagct gaactctttc atcacccagt attctactgg ccaagtcagc   2040

gtggagattg agtgggagct gcagaaggaa aacagcaagc gctggaaccc ggagatccag   2100

tacacttcca actattacaa gtctaataat gttgaatttg ctgttaatac tgaaggtgta   2160

tatagtgaac cccgccccat tggcaccaga tacctgactc gtaatctgta a            2211


<210> SEQ ID NO 26
<211> LENGTH: 546
<212> TYPE: PRT
<213> ORGANISM: Homo sapiens

<400> SEQUENCE: 26

Met Pro Gly Phe Leu Val Arg Ile Leu Pro Leu Leu Leu Val Leu Leu
1               5                   10                  15

Leu Leu Gly Pro Thr Arg Gly Leu Arg Asn Ala Thr Gln Arg Met Phe
            20                  25                  30

Glu Ile Asp Tyr Ser Arg Asp Ser Phe Leu Lys Asp Gly Gln Pro Phe
        35                  40                  45

Arg Tyr Ile Ser Gly Ser Ile His Tyr Ser Arg Val Pro Arg Phe Tyr
    50                  55                  60

Trp Lys Asp Arg Leu Leu Lys Met Lys Met Ala Gly Leu Asn Ala Ile
65                  70                  75                  80

Gln Thr Leu Pro Gly Ser Cys Gly Gln Val Val Gly Ser Pro Ser Ala
                85                  90                  95

Gln Asp Glu Ala Ser Pro Leu Ser Glu Trp Arg Ala Ser Tyr Asn Ser
            100                 105                 110

Ala Gly Ser Asn Ile Thr Asp Ala Phe Leu Ser Gln Arg Lys Cys Glu
        115                 120                 125

Pro Lys Gly Pro Leu Ile Asn Ser Glu Phe Tyr Thr Gly Trp Leu Asp
    130                 135                 140

His Trp Gly Gln Pro His Ser Thr Ile Lys Thr Glu Ala Val Ala Ser
145                 150                 155                 160

Ser Leu Tyr Asp Ile Leu Ala Arg Gly Ala Ser Val Asn Leu Tyr Met
                165                 170                 175

Phe Ile Gly Gly Thr Asn Phe Ala Tyr Trp Asn Gly Ala Asn Ser Pro
            180                 185                 190
```

-continued

```
Tyr Ala Ala Gln Pro Thr Ser Tyr Asp Tyr Asp Ala Pro Leu Ser Glu
        195                 200                 205

Ala Gly Asp Leu Thr Glu Lys Tyr Phe Ala Leu Arg Asn Ile Ile Gln
    210                 215                 220

Lys Phe Glu Lys Val Pro Glu Gly Pro Ile Pro Pro Ser Thr Pro Lys
225                 230                 235                 240

Phe Ala Tyr Gly Lys Val Thr Leu Glu Lys Leu Lys Thr Val Gly Ala
                245                 250                 255

Ala Leu Asp Ile Leu Cys Pro Ser Gly Pro Ile Lys Ser Leu Tyr Pro
            260                 265                 270

Leu Thr Phe Ile Gln Val Lys Gln His Tyr Gly Phe Val Leu Tyr Arg
        275                 280                 285

Thr Thr Leu Pro Gln Asp Cys Ser Asn Pro Ala Pro Leu Ser Ser Pro
    290                 295                 300

Leu Asn Gly Val His Asp Arg Ala Tyr Val Ala Val Asp Gly Ile Pro
305                 310                 315                 320

Gln Gly Val Leu Glu Arg Asn Asn Val Ile Thr Leu Asn Ile Thr Gly
                325                 330                 335

Lys Ala Gly Ala Thr Leu Asp Leu Leu Val Glu Asn Met Gly Arg Val
            340                 345                 350

Asn Tyr Gly Ala Tyr Ile Asn Asp Phe Lys Gly Leu Val Ser Asn Leu
        355                 360                 365

Thr Leu Ser Ser Asn Ile Leu Thr Asp Trp Thr Ile Phe Pro Leu Asp
    370                 375                 380

Thr Glu Asp Ala Val Arg Ser His Leu Gly Gly Trp Gly His Arg Asp
385                 390                 395                 400

Ser Gly His His Asp Glu Ala Trp Ala His Asn Ser Ser Asn Tyr Thr
                405                 410                 415

Leu Pro Ala Phe Tyr Met Gly Asn Phe Ser Ile Pro Ser Gly Ile Pro
            420                 425                 430

Asp Leu Pro Gln Asp Thr Phe Ile Gln Phe Pro Gly Trp Thr Lys Gly
        435                 440                 445

Gln Val Trp Ile Asn Gly Phe Asn Leu Gly Arg Tyr Trp Pro Ala Arg
    450                 455                 460

Gly Pro Gln Leu Thr Leu Phe Val Pro Gln His Ile Leu Met Thr Ser
465                 470                 475                 480

Ala Pro Asn Thr Ile Thr Val Leu Glu Leu Glu Trp Ala Pro Cys Ser
                485                 490                 495

Ser Asp Asp Pro Glu Leu Cys Ala Val Thr Phe Val Asp Arg Pro Val
            500                 505                 510

Ile Gly Ser Ser Val Thr Tyr Asp His Pro Ser Lys Pro Val Glu Lys
        515                 520                 525

Arg Leu Met Pro Pro Pro Pro Gln Lys Asn Lys Asp Ser Trp Leu Asp
    530                 535                 540

His Val
545
```

COMPOSITIONS USEFUL FOR TREATING GM1 GANGLIOSIDOSIS

CROSS-REFERENCE TO RELATED APPLICATIONS

This application is a National Stage Entry under 35 U.S.C. 371 of International Patent Application No. PCT/US2019/053797, filed Sep. 30, 2019, which claims priority to U.S. Provisional Patent Application No. 62/739,811, filed Oct. 1, 2018, and U.S. Provisional Patent Application No. 62/835,178, filed Apr. 17, 2019, which are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "18-8537PCT_SequenceListing_ST25.txt", dated Aug. 29, 2019 and is 144,703 bytes in size.

BACKGROUND OF THE INVENTION

GM1 gangliosidosis, henceforth referred to as GM1, is a recessive lysosomal storage disease caused by mutations in the GLB1 gene which encodes lysosomal acid beta galactosidase (β-gal), an enzyme that catalyzes the first step in the degradation of GM1 ganglioside and keratan sulfate (Brunetti-Pierri and Scaglia, 2008, GM1 gangliosidosis: Review of clinical, molecular, and therapeutic aspects, *Molecular Genetics and Metabolism,* 94: 391-96). The GLB1 gene is located on chromosome 3 and leads to two alternatively spliced mRNAs, a 2.5 kb transcript encoding the β-gal lysosomal enzyme and a 2.0 kb transcript encoding the elastin binding protein (EBP) (Oshima et al. 1988, Cloning, sequencing, and expression of cDNA for human β-galactosidase, Biochemical and Biophysical Research Communications, 157: 238-44; Morreau et al. 1989, Alternative splicing of beta-galactosidase mRNA generates the classic lysosomal enzyme and a beta-galactosidase-related protein, *Journal of Biological Chemistry,* 264: 20655-63). β-gal is synthesized as an 85 kDa precursor that is post-translationally glycosylated to an 88 kDa form and processed into the mature 64 kDa lysosomal enzyme (D'Azzo et al. 1982, Molecular defect in combined beta-galactosidase and neuraminidase deficiency in man, *Proceedings of the National Academy of Sciences,* 79: 4535-39). Within lysosomes the enzyme is complexed with protective protein cathepsin A (PPCA) and neuraminidase hydrolases.

In patients carrying GLB1 alleles that produce little or no residual β-gal, GM1 ganglioside accumulates in neurons throughout the brain, resulting in a rapidly progressive neurodegenerative disease (Brunetti-Pierri and Scaglia 2008). While the molecular mechanisms leading to disease pathogenesis are still not well understood, hypotheses include neuronal cell death and demyelination accompanied by astrogliosis and microgliosis in areas of severe neuronal vacuolation, neuronal apoptosis (Tessitore et al. 2004, GM1-Ganglioside-Mediated Activation of the Unfolded Protein Response Causes Neuronal Death in a Neurodegenerative Gangliosidosis, *Molecular Cell,* 15: 753-66), abnormal axoplasmic transport resulting in myelin deficiency (van der Voorn et al. 2004, The leukoencephalopathy of infantile GM1 gangliosidosis: oligodendrocytic loss and axonal dysfunction, *Acta Neuropathologica,* 107: 539-45), disturbed neuronal-oligodendroglial interactions (Folkerth 1999, Abnormalities of Developing White Matter in Lysosomal Storage Diseases, *Journal of Neuropathology and Experimental Neurology,* 58: 887-902; Kaye et al. 1992, Dysmyelinogenesis in animal model of GM1 gangliosidosis', Pediatric Neurology, 8: 255-61), and inflammatory responses (Jeyakumar et al. 2003, Central nervous system inflammation is a hallmark of pathogenesis in mouse models of GM1 and GM2 gangliosidosis, Brain, 126: 974-87).

There are currently no disease-modifying therapies for GM1. Supportive care and symptomatic treatments including feeding tube placement, respiratory therapy and anti-epileptic drugs are current therapeutic approaches (James Utz et al. 2017, Infantile gangliosidoses: Mapping a timeline of clinical changes, *Molecular Genetics and Metabolism,* 121: 170-79). Substrate reduction therapy (SRT) with miglustat, a glucosylceramide synthase inhibitor, has been evaluated in GM1 and GM2 patients. Although miglustat is generally well tolerated, it has not resulted in marked improvement in symptom management or disease progression and some patients experience dose limiting gastrointestinal side effects (Shapiro et al., 2009, Regier et al., 2016b). When used in combination with a ketogenic diet, miglustat has been shown to be well tolerated and to increase survival in some patients (James Utz et al., 2017). However, it should be noted that no randomized controlled studies with miglustat have been conducted and miglustat is not approved for the treatment of GM1 gangliosidosis. There is limited experience with haematopoietic stem cell transplantation (HSCT) with bone marrow or umbilical cord blood in this disease. Bone marrow transplant performed in a patient with Type 2 GM1 resulted normalization of white cell β-galactosidase levels in a patient with presymptomatic juvenile onset GM1-gangliosidosis, did not improve long-term clinical outcome (Shield et al., 2005, Bone marrow transplantation correcting β-galactosidase activity does not influence neurological outcome in juvenile GM1-gangliosidosis. *Journal of Inherited Metabolic Disease.* 28(5):797-798). The slow time to effect of HSCT make it not suitable for rapidly progressive Type 1 GM1 disease (Peters and Steward, 2003, Hematopoietic cell transplantation for inherited metabolic diseases: an overview of outcomes and practice guidelines. *Bone Marrow Transplantation.* 31:229).

Adeno-associated virus (AAV), a member of the Parvovirus family, is a small non-enveloped, icosahedral virus with single-stranded linear DNA (ssDNA) genomes of about 4.7 kilobases (kb) long. The wild-type genome comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which self-assemble to form a capsid of an icosahedral symmetry.

AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

What is desirable are alternative therapeutics for treatment of conditions associated with abnormal GLB1 gene.

SUMMARY OF THE INVENTION

A therapeutic, recombinant (r), replication-defective, adeno-associated virus (AAV) is provided which is useful for treating and/or reducing the symptoms associated with GM1 gangliosidosis in human patients in need thereof. The rAAV is desirably replication-defective and carries a vector genome comprising a GLB1 gene encoding human(h) β-galactosidase under the control of regulatory sequences which direct its expression in targeted human cells, which may be termed as rAAV.GLB1 as used herein. In certain embodiments, the rAAV comprises an AAVhu68 capsid. This is rAAV is termed herein, rAAVhu68.GLB1, but in certain instances the terms rAAVhu68.GLB1 vector, rAAVhu68.hGLB1, rAAVhu68.hGLB1 vector, AAVhu68.GLB1, or AAVhu68.GLB1 vector are used interchangeable to reference the same construct. In certain embodiments, the vector genome is entirely exogenous to the AAVhu68 capsid, as it contains no AAVhu68 genomic sequences. In certain embodiments, a capsid other than the AAVhu68 capsid may be utilized. In a further embodiment, the AAV capsid is suitable for delivering a vector genome into the central nervous system (CNS, for example, neurons, glial cells, epithelial cells or other cells in the CNS). Additionally, provided are methods, vectors (viral or non-viral vectors, such as plasmids), and cells for use in production (for example, generation and/or purification) of the rAAV.

In certain embodiments, the GLB1 gene encodes a signal peptide and the mature GLB1 amino acid sequence of amino acids 24 to 677 of SEQ ID NO: 4 or a functional fragment thereof. In certain embodiments, the native human GLB1 signal peptide is used, e.g., the amino acid sequence of amino acids 1 to 23 of SEQ ID NO: 4.

In certain embodiments, the GLB1 gene has a nucleic acid sequence selected from: SEQ ID NO: 5, SEQ ID NO: 6, SEQ ID NO: 7 or SEQ ID NO: 8, or a sequence at least 95% to 99.9% identical to SEQ ID NO: 6, SEQ ID NO: 7 or SEQ ID NO: 8. In a further embodiment, the GLB1 nucleic acid sequence encodes amino acids 24 to 677 of SEQ ID NO: 4 or a functional fragment thereof. In another embodiment, the GLB1 nucleic acid sequence encodes an amino acid sequence of SEQ ID NO: 4 or a functional fragment thereof.

In certain embodiments, the regulatory sequences comprise a human ubiquitin C (UbC) promoter.

In certain embodiments, the vector genome has a sequence selected from SEQ ID NO: 12, SEQ ID NO: 13, SEQ ID NO: 14 or SEQ ID NO: 15.

In certain embodiments, an aqueous pharmaceutical composition is provided which comprises a formulation buffer and the rAAV.GLB1 (for example, rAAVhu68.GLB1). In certain embodiments, the formulation buffer comprises: an artificial cerebrospinal fluid comprising buffered saline and one or more of sodium, calcium, magnesium, potassium, or mixtures thereof; and a surfactant. In certain embodiments, the surfactant comprises about 0.0005% to about 0.001% of the suspension. In a further embodiment, the percentage (%) is calculated based on weight (w) ratio (i.e., w/w). In certain embodiments, the composition is at a pH of 7.2 to 7.8. In certain embodiments, the composition is at a pH of 6.2 to 7.7. In certain embodiment, the composition is at a pH of 6.0 to 7.5. In one embodiment, the pH is about 7.

In certain embodiments, a method of treating patients having GM1 gangliosidosis comprising administering a rAAV.GLB1 (for example, rAAVhu68.GLB1) as described herein, or a composition containing same as provided. The method involves delivering the rAAV.GLB1 to a human patient having GM1 gangliosidosis. In certain embodiments, the rAAV.GLB1 or composition is administered via a CT-guided sub-occipital injection into the cisterna magna. In certain embodiments, the method involves delivering the rAAV.GLB1 or composition to a human patient in a single dose.

In certain embodiments, a rAAV.GLB1 (such as, rAAVhu68.GLB1) or a composition comprising the same is administrable to a patient via an intra-cisterna magna injection (ICM). In certain embodiments, a rAAV.GLB1 (for example, rAAVhu68.GLB1) or a composition comprising the same is provided which is administrable to a patient having infantile gangliosidosis who is 18 months of age or younger. A rAAV.GLB1 (for example, rAAVhu68.GLB1) or a composition comprising the same is provided which is administrable to a patient in need thereof to ameliorate symptoms of GM1 gangliosidosis, for example, GM1 neurological symptoms. In certain embodiments, the amelioration of GM1 gangliosidosis include increased average life span, decreased need for feeding tube, reduction in seizure incidence and frequency, reduction in progression towards neurocognitive decline and/or improvement in neurocognitive development.

These and other aspects of the invention are apparent from the following detailed description of the invention.

BRIEF DESCRIPTION OF THE DRAWINGS

FIGS. 3A-3E illustrate serum and peripheral organ β-gal activity. β-gal activity was measured in serum (FIG. 3A) as well as lung (FIG. 3B), liver (FIG. 3C), heart (FIG. 3D) and spleen samples (FIG. 3E), respectively, using a fluorogenic substrate. PBS: phosphate buffered saline (vehicle), AAV:

Adeno-associated virus (AAVhu68.UbC.hGLB1). *$p<0.05$, **$p<0.01$ Kruskal-Wallis test followed by Dunn's test. NS: not significant.

Figure 4A:
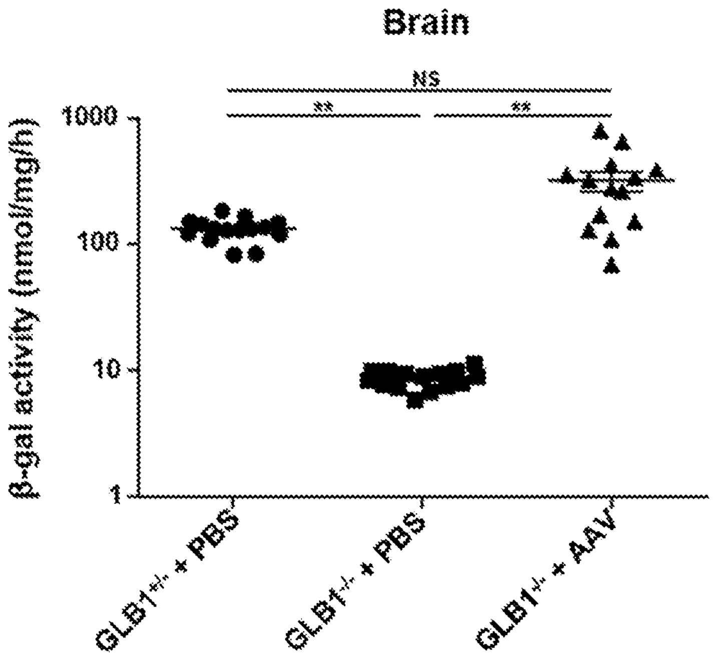
Figure 4B:
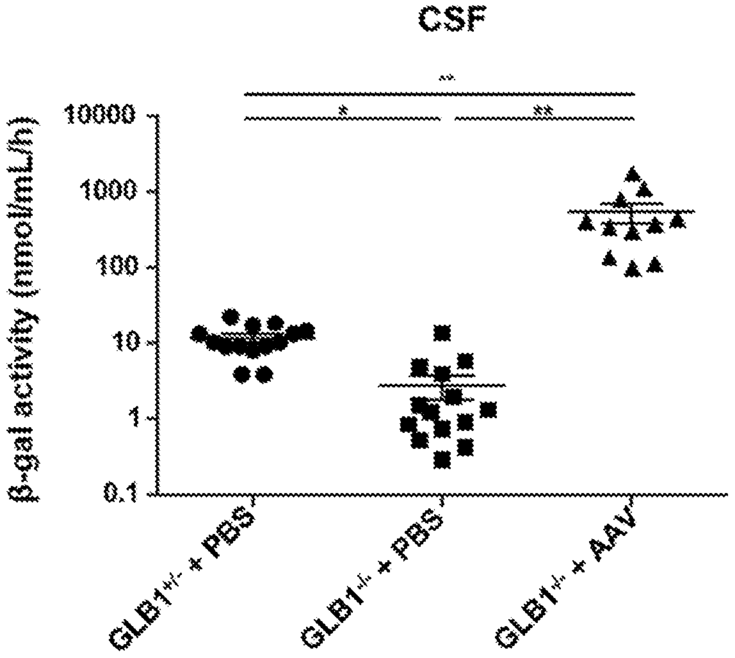

FIGS. 4A-4B illustrate β-gal activity in brain and CSF. Brain (frontal cortex) and CSF were collected at necropsy and β-gal activity measured using a fluorogenic substrate. PBS: phosphate buffered saline (vehicle), AAV: Adeno-associated virus (AAVhu68.UbC.hGLB1). *$p<0.05$, **$p<0.01$ Kruskal-Wallis test followed by Dunn's test. NS: not significant.

Figure 5:
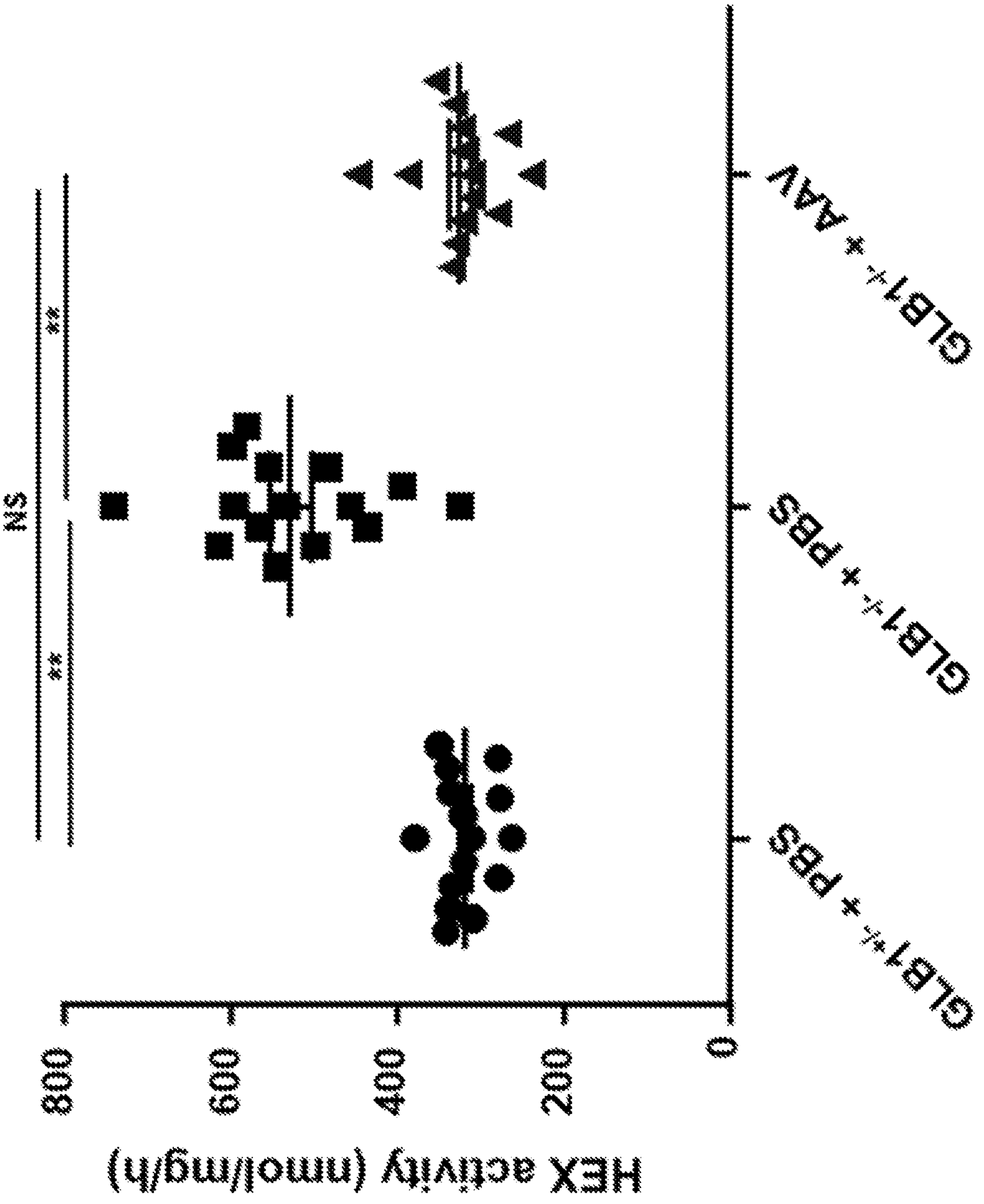

FIG. 5 shows reduction of hexosaminidase (HEX) activity in brains of rAAVhu68.GLB1-treated GLB1$^{-/-}$ mice. Brain (frontal cortex) was collected at necropsy and HEX activity measured using a fluorogenic substrate. PBS: phosphate buffered saline (vehicle), AAV: Adeno-associated virus (AAVhu68.UbC.hGLB1). *$p<0.05$, **$p<0.01$ Kruskal-Wallis test followed by Dunn's test. NS: not significant.

Figure 6:
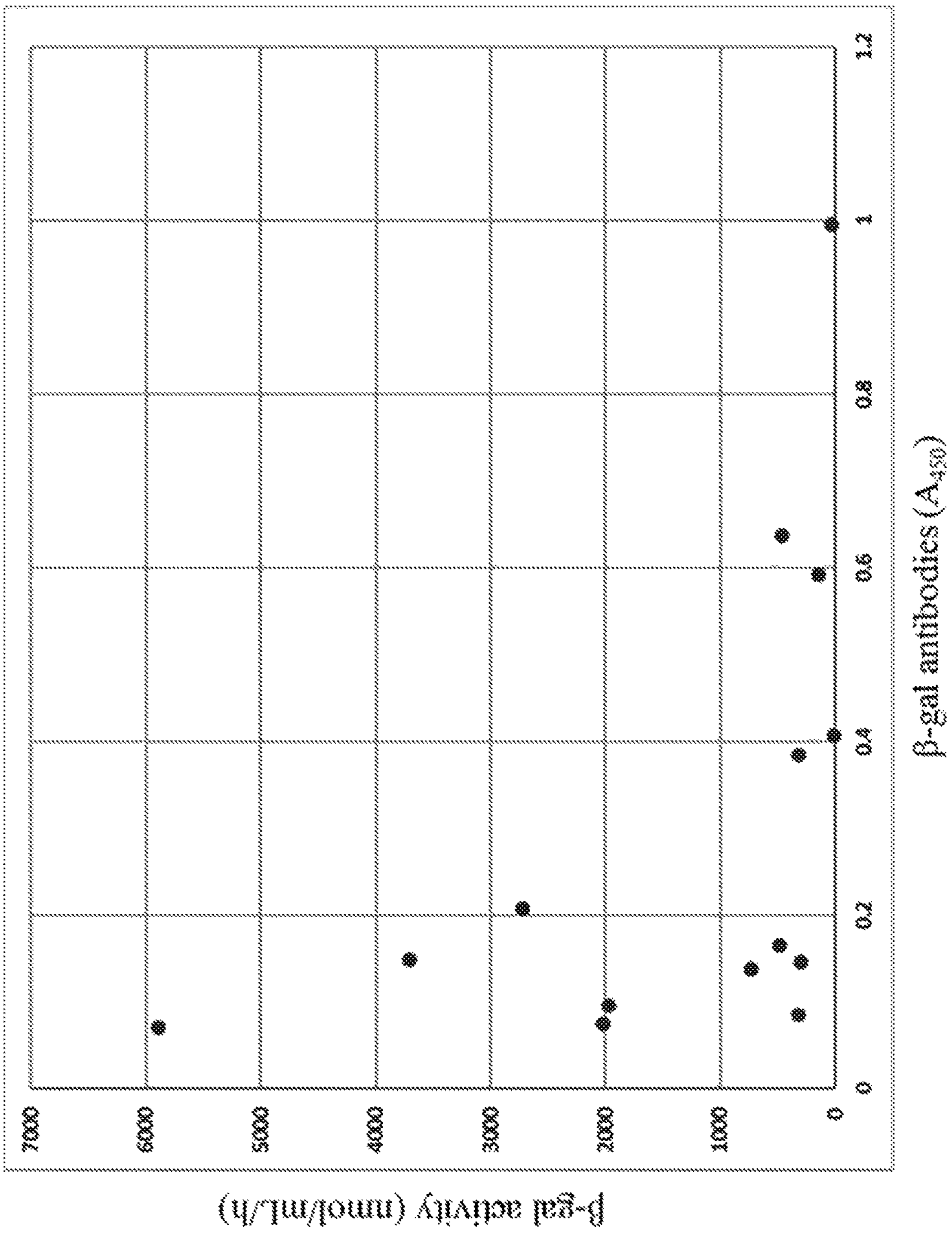

FIG. 6 shows the correlation between β-gal activity and anti-β-gal antibodies. β-gal activity and serum anti-β-gal antibodies were measured in serum samples collected from AAV-treated mice at the time of necropsy. Each point represents an individual animal.

FIGS. 7A-7G show correction of gait abnormalities in AAV-treated GLB1$^{-/-}$ mice. FIGS. 7A and 7B show that untreated GLB1$^{-/-}$ mice (n=12) and GLB1$^{-/-}$ controls (n=22) with an average age of 5 months were evaluated using the CatWalk system on two consecutive days. Average walking speed (FIG. 7A) and length of the hind paw prints (FIG. 7B) were quantified for each animal across at least 3 trials. $p<0.01$ Mann Whitney test. FIGS. 7C and 7D show that four-month-old GLB1$^{-/-}$ (n=15) or GLB1$^{-/-}$ (n=15) mice treated with vehicle and AAV-treated GLB1$^{-/-}$ mice (n=14) were evaluated using the CatWalk system. Average walking speed (FIG. 7C) and length of the hind paw prints (FIG. 7**D) were quantified for each animal across at least 3 trials on the second day of testing. *$p<0.05$, $p<0.01$ Kruskal-Wallis test followed by Dunn's test. NS: not significant. FIGS. 7E-G show representative hind paw prints for AAV-treated GLB1$^{-/-}$ mice (FIG. 7G) and vehicle-treated GLB1$^{-/-}$ (FIG. 7E) and GLB1$^{-/-}$ (FIG. 7**F) controls.

FIGS. 8A and 8B show correlation between walking speed and gait parameters. GLB1$^{-/-}$ controls (n=22) were evaluated using the CatWalk system on two consecutive days. Gait parameters measured in at least three trials on the second day of testing were recorded. Correlation analysis demonstrated a strong correlation between walking speed and gait parameters such as stride length (Spearman r=0.7432, $p<0.001$, FIG. 8A). In contrast, hind paw print length was speed independent (Spearman r=−0.1239, p=0.423, FIG. 8B).

FIGS. 9A-9F provide β-gal activity (FIG. 9A), body weight (FIG. 9B), neurological examination score (neuro exam score, FIG. 9C), length of hind paw print (FIG. 9D), and swing time (FIG. 9E) and stride length (FIG. 9F) of hind limb of GLB1$^{-/-}$ mice received one of 4 doses of rAAVhu68.UbC.GLB1 ($1.3\times10^{11}$ GC, $4.4\times10^{10}$ GC, $1.3\times10^{10}$ GC or $4.4\times10^{9}$ GC) or vehicle by ICV injection. GLB1$^{-/-}$ mice administered with vehicle (Het+Vehicle serves as controls. More details are provided in Example 4, Section A.

FIGS. 10A-10B provides an alignment showing the amino acid sequence of the vp1 capsid protein of AAVhu68 (SEQ ID NO: 2) (labelled hu.68.vp1 in alignment), with AAV9 (SEQ ID NO: 20), AAVhu31 (labelled hu.31 in alignment, SEQ ID NO: 21) and AAVhu32 (labelled hu.32 in alignment, SEQ ID NO: 22). Compared to AAV9, AAVhu31 and AAVhu32, two mutations (A67E and A157V) were found critical in AAVhu68 and circled in the FIG.

FIGS. 11A-11E provide an alignment of the nucleic acid sequence encoding the vp1 capsid protein of AAVhu68 (SEQ ID NO: 1), with AAV9 (SEQ ID NO: 23), AAVhu31 (SEQ ID NO: 24) and AAVhu32 (SEQ ID NO: 25).

Figure 12A:
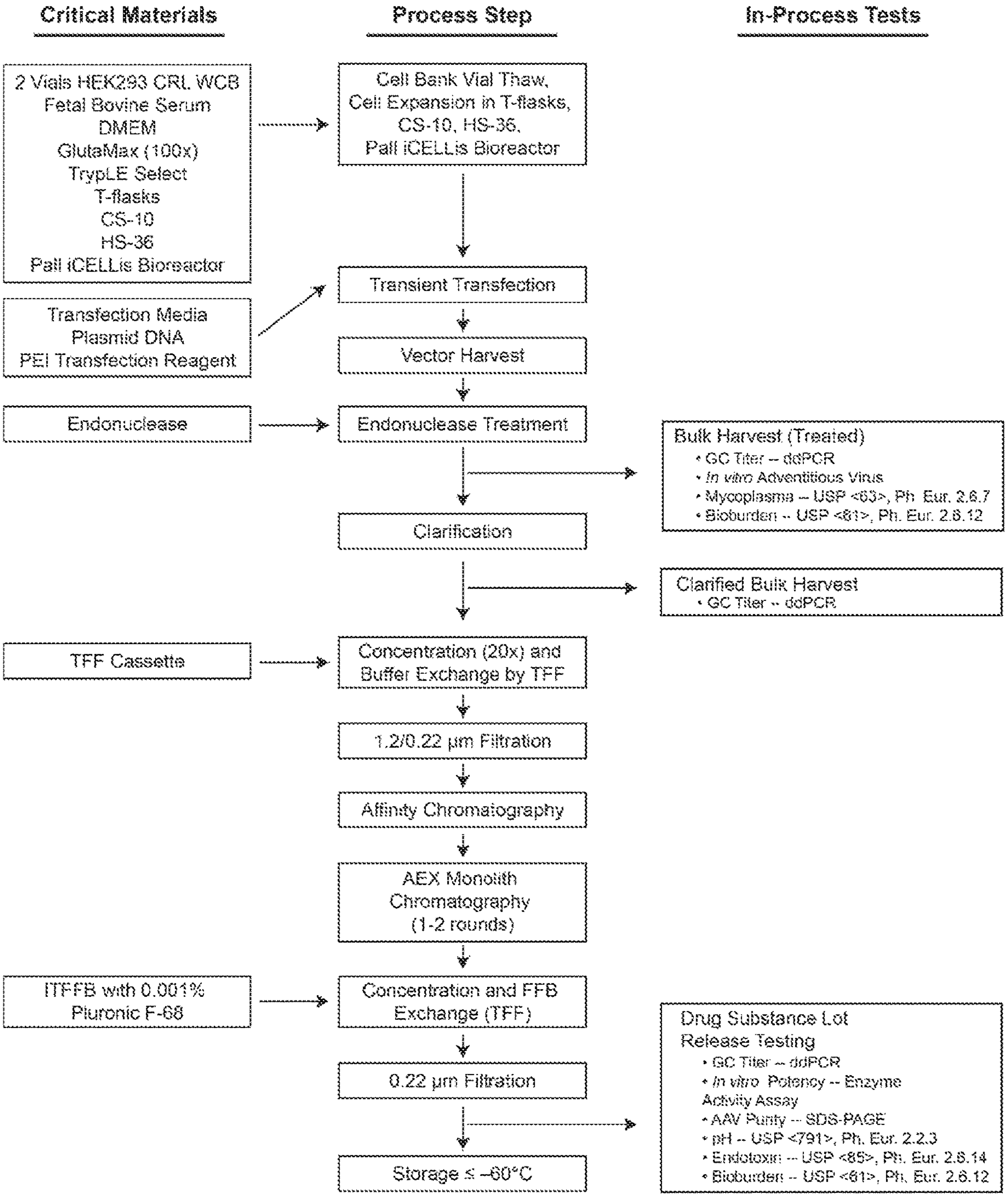

FIG. 12A provides an illustrative flow chart of manufacturing process for producing rAAVhu68.GLB1 drug substance. AEX, anion exchange; CRL, Charles River Laboratories; ddPCR, droplet digital polymerase chain reaction; DMEM, Dulbecco's modified Eagle medium; DNA, deoxyribonucleic acid; FFB, final formulation buffer; GC, genome copies; HEK293, human embryonic kidney 293 cells; ITFFB, intrathecal final formulation buffer; PEI, polyethylenimine; Ph. Eur., European Pharmacopoeia; SDS-PAGE, sodium dodecyl sulfate polyacrylamide gel electrophoresis; TFF, tangential flow filtration; USP, United States Pharmacopeia; WCB, working cell bank.

Figure 12B:
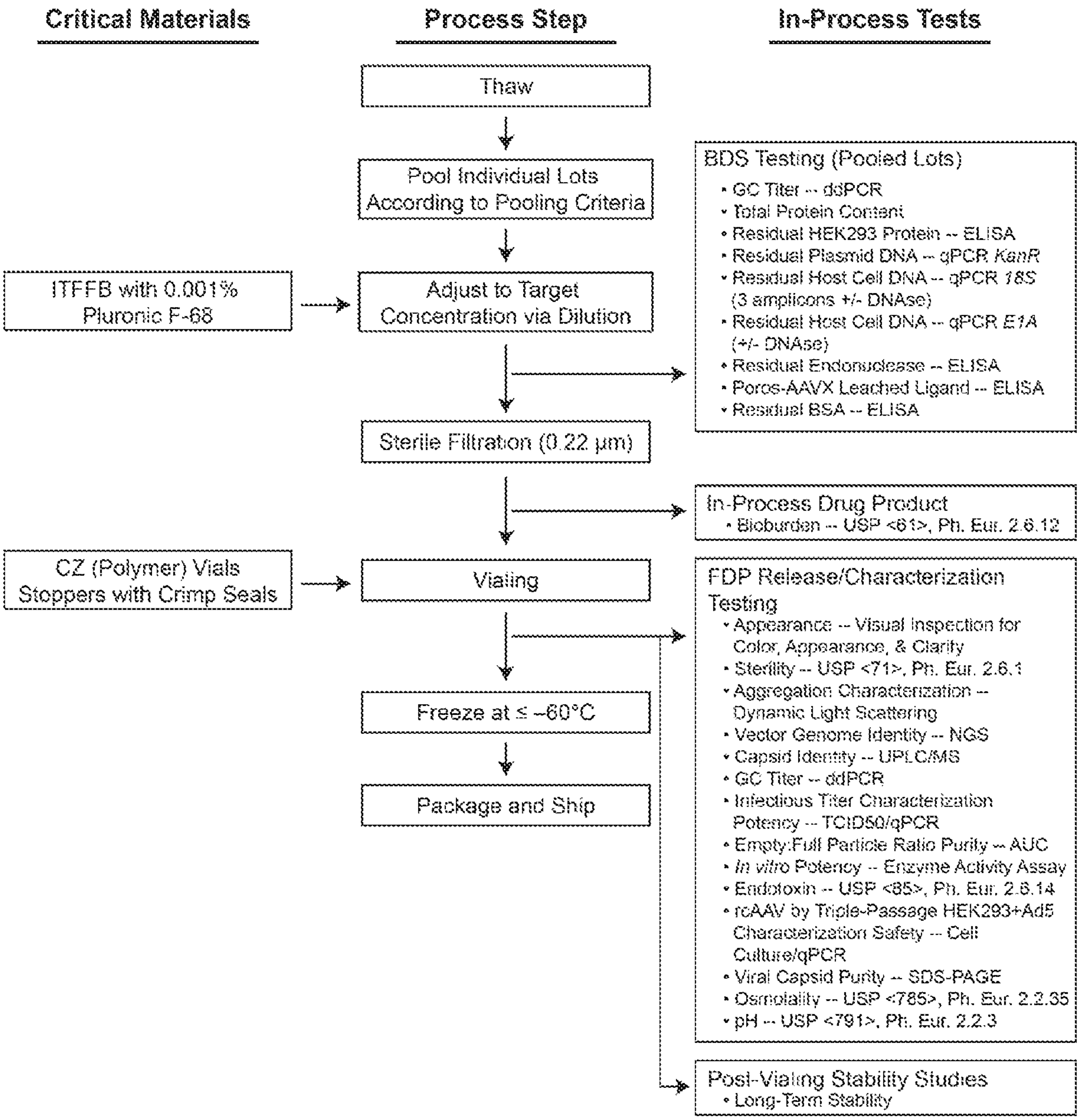

FIG. 12B provides an illustrative flow chart for manufacturing process for producing rAAVhu68.GLB1 drug product. Ad5, adenovirus serotype 5; AUC, analytical ultracentrifugation; BDS, bulk drug substance; BSA, bovine serum albumin; CZ, Crystal Zenith; ddPCR, droplet digital polymerase chain reaction; E1A, early region 1A (gene); ELISA, enzyme-linked immunosorbent assay; FDP, final drug product; GC, genome copies; HEK293, human embryonic kidney 293 cells; ITFFB, intrathecal final formulation buffer; KanR, kanamycin resistance (gene); MS, mass spectrometry; NGS, next-generation sequencing; Ph. Eur., European Pharmacopoeia; qPCR, quantitative polymerase chain reaction; SDS-PAGE, sodium dodecyl sulfate polyacrylamide gel electrophoresis; $TCID_{50}$ 50% tissue culture infective dose; UPLC, ultra-performance liquid chromatography; USP, United States Pharmacopeia.

DETAILED DESCRIPTION OF THE INVENTION

Adeno-associated virus (AAV) based compositions and methods for treating GM1 gangliosidosis (GM1) are provided herein. An effective amount of genome copies (GC) of a recombinant AAV (rAAV) having an AAVhu68 capsid and carrying a vector genome encoding the normal human β-galactosidase (GLB1) enzyme (rAAVhu68.GLB1) is delivered to the patient. Desirably, this rAAVhu68.GLB1 is formulated with an aqueous buffer. In certain embodiments, the suspension is suitable for intrathecal injection. In certain embodiments, rAAVhu68.GLB1 is AAVhu68.UbC.GLB1 (also termed as AAVhu68.UbC.hGLB1), in which the GLB1 gene (i.e., β-galactosidase (also termed as GLB1 enzyme, β-gal, or galactosidase as used herein) coding sequence) is under the control of regulatory sequences which include a promoter derived from human ubiquitin C (UbC). In certain embodiments, the compositions are delivered via an intra-cisterna magna injection (ICM).

Nucleic acid sequences encoding the capsid of a clade F adeno-associated virus, which is termed herein AAVhu68, are utilized in the production of the AAVhu68 capsid and recombinant AAV (rAAV) carrying the vector genome. As used herein, the term "vector genome" refers to a nucleic acid molecule which is packaged in a viral capsid, for example, an AAV capsid, and is capable of being delivered to a host cell or a cell in a patient. In certain embodiments, the vector genome is an expression cassette having inverted terminal repeat (ITR) sequences necessary for packaging the vector genome into the AAV capsid at the extreme 5' and 3' end and containing therebetween a GLB1 gene as described herein operably linked to sequences which direct expression thereof. Additional details relating to AAVhu68 are provided in WO 2018/160582, incorporated by reference in its entirety herein, and in this detailed description. The rAAVhu68.GLB1 described herein are well suited for delivery of the vector genome comprising the GLB1 gene to cells within the central nervous system (CNS), including brain, hippocampus, motor cortex, cerebellum, and motor neurons. These rAAVhu68.GLB1 may be used for targeting other cells within the CNS and certain other tissues and cells outside the CNS. Alternatively, AAVhu68 capsid may be replaced by another capsid which is also suitable for delivering a vector genome to the CNS, for example, AAVcy02, AAV8, AAVrh43, AAV9, AAVrh08, AAVrh10, AAVbb01, AAVhu37, AAVrh20, AAVrh39, AAV1, AAVhu48, AAVcy05, AAVhu11, AAVhu32, or AAVpi02.

I. GM1 and the Therapeutic GLB1 Gene

GM1 gangliosidosis (i.e., GM1) can be classified into three types based on the clinical phenotype: (1) type 1 or infantile form with onset from birth to 6 months, rapidly progressive with hypotonia, severe central nervous system (CNS) degeneration and death by 1-2 years of age; (2) type 2 late infantile or juvenile with onset from 7 months to 3 years, lag in motor and cognitive development, and slower progression; and (3) type 3 adult or chronic variant with late onset (3-30 years), a progressive extrapyramidal disorder due to local deposition of glycosphingolipid in the caudate nucleus (Brunetti-Pierri and Scaglia, 2008. GM1 gangliosidosis: Review of clinical, molecular, and therapeutic aspects, *Molecular Genetics and Metabolism,* 94: 391-96). Infantile GM1 subjects with symptom onset before 6 months of age uniformly exhibit rapid and predictable progression of both motor and cognitive impairment. The majority of patients die within the first few years of life (median survival 46 months, James Utz et al., 2017). Despite a shared underlying pathophysiology, the adult (Type 3) GM1 phenotype is variable and disease course is notably milder. Most patients with Type 3 GM1 first develop neurological symptoms in late childhood, with little subsequent progression in adulthood.

The severity of each type is inversely related to the residual activity of the mutant β-gal (Brunetti-Pierri and Scaglia, 2008) which is encoded by a GLB1 gene. Over 130 disease-causing GLB1 mutations have been identified in human (Hofer et al., 2010, Phenotype determining alleles in GM1 gangliosidosis patients bearing novel GLB1 mutations. *Clinical Genetics.* 78(3):236-246; and Caciotti et al., 2011, M1 gangliosidosis and Morquio B disease: An update on genetic alterations and clinical findings. *Biochimica et Biophysica Acta* (*BBA*)—*Molecular Basis of Disease.* 1812 (7):782-790). While a number of GLB1 mutations have been genetically and biochemically analyzed and correlated with clinical phenotype (Gururaj et al., 2005, Magnetic Resonance Imaging Findings and Novel Mutations in GM1 Gangliosidosis. *Journal of Child Neurology.* 20(1):57-60; Caciotti et al., 2011; and Sperb et al., 2013, Genotypic and phenotypic characterization of Brazilian patients with GM1 gangliosidosis. *Gene.* 512(1):113-116), many GLB1 mutations remain uncharacterized. Broadly speaking the genotype of the patient results in varying amounts of residual enzyme activity, but generally speaking, the higher the residual enzyme activity is, the less severe the phenotype is (Ou et al., 2018, SAAMP 2.0: An algorithm to predict genotype-phenotype correlation of lysosomal storage diseases. *Clinical Genetics.* 93(5):1008-1014). Diagnosis of GM1 is confirmed by either biochemical assay of β-gal and neuraminidase and/or by GLB1 molecular analysis. However, there are limitations to the use of genotype-phenotype correlations in predicting the clinical presentation of an affected individual, as the residual enzyme activity per se cannot predict the disease subtypes caused by mutations in the GLB1 gene (Hofer et al., 2010, Caciotti et al., 2011, Ou et al., 2018). The predictive value is best for individuals bearing two severe mutations (i.e. mutations that show no GLB1 enzyme activity), who commonly present with a severe early onset phenotype (Caciotti et al., 2011, Sperb et al., 2013). Data on sibling concordance, although sparse, indicate that the clinical course in sibling with infantile GM1 is similar in terms of time to onset and prevailing disease manifestations (Gururaj et al., 2005).

The gene therapy vector provided herein, i.e., rAAV. GLB1 (for example, rAAVhu68.GLB1, rAAVhu68. UbC. GLB1), or the composition comprising the same is useful for treatment of conditions associated with deficiencies in normal levels of functional beta-galactosidase. As used herein, the gene therapy vector refers to a rAAV as described herein which is suitable for use in treating a patient. In certain embodiments, the gene therapy vector or the composition provided herein is useful for treating Type 1 of GM1. In certain embodiments, the gene therapy vector or the composition provided herein is useful for treating Type 2 of GM1. In certain embodiments, the gene therapy vector or the composition provided herein is useful for treating Type 3 of GM1. In certain embodiments, the gene therapy vector or the composition provided herein is useful for treating Type 1 and Type 2 of GM1. In certain embodiments, the gene therapy vector or the composition provided herein is useful for treating GM1 patient who is 18 months of age or younger. In certain embodiments, the gene therapy vector or the composition provided herein is for treatment of GM1 which excludes Type 3. In certain embodiments, the gene therapy vector or the composition provided herein is useful for treatment of neurological conditions associated with deficiencies in normal levels of functional β-galactosidase. In certain embodiments, the gene therapy vector or the composition provided herein is useful for amelioration of symptoms associated with GM1 gangliosidosis. In certain embodiments, the gene therapy vector or the composition provided herein is useful for amelioration of neurological symptoms associated with GM1 gangliosidosis.

In certain embodiments, the patient has infantile gangliosidosis and is 18 months of age or younger. In certain embodiments, the patients receiving the rAAV.GLB1 are 1 month to 18 months of age. In certain embodiments, the patients receiving the rAAV.GLB1 are four months to 18 months of age. In certain embodiments, the infant is under four months of age. In certain embodiments, the patients receiving the rAAV.GLB1 are about 1, about 2, about 3, about 4, about 5, about 6, about 7, about 8, about 9, about 10, about 11, about 12, about 13, about 14, about 15, about 16, about 17, or about 18 months of age. In certain embodiments, the patient is a toddler, e.g., 18 months to 3 years of age. In certain embodiments, the patient receiving the rAAV.GLB1 is from 3 years to 6 years of age, from 3 years to 12 years of age, from 3 years to 18 years of age, from 3 years to 30 years of age. In certain embodiments, patients are older than 18 years of age.

In certain embodiments, amelioration of symptoms associated with GM1 gangliosidosis are observed following treatment, including, e.g., increased life span (survival); decreased need for feeding tube; reduction in seizure incidence, frequency, and length, delayed onset of seizures; improved quality of life, for example, as measured by PedsQL; reduction in progression towards neurocognitive decline and/or improvement in neurocognitive development, e.g., improved development or improvement in adaptive behaviors, cognition, language (receptive and expressive communication), and motor function (gross motor, fine motor), as measured by the Bayley Scales of Infant and Toddler Development, Third Edition (BSID-III) and the Vineland Adaptive Behavior Scales, Second Edition (Vineland-II); earlier age-at-achievement and later age-at-loss for motor milestones; delayed increasement of brain tissue volume (cerebral cortex and other smaller structures) and ventricular volume, delayed size decrease of brain substructures including the corpus callosum, caudate and putamen as well as the cerebellar cortex, and stabilization in brain atrophy and volumetric changes; delayed progression of abnormal T1/T2 signal intensity in the thalamus and basal ganglia; increased β-gal enzyme (GLB1) activity in CSF and serum; reduction of CSF GM1 concentration; reduction of serum and/or urine keratan sulfate levels, decreased hexosaminidase activity; reduce inflammatory response in the brain; delayed abnormal liver and spleen volume; delayed abnormal EEG and visual evoked potentials (VEP); and/or improvements in dysphagia, gait function, motor skills, language and/or respiratory function.

In certain embodiments, the patient receives a co-therapy following rAAV.GLB1 injection for which they would not have been eligible without the AAV therapy described herein. Such co-therapies may include enzyme replacement therapy, substrate reduction therapy (e.g., with miglustat (OGT 918, N-butyl-deoxynojirimycin), tanganil (acetyl-DL-leucine) treatment, respiratory therapy, feeding tube use, anti-epileptic drugs), or haematopoietic stem cell transplantation (HSCT) with bone marrow or umbilical cord blood.

Optionally, an immunosuppressive co-therapy may be used in a subject in need. Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor- (CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent. In certain embodiments, the immunosuppressive therapy may be started 0, 1, 2, 3, 4, 5, 6, 7, or more days prior to or after the rAAV.GLB1 administration. Such immunosuppressive therapy may involve administration of one, two or more drugs (e.g., glucocorticoids, prednelisone, micophenolate mofetil (MMF) and/or sirolimus (i.e., rapamycin)). Such immunosuppressive drugs may be administrated to a patient/subject in need once, twice or for more times at the same dose or an adjusted dose. Such therapy may involve co-administration of two or more drugs, the (e.g., prednelisone, micophenolate mofetil (MMF) and/or sirolimus (i.e., rapamycin)) on the same day. One or more of these drugs may be continued after the rAAV.GLB1 administration, at the same dose or an adjusted dose. Such therapy may be for about 1 week (7 days), about 60 days, or longer, as needed. In certain embodiments, a tacrolimus-free regimen is selected.

In certain embodiments, an "effective amount" of rAAV.GLB1 (for example, rAAV.GLB1, rAAV.UbC.GLB1) as provided herein is the amount which achieves amelioration of symptoms associated with GM1 gangliosidosis. In certain embodiments, an "effective amount" of rAAV.GLB1 as provided herein is the amount which achieves one or more of the following endpoints: increased GLB1 pharmacodynamics and biological activity in Cerebrospinal fluid (CSF), increased GLB1 pharmacodynamics and biological activity in serum, increased average life span (survival) of the patient, delayed disease progression of GM1 gangliosidosis (assessed by one or more of age at achievement, age at loss and percentage of patients maintaining or acquiring age-appropriate developmental and motor milestones), and improvements in neurocognitive development based on one or more of change in age-equivalent cognitive, gross motor, fine motor, receptive and expressive communication scores of the Bayley Scales of Infant and Toddler Development (BSID, for example, BSID Third Edition (BSID-III)), change in standard score for each domain of the Vineland Adaptive Behavior Scales. For older children and adults, an "effective amount" of rAAV.GLB1 as provided herein may in some embodiments be an amount that improves dysphagia, gait function, motor skills, language and/or respiratory function, change in standard scores for each domain of the Vineland Adaptive Behavior Scales, Second Edition (Vineland-II), decreased seizure frequency and age of seizure onset, improved probability of feeding tube independence at 24 months of age. Examples of age-appropriate developmental and motor milestones are provided by World Health Organization (WHO). See, e.g., Wijnhoven T. M., et al. (2004). Assessment of gross motor development in the WHO Multicentre Growth Reference Study. *Food Nutr Bull.* 25(1 Suppl):537-45, as well as in the table below. In certain embodiments, an "effective amount" of rAAV.GLB1 (such as, rAAVhu68, GLB1) as provided herein is the amount which achieves pharmacodynamic effects of rAAV.GLB1 on CSF and serum GLB1 activity, CSF GM1 concentration, and serum and urine keratan sulfate; changes in brain MRI; monitoring liver and spleen volume; monitoring on EEG and visual evoked potentials (VEP).

| Gross Motor Milestone | Multicenter Growth Reference Study Performance Criteria |
|---|---|
| Sitting without support | Child sits up straight with the head erect for at least 10 seconds. Child does not use arms or hands to balance body or support position. |
| Hands-and-knees crawling | Child alternately moves forward or backward on hands and knees. The stomach does not touch the supporting surface. There are continuous and consecutive movements, at least three in a row. |
| Standing with assistance | Child stands in upright position on both feet, holding onto a stable object (e.g, furniture) with both hands without leaning on it. The body does not ouch the stable object, and the legs support most of the body weight. Child thus stands with assistance for at least 10 seconds. |
| Walking with assistance | Child is in upright position with the back straight. Child makes sideways or forward steps by holding on a stable object (e.g., furniture) with one of both hands. One leg moves forward while the other supports part of the body weight. Child takes at least five steps in this manner. |
| Standing alone | Childs stands in upright position on both feed (not on the toes) with the back straight. The legs support 100% of the child's weigh. There is no contact with a person or objects. Child stands alone for at least 10 seconds. |
| Walking alone | Child takes at least five steps independently in upright position with the back straight. One leg moves forward while the other supports most of the body weight. There is no contact with a person or object. |

Adapted from (Wijnhoven et al., 2004, Assessment of gross motor development in the WHO Multicentre Growth Reference Study." Food Nutr Bull. 25(1 Suppl): 537-45). Abbreviations: WHO, World Health Organization.

The rAAV.GLB1 described herein, and compositions comprising the same, contain a GLB1 gene (i.e., β-gal coding sequence) which encodes and expresses human β-galactosidase (a which may be also termed as normal GLB1 enzyme) or a functional fragment thereof. GLB1 enzyme catalyzes the hydrolysis of β-galactoside into monosaccharides. The amino acid sequence of human β-galactosidase (2034 bp, 677 aa, Genbank 4AAA51819.1, EC3.2.1.23) is reproduced herein as SEQ ID NO: 4, which is also recognized as β-galactosidase, Isoform 1. See, for example, UniProtKB-P16278 (BGAL_HUMAN). In certain embodiments, the GLB1 enzyme may have a sequence of amino acid 24 to amino acid 677 of SEQ ID NO: 4 (i.e., mature GLB1 enzyme without signal peptide). In certain embodiments, the GLB1 enzyme may have a sequence of amino acid 31 to amino acid 677 of SED ID NO: 4 (i.e., β-galactosidase, Isoform 3). In certain embodiments, the GLB1 enzyme is Isoform 2 having an amino acid sequence of SEQ ID NO: 26. Any fragment that retains the function of the full length β-galactosidase may be encoded by the GLB1 gene as described herein, and is referred to as a "functional fragment". For example, a functional fragment of β-galactosidase may have at least about 25%, 50%, 60%, 70%, 80%, 90%, 100% or more of the activity of the full length β-galactosidase (i.e., the normal GLB1 enzyme which may be β-galactosidase having a sequence of amino acid 24 to amino acid 677 SEQ ID NO: 4, or any one of the three isoforms). Methods of evaluating the β-galactosidase activity can be found in the Examples as well as in publications. See, for example, Radoslaw Kwapiszewski, Determination of Acid β-Galactosidase Activity: Methodology and Perspectives. Indian J Clin Biochem. 2014 January; 29(1): 57-62. In certain embodiments, the functional fragment is a truncated β-galactosidase, which lacks about 1, 2, 3, 4, 5, 6, 7, 8, 9, 10, 11, 12, 13, 14, 15, 16, 17, 18, 19, 20, 21, 22, 23, 24, 25, 30 or more amino acids at the N terminal and/or C terminal of the full length β-galactosidase. In certain embodiments, the functional fragment contains about 1, 2, 3, 4, 5, 6, 7, 8, 9, 10, 11, 12, 13, 14, 15, 16, 17, 18, 19, 20, 21, 22, 23, 24, 25, 30 or more conservative amino acid substitution(s) compared to the full length β-galactosidase. As used herein, a conservative amino acid substitution is an amino acid replacement in a protein that changes a given amino acid to a different amino acid with similar biochemical properties (e.g. charge, hydrophobicity and size).

In one embodiment, the GLB1 gene has the sequence of SEQ ID NO: 5. In certain embodiments, the GLB1 gene is engineered to have the sequence of SEQ ID NO: 6. In certain embodiments, the GLB1 gene is engineered to have the sequence of SEQ ID NO: 7. In certain embodiments, the GLB1 gene is engineered to have the sequence of SEQ ID NO: 8. In certain embodiments, the GLB1 gene is engineered to have a sequence which is at least 95% identical to 99.9% identical to SEQ ID NO: 6. In certain embodiments, the GLB1 gene is engineered to have a sequence which is at least about 95%, at least about 96%, at least about 97%, at least about 98%, at least about 99% or at least about 99.9% identical to SEQ ID NO: 6. In certain embodiments, the GLB1 gene is engineered to have a sequence which is at least 95% identical to 99.9% identical to SEQ ID NO: 7. In certain embodiments, the GLB1 gene is engineered to have a sequence which is at least about 95%, at least about 96%, at least about 97%, at least about 98%, at least about 99% or at least about 99.9% identical to SEQ ID NO: 7. In certain embodiments, the GLB1 gene is engineered to have a sequence which is at least 95% identical to 99.9% identical to SEQ ID NO: 8. In certain embodiments, the GLB1 gene is engineered to have a sequence which is at least about 95%, at least about 96%, at least about 97%, at least about 98%, at least about 99% or at least about 99.9% identical to SEQ ID NO: 8. In a further embodiment, the engineered sequence encodes a full length β-galactosidase or a functional fragment thereof. In yet a further embodiment, the engineered sequence encodes amino acid 24 to amino acid 677 of SEQ ID NO: 4 or a functional fragment thereof. In another embodiment, the engineered sequence encodes an amino acid sequence of SEQ ID NO: 4 or a functional fragment thereof.

In certain embodiments, the GLB1 gene encodes a GLB1 enzyme which comprises a signal (leader) peptide and the GLB1 mature protein, amino acids 24 to 677 of SEQ ID NO: 4. The leader sequence is preferably of human origin or a derivative of a human leader sequence, and is be about 15 to about 28 amino acids, preferably about 20 to 25 amino acids, or about 23 amino acids in length. In certain embodiments, the signal peptide is the native signal peptide (amino acids 1 to 23 of SEQ ID NO: 4). In certain embodiments, the GLB1 enzyme comprises an exogenous leader sequence in the place of the native leader sequence (amino acids 1-23 of SEQ ID NO:4). In another embodiment, the leader may be from a human IL2 or a mutated leader. In another embodiment, a human serpinF1 secretion signal may be used as a leader peptide.

II. AAVhu68

AAVhu68 (previously termed AAV3G2) varies from another Clade F virus AAV9 by two encoded amino acids at positions 67 and 157 of vp1, based on the numbering of SEQ ID NO: 2. In contrast, the other Clade F AAV (AAV9, hu31, hu31) have an Ala at position 67 and an Ala at position 157. Provided are novel AAVhu68 capsids and/or engineered AAV capsids having valine (Val or V) at position 157 based on the numbering of SEQ ID NO: 2 and optionally, a glutamic acid (Glu or E) at position 67 based on the numbering of SEQ ID NO: 2.

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, *J Virol*, 2004 June; 78(10): 6381-6388, which identifies Clades A, B, C, D, E and F, and provides nucleic acid sequences of novel AAV, GenBank Accession Numbers AY530553 to AY530629. See, also, WO 2005/033321.

In certain embodiments, an AAVhu68 capsid is further characterized by one or more of the following. AAVhu68 capsid proteins comprise: AAVhu68 vp1 proteins produced by expression from a nucleic acid sequence which encodes the predicted amino acid sequence of 1 to 736 of SEQ ID NO: 2, vp1 proteins produced from SEQ ID NO: 1, or vp1 proteins produced from a nucleic acid sequence at least 70% identical to SEQ ID NO: 1 which encodes the predicted amino acid sequence of 1 to 736 of SEQ ID NO: 2; AAVhu68 vp2 proteins produced by expression from a nucleic acid sequence which encodes the predicted amino acid sequence of at least about amino acids 138 to 736 of SEQ ID NO: 2, vp2 proteins produced from a sequence comprising at least nucleotides 412 to 2211 of SEQ ID NO: 1, or vp2 proteins produced from a nucleic acid sequence at least 70% identical to at least nucleotides 412 to 2211 of SEQ ID NO: 1 which encodes the predicted amino acid sequence of at least about amino acids 138 to 736 of SEQ ID NO: 2; and/or AAVhu68 vp3 proteins produced by expression from a nucleic acid sequence which encodes the predicted amino acid sequence of at least about amino acids 203 to 736 of SEQ ID NO: 2, vp3 proteins produced from a sequence comprising at least nucleotides 607 to 2211 of SEQ ID NO: 1, or vp3 proteins produced from a nucleic acid sequence at least 70% identical to at least nucleotides 607 to 2211 of SEQ ID NO: 1 which encodes the predicted amino acid sequence of at least about amino acids 203 to 736 of SEQ ID NO: 2.

The AAVhu68 vp1, vp2 and vp3 proteins are typically expressed as alternative splice variants encoded by the same nucleic acid sequence which encodes the full-length vp1 amino acid sequence (amino acid (aa) 1 to 736). Optionally the vp1-encoding sequence is used alone to express the vp1, vp2 and vp3 proteins. Alternatively, this sequence may be co-expressed with one or more of a nucleic acid sequence which encodes the AAVhu68 vp3 amino acid sequence (about aa 203 to 736) without the vp1-unique region (about aa 1 to about aa 137) and/or vp2-unique regions (about aa 1 to about aa 202), or a strand complementary thereto, the corresponding mRNA or tRNA (for example, the mRNA transcribed from about nucleotide (nt) 607 to about nt 2211 of SEQ ID NO: 1), or a sequence at least 70% to at least 99% (e.g., at least 85%, at least 90%, at least 95%, at least 97%, at least 98% or at least 99%) identical to SEQ ID NO: 1 which encodes aa 203 to 736 of SEQ ID NO: 2. Additionally, or alternatively, the vp1-encoding and/or the vp2-encoding sequence may be co-expressed with the nucleic acid sequence which encodes the AAVhu68 vp2 amino acid sequence of SEQ ID NO: 2 (about aa 138 to 736) without the vp1-unique region (about aa 1 to about 137), or a strand complementary thereto, the corresponding mRNA or tRNA (for example, the mRNA transcribed from nt 412 to 2211 of SEQ ID NO: 1), or a sequence at least 70% to at least 99% (e.g., at least 85%, at least 90%, at least 95%, at least 97%, at least 98% or at least 99%) identical to SEQ ID NO: 1 which encodes about aa 138 to 736 of SEQ ID NO: 2.

As described herein, a rAAVhu68 has a rAAVhu68 capsid produced in a production system expressing capsids from an AAVhu68 nucleic acid sequence which encodes the vp1 amino acid sequence of SEQ ID NO: 2, and optionally additional nucleic acid sequences, e.g., encoding a vp 3 protein free of the vp1 and/or vp2-unique regions. The rAAVhu68 resulting from production using a single nucleic acid sequence vp1 produces the heterogenous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO: 2. These subpopulations include, at a minimum, deamidated asparagine (N or Asn) residues. For example, asparagines in asparagine—glycine pairs are highly deamidated.

In one embodiment, the AAVhu68 vp1 nucleic acid sequence has the sequence of SEQ ID NO: 1, or a strand complementary thereto, e.g., the corresponding mRNA or tRNA. In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 2 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 1). In certain embodiments, also provided is a nucleic acid sequence which encodes the AAVhu68 vp2 amino acid sequence of SEQ ID NO: 2 (about aa 138 to 736) without the vp1-unique region (about aa 1 to about 137), or a strand complementary thereto, the corresponding mRNA or tRNA (nt 412 to 2211 of SEQ ID NO: 1).

However, other nucleic acid sequences which encode the amino acid sequence of SEQ ID NO: 2 may be selected for use in producing rAAVhu68 capsids. In certain embodiments, the nucleic acid sequence has the nucleic acid sequence of SEQ ID NO: 1 or a sequence at least 70% to 99% identical, at least 75%, at least 80%, at least 85%, at least 90%, at least 95%, at least 97%, at least 99%, identical to SEQ ID NO: 1 which encodes SEQ ID NO: 2. In certain embodiments, the nucleic acid sequence has the nucleic acid sequence of SEQ ID NO: 1 or a sequence at least 70% to 99%, at least 75%, at least 80%, at least 85%, at least 90%, at least 95%, at least 97%, at least 99%, identical to about nt 412 to about nt 2211 of SEQ ID NO: 1 which encodes the vp2 capsid protein (about aa 138 to 736) of SEQ ID NO: 2. In certain embodiments, the nucleic acid sequence has the nucleic acid sequence of about nt 607 to about nt 2211 of SEQ ID NO:1 or a sequence at least 70% to 99%, at least 75%, at least 80%, at least 85%, at least 90%, at least 95%, at least 97%, at least 99%, identical to nt 607 to about nt 2211 of SEQ ID NO: 1 which encodes the vp3 capsid protein (about aa 203 to 736) of SEQ ID NO: 2.

It is within the skill in the art to design nucleic acid sequences encoding this AAVhu68 capsid, including DNA (genomic or cDNA), or RNA (e.g., mRNA). In certain embodiments, the nucleic acid sequence encoding the AAVhu68 vp1 capsid protein is provided in SEQ ID NO: 1. See, also, FIGS. 11A-11E. In other embodiments, a nucleic acid sequence of 70% to 99.9% identity to SEQ ID NO: 1 may be selected to express the AAVhu68 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 1. Such nucleic acid sequences may be codon-optimized for expression in a selected system (i.e., cell type) can be designed by various methods. This optimization may be performed using methods which are available on-line (e.g., GeneArt), published methods, or a company which provides codon optimizing services, e.g., DNA2.0 (Menlo Park, CA). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence and produce a nucleic acid fragment of a codon-optimized coding region which encodes the polypeptide. A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair.

The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, the AAVhu68 capsid is produced using a nucleic acid sequence of SEQ ID NO: 1 or a sequence at least 70%, at least 75%, at least 80%, at least 85%, at least 90%, at least 95%, at least 97%, at least 99%, which encodes the vp1 amino acid sequence of SEQ ID NO: 2 with a modification (e.g., deamidated amino acid) as described herein. In certain embodiments, the vp1 amino acid sequence is reproduced in SEQ ID NO: 2.

As used herein when used to refer to vp capsid proteins, the term "heterogenous" or any grammatical variation thereof, refers to a population consisting of elements that are not the same, for example, having vp1, vp2 or vp3 monomers (proteins) with different modified amino acid sequences. SEQ ID NO: 2 provides the encoded amino acid sequence of the AAVhu68 vp1 protein. The term "heterogenous" as used in connection with vp1, vp2 and vp3 proteins (alternatively termed isoforms), refers to differences in the amino acid sequence of the vp1, vp2 and vp3 proteins within a capsid. The AAV capsid contains subpopulations within the vp1 proteins, within the vp2 proteins and within the vp3 proteins which have modifications from the predicted amino acid residues. These subpopulations include, at a minimum, certain deamidated asparagine (N or Asn) residues. For example, certain subpopulations comprise at least one, two, three or four highly deamidated asparagines (N) positions in asparagine—glycine pairs and optionally further comprising other deamidated amino acids, wherein the deamidation results in an amino acid change and other optional modifications.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine—glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, at least 97%, at least 99%, or up to about 100% deamidated at a referenced amino acid position, as compared to the predicted amino acid sequence at the reference amino acid position (e.g., at least 80% of the asparagines at amino acid 57 based on the numbering of SEQ ID NO: 2 (AAVhu68) may be deamidated based on the total vp1 proteins may be deamidated based on the total vp1, vp2 and vp3 proteins). Such percentages may be determined using 2D-gel, mass spectrometry techniques, or other suitable techniques.

Without wishing to be bound by theory, the deamidation of at least highly deamidated residues in the vp proteins in the AAV capsid is believed to be primarily non-enzymatic in nature, being caused by functional groups within the capsid protein which deamidate selected asparagines, and to a lesser extent, glutamine residues. Efficient capsid assembly of the majority of deamidation vp1 proteins indicates that either these events occur following capsid assembly or that deamidation in individual monomers (vp1, vp2 or vp3) is well-tolerated structurally and largely does not affect assembly dynamics. Extensive deamidation in the VP1-unique (VP1-u) region (~aa 1-137), generally considered to be located internally prior to cellular entry, suggests that VP deamidation may occur prior to capsid assembly. The deamidation of N may occur through its C-terminus residue's backbone nitrogen atom conducts a nucleophilic attack to the Asn's side chain amide group carbon atom. An intermediate ring-closed succinimide residue is believed to form. The succinimide residue then conducts fast hydrolysis to lead to the final product aspartic acid (Asp) or iso aspartic acid (IsoAsp). Therefore, in certain embodiments, the deamidation of asparagine (N or Asn) leads to an Asp or IsoAsp, which may interconvert through the succinimide intermediate e.g., as illustrated below.

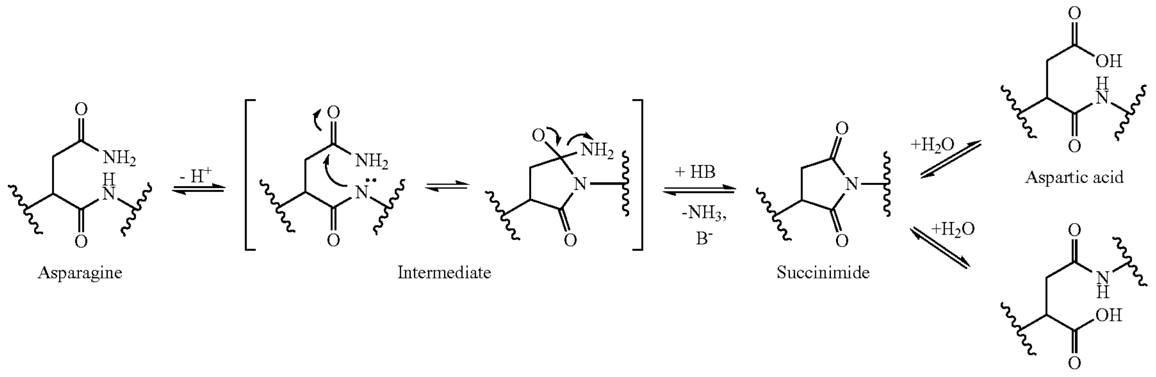

Asparagine Intermediate Succinimide Aspartic acid Iso aspartic acid

As provided herein, each deamidated N in the VP1, VP2 or VP3 may independently be aspartic acid (Asp), isoaspartic acid (isoAsp), aspartate, and/or an interconverting blend of Asp and isoAsp, or combinations thereof. Any suitable ratio of α- and isoaspartic acid may be present. For example, in certain embodiments, the ratio may be from 10:1 to 1:10 aspartic to isoaspartic, about 50:50 aspartic:isoaspartic, or about 1:3 aspartic:isoaspartic, or another selected ratio.

In certain embodiments, one or more glutamine (Q) may deamidates to glutamic acid (Glu), i.e., α-glutamic acid, γ-glutamic acid (Glu), or a blend of α- and γ-glutamic acid, which may interconvert through a common glutarinimide intermediate. Any suitable ratio of α- and γ-glutamic acid may be present. For example, in certain embodiments, the ratio may be from 10:1 to 1:10 α to γ, about 50:50 α:γ, or about 1:3 α:γ, or another selected ratio.

In certain embodiments, an AAV capsid contains subpopulations of vp1, vp2 and vp3 having at least 4 to at least about 25 deamidated amino acid residue positions, of which at least 1% to 10% are deamidated as compared to the encoded amino acid sequence of the vp proteins. The majority of these may be N residues. However, Q residues may also be deamidated.

In certain embodiments, a rAAV has an AAV capsid having vp1, vp2 and vp3 proteins having subpopulations comprising combinations of two, three, four or more deamidated residues at the positions set forth in the table provided in Example 1 and incorporated herein by reference. Deamidation in the rAAV may be determined using 2D gel electrophoresis, and/or mass spectrometry (MS), and/or protein modelling techniques. Online chromatography may be performed with an Acclaim PepMap column and a Thermo

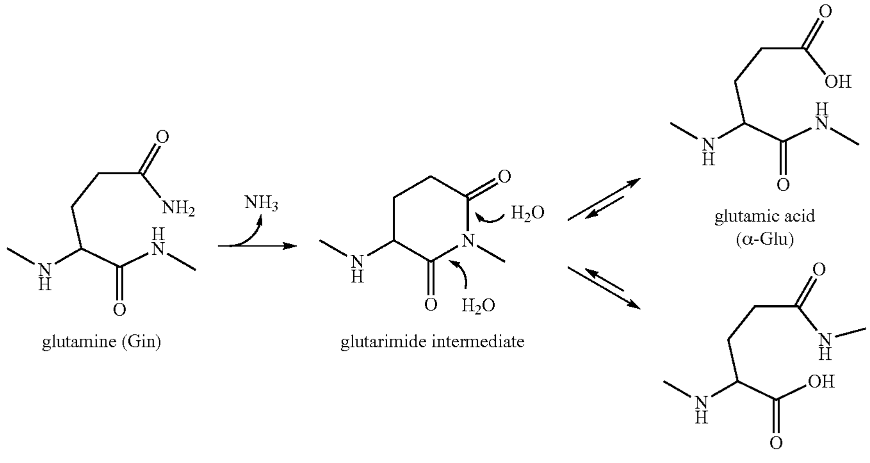

glutamine (Gin) glutarimide intermediate glutamic acid (α-Glu) isoglutamic acid (γ-Glu)

Thus, an rAAV includes subpopulations within the rAAV capsid of vp1, vp2 and/or vp3 proteins with deamidated amino acids, including at a minimum, at least one subpopulation comprising at least one highly deamidated asparagine. In addition, other modifications may include isomerization, particularly at selected aspartic acid (D or Asp) residue positions. In still other embodiments, modifications may include an amidation at an Asp position.

UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value of 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. BioPharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule +0.984 Da (the mass difference between —OH and —$NH_2$ groups). The percent deamidation of a particular peptide is determined by the mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It is understood by one of skill in the art that a number of variations on these illustrative methods can be used. For example, suitable mass spectrometers may include, e.g, a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

In addition to deamidations, other modifications may occur do not result in conversion of one amino acid to a different amino acid residue. Such modifications may include acetylated residues, isomerizations, phosphorylations, or oxidations. Modulation of Deamidation: In certain embodiments, the AAV is modified to change the glycine in an asparagine-glycine pair, to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain amine groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAV amino acid sequence. In certain embodiments, such modifications are not made in all four of the asparagine—glycine pairs. Thus, a method for reducing deamidation of AAV and/or engineered AAV variants having lower deamidation rates. Additionally, or alternative one or more other amide amino acids may be changed to a non-amide amino acid to reduce deamidation of the AAV. In certain embodiments, a mutant AAV capsid as described herein contains a mutation in an arginine—glycine pair, such that the glycine is changed to an alanine or a serine. A mutant AAV capsid may contain one, two or three mutants where the reference AAV natively contains four NG pairs. In certain embodiments, an AAV capsid may contain one, two, three or four such mutants where the reference AAV natively contains five NG pairs. In certain embodiments, a mutant AAV capsid contains only a single mutation in an NG pair. In certain embodiments, a mutant AAV capsid contains mutations in two different NG pairs. In certain embodiments, a mutant AAV capsid contains mutation is two different NG pairs which are located in structurally separate location in the AAV capsid. In certain embodiments, the mutation is not in the VP1-unique region. In certain embodiments, one of the mutations is in the VP1-unique region. Optionally, a mutant AAV capsid contains no modifications in the NG pairs, but contains mutations to minimize or eliminate deamidation in one or more asparagines, or a glutamine, located outside of an NG pair.

In certain embodiments, a method of increasing the potency of a rAAV is provided which comprises engineering an AAV capsid which eliminating one or more of the NGs in the wild-type AAV capsid. In certain embodiments, the coding sequence for the "G" of the "NG" is engineered to encode another amino acid. In certain examples below, an "S" or an "A" is substituted. However, other suitable amino acid coding sequences may be selected. See, the table of Example 1, incorporated herein by reference.

In the AAVhu68 capsid protein, 4 residues (N57, N329, N452, N512) routinely display levels of deamidation >70% and it most cases >90% across various lots. Additional asparagine residues (N94, N253, N270, N304, N409, N477, and Q599) also display deamidation levels up to ~20% across various lots. The deamidation levels were initially identified using a trypsin digest and verified with a chymotrypsin digestion.

The AAVhu68 capsid contains subpopulations within the vp1 proteins, within the vp2 proteins and within the vp3 proteins which have modifications from the predicted amino acid residues in SEQ ID NO: 2. These subpopulations include, at a minimum, certain deamidated asparagine (N or Asn) residues. For example, certain subpopulations comprise at least one, two, three or four highly deamidated asparagines (N) positions in asparagine—glycine pairs in SEQ ID NO: 2 and optionally further comprising other deamidated amino acids, wherein the deamidation results in an amino acid change and other optional modifications. SEQ ID NO: 3 provide an amino acid sequence of a modified AAVhu68 capsid, illustrating positions which may have some percentage of deamidated or otherwise modified amino acids. The various combinations of these and other modifications are described herein.

In other embodiments, the method involves increasing yield of a rAAV and thus, increasing the amount of an rAAV which is present in supernatant prior to, or without requiring cell lysis. This method involves engineering an AAV VP1 capsid gene to express a capsid protein having Glu at position 67, Val at position 157, or both based on an alignment having the amino acid numbering of the AAVhu68 vp1 capsid protein. In other embodiments, the method involves engineering the VP2 capsid gene to express a capsid protein having the Val at position 157. In still other embodiments, the rAAV has a modified capsid comprising both vp1 and vp2 capsid proteins Glu at position 67 and Val at position 157.

As used herein, an "AAV9 capsid" is a self-assembled AAV capsid composed of multiple AAV9 vp proteins. The AAV9 vp proteins are typically expressed as alternative splice variants encoded by a nucleic acid sequence of SEQ ID NO: 23 or a sequence at least 70%, at least 75%, at least 80%, at least 85%, at least 90%, at least 95%, at least 97%, at least 99% thereto, which encodes the vp1 amino acid sequence of GenBank accession: AAS99264. In certain embodiments, "AAV9 capsid" includes an AAV having an amino acid sequence which is 99% identical to AAS99264 or 99% identical to SEQ ID NO: 20. See, also U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809.

Methods of generating the capsid, coding sequences therefore, and methods for production of rAAV have been described. See, e.g., Gao, et al, Proc. Natl. Acad. Sci. U.S.A. 100 (10), 6081-6086 (2003) and US 2013/0045186A 1.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13): 2682-2690 (1999).

III. rAAV

Recombinant adeno-associated virus (rAAV) has been described as suitable vehicles for gene delivery. Typically, an exogenous expression cassette comprising the transgene (for example, the GLB1 gene) for delivery by the rAAV replaces the functional rep genes and the cap gene from the native AAV source, resulting in a replication-incompetent vector. These rep and cap functions are provided in trans during the vector production system but absent in the final rAAV.

As indicated above, a rAAV is provided which has an AAV capsid and a vector genome which comprises, at a minimum, AAV inverted terminal repeats (ITRs) required to package the vector genome into the capsid, a GLB1 gene and regulatory sequences which direct expression therefor. In certain embodiments, the AAV capsid is from AAVhu68. The examples herein utilize a single-stranded AAV vector genome, but in certain embodiments, a rAAV may be utilized in the invention which contains self-complementary (sc) AAV vector genome.

The regulatory control elements necessary are operably linked to the gene (e.g., GLB1) in a manner which permits its transcription, translation and/or expression in a cell which takes up the rAAV. As used herein, "operably linked"

sequences include both expression control sequences that are contiguous with the gene of interest and expression control sequences that act in trans or at a distance to control the gene of interest. Such regulatory sequences typically include, e.g., one or more of a promoter, an enhancer, an intron, a polyA, a self-cleaving linker (e.g., furin, furin-F2A, an IRES). The examples below utilize CB7 promoter (e.g., SEQ ID NO: 10), EF1a promoter (e.g., SEQ ID NO: 11), or human ubiquitin C (UbC) promoter (e.g., SEQ ID NO: 9) for expression of the GLB1 gene. However, in certain embodiments, other promoters, or an additional promoter, may be selected.

In certain embodiments, in addition to the GLB1 gene, a non-AAV sequence encoding another one or more of gene products may be included. Such gene products may be, e.g., a peptide, polypeptide, protein, functional RNA molecule (e.g., miRNA, miRNA inhibitor) or other gene product, of interest. Useful gene products may include miRNAs. minRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mnRNAs based upon their complementarity to the mature miRNA.

The AAV vector genome typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are about 145 base pairs (bp) in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences are from AAV2. A shortened version of the 5' ITR, termed AITR, has been described in which the D-sequence and terminal resolution site (trs) are deleted. In other embodiments, the full-length AAV 5' and 3' ITRs are used. However, ITRs from other AAV sources may be selected. Where the source of the ITRs is from AAV2 and the AAV capsid is from another AAV source, the resulting rAAV may be termed pseudotyped. However, other configurations of these elements may be suitable.

In certain embodiments, an additional or alternative promoter sequence may be included as part of the expression control sequences (regulatory sequences), e.g., located between the selected 5' ITR sequence and the coding sequence. Constitutive promoters, regulatable promoters (see, e.g., WO 2011/126808 and WO 2013/04943), tissue specific promoters (for example, a neuron specific promoter or a glial cell specific promoter, or a CNS specific promoter), or a promoter responsive to physiologic cues may be utilized in the rAAVs described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. Other suitable promoter may include a CB7 promoter. In addition to a promoter, a vector genome may contain one or more other appropriate transcription initiation sequences, transcription termination sequences, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the regulatory sequences comprise one or more expression enhancers. In one embodiment, the regulatory sequences contain two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. In certain embodiments, the intron is a chimeric intron (CI)— a hybrid intron consisting of a human beta-globin splice donor and immunoglobulin G (IgG) splice acceptor elements. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence (see, e.g., MA Zanta-Boussif, et al, *Gene Therapy* (2009) 16: 605-619). In certain embodiments, no WPRE sequence is present.

In certain embodiments, vector genomes are constructed which comprise a 5' AAV ITR—promoter—optional enhancer—optional intron—GLB1 gene—polyA—3' ITR. In certain embodiments, the ITRs are from AAV2. In certain embodiments, more than one promoter is present. In certain embodiments, the enhancer is present in the vector genome. In certain embodiments, more than one enhancer is present. In certain embodiments, an intron is present in the vector genome. In certain embodiments, the enhancer and intron are present. In certain embodiments, the intron is a chimeric intron (CI)— a hybrid intron consisting of a human beta-globin splice donor and immunoglobulin G (IgG) splice acceptor elements. In certain embodiments, the polyA is an SV40 poly A (i.e., a polyadenylation (PolyA) signal derived from Simian Virus 40 (SV40) late genes). In certain embodiments, the polyA is a rabbit beta-globin (RBG) poly A. In certain embodiments, the vector genome comprises a 5' AAV ITR—CB7 promoter—GLB1 gene—RBG poly A—3' ITR. In certain embodiments, the vector genome comprises a 5' AAV ITR—EF1a promoter—GLB1 gene—SV40 poly A—3' ITR. In certain embodiments, the vector genome comprises a 5' AAV ITR—UbC promoter—GLB1 gene—SV40 poly A—3' ITR. In certain embodiments, the GLB1 gene has SEQ ID NO: 5. In certain embodiments, the GLB1 gene has SEQ ID NO: 6. In certain embodiments, the GLB1 gene has SEQ ID NO: 7. In certain embodiments, the GLB1 gene has SEQ ID NO: 8. In certain embodiments, the vector genome has the sequence of SEQ ID NO: 12 or a sequence at least about 85%, 90%, 91%, 92%, 93%, 94%, 95%, 96%, 97%, 98%, or 99%, to about 99.9% identical thereto. In certain embodiments, the vector genome has the sequence of SEQ ID NO: 13 or a sequence at least about 85%, 90%, 91%, 92%, 93%, 94%, 95%, 96%, 97%, 98%, or 99%, to about 99.9% identical thereto. In certain embodiments, the vector genome has the sequence of SEQ ID NO: 14 or a sequence at least about 85%, 90%, 91%, 92%, 93%, 94%, 95%, 96%, 97%, 98%, or 99%, to about 99.9% identical thereto. In certain embodiments, the vector genome has the sequence of SEQ ID NO: 15 or a sequence at least about 85%, 90%, 91%, 92%, 93%, 94%, 95%, 96%, 97%, 98%, or 99%, to about 99.9% identical thereto. In certain embodiments, the vector genome has the sequence of SEQ ID NO: 16 or a sequence at least about 85%, 90%, 91%, 92%, 93%, 94%, 95%, 96%, 97%, 98%, or 99%, to about 99.9% identical thereto.

IV. rAAV Production

For use in producing an AAV viral vector (e.g., a recombinant (r) AAV), the vector genomes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art. An illustrative production process is provided in FIGS. 12A-12B.

Methods for generating and isolating AAVs suitable for use as vectors are known in the art. See generally, e.g., Grieger & Samulski, 2005, Adeno-associated virus as a gene therapy vector: Vector development, production and clinical applications, *Adv. Biochem. Engin/Biotechnol.* 99: 119-145; Buning et al., 2008, Recent developments in adeno-associated virus vector technology, *J. Gene Med.* 10:717-733; and the references cited below, each of which is incorporated herein by reference in its entirety. For packaging a gene into virions, the ITRs are the only AAV components required in cis in the same construct as the nucleic acid molecule containing the gene. The cap and rep genes can be supplied in trans.

In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product (for example, β-gal). These empty capsids are non-functional to transfer the gene of interest to a host cell. In certain embodiment, the rAAV.GLB1 or the composition as described herein may be at least about 80%, 85%, 90%, 95%, 96%, 97%, 98%, 99% or 99.9% free from an AAV intermediate, i.e., containing less than 20%, 15%, 10%, 5%, 4%, 3%, 2%, 1%, or 0.1% AAV intermediates.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAV (such as rAAVhu68) is provided. Such a cell culture contains a nucleic acid which expresses the AAVcapsid protein in the host cell; a nucleic acid molecule suitable for packaging into the AAVcapsid, e.g., a vector genome which contains AAV ITRs and a GLB1 gene operably linked to regulatory sequences which direct expression of the gene in a cell (for example, a cell in a patient in need); and sufficient AAV rep functions and adenovirus helper functions to permit packaging of the vector genome into the recombinant AAV capsid. In one embodiment, the cell culture is composed of mammalian cells (e.g., human embryonic kidney 293 cells, among others) or insect cells (e.g., *Spodoptera frugiperda* (Sf9) cells). In certain embodiments, baculovirus provides the helper functions necessary for packaging the vector genome into the recombinant AAVhu68 capsid.

Optionally the rep functions are provided by an AAV other than the capsid source AAV, AAVhu68. In certain embodiments, at least parts of the rep functions are from AAVhu68. In another embodiment, the rep protein is a heterologous rep protein other than AAVhu68 rep, for example but not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. Any of these AAVhu68 or mutant AAV capsid sequences may be under the control of exogenous regulatory control sequences which direct expression thereof in a host cell.

In one embodiment, cells are manufactured in a suitable cell culture (e.g., HEK 293 or Sf9) or suspension. Methods for manufacturing the gene therapy vectors described herein include methods well known in the art such as generation of plasmid DNA used for production of the gene therapy vectors, generation of the vectors, and purification of the vectors. In some embodiments, the gene therapy vector is a rAAV and the plasmids generated are an AAV cis-plasmid encoding the AAV vector genome comprising the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, Adenovirus-adeno-associated virus hybrid for large-scale recombinant adeno-associated virus production, *Human Gene Therapy* 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the rAAV harvest, diafiltration of the rAAV harvest, microfluidization of the rAAV harvest, nuclease digestion of the rAAV harvest, filtration of microfluidized intermediate, crude purification by chromatography, crude purification by ultracentrifugation, buffer exchange by tangential flow filtration, and/or formulation and filtration to prepare bulk rAAV.

A two-step affinity chromatography purification at high salt concentration followed anion exchange resin chromatography are used to purify the rAAV drug product and to remove empty capsids. These methods are described in more detail in WO 2017/160360, International Patent Application No. PCT/US2016/065970, filed Dec. 9, 2016 and its priority documents, US Patent Application Nos. 62/322,071, filed Apr. 13, 2016 and 62/226,357, filed Dec. 11, 2015 and entitled "Scalable Purification Method for AAV9", which is incorporated by reference herein.

To calculate empty and full particle content, VP3 band volumes for a selected sample (e.g., in examples herein an iodixanol gradient-purified preparation where # of genome copies (GC)=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and x 100 gives the percentage of empty particles.

Generally, methods for assaying for empty capsids and rAAV particles with packaged vector genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the rAAV is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAVhu68 particles having packaged genomic sequences from genome-deficient AAVhu68 intermediates involves subjecting a suspension comprising recombinant AAVhu68 viral particles and AAVhu68 capsid intermediates to fast performance liquid chromatography, wherein the AAVhu68 viral particles and AAVhu68 intermediates are bound to a strong anion exchange resin equilibrated at a pH of about 10.2, and subjected to a salt gradient while monitoring eluate for ultraviolet absorbance at about 260 nanometers (nm) and about 280 nm. Although less optimal for rAAVhu68, the pH may be in the range of about 10.0 to 10.4. In this method, the AAVhu68 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/hu68 serotype. Under these ionic conditions, a significant percentage of residual cellular DNA and proteins flow through the column, while AAV particles are efficiently captured.

Also provided herein is a production vector (such as a plasmid) or a host cell for producing the vector genome and/or the rAAV.GLB1 as described herein. As used herein, a production vector carrying a vector genome to a host cell for generating and/or packaging a gene therapy vector as described herein.

The rAAV.GLB1 (for example, rAAVhu68.GLB1) is suspended in a suitable physiologically compatible composition (e.g., a buffered saline). This composition may be frozen for storage, later thawed and optionally diluted with a suitable diluent. Alternatively, the rAAV.GLB1 may be prepared as a composition which is suitable for delivery to a patient without proceeding through the freezing and thawing steps.

V. Compositions and Uses

Provided herein are compositions containing at least one rAAV stock (e.g., an rAAVhu68 stock or a mutant rAAVhu68 stock) and an optional carrier, excipient and/or preservative. An rAAV stock refers to a plurality of rAAV which are the same, e.g., such as in the amounts described below in the discussion of concentrations and dosage units.

In particular, the composition is for the treatment of GM1 gangliosidosis. In one embodiment, the composition is suitable for administration to a patient having GM1 gangliosidosis or a patient having infantile gangliosidosis who is 18 months of age or younger. In one embodiment, the composition is suitable for administration to a patient in need thereof to ameliorate symptoms of GM1 gangliosidosis, or ameliorate neurological symptoms of GM1 gangliosidosis. In some embodiments, the composition is for use in the manufacture of a medication for the treatment of GM1 gangliosidosis.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

In certain embodiments, provided herein is a composition comprising the rAAV.GLB1 as described herein and a pharmaceutically acceptable carrier. The phrase "pharmaceutically-acceptable" refers to molecular entities and compositions that do not produce an allergic or similar untoward reaction when administered to a host.

In certain embodiments, provided herein is a composition comprising the rAAV.GLB1 as described herein and a delivery vehicle. Delivery vehicles such as liposomes, nanocapsules, microparticles, microspheres, lipid particles, vesicles, and the like, may be used for the introduction of the compositions of the present invention into suitable host cells. In particular, the rAAV delivered vector genomes may be formulated for delivery either encapsulated in a lipid particle, a liposome, a vesicle, a nanosphere, or a nanoparticle or the like.

In one embodiment, a composition includes a final formulation suitable for delivery to a subject/patient, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. In one embodiment, the surfactant may be present in an amount up to about 0.0005% to about 0.001% (based on weight ratio, w/w %) of the suspension. In another embodiment, the surfactant may be present in an amount up to about 0.0005% to about 0.001% (based on volume ratio, v/v %) of the suspension. In yet another embodiment, the surfactant may be present in an amount up to about 0.0005% to about 0.001% of the suspension, wherein n % indicates n gram per 100 mL of the suspension.

The rAAV.GLB1 is administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., brain, CSF, the liver (optionally via the hepatic artery), lung, heart, eye, kidney), oral, inhalation, intranasal, intrathecal, intratracheal, intraarterial, intraocular, intravenous, intramuscular, subcutaneous, intradermal, intraparenchymal, intracerebroventricular, intrathecal, ICM, lumbar puncture and other parenteral routes of administration. Routes of administration may be combined, if desired.

Dosages of the rAAV.GLB1 depend primarily on factors such as the condition being treated, the age, weight and health of the patient, and can thus vary among patients. For example, a therapeutically effective human dosage of the rAAV.GLB1 is generally in the range of from about 25 to about 1000 microliters to about 100 mL of solution containing concentrations of from about $1\times10^9$ to $1\times10^{16}$ vector genome copies. In certain embodiments, a volume of about 1 mL to about 15 mL, or about 2.5 mL to about 10 mL, or about 5 mL suspension is delivered. In certain embodiments, a volume of about 1, about 2, about 3, about 4, about 5, about 6, about 7, about 8, about 9, about 10, about 11, about 12, about 13, about 14, or about 15 mL suspension is delivered.

In some embodiments, the composition is for administration in a single dose. In some embodiments, the composition is for administration in multiple doses.

In certain embodiments, a dose from about $8\times10^{12}$ genome copies (GC) of rAAV.GLB1 per patient to about $3\times10^{14}$ GC of rAAV.GLB1 per patient is administered in the volume described herein. In certain embodiments, a dose from about $2\times10^{12}$ GC of rAAV.GLB1 per patient to about $3\times10^{14}$ GC of rAAV.GLB1 per patient, or from about $2\times10^{13}$ GC of rAAV.GLB1 per patient to about $3\times10^{14}$ GC of rAAV.GLB1 per patient, or from about $8\times10^{13}$ GC of rAAV.GLB1 per patient to about $3\times10^{14}$ GC of rAAV.GLB1 per patient, or about $9\times10^{13}$ GC of rAAV.GLB1 per patient, or about $8.9\times10^{12}$ to $2.7\times10^{14}$ GC total is administered in the volume.

In certain embodiments, a dose from $1\times10^{10}$ GC of rAAV.GLB1 per g brain mass (GC/g brain mass) to $3.4\times10^{11}$ GC/g brain mass is administered in the volume as described herein. In certain embodiments, a dose from $3.4\times10^{10}$ GC/g brain mass to $3.4\times10^{11}$ GC/g brain mass, or from $1.0\times10^{11}$ GC/g brain mass to $3.4\times10^{11}$ GC/g brain mass, or about $1.1\times10^{11}$ GC/g brain mass, or from about $1.1\times10^{10}$ GC/g brain mass to about $3.3\times10^{11}$ GC/g brain mass is administered in the volume. In certain embodiments, a dose of about $3.0\times10^{9}$, about $4.0\times10^{9}$, about $5.0\times10^{9}$, about $6.0\times10^{9}$, about $7.0\times10^{9}$, about $8.0\times10^{9}$, about $9.0\times10^{9}$, about $1.0\times10^{11}$, about $1.1\times10^{11}$, about $1.5\times10^{11}$, about $2.0\times10^{11}$, about $2.5\times10^{10}$, about $3.0\times10^{10}$, about $3.3\times10^{10}$, about $3.5\times10^{10}$, about $4.0\times10^{10}$, about $4.5\times10^{10}$, about $5.0\times10^{10}$, about $5.5\times10^{10}$, about $6.0\times10^{10}$, about $6.5\times10^{10}$, about $7.0\times10^{10}$, about $7.5\times10^{10}$, about $8.0\times10^{10}$, about $8.5\times10^{10}$, about $9.0\times10^{10}$, about $9.5\times10^{10}$, about $1.0\times10$, about $1.1\times10^{11}$, about $1.5\times10^{11}$, about $2.0\times10^{11}$, about $2.5\times10^{11}$, about $3.0\times10^{11}$, about $3.3\times10^{11}$, about $3.5\times10^{11}$, about $4.0\times10^{11}$, about $4.5\times10^{11}$, about $5.0\times10^{11}$, about $5.5\times10^{11}$, about $6.0\times10^{11}$, about $6.5\times10^{11}$, about $7.0\times10^{11}$, about $7.5\times10^{11}$, about $8.0\times10^{11}$, about $8.5\times10^{11}$, about $9.0\times10^{11}$ GC per gram brain mass is administered in the volume. In certain embodiments, the dose reflects the minimum effective dose shown in a GM1 animal model and adjusted for use in a human patient based on genome copies per gram brain mass. In one embodiment, the dose for use in a human patient is calculated using the assumed brain masses listed in the table below.

| Subject Age | Assumed brain mass (g) |
|---|---|
| ≥4 to <9 months | 600 |
| ≥9 to <18 months | 1000 |
| ≥18 months to <3 years | 1100 |
| ≥3 years | 1300 |

The dosage is adjusted to balance the therapeutic benefit against any side effects and such dosages may vary depending upon the therapeutic application for which the rAAV.GLB1 is employed. The levels of expression of the transgene product (for example, β-gal) can be monitored to determine the frequency of dosage resulting in rAAV.GLB1, preferably rAAV containing the minigene (for example, the GLB1 gene). Optionally, dosage regimens similar to those described for therapeutic purposes may be utilized for immunization using the compositions of the invention.

The replication-defective virus compositions can be formulated in dosage units to contain an amount of replication-defective virus (for example, rAAV.GLB1, rAAVhu68.GLB1, or rAAVhu68.UbC.GLB1) that is in the range of about $1.0\times10^{9}$ GC to about $1.0\times10^{16}$ GC (to treat an subject) including all integers or fractional amounts within the range, and preferably $1.0\times10^{12}$ GC to $1.0\times10^{14}$ GC for a human patient. In one embodiment, the compositions are formulated to contain at least $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ GC per dose including all integers or fractional amounts within the range. In another embodiment, the compositions are formulated to contain at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per dose including all integers or fractional amounts within the range. In another embodiment, the compositions are formulated to contain at least $1\times10^{11}$, $2\times10^{11}$, $3\times10^{11}$, $4\times10^{11}$, $5\times10^{11}$ $6\times10^{11}$, $7\times10^{11}$, $8\times10^{11}$, or $9\times10^{11}$ GC per dose including all integers or fractional amounts within the range. In another embodiment, the compositions are formulated to contain at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, for human application the dose can range from $1\times10^{10}$ to about $1\times10^{12}$ GC per dose including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is from about 700 to 1000 μL.

In certain embodiments, the dose may be in the range of about $1\times10^9$ GC/g brain mass to about $1\times10^{12}$ GC/g brain mass. In certain embodiments, the dose may be in the range of about $3\times10^{10}$ GC/g brain mass to about $3\times10^{11}$ GC/g brain mass. In certain embodiments, the dose may be in the range of about $5\times10^{10}$ GC/g brain mass to about $1.85\times10^{11}$ GC/g brain mass.

In one embodiment, the viral constructs may be delivered in doses of from at least about least $1\times10^9$ GC to about $1\times10^5$, or about $1\times10^{11}$ to $5\times10^{11}$ GC. Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage may be adjusted to balance the therapeutic benefit against any side effects and such dosages may vary depending upon the therapeutic application for which the rAAV.GLB1 is employed.

The above-described rAAV.GLB1 may be delivered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.0 to 7.5, or pH 6.2 to 7.7, or pH 6.5 to 7.5, pH 7.0 to 7.7, or pH 7.2 to 7.8, or about 7.0. In certain embodiments, the formulation is adjusted to a pH of about 6.0, about 6.1, about 6.2, about 6.3, about 6.4, about 6.5, about 6.6, about 6.7, about 6.8, about 6.9, about 7.0, about 7.1, about 7.2, about 7.3 about 7.4, about 7.5, about 7.6, about 7.7, or about 7.8. In certain embodiments, a pH of about 7.28 to about 7.32, about 6.0 to about 7.5, about 6.2 to about 7.7, about 7.5 to about 7.8, about 6.0, about 6.1, about 6.2, about 6.3, about 6.4, about 6.5, about 6.6, about 6.7, about 6.8, about 6.9, about 7.0, about 7.1, about 7.2, about 7.3 about 7.4, about 7.5, about 7.6, about 7.7, or about 7.8 may be desired for intrathecal delivery; whereas for intravenous delivery, a pH of about 6.8 to about 7.2 may be desired. However, other pHs within the broadest ranges and these subranges may be selected for other route of delivery.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Poloxamer 188 (also known under the commercial names Pluronic® F68 [BASF], Lutrol® F68, Synperonic® F68, Kolliphor® P188) which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate·$7H_2O$), potassium chloride, calcium chloride (e.g., calcium chloride·$2H_2O$), dibasic sodium phosphate, and mixtures thereof, in water. Suitably, for intrathecal delivery, the osmolarity is within a range compatible with cerebrospinal fluid (e.g., about 275 milliosmoles/liter (mOsm/L) to about 290 mOsm/L); see, e.g., emedicine.medscape.com/-article/2093316-overview. Optionally, for intrathecal delivery, a commercially available diluent may be used as a suspending agent, or in combination with another suspending agent and other optional excipients. See, e.g., Elliotts B® solution [Lukare Medical]. Each 10 mL of Elliotts B Solution contains:

| | |
|---|---|
| Sodium Chloride, USP | 73 mg |
| Sodium Bicarbonate, USP | 19 mg |
| Dextrose, USP | 8 mg |
| Magnesium Sulfate•$7H_2O$, USP | 3 mg |
| Potassium Chloride, USP | 3 mg |
| Calcium Chloride•$2H_2O$, USP | 2 mg |
| Sodium Phosphate, dibasic•$7H_2O$, USP | 2 mg |
| Water for Injection, USP | qs 10 mL |

Concentration of Electrolytes:

| | | | |
|---|---|---|---|
| Sodium | 149 mEq/liter | Bicarbonate | 22.6 mEq/liter |
| Potassium | 4.0 mEq/liter | Chloride | 132 mEq/liter |
| Calcium | 2.7 mEq/liter | Sulfate | 2.4 mEq/liter |
| Magnesium | 2.4 mEq/liter | Phosphate | 1.5 mEq/liter |

The formulae and molecular weights of the ingredients are:

| INGREDIENT | MOLECULAR FORMULA | MOLECULAR WEIGHT |
|---|---|---|
| Sodium Chloride | $NaCl$ | 58.44 |
| Sodium Bicarbonate | $NaHCO_3$ | 84.01 |
| Dextrose | $C_6H_{12}O_6$ | 180.16 |
| Magnesium Sulfate•$7H_2O$ | $Mg_2SO_4$•$7H_2O$ | 246.48 |
| Potassium Chloride | $KCl$ | 74.55 |
| Calcium Chloride•$2H_2O$ | $CaCl_2$•$2H_2O$ | 147.01 |
| Sodium Phosphate, dibasic•$7H_2O$ | $Na_2HPO_4$•$7H_2O$ | 268.07 |

The pH of Elliotts B Solution is 6 to 7.5, and the osmolarity is 288 mOsmol per liter (calculated).

In certain embodiments, the intrathecal final formulation buffer (ITFFB) formulation buffer comprises an artificial cerebrospinal fluid comprising buffered saline and one or more of sodium, calcium, magnesium, potassium, or mixtures thereof; and a surfactant. In certain embodiments, the surfactant comprises about 0.0005% to about 0.001% of the suspension. In a further embodiment, the percentage (%) is calculated based on weight (w) ratio (i.e., w/w).

In certain embodiments, the composition containing the rAAVhu68.GLB1 (e.g., the ITFFB formulation) is at a pH in the range of 6.0 to 7.5, or 6.2 to 7.7, or 6.8 to 8, or 7.2 to 7.8, or 7.5 to 8. In certain embodiments, the final formulation is at a pH of about 7, or 7 to 7.4, or 7.2. In certain embodiments, for intrathecal delivery, a pH above 7.5 may be desired, e.g., 7.5 to 8, or 7.8.

In certain embodiments, a pH of about 7 is desired for intrathecal delivery as well as other delivery routes.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. In certain embodiment, the aqueous solution may have a pH of 7.2. In certain embodiment, the aqueous solution may have a pH of about 7.

In another embodiment, the formulation may contain a buffered saline aqueous solution comprising 1 mM Sodium Phosphate ($Na_3PO_4$), 150 mM sodium chloride (NaCl), 3 mM potassium chloride (KCl), 1.4 mM calcium chloride ($CaCl_2$)), 0.8 mM magnesium chloride ($MgCl_2$), and 0.001% poloxamer (e.g., Kolliphor®) 188. In certain embodiments, the formulation has a pH of about 7.2. In certain embodiments, the formulation has a pH of about 7. See, e.g., harvardapparatus.com/harvard-apparatus-perfusion-fluid.html. In certain embodiments, Harvard's buffer is preferred due to better pH stability observed with Harvard's buffer. The table below provides a comparison of Harvard's buffer and Elliot's B buffer.

Cerebrospinal Fluid (CSF) Compositions

| Component | Units | CSF | Elliot's B | Harvard's |
|---|---|---|---|---|
| $Na^+$ | mEq/L | 117-137 | 149 | 150 |
| $K^+$ | mEq/L | 2.3-4.6 | 4.0 | 3.0 |
| $Mg^+$ | mEq/L | 2.2 | 2.4 | 0.8 |
| $Ca^{2+}$ | mEq/L | 2.2 | 2.7 | 1.4 |
| $Cl^-$ | mEq/L | 113-127 | 132 | 155 |
| $HCO_3^-$ | mEq/L | 22.9 | 22.6 | 0 |
| Phos | mg/dL | 1.2-2.1 | 1.5 | 1.0 |
| Glucose | mg/dL | 45-80 | 80 | — |
| Pluronic | % | — | 0.001% (added) | 0.001% (added) |
| Osmolarity | mOsm/L | 295 | 288 | 290 |
| pH | | 7.31 | 6.0-7.5* Drift to 9+ (8.2+ w/o titratn) | 7.2 (titrated to) |

In certain embodiments, the formulation buffer is artificial CSF with Pluronic F68. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery. In one embodiment, the composition is formulated for administration via an intra-cisterna magna injection (ICM). In one embodiment, the composition is formulated for administration via a CT-guided sub-occipital injection into the cisterna magna.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube.

In certain embodiments, an aqueous composition comprising a formulation buffer and an rAAV.GLB1 (for example, rAAVhu68.GLB1) as provided herein is delivered to a patient in need thereof. In certain embodiments, the rAAV.GLB1 has an AAV capsid (for example, an AAVhu68 capsid) and a vector genome comprising a 5' AAV ITR—promoter—optional enhancer—optional intron—GLB1 gene—polyA—3' ITR. In certain embodiments, the ITRs are from AAV2. In certain embodiments, more than one promoter is present. In certain embodiments, the enhancer is present in the vector genome. In certain embodiments, more than one enhancer is present. In certain embodiments, an intron is present in the vector genome. In certain embodiments, the enhancer and intron are present. In certain embodiments, the polyA is an SV40 poly A. In certain embodiments, the polyA is a rabbit beta-globin (RBG) poly A. In certain embodiments, the vector genome comprises a 5' AAV ITR—CB7 promoter—GLB1 gene—RBG poly A—3' ITR. In certain embodiments, the vector genome comprises a 5' AAV ITR—EF1a promoter—GLB1 gene—SV40 poly A—3' ITR. In certain embodiments, the vector genome comprises a 5' AAV ITR—UbC promoter—GLB1 gene—SV40 poly A—3' ITR. In certain embodiments, the GLB1 gene has SEQ ID NO: 5. In certain embodiments, the GLB1 gene has SEQ ID NO: 6. In certain embodiments, the GLB1 gene has SEQ ID NO: 7. In certain embodiments, the GLB1 gene has SEQ ID NO: 8. In certain embodiments, the vector genome has the sequence of SEQ ID NO: 12. In certain embodiments, the vector genome has the sequence of SEQ ID NO: 13. In certain embodiments, the vector genome has the sequence of SEQ ID NO: 14. In certain embodiments, the vector genome has the sequence of SEQ ID NO: 15. In certain embodiments, the vector genome has the sequence of SEQ ID NO: 16.

In certain embodiments, the final formulation buffer comprises an artificial cerebrospinal fluid comprising buffered saline and one or more of sodium, calcium, magnesium, potassium, or mixtures thereof; and a surfactant. In certain embodiments, the surfactant is about 0.0005% to about 0.001% of the suspension. In certain embodiments, the surfactant is Pluronic F68. In certain embodiments, the Pluronic F68 is present in an amount of about 0.0001% of the suspension. In certain embodiments, the composition is at a pH in the range of 7.5 to 7.8 for intrathecal delivery. In certain embodiments, the composition is at a pH in the range of 6.2 to 7.7, or 6.9 to 7.5, or about 7 for intrathecal delivery. In one embodiment, the percentage (%) is calculated based on weight ratio or volume ratio. In another embodiment, the percentage represents "gram per 100 ml of final volume".

In certain embodiments, treatment of the composition described herein has minimal to mild asymptomatic degeneration of DRG sensory neurons in animals and/or in human patients, well-tolerated with respect to sensory nerve toxicity and subclinical sensory neuron lesions.

In certain embodiment, the composition described herein is useful in improving functional and clinical outcomes in the subject/patient treated. Such outcomes may be measured at about 30 days, about 60 days, about 90 days, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 2.5 years, about 3 years, about 3.5 years, about 4 years, about 4.5 years and then yearly up to the about 5 years after administration of the composition. Measurement frequency may be about every 1 month, about every 2 months, about every 3 months, about every 4 months, about every 5 months, about every 6 months, about every 7 months, about every 8 months, about every 9 months, about every 10 months, about every 11 months, or about every 12 months.

In certain embodiments, the composition described herein shows pharmacodynamics and clinical efficacy measured in treated subjects compared to untreated controls.

In certain embodiments, the pharmacodynamics efficacy, clinical efficacy, functional outcomes, or clinical outcomes may be measured via one or more of the following: (1) survival, (2) feeding tube independence, (3) seizure diary, e.g., incidence, onset, frequency, length, and type of seizure, (4) quality of life, for example, as measured by PedsQL, (5) neurocognitive and behavioral development, (6) β-gal enzyme expression or activity, for example in serum or CSF, and (7) other parameters as described herein. The Bayley Scales of Infant Development and Vineland Scales may be used to quantify the effects of the composition on development and/or changes in adaptive behaviors, cognition, language, motor function, and health-related quality of life.

In certain embodiments, the neurocognitive development is based on one of more of the following: change in age equivalent cognitive, gross motor, fine motor, receptive and expressive communication scores of the Bayley Scales of Infant and Toddler Development; change in standard scores for each domain of the Vineland Adaptive Behavior Scales; and pediatric quality of life by change in total score on the Pediatric Quality of Life Inventory- and the Pediatric Quality of Life Inventory Infant Scale (PedsQL and PedsQL-IS).

BSID (Bayley Scale of Infant Development): is used primarily to assess the development of infants and toddlers, ages 1-42 months (Albers and Grieve, 2007, Test Review: Bayley, N. (2006). Bayley Scales of Infant and Toddler Development—Third Edition. San Antonio, TX: Harcourt Assessment. Journal of Psychoeducational Assessment. 25(2):180-190). It consists of a standardized series of developmental play tasks and derives a developmental quotient by converting raw scores of successfully completed items to scale scores and composite scores and comparing the scores with norms taken from typically developing children of the same age. The Bayley-III has 3 main subtests; a Cognitive Scale, which includes items such as attention to familiar and unfamiliar objects, looking for a fallen object, and pretend play; a Language Scale, which assesses understanding and expression of language (e.g. ability to follow directions and naming objects); and a Motor Scale that measures gross and fine motor skills (e.g. grasping, sitting, stacking blocks, and climbing stairs). The most current version is the BSID-III Vineland: Assesses adaptive behavior from birth through adulthood (0-90 years) across five domains: communication, daily living skills, socialization, motor skills, and maladaptive behavior. The most current version is the Vineland III. Improvements from the Vineland-II to the Vineland-III incorporate questions to enable better understanding of developmental disabilities.

The BSID and Vineland were chosen based on data from the only prospective study of infantile GM1 gangliosidosis patients (Brunetti-Pierri and Scaglia, 2008, GM1 gangliosidosis: Review of clinical, molecular, and therapeutic aspects. Molecular Genetics and Metabolism. 94(4):391-396). Age-equivalent scores on the BSID-III showed a decline to the floor of the testing scale by 28 months of age for both cognitive and gross motor domains, and the scores on the Vineland-II adaptive behavior scale remained measurable, albeit far below normal, by 28 months of age. While these tools showed floor effects they were shown to be appropriate scales for measuring developmental changes in this severely impaired population, the cross-cultural validity of the scales make them appropriate for international studies.

PedsQOL and PedsQL-IS: As is the case with severe pediatric diseases, the burden of the disease on the family is significant. The Pediatric Quality of Life Inventory™ is a validated a tool that assesses quality of life in children and their parents (by parent proxy reports). It has been validated in healthy children and adolescents and has been used in various pediatric diseases (Iannaccone et al., 2009, The PedsQL in pediatric patients with Spinal Muscular Atrophy: feasibility, reliability, and validity of the Pediatric Quality of Life Inventory Generic Core Scales and Neuromuscular Module. *Neuromuscular disorders: NMD.* 19(12):805-812; Absoud et al., 2011, Paediatric UK demyelinating disease longitudinal study (PUDDLS)." BMC Pediatrics. 11(1):68; and Consolaro and Ravelli, 2016, Chapter 5—Assessment Tools in Juvenile Idiopathic Arthritis. Handbook of Systemic Autoimmune Diseases. R. Cimaz and T. Lehman, Elsevier. 11: 107-127). Therefore, the PedsQL is included to evaluate the impact of rAAV.GLB1 on the quality of life of the patient and their family. It can be applied to parents of children age 2 and above and may therefore be informative as the children age over the 5 year follow-up period. The Pediatric Quality of Life Inventory™ Infant Scale (Vari et al., 2011, "The PedsQL™ Infant Scales: feasibility, internal consistency reliability, and validity in healthy and ill infants." Quality of Life Research. 20(1):45-55) is a validated modular instrument completed by parents and designed to measure health-related quality of life instrument specifically for healthy and ill infants ages 1-24 months.

Given the severity of disease in the target population, subjects may have achieved motor skills by enrollment, developed and subsequently lost other motor milestones, or not yet shown signs of motor milestone development. Assessments tracks age-at-achievement and age-at-loss for all milestones. Motor milestone achievement is defined for six gross milestones based on the WHO criteria outlined in the Table provided herein under Section I GM1 and the therapeutic GLB1 gene. Given that subjects with infantile GM1 gangliosidosis can develop symptoms within the months of life, and acquisition of the first WHO motor milestone (sitting without support) typically does not manifest before 4 months of age (median: 5.9 months of age), this endpoint may lack sensitivity to evaluate the extent of therapeutic benefit, especially in subjects who had more overt symptoms at the time of treatment. For this reason, assessment of age-appropriate developmental milestones that can be applied to infants are also be included (Scharf et al., 2016, Developmental Milestones. Pediatr Rev. 37(1):25-37; quiz 38, 47). One shortcoming is that the published tool is intended for use by clinicians and parents, and organizes skills around the typical age of milestone acquisition without referencing normal ranges. However, the data may be informative for summarizing retention, acquisition, or loss of developmental milestones over time relative to untreated children with infantile GM1 disease or the typical time of acquisition in neurotypical children.

As the disease progresses children can develop seizures. The onset of seizure activity enables us to determine whether treatment with rAAV.GLB1 can either prevent or delay onset of seizures or decrease the frequency of seizure events in this population. Parents are asked to keep seizure diaries, which tracks onset, frequency, length, and type of seizure.

In certain embodiments, the pharmacodynamics efficacy, clinical efficacy, functional outcomes, or clinical outcomes may also include CNS manifestations of the disease, for example, volumetric changes measured on MRI over time. The infantile phenotype of all gangliosidoses was shown to have a consistent pattern of macrocephaly and rapidly increasing intracranial MRI volume with both brain tissue volume (cerebral cortex and other smaller structures) and ventricular volume. Additionally, various smaller brain substructures including the corpus callosum, caudate and putamen as well as the cerebellar cortex generally decrease in size as the disease progresses (Regier et al., 2016s, and Nestrasil et al., 2018, as cited herein). Treatment with rAAV.GLB1 can slow or cease the progression of CNS disease manifestations with evidence of stabilization in atrophy and volumetric changes. Changes (normal/abnormal) in T1/T2 signal intensity in the thalamus and basal ganglia may also be included based on reported evidence for changes in the thalamic structure in patients with GM1 and GM2 gangliosidosis (Kobayashi and Takashima, 1994, Thalamic hyperdensity on CT in infantile GM1-gangliosidosis." Brain and Development. 16(6):472-474). In certain embodiments, the pharmacodynamics efficacy, clinical efficacy, functional outcomes, or clinical outcomes may include changes in total brain volume, brain substructure volume, and lateral ventricle volume as measured by MRI; and/or changes in T1/T2 signal intensity in the thalamus and basal ganglia activity.

Alternatively or additionally, the pharmacodynamics efficacy, clinical efficacy, functional outcomes, or clinical outcomes may include biomarkers, for example, pharmacodynamics and biological activity of rAAV.GLB1, β-gal enzyme (GLB1) activity, which can be measured in CSF and serum, CSF GM1 concentration, serum and urine keratan sulfate levels, reduction of hexosaminidase activity, and brain MRI, which demonstrates consistent, rapid atrophy in infantile GM1 gangliosidosis (Regier et al., 2016b, as cited herein).

In certain embodiments, the composition described herein is useful in slowing down disease progression, for example, as assessed by age at achievement, age at loss, and percentage of children maintaining or acquiring age-appropriate developmental and motor milestones (as defined by World Health Organization [WHO] criteria).

In certain embodiments, the pharmacodynamics efficacy, clinical efficacy, functional outcomes, or clinical outcomes may include liver and spleen volume; and/or EEG and visual evoked potentials (VEP).

VI. Apparatus and Method for Delivery of a Pharmaceutical Composition into Cerebrospinal Fluid In one aspect, the rAAV or composition provided herein may be administered intrathecally via the method and/or the device provided in this section and described in WO 2018/160582, which is incorporated by reference herein. Alternatively, other devices and methods may be selected.

In certain embodiments, the method comprises the steps of CT-guided sub-occipital injection via spinal needle into the cisterna magna of a patient. As used herein, the term Computed Tomography (CT) refers to radiography in which a three-dimensional image of a body structure is constructed by computer from a series of plane cross-sectional images made along an axis.

On the day of treatment, the appropriate concentration of rAAV.GLB1 is be prepared. A syringe containing 5.6 mL of rAAV.GLB1 at the appropriate concentration is delivered to the procedure room. The following personnel are present for study drug administration: interventionalist performing the procedure; anesthesiologist and respiratory technician(s); nurses and physician assistants; CT (or operating room) technicians; site research coordinator. Prior to drug administration, a lumbar puncture is performed to remove a predetermined volume of CSF and then to inject iodinated contrast intrathecally (IT) to aid in visualization of relevant anatomy of the cisterna magna. Intravenous (IV) contrast may be administered prior to or during needle insertion as an alternative to the intrathecal contrast. The decision to used IV or IT contrast is at the discretion of the interventionalist. The subject is anesthetized, intubated, and positioned on the procedure table. The injection site are prepped and draped using sterile technique. A spinal needle (22-25 G) are advanced into the cisterna magna under fluoroscopic guidance. A larger introducer needle may be used to assist with needle placement. After confirmation of needle placement, the extension set are attached to the spinal needle and allowed to fill with CSF. At the discretion of the interventionalist, a syringe containing contrast material may be connected to the extension set and a small amount injected to confirm needle placement in the cisterna magna. After the needle placement is confirmed by CT guidance+/−contrast injection, a syringe containing 5.6 mL of rAAV.GLB1 is connected to the extension set. The syringe contents are slowly injected over 1-2 minutes, delivering a volume of 5.0 mL. The needle is slowly removed from the subject.

Additional or alternate routes of administration to the intrathecal method described herein include, for example, systemic, oral, intravenous, intraperitoneal, subcutaneous, or intramuscular administration.

In one embodiment, doses may be scaled by brain mass, which provides an approximation of the size of the CSF compartment. In a further embodiment, dose conversions are based on a brain mass of 0.4 g for an adult mouse, 90 g for a juvenile rhesus macaque, and 800 g for children 4-18 months of age. The following table provides illustrative doses for a murine MED study, NHP toxicology study, and equivalent human doses.

| Dose (GC/g brain mass) | Mouse (GC) | NHP (GC) | Human (GC) |
|---|---|---|---|
| $3.33 \times 10^{11}$ | $1.30 \times 10^{11}$ | $3.00 \times 10^{13}$ | $2.70 \times 10^{14}$ |
| $1.11 \times 10^{11}$ | $4.40 \times 10^{10}$ | $1.00 \times 10^{13}$ | $8.90 \times 10^{13}$ |
| $3.33 \times 10^{10}$ | $1.30 \times 10^{10}$ | $3.00 \times 10^{12}$ | $2.70 \times 10^{13}$ |
| $1.11 \times 10^{10}$ | $4.40 \times 10^{9}$ | — | $8.90 \times 10^{12}$ |

In certain embodiments, a rAAV.GLB1 is administered to a subject in a single dose. In certain embodiments, multiple doses (for example 2 doses) may be desired. For example, for infants under 6 months, multiple doses delivered days, weeks, or months, apart may be desired.

In certain embodiments, a single dose of rAAV.GLB1 is from about $1\times10^{9}$ GC/g brain mass to about $5\times10^{11}$ GC/g brain mass. In certain embodiments, a single dose of rAAV.GLB1 is from about $1\times10^{9}$ GC/g brain mass to about $3\times10^{11}$ GC. In certain embodiments, a single dose of rAAV.GLB1 is from about $1\times10^{10}$ GC/g brain mass to about $3\times10^{11}$ GC/g brain mass. In certain embodiments, the dose of rAAV.GLB1 is from $1\times10^{10}$ GC/brain mass to $3.33\times10^{11}$ GC/brain mass. In certain embodiments, the dose of rAAV.GLB1 is from $1\times10^{11}$ GC/brain mass to $3.33\times10^{11}$ GC/brain mass. In certain embodiments, a single dose of rAAV.GLB1 is from $1.11\times10^{10}$ GC/g brain mass to $3.33\times10^{11}$ GC/g brain mass.

In certain embodiments, a single dose of rAAV.GLB1 is from $1\times10^{10}$ GC/g brain mass to $3.4\times10^{11}$ GC/g brain mass. In certain embodiments, a single dose of rAAV.GLB1 is from $3.4\times10^{10}$ GC/g brain mass to $3.4\times10^{11}$ GC/g brain mass. In certain embodiments, a single dose of rAAV.GLB1 is from $1.0\times10^{11}$ GC/g brain mass to $3.4\times10^{11}$ GC/g brain mass. In certain embodiments, a single dose of rAAV.GLB1 is about $1.1\times10^{11}$ GC/g brain mass. In certain embodiments, a single dose of rAAV.GLB1 is at least $1.11\times10^{10}$ GC/g brain mass. In other embodiments, different doses may be selected.

In preferred embodiments, the subject is a human patient. In this case, a single dose of rAAV.GLB1 is from about $1\times10^{12}$ GC to about $3\times10^{11}$ GC. In certain embodiments, a single dose of rAAV.GLB1 is from $9\times10^{12}$ GC to $3\times10^{11}$ GC. In certain embodiments, the dose of rAAV.GLB1 is from $5\times10^{13}$ GC to $3\times10^{14}$ GC. In certain embodiments, a single dose of rAAV.GLB1 is from $8.90\times10^{13}$ GC to $2.70\times10^{14}$ GC. In certain embodiments, a single dose of rAAV.GLB1 is from $8\times10^{12}$ genome copies (GC) per patient to $3\times10^{14}$ GC per patient. In certain embodiments, a single dose of rAAV.GLB1 is from $2\times10^{13}$ GC per patient to $3\times10^{14}$ GC per patient. In certain embodiments, a single dose of rAAV.GLB1 is from $8\times10^{13}$ GC per patient to $3\times10^{14}$ GC per patient. In certain embodiments, a single dose of rAAV.GLB1 is about $9\times10^{13}$ GC per patient. In certain embodiments, a single dose of rAAV.GLB1 is at least $8.90\times10^{13}$ GC. In other embodiments, different doses may be selected.

The compositions can be formulated in dosage units to contain an amount of AAV that is in the range from about $1\times10^{9}$ genome copies (GC) to about $5\times10^{14}$ GC (to treat an average subject of 70 kg in body weight). In some embodiments, the composition is formulated in dosage unit to contain an amount of AAV in the range from $1\times10^{9}$ genome copies (GC) to $5\times10^{13}$ GC; from $1\times10^{10}$ genome copies (GC) to $5\times10^{14}$ GC; from $1\times10^{11}$ GC to $5\times10^{11}$ GC; from $1\times10^{1}$ GC to $5\times10^{11}$ GC; from $1\times10^{13}$ GC to $5\times10^{11}$ GC; from $8.9\times10^{13}$ GC to $5\times10^{14}$ GC; or from $8.9\times10^{13}$ GC to $2.7\times10^{14}$ GC. In certain embodiments, the composition is formulated in dosage unit to contain an amount of AAV at least $1\times10^{13}$ GC, $2.7\times10^{13}$ GC, or $8.9\times10^{13}$ GC.

In one embodiment, a spinal tap is performed in which from about 15 mL (or less) to about 40 mL CSF is removed and in which rAAV.GLB1 is admixed with the CSF and/or suspended in a compatible carrier and delivered to the subject. In one example, the rAAV.GLB1 concentration is from $1\times10^{10}$ genome copies (GC) to $5\times10^{14}$ GC; from $1\times10^{11}$ GC to $5\times10^{14}$ GC; from $1\times10^{12}$ GC to $5\times10^{14}$ GC; from $1\times10^{13}$ GC to $5\times10^{14}$ GC; from $8.9\times10^{13}$ GC to $5\times10^{14}$ GC; or from $8.9\times10^{13}$ GC to $2.7\times10^{14}$ GC, but other amounts such as about $1\times10^{9}$ GC, about $5\times10^{9}$ GC, about $1\times10^{10}$ GC, about $5\times10^{10}$ GC, about $1\times10^{11}$ GC, about $5\times10^{11}$ GC, about $1\times10^{12}$ GC, about $5\times10^{12}$ GC, about $1.0\times10^{13}$ GC, about $5\times10^{13}$ GC, about $1.0\times10^{14}$ GC, or about $5\times10^{14}$ GC. In certain embodiments, the concentration in GC is illustrated as GC per spinal tap. In certain embodiments, the concentration in CG is illustrated as GC per mL.

A co-therapy may be delivered with the rAAV.GLB1 compositions provided herein. Co-therapies such as described earlier in this application are incorporated herein by reference.

One such co-therapy may be an immune modulator. Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor- (CD25-) or CD3-directed antibodies, anti-IL-2 antibodies, cyclosporin, tacrolimus, sirolimus, IFN-β, IFN-γ, an opioid, or TNF-α (tumor necrosis factor-alpha) binding agent. In certain embodiments, the immunosuppressive therapy may be started prior to the gene therapy administration. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week, about 15 days, about 30 days, about 45 days, 60 days, or longer, as needed.

For example, when nutrition is a concern in GM1, placement of a gastrostomy tube is appropriate. As respiratory function deteriorates, tracheotomy or noninvasive respiratory support is offered. A power chair and other equipment may improve quality of life.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

In some embodiments, the administration of the AAV or composition ameliorates symptoms of GM1 gangliosidosis, or ameliorated neurological symptoms of GM1 gangliosidosis. In some embodiments, following treatment, the patient has one or more of increased average life span, decreased need for feeding tube, reduction in seizure incidence and frequency, reduction in progression towards neurocognitive decline and/or improvement in neurocognitive development.

As used herein, an "expression cassette" refers to a nucleic acid molecule which comprises a coding sequence, promoter, and may include other regulatory sequences therefor. In certain embodiments, a vector genome may contain two or more expression cassettes. In other embodiments, the term "transgene" may be used interchangeably with "expression cassette". Typically, such an expression cassette for generating a viral vector contains the coding sequence for the gene product described herein flanked by packaging signals of the viral genome and other expression control sequences such as those described herein.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

A "replication-defective virus" or "viral vector" refers to a synthetic or artificial viral particle in which a vector genome comprising an expression cassette containing a gene of interest (for example, GLB1) is packaged in a viral capsid (e.g., AAV or bocavirus) or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the gene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

As used herein, an "effective amount" refers to the amount of the rAAV composition which delivers and expresses in the target cells an amount of the gene product from the vector genome. An effective amount may be determined based on an animal model, rather than a human patient. Examples of a suitable murine or NHP model are described herein.

It is to be noted that the term "a" or "an", refers to one or more, for example, "an enhancer", is understood to represent one or more enhancer(s). As such, the terms "a" (or "an"), "one or more," and "at least one" is used interchangeably herein.

As described above, the term "about" when used to modify a numerical value means a variation of ±10%, unless otherwise specified.

As described above, the terms "increase" "decrease" "reduce" "ameliorate" "improve" "delay" "earlier" "slow" "cease" or any grammatical variation thereof, or any similar terms indication a change, means a variation of about 5 fold, about 2 fold, about 1 fold, about 90%, about 80%, about 70%, about 60%, about 50%, about 40%, about 30%, about 20%, about 10%, about 5% compared to the corresponding reference (e.g., untreated control, corresponding level of a GM1 patient or a GM1 patient at a certain stage or a healthy subject or a healthy human without GM1)), unless otherwise specified.

"Patient" or "subject" as used herein refer to a mammalian animal, including a human, a veterinary or farm animal, a domestic animal or pet, and animals normally used for clinical research. In one embodiment, the subject of these methods and compositions is a human. In certain embodiments, the patient has GM1.

Unless defined otherwise in this specification, technical and scientific terms used herein have the same meaning as commonly understood by one of ordinary skill in the art and by reference to published texts, which provide one skilled in the art with a general guide to many of the terms used in the present application.

EXAMPLES

The following examples are illustrative only and are not intended to limit the present invention.

Example 1: AAVhu68+Deamidation

AAVhu68 was analyzed for modifications. Briefly, AAVhu68 were produced using vector genomes which are not relevant to this study, each produced using conventional triple transfection methods in 293 cells. For a general description of these techniques, see, e.g., Bell C L, et al., The AAV9 receptor and its modification to improve in vivo lung gene transfer in mice. *J Clin Invest.* 2011; 121:2427-2435. Briefly, for example, a plasmid encoding the sequence to be packaged (a transgene expressed from a chicken β-actin promoter, an intron and a poly A derived from Simian Virus 40 (SV40) late gene) flanked by AAV2 inverted terminal repeats, was packaged by triple transfection of HEK293 cells with plasmids encoding the AAV2 rep gene and the AAVhu68 cap gene and an adenovirus helper plasmid (pAdAF6). The resulting AAV viral particles can be purified using CsCl gradient centrifugation, concentrated, and frozen for later use.

Denaturation and alkylation: To 100 μg of the thawed viral preparation (protein solution), add 2 μl of 1M Dithiothreitol (DTT) and 2 μl of 8M guanidine hydrochloride (GndHCl) and incubate at 90° C. for 10 minutes. Allow the solution to cool to room temperature then add 5 µl of freshly prepared 1M iodoacetamide (IAM) and incubate for 30 minutes at room temperature in the dark. After 30 minutes, quench alkylation reaction by adding 1 µl of 1M DTT.

Digestion: To the denatured protein solution add 20 mM Ammonium Bicarbonate, pH 7.5-8 at a volume that dilutes the final GndHCl concentration to 800 mM. Add trypsin solution for a 1:20 trypsin to protein ratio and incubate at 37° C. overnight. After digestion, add TFA to a final of 0.5% to quench digestion reaction.

Mass Spectrometry: Approximately 1 microgram of the combined digestion mixture is analyzed by UHPLC-MS/MS. LC is performed on an UltiMate 3000 RSLCnano System (Thermo Scientific). Mobile phase A is MilliQ water with 0.1% formic acid. Mobile phase B is acetonitrile with 0.1% formic acid. The LC gradient is run from 4% B to 6% B over 15 min, then to 10% B for 25 min (40 minutes total), then to 30% B for 46 min (86 minutes total). Samples are loaded directly to the column. The column size is 75 cm×15 um I.D. and is packed with 2 micron C18 media (Acclaim PepMap). The LC is interfaced to a quadrupole-Orbitrap mass spectrometer (Q-Exactive HF, Thermo Scientific) via nanoflex electrospray ionization using a source. The column is heated to 35° C. and an electrospray voltage of 2.2 kV is applied. The mass spectrometer is programmed to acquire tandem mass spectra from top 20 ions. Full MS resolution to 120,000 and MS/MS resolution to 30,000. Normalized collision energy is set to 30, automatic gain control to 1e5, max fill MS to 100 ms, max fill MS/MS to 50 ms.

Data Processing: Mass spectrometer RAW data files were analyzed by BioPharma Finder 1.0 (Thermo Scientific). Briefly, all searches required 10 ppm precursor mass tolerance, 5 ppm fragment mass tolerance, tryptic cleavage, up to 1 missed cleavages, fixed modification of cysteine alkylation, variable modification of methionine/tryptophan oxidation, asparagine/glutamine deamidation, phosphorylation, methylation, and amidation.

In the following table, T refers to the trypsin and C refers to chymotrypsin.

| Modification AAVhu68 | | | | | | | | | | | | |
|---|---|---|---|---|---|---|---|---|---|---|---|---|
| Enzyme | T | T | T | T | C | C | C | C | T | T | T | |
| % Coverage | 93.6 | 92 | 93.1 | 92.5 | 90.2 | 89.7 | 91.1 | 88.9 | 98.9 | 97 | 94.6 | 92.4 |
| +Deamidation (Deamid) | | | | | | | | | | | | |
| ~N35 | | | | | | | | | | | | |
| N57 + Deamid | 87.6 | 95.5 | 89.3 | 88.2 | 90.5 | 96.3 | 86.4 | 84.8 | 100.0 | 100.0 | 99.0 | 92.7 |
| N66 + Deamid | 4.7 | | | | | | | | | | | |
| N94 + Deamid | 11.3 | 10.9 | 11.0 | 5.3 | 11.6 | 10.4 | 10.8 | 5.6 | 5.0 | 11.1 | 5.4 | 16.0 |
| N113 + Deamid | | | 1.8 | | | | | | | | | |
| ~N253 + Deamid | 17.7 | 22.0 | 21.1 | 15.0 | 17.0 | 22.6 | 20.5 | 15.6 | 4.2 | 5.5 | | |
| Q259 + Deamid | 35.2 | 25.6 | 21.0 | | 35.4 | 26.3 | 20.9 | 9.2 | | | | |
| ~N270 + Deamid | 16.4 | 25.1 | 23.2 | 16.6 | 15.9 | 24.9 | 23.5 | 16.1 | 0.2 | | | |
| ~N304 + Deamid | 2.6 | 2.9 | 2.8 | 1.3 | 2.5 | 2.8 | 2.9 | 1.3 | 16.6 | 10.3 | | |
| ~N314 + Deamid | | | | | | | | | 6.5 | | | |
| N319 + Deamid | 0.3 | 2.8 | 2.8 | 0.2 | | 2.9 | 2.8 | 0.2 | | | | |
| N329 + Deamid | 72.7 | 85.6 | 89.1 | 86.8 | 71.0 | 87.2 | 88.7 | 84.7 | 85.5 | 79.4 | 78.9 | 91.8 |
| N336 + Deamid | | 30.8 | 9.3 | 100.0 | | 31.0 | 9.2 | 95.7 | | | | |
| ~N409 + Deamid | 21.3 | 22.9 | 23.9 | 24.0 | 22.0 | 23.4 | 24.7 | 24.2 | | | | |
| N452 + Deamid | 98.8 | 99.7 | 99.2 | 100.0 | 98.9 | 97.3 | 98.1 | 95.2 | 98.2 | 68.7 | 67.4 | 49.4 |
| N477 + Deamid | 4.4 | 4.3 | 4.3 | 2.6 | 4.5 | 4.4 | 4.3 | 2.6 | | | 0.8 | |
| N512 + Deamid | 97.5 | 97.9 | 95.3 | 95.7 | 92.2 | 91.8 | 99.2 | 96.1 | 99.7 | 98.2 | 87.9 | 75.7 |
| ~N515 + Deamid | 8.2 | 21.0 | 16.0 | | 8.3 | 21.0 | 16.5 | 0.0 | 2.5 | 3.0 | | 15.1 |
| ~Q599 + Deamid | 4.0 | 15.4 | 10.1 | 13.6 | 4.0 | 15.5 | 10.0 | 13.8 | 15.8 | | | |
| N628 + Deamid | 5.3 | | 5.6 | | 5.4 | 0.0 | 5.4 | 0.0 | | | | |
| N651 + Deamid | 0.9 | 1.6 | 1.6 | | | | | | 0.5 | | | |
| N663 + Deamid | 3.4 | | 3.5 | 3.7 | 3.4 | 0.0 | 3.4 | 3.6 | | | | |
| N709 + Deamid | 0.6 | 0.8 | 20.2 | 0.6 | 0.6 | 0.8 | 19.8 | 0.6 | 0.3 | 1.3 | 0.1 | 0.2 |
| N735 | | | | | | | | | 25.0 | 42.7 | | 21.7 |
| +Acetylation (Ac): | | | | | | | | | | | | |
| K332 + Ac | | | | 100.0 | | | | | | | | |
| ~K693 + Ac | 13.0 | | 13.5 | | | | | | | | | |
| ~K666 + Ac | | | | 93.8 | | | | | | | | |
| ~K68 + Ac | | 59.2 | | | | | | | | | | |
| +Isomerization (Iso): | | | | | | | | | | | | |
| D97 + Iso | 0.5 | 0.4 | 0.4 | 0.2 | 0.5 | | 0.4 | 0.2 | | | | |
| D107 + Iso | | 0.3 | | 0.3 | | 0.3 | | | | | | |
| D384 + Iso | 0.8 | | | | 0.9 | | | | | | | |
| +Phosphorylation (Phos) | | | | | | | | | | | | |
| S149 + Phos | 5.8 | 5.7 | 5.2 | 9.8 | 5.7 | 5.9 | 5.2 | 9.9 | | | | |
| ~S499 + Phos | | | | 30.6 | | | | | | | | |
| ~T569 + Phos | 0.9 | | | | | | | | | | | |
| ~S586 + Phos | | 3.6 | | | | | | | | | | |
| +Oxidation | | | | | | | | | | | | |
| ~W23 + Oxi | | 4.7 | 5.5 | | | 4.8 | 5.5 | | | | | |
| W247 + Oxi | 1.5 | 0.4 | 0.7 | | 1.4 | | | | | | | |
| W247 + Oxi to kynurenine | | 0.1 | | | | 0.1 | | | | | | |
| W306 + Oxi | 0.7 | 0.9 | 1.6 | 1.8 | 0.7 | 1.0 | 1.6 | 1.8 | | | | |
| W306 + Oxidation | | | 0.3 | | | | 0.3 | | | | | |

-continued

| | | | | | | | | |
|---|---|---|---|---|---|---|---|---|
| to kynurenine | | | | | | | | |
| M404 + Oxi | 0.1 | | 0.2 | | 0.1 | | 0.2 | |
| M436 + Oxi | 4.9 | | 10.2 | 23.0 | 4.8 | | 10.2 | 22.6 |
| ~M518 + Oxi | 29.9 | | 1.5 | 10.6 | 29.9 | | 1.5 | 10.5 |
| ~M524 + Oxi | 18.8 | 31.6 | 52.7 | | 18.4 | 31.1 | 52.5 | 14.2 |
| M559 + Oxi | 19.0 | 21.6 | 19.6 | 20.9 | 19.6 | 21.3 | 20.1 | 20.9 |
| ~M605 + Oxi | 12.2 | 15.2 | | | 12.8 | 14.8 | | |
| W619 + Oxi | 1.0 | | 0.6 | 1.5 | 1.0 | | 0.6 | 1.5 |
| W619 + Oxidation | | | 20.3 | | | | | |
| ~M640 + Oxi | 23.5 | 64.2 | 24.6 | | 22.4 | 21.1 | 25.6 | |
| W695 + Oxi | 0.3 | | 0.4 | 0.4 | 0.3 | | 0.4 | 0.4 |
| +Amidation | | | | | | | | |
| ~D297 + Amidation | | 72.9 | | 73.3 | | | | |

In the case of the AAVhu68 capsid protein, 4 residues (N57, N329, N452, N512) routinely display levels of deamidation >70% and it most cases >90% across various lots. Additional asparagine residues (N94, N253, N270, N304, N409, N477, and Q599) also display deamidation levels up to ~20% across various lots. The deamidation levels were initially identified using a trypsin digest and verified with a chymotrypsin digestion.

Accordingly, AAV comprising AAVhu68 capsid proteins can include a heterogeneous population of capsid proteins because the AAV can contain AAVhu68 capsid proteins displaying different levels of deamidation. The heterogenous population of AAVhu68 vp1 proteins having various levels of deamidation can be vp1 proteins produced by expression from a nucleic acid sequence which encodes the predicted amino acid sequence of 1 to 736 of SEQ ID NO:2, vp1 proteins produced from SEQ ID NO: 1, or vp1 proteins produced from a nucleic acid sequence at least 70% identical to SEQ ID NO:1 which encodes the predicted amino acid sequence of 1 to 736 of SEQ ID NO:2. The heterogenous population of AAVhu68 vp2 proteins having various levels of deamidation can be vp2 proteins produced by expression from a nucleic acid sequence which encodes the predicted amino acid sequence of at least about amino acids 138 to 736 of SEQ ID NO:2, vp2 proteins produced from a sequence comprising at least nucleotides 412 to 2211 of SEQ ID NO:1, or vp2 proteins produced from a nucleic acid sequence at least 70% identical to at least nucleotides 412 to 2211 of SEQ ID NO:1 which encodes the predicted amino acid sequence of at least about amino acids 138 to 736 of SEQ ID NO:2. The heterogenous population of AAVhu68 vp3 proteins having various levels of deamidation can be vp3 produced by expression from a nucleic acid sequence which encodes the predicted amino acid sequence of at least about amino acids 203 to 736 of SEQ ID NO:2, vp3 proteins produced from a sequence comprising at least nucleotides 607 to 2211 of SEQ ID NO: 1, or vp3 proteins produced from a nucleic acid sequence at least 70% identical to at least nucleotides 607 to 2211 of SEQ ID NO:1 which encodes the predicted amino acid sequence of at least about amino acids 203 to 736 of SEQ ID NO:2.

Adult Rhesus macaques were ICM-administered AAVhu68.CB7.CI.eGFP.WPRE.rBG ($3.00\times10^{13}$ GC) and necropsied 28 days later to assess vector transduction. Transduction of AAVhu68 was observed in widespread areas of the brain (data not shown). Thus, the AAVhu68 capsid provides the possibility of cross-correction in the CNS.

Example 2: Manufacturing—Components and Materials

Vectors are constructed from cis-plasmids containing a coding sequence for human GLB1 expressed from the chicken beta actin promoter with a cytomegalovirus enhancer (CB7) [SEQ ID NO: 10], human elongation initiation factor 1 alpha promoter (EF1a) [SEQ ID NO: 11] or human ubiquitin C promoter (UbC) [SEQ ID NO: 9] (1229 bp, GenBank #D63791.1)] flanked by AAV2 inverted terminal repeats. Various coding sequences for human GLB1 [aa sequence of SEQ ID NO: 4] are constructed. The wild-type sequence is reproduced in SEQ ID NO: 5. Various engineered GLB1 coding sequences were generated and are provided in SEQ ID NO: 6, 7, or 8.

The vectors are packaged in an AAV serotype hu68 capsid by triple transfection of adherent HEK 293 cells and purified by iodixanol gradient centrifugation as previously described in Lock, M., et al. Rapid, Simple, and Versatile Manufacturing of Recombinant Adeno-Associated Viral Vectors at Scale. Human Gene Therapy 21, 1259-1271 (2010). The AAV serotype Hu68 capsid was described in WO2018/160582 which is incorporated by reference in its entirety herein.

More particularly, AAVhu68.GLB1 are produced by triple plasmid transfection of human HEK293 WCB cells with: 1) the AAV cis vector genome plasmid, 2) the AAV trans plasmid termed pAAV2/hu68.KanR encoding the AAV2 replicase (rep) and AAVhu68 capsid (cap), and 3) the helper adenovirus plasmid termed pAdAF6.KanR.

Description of Sequence Elements of the AAV cis Vector Genome Plasmid:

- Inverted Terminal Repeat (ITR): The ITRs are identical, reverse complementary sequences derived from AAV2 (130 bp, GenBank #NC001401) that flank all components of the vector genome. The ITR sequences function as both the origin of vector DNA replication and the packaging signal of the vector genome, when AAV and adenovirus helper functions are provided in trans. As such, the ITR sequences represent the only cis sequences required for vector genome replication and packaging.
- Promoter: Regulatory element derived from human ubiquitin C (UbC) promoter: This ubiquitous promoter (1229 bp, GenBank #D63791.1) was selected to drive transgene expression in any CNS cell type.
- Coding sequence: GLB1 gene, based on maximized human codon usage, encodes beta-galactosidase. GLB1 enzyme catalyzes the hydrolysis of β-linked galactose from gangliosides (2034 bp, 677 aa, Genbank #AAA51819.1, EC3.2.1.23).
- Chimeric intron (CI)—a hybrid intron consisting of a human beta-globin splice donor and immunoglobulin G (IgG) splice acceptor elements
- SV40 polyadenylation signal (239 bp, Genbank #KP659662.1): The SV40 polyadenylation signal facilitates efficient polyadenylation of the gene mRNA in cis. This element functions as a signal for transcriptional termination, a specific cleavage event at the 3' end of the nascent transcript and addition of a long polyadenyl tail.

AAVhu68 Trans Plasmid: pAAV2/hu68.KanR

The AAV2/hu68 trans plasmid pAAV2/hu68.KanR was constructed in the laboratory of Dr. James M. Wilson at the University of Pennsylvania. The AAV2/hu68 trans plasmid encodes the four wild type (WT) AAV2 replicase (Rep) proteins required for the replication and packaging of the AAV vector genome. The AAV2/hu68 trans plasmid also encodes three WT AAVhu68 virion protein capsid (Cap) proteins, which assemble into a virion shell of the AAV serotype hu68 to house the AAV vector genome. The AAVhu68 sequence was obtained from human heart tissue DNA.

Figure 1A:
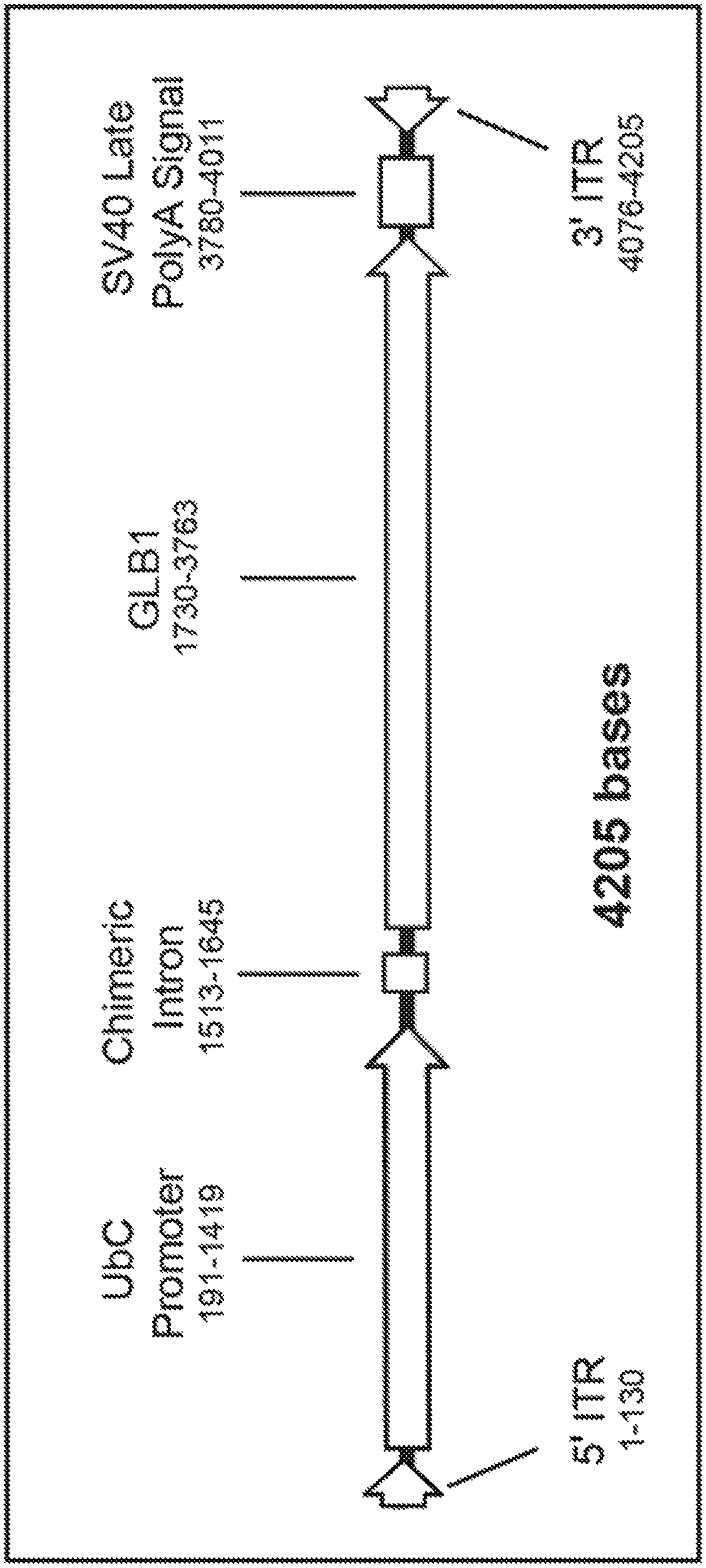
FIG. 1A provides a schematic of an AAV vector genome showing 5' ITR, human ubiquitin C (UbC) promoter, chimeric intron, GLB1 gene encoding human β-galactosidase (β-gal), SV40 late polyA signal, and 3' ITR (i.e., "AAVhu68.Ubc.hGLB1co.SV40").
Figure 1B:
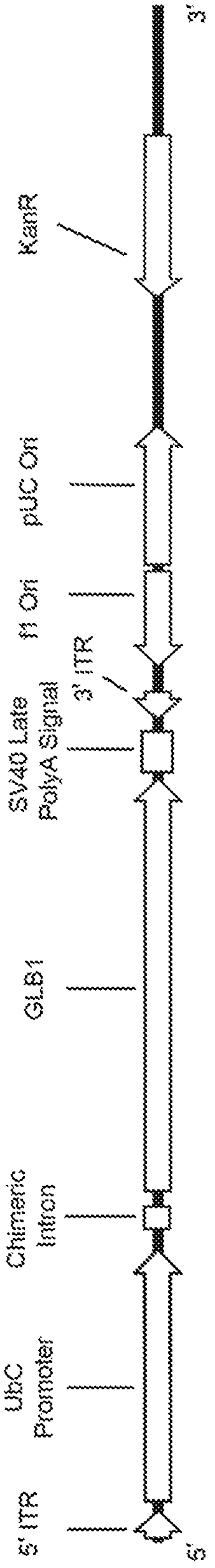
FIG. 1B provides a schematic of a cis-plasmid containing an AAV vector genome carried by the cis plasmid, pAAV.UbC.hGLB1co.SV40.KanR. GLB1, β-galactosidase; ITR, inverted terminal repeats; KanR, kanamycin resistance; Ori, origin of replication; PolyA, polyadenylation; and UbC, ubiquitin C.
Figure 1C:
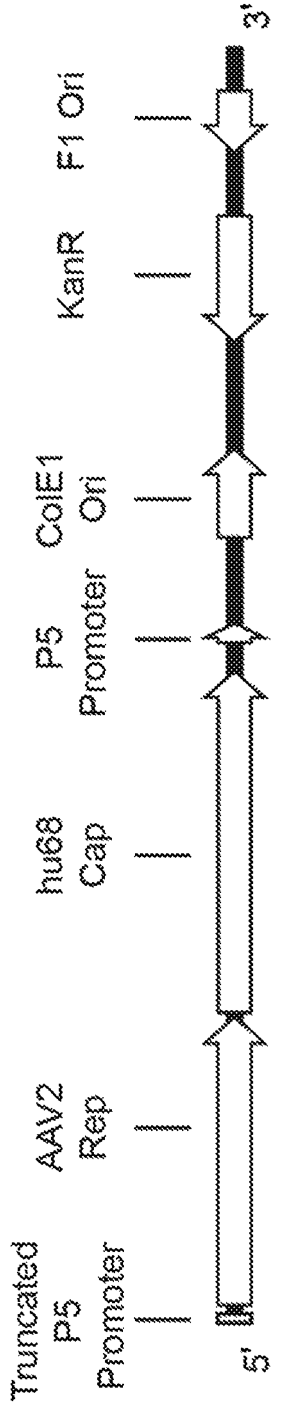
FIG. 1C provides a schematic of a trans-plasmid comprising a coding sequence for a full-length AAV2 replicase (AAV2 Rep) encoding four proteins and the AAVhu68 VP1 capsid gene (which encodes VP1, VP2 and VP3 proteins). AAV2, adeno-associated virus serotype 2; AAVhu68, adeno-associated virus serotype hu68; Cap, capsid; KanR, kanamycin resistance; Ori, origin of replication; and Rep, replicase.

To create the AAV2/hu68 trans plasmid, the AAV9 cap gene from plasmid pAAV2/9n which encodes the wild type AAV2 rep and AAV9 cap genes on a plasmid backbone derived from the pBluescript KS vector was removed and replaced with the AAVhu68 cap gene. The ampicillin resistance (AmpR) gene was also replaced with the kanamycin resistance (KanR) gene, yielding pAAV2/hu68.KanR. The AAV p5 promoter, which normally drives rep expression, is moved from the 5' end of rep to the 3' end of cap, leaving behind a truncated p5 promoter upstream of rep. This truncated promoter serves to down-regulate expression of rep and, consequently, maximize vector production (FIG. 1C). All component parts of the plasmid have been verified by direct sequencing.

pAdDeltaF6(KanR) Adenovirus Helper Plasmid

Plasmid pAdDeltaF6(KanR) is 15,774 bp in size. The plasmid contains the regions of adenovirus genome that are important for AAV replication, namely E2A, E4, and VA RNA (the adenovirus E1 functions are provided by the HEK293 cells), but does not contain other adenovirus replication or structural genes. The plasmid does not contain the cis elements critical for replication such as the adenoviral inverted terminal repeats and therefore, no infectious adenovirus is expected to be generated. The plasmid was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 kb to 12 kb. Finally, the ampicillin resistance gene was replaced by the kanamycin resistance gene to create pAdeltaF6 (KanR). The E2, E4 and VAI adenoviral genes which remain in this plasmid, along with E1, which is present in HEK293 cells, are necessary for AAV vector production.

AAVhu68.GM1 are manufactured by transient transfection of HEK293 cells followed downstream purification. A manufacturing process flow diagram is shown in FIGS. 12A—12B. The major reagents entering into the preparation of the product are indicated on the left side of the diagram and in-process quality assessments are depicted on the right side of the diagram. A description of each production and purification step is also provided.

Cell Culture and Harvest: The cell culture and harvest manufacturing process comprise four main manufacturing steps: cell seeding and expansion, transient transfection, vector harvest and vector clarification (FIG. 12A).

Cell Seeding and Expansion: A fully characterized HEK293 cell line is used for the production process.

Transient Transfection: Following approximately 4 days of growth (DMEM media+10% FBS), cell culture media is replaced with fresh, serum-free DMEM media and the cells are transfected with the 3 production plasmids using a polyethyleneimine (PEI)-based transfection method. Initially, a DNA/PEI mixture is prepared containing cis (vector genome) plasmid, trans (rep and cap genes) plasmid, and helper plasmid in a ratio with GMP-grade PEI (PEIPro HQ, PolyPlus Transfection SA). This plasmid ratio was determined to be optimal for AAV production in small-scale optimization studies. After mixing well, the solution is allowed to sit at room temperature for up to 25 minutes, then added to serum-free media to quench the reaction, and finally added to the iCELLis bioreactor. The reactor is temperature- and DO-controlled, and cells are incubated for 5 days.

Vector Harvesting: Transfected cells and media are harvested from the PALL iCELLis bioreactor using disposable bioprocess bags by aseptically pumping the medium out of the bioreactor. Following the harvest, detergent, endonuclease, and $MgCl_2$ (a co-factor for the endonuclease) are added to release vector and digest unpackaged DNA. The product (in a disposable bioprocess bag) is incubated at 37° C. for 2 hours in a temperature-controlled single-use mixer to provide sufficient time for enzymatic digestion of residual cellular and plasmid DNA present in the harvest as a result of the transfection procedure. This step is performed to minimize the amount of residual DNA in the final vector drug product (DP). Following incubation, NaCl is added to a final concentration of 500 mM to aid in the recovery of the product during filtration and downstream tangential flow filtration (TFF).

Vector Clarification: Cells and cellular debris are removed from the product using a pre-filter and depth filter capsule (1.2/0.22 μm) connected in series as a sterile, closed tubing and bag set that is driven by a peristaltic pump. Clarification assures that downstream filters and chromatography columns are protected from fouling and bioburden reduction filtration ensures that, at the end of the filter train, any bioburden potentially introduced during the upstream production process is removed before downstream purification.

Purification Process: The purification process comprises four main manufacturing steps: concentration and buffer exchange by TFF, affinity chromatography, anion exchange chromatography, and concentration and buffer exchange by TFF. These process steps are depicted in the overview process diagram (FIG. 12B). General descriptions of each of these processes are provided below Large-Scale Tangential Flow Filtration: Volume reduction (20-fold) of the clarified product is achieved by TFF using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface, preventing membrane pore fouling and product loss through binding to the membrane. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This diafiltration results in a modest purification of the clarified product, but also achieves buffer exchange compatible with the subsequent affinity column chromatography step. Accordingly, we utilize a 100 kDa, PES membrane for concentration that is then diafiltered with a minimum of 4 diavolumes of a buffer composed of 20 mM Tris pH 7.5 and 400 mM NaCl. The diafiltered product is then further clarified with a 1.2/0.22 μm depth filter capsule to remove any precipitated material.

Affinity Chromatography: The diafiltered product is applied to a Poros' Capture-Select™ AAV affinity resin (Life Technologies) that efficiently captures the AAVhu68 serotype. Under these ionic conditions, a significant percentage of residual cellular DNA and proteins flow through the column, while AAV particles are efficiently captured. Following application, the column is treated with 5 volumes of a low salt endonuclease solution (250 U/mL endonuclease, 20 mM Tris pH 7.5 and 40 mM NaCl, 1.5 mM $MgCl_2$) to remove any remaining host cell and plasmid nucleic acid. The column is washed to remove additional feed impurities followed by a low pH step elution (400 mM NaCl, 20 mM Sodium Citrate, pH 2.5) that is immediately neutralized by collection into a 1/10th volume of a neutralization buffer (200 mM Bis Tris Propane, pH 10.2).

Anion Exchange Chromatography: To achieve further reduction of in-process impurities including empty AAV particles, the Poros AAV elution pool is diluted 50-fold (20 mM Bis Tris Propane, 0.001% Pluronic F68, pH 10.2) to reduce ionic strength and enable binding to a CIMultus™ QA monolith matrix (BIA Separations). Following a low-salt wash, vector product is eluted using a 60 column volume (CV) NaCl linear salt gradient (10-180 mM NaCl). This shallow salt gradient effectively separates capsid particles without a vector genome (empty particles) from particles containing vector genome (full particles) and results in a preparation enriched for full particles. The full particle peak eluate is collected, neutralized and diluted 20-fold in 20 mM Bis Tris Propane, 0.001% Pluronic F68, pH 10.2 and reapplied to the same column, which has been cleaned in place. The 10-180 mM NaCl salt gradient is reapplied and the appropriate full particle peak is collected. The peak area is assessed and compared to previous data for determination of the approximate vector yield.

Concentration and Buffer Exchange by Hollow Fiber Tangential Flow Filtration: The pooled anion exchange intermediate is concentrated, and buffer exchanged using TFF. In this step, a 100 kDa membrane hollow fiber TFF membrane is used. During this step, the product is brought to a target concentration and then buffer exchanged into the Intrathecal Final Formulation Buffer (ITFFB, i.e., artificial CSF with 0.001% Pluronic® F68). The product is sterile-filtered (0.22 μm), stored in sterile containers, and frozen at <−60° C. in a quarantine location until release for final fill.

Final Fill: The frozen product is thawed, pooled, and adjusted to the target concentration (dilution or concentrating step via TFF) using the final formulation buffer. The product is terminally filtered through a 0.22 μm filter and filled into sterile West Pharmaceutical's Crystal Zenith (cyclic olefin polymer) vials and stoppers with crimp seals at a fill volume to be determined. Vials are individually labeled. Labeled vials are stored at ≤60° C.

Example 3

An optimized AAV vector expressing human β-gal was developed and the impact of vector administration into the CSF was evaluated on brain enzyme activity, lysosomal storage lesions and neurological signs using a murine disease model.

A. Materials and Methods:

Animal procedures: All animal procedures were approved by the Institutional Animal Care and Use Committee of the University of Pennsylvania. GLB1 knockout mice were obtain from RIKEN BioResource Research Center. Mice were maintained as heterozygous carriers on a C57BL/6J background. For ICV injections, vectors were diluted in sterile phosphate buffered saline (Gibco) to a volume of 5 μL, and injections were performed freehand on isoflurane anesthetized mice using a custom gastight syringe (Hamilton) and a cemented 10 mm 27-gauge needle, with plastic tubing attached to the needle base to limit penetration to a depth of 3 mm. Submandibular blood collection was performed on isoflurane anesthetized mice. Blood was collected in serum separator tubes, allowed to clot, and separated by centrifugation before aliquoting and freezing at ≤−60° C. At the time of necropsy, mice were sedated with ketamine and xylazine and CSF was collected by suboccipital puncture using a 32-gauge needle connected to polyethylene tubing. Euthanasia was performed by cervical dislocation. CSF, heart, lung, liver and spleen were immediately frozen on dry ice and stored at ≤−60° C. Brains were removed, and a coronal slice of the frontal lobe was collected and frozen for biochemical studies. The remaining brain was used for histological analysis.

Vectors were generated as described in Examples 1 and 2.

Empty:Full Particle Ratio: Vector samples are loaded into cells with two-channel charcoal-epon centerpieces with 12 mm optical path length. The supplied dilution buffer is loaded into the reference channel of each cell. The loaded cells are then placed into an AN-60Ti analytical rotor and loaded into a Beckman-Coulter ProteomeLab XL-I analytical ultracentrifuge equipped with both absorbance and RI detectors. After full temperature equilibration at 20° C., the rotor is brought to the final run speed of 12,000 rpm. Absorbance at 280 nm scans are recorded approximately every 3 minutes for approximately 5.5 hours (110 total scans for each sample). The raw data is analyzed using the c(s) method and implemented in the analysis program SEDFIT. The resultant size distributions are graphed and the peaks integrated. The percentage values associated with each peak represent the peak area fraction of the total area under all peaks and are based upon the raw data generated at 280 nm; many labs use these values to calculate empty:full particle ratios. However, because empty and full particles have different extinction coefficients at this wavelength, the raw data can be adjusted accordingly. The ratio of the empty particle and full monomer peak values both before and after extinction coefficient adjustment is used to determine the empty:full particle ratio.

Replication-competent AAV Assay: A sample is analyzed for the presence of replication-competent AAV2/hu68 (rcAAV) that could potentially arise during the production process. The cell-based component consists of inoculating monolayers of HEK293 cells (P1) with dilutions of the test sample and wild type (WT) human adenovirus type 5 (Ad5). The maximal amount of the product tested is $1.0\times10^{10}$ GC of the vector product. Due to the presence of adenovirus, rcAAV amplifies in the cell culture. After 2 days, a cell lysate is generated and Ad5 is heat-inactivated. The clarified lysate is then passed onto a second round of cells (P2) to enhance sensitivity (again in the presence of Ad5). After 2 days, a cell lysate is generated, and Ad5 is heat-inactivated. The clarified lysate is then passed onto a third round of cells (P3) to maximize sensitivity (again in the presence of Ad5). After 2 days, cells are lysed to release DNA, which is then subjected to qPCR to detect AAVhu68 cap sequences. Amplification of AAVhu68 cap sequences in an Ad5-dependent manner indicates the presence of rcAAV. The use of a AAV2/hu68 surrogate positive control containing AAV2 rep and AAVhu68 cap genes enables the limit of detection of the assay to be determined (0.1, 1, 10, and 100 IU). Using a serial dilution of rAAV ($1.0\times10^{10}$, $1.0\times10^{9}$, $1.0\times10^{8}$, and $1.0\times10^{7}$ GC), the approximate quantity of rcAAV present in the test sample can be quantitated.

In Vitro Potency: To relate the ddPCR GC titer to gene expression, an in vitro relative potency bioassay is performed. Briefly, cells are plated in a 96-well plate and incubated at 37° C./5% $CO_2$ overnight. The next day, cells are infected with serially diluted AAV vector and are incubated at 37° C./5% $CO_2$ for up to 3 days. Cell supernatant is collected and analyzed for β-gal activity based on cleavage of a fluorogenic substrate.

Total Protein, Capsid Protein, Protein Purity and Capsid Protein Ratio: Vector samples are first quantified for total protein against a bovine serum albumin (BSA) protein standard curve using a bicinchoninic acid (BCA) assay. The determination is made by mixing equal parts of sample with a Micro-BCA reagent provided in the kit. The same procedure is applied to dilutions of a BSA standard. The mixtures are incubated at 60° C. and absorbance measured at 562 nm. A standard curve is generated from the standard absorbance of the known concentrations using a 4-parameter fit. Unknown samples are quantified according to the 4-parameter regression. To provide a semi-quantitative determination of rAAV purity, the samples are normalized for genome titer, and $5.0\times10^{9}$ GC is separated by sodium dodecyl sulfate polyacrylamide gel electrophoresis (SDS-PAGE) under reducing conditions. The SDS-PAGE gel is then stained with SYPRO Ruby dye. Any impurity bands are quantified by densitometry. Stained bands that appear in addition to the three AAV-specific proteins (VP1, VP2, and VP3) are considered protein impurities. The impurity mass percent as well as approximate molecular weight of contaminant bands are reported. The SDS-PAGE gel is also used to quantify the VP1, VP2, and VP3 proteins and determine their ratio.

Enzyme activity assays: Tissues were homogenized in 0.9% NaCl, pH 4.0 use a steel bead homogenizer (TissueLyzer, Qiagen). After 3 freeze-thaw cycles, samples were clarified by centrifugation and protein content was quantified by BCA assay. Serum samples were used directly for enzyme assays. For the β-gal activity assay, 1 μL sample was combined with 99 μL of 0.5 mM 4-Methylumbelliferyl β-D-galactopyranoside (Sigma M1633) in 0.15 M NaCl, 0.05% Triton-X100, 0.1 M sodium acetate, pH 3.58. The reaction was incubated at 37° C. for 30 minutes, then stopped by addition of 150 μL of 290 mM glycine, 180 mM sodium citrate, pH 10.9. Fluorescence was compared to standard dilutions of 4 MU. β-gal activity is expressed as nmol 4 MU liberated per hour per mg of protein (tissues) or per ml of serum or CSF. The HEX assay was performed in the same manner as the β-gal activity assay using 1 mM 4-Methylumbelliferyl N-acetyl-β-D-glucosaminide (Sigma M2133) as substrate and sample volumes of 1 μL for tissue lysates and 2 μL for serum.

Histology: Brains were fixed overnight in 4% paraformaldehyde, equilibrated in 15% and 30% sucrose, then frozen in OCT embedding medium. Cryosections were stained with filipin (Sigma, 10 μg/mL) or antibodies against GFAP or LAMP1.

Anti-β-gal antibody ELISA: High binding polystyrene ELISA plates were coated overnight with 100 μL per well of recombinant human β-gal (R&D Systems) at a concentration of 1 μg/mL in PBS. Plates were washed and blocked for 2 hours at room temperature with 2% bovine serum albumin in PBS. Duplicate wells were incubated with serum samples diluted 1:1,000 in PBS for one hour at room temperature. Plates were washed, incubated for one hour with a horseradish peroxidase-conjugated anti-mouse IgG polyclonal antibody diluted 1:5,000 in blocking solution, and developed using TMB substrate.

Gait analysis: Gait analysis was performed using the CatWalk XT system (Noldus) according to the manufacturer's instructions. Mice were tested on two consecutive days. At least 3 complete trials were acquired for each animal on each day of testing. Trials lasting more than 5 seconds, or trials in which the animal did not traverse the entire length of the apparatus before stopping or turning around were excluded from analysis.

Figure 2A:
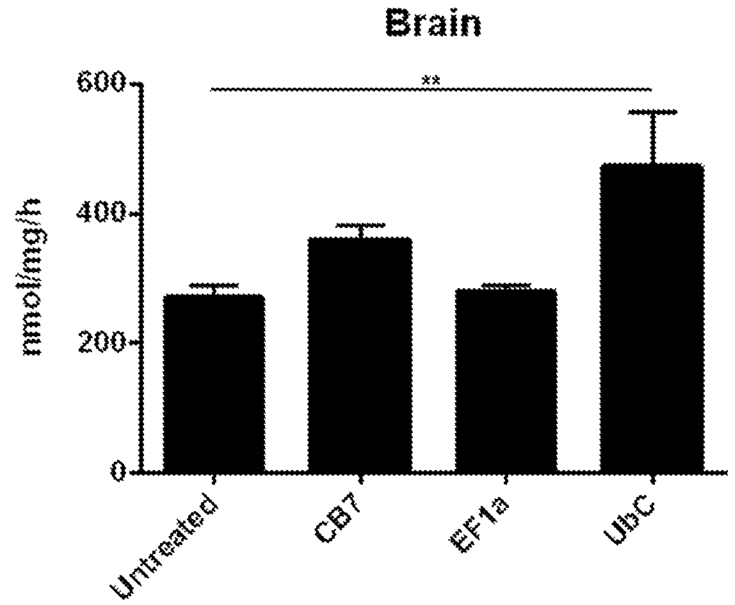
FIGS. 2A and 2B illustrate β-gal activity in brain and cerebrospinal fluid (CSF), respectively, of wild-type mice treated with rAAVhu68.GLB1 expressing human β-gal using different promoters. Wild-type mice were treated with a single ICV injection of rAAVhu68.GLB1 expressing human GLB1 from a CB7, EF1a or UbC promoter (n=10 per group). Untreated wild-type mice (n=5) served as controls. Brain (frontal cortex) and CSF were collected 14 days after rAAVhu68.GLB1 administration, and β-gal activity was measured using a fluorogenic substrate. *$p<0.05$, $p<0.01$, *$p<0.001$, Kruskal-Wallis test followed by Dunn's test.
Figure 2B:
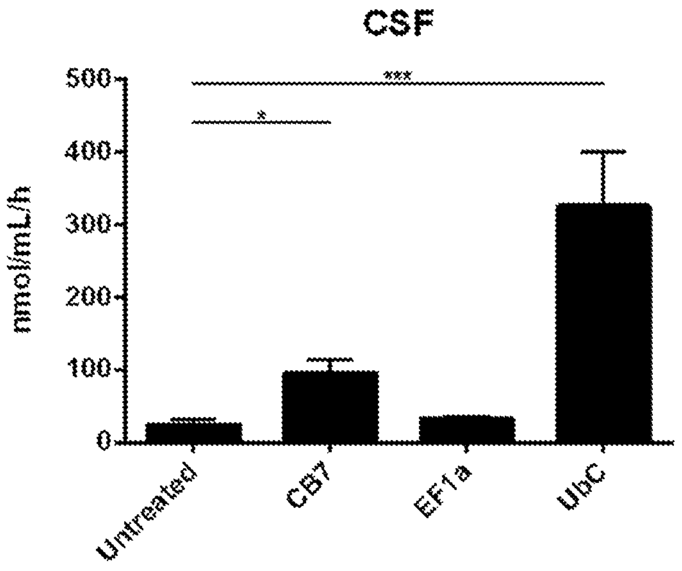

B. Results:

Transgene cassettes were designed consisting of a human GLB1 cDNA driven by chicken beta actin promoter with a cytomegalovirus enhancer (CB7), human elongation initiation factor 1 alpha promoter (EF1a) or human ubiquitin C promoter (UbC). Each cassette was packaged in an AAVhu68 capsid, and a single dose of $10^{11}$ genome copies (GC) was administered by intracerebroventricular (ICV) injection to wild-type mice. Two weeks after injection, β-gal activity was measured in brain and CSF (FIGS. 2A—2B). The vector carrying the UbC promoter achieved statistically significant elevations in β-gal activity in both the brain and CSF, with enzyme activity nearly 2-fold greater than that of untreated wild-type mice in the brain, and 10-fold greater in CSF. The AAVhu68.UbC.hGLB1 vector was therefore selected for further studies.

Efficacy of the optimized vector was assessed in the $GLB1^{-/-}$ mouse model. Mouse models of GM1 gangliosidosis have been developed by targeted insertion of neomycin resistance cassettes into the $6^{th}$ and/or $15^{th}$ exons of the GLB1 gene. Hahn, C. N., et al. Generalized CNS disease and massive GM1-ganglioside accumulation in mice defective in lysosomal acid beta-galactosidase. Human molecular genetics 6, 205-211 (1997) and Matsuda, J., et al. Beta-galactosidase-deficient mouse as an animal model for GM1-gangliosidosis. Glycoconjugate journal 14, 729-736 (1997). Similar to infantile GM1 gangliosidosis patients, these mice express no functional β-gal and exhibit rapid accumulation of GM1 ganglioside in the brain. Brain GM1 storage is already apparent in the first weeks of life, and by 3 months of age, $GLB1^{-/-}$ mice have a similar degree of GM1 accumulation in the brain to that of an 8-month-old infantile GM1 patient (Hahn 1997, as cited above). The clinical phenotype of the $GLB1^{-/-}$ mouse most closely models that of infantile GM1 gangliosidosis, with motor abnormalities appearing by 4 months of age and severe neurological symptoms (e.g., ataxia or paralysis) necessitating euthanasia presenting by 10 months of age (Hahn 1997; Matsuda 1997, as cited above). The $GLB1^{-/-}$ mouse model does not exhibit any peripheral organ involvement, unlike infantile GM1 patients who often develop bone deformities and hepatosplenomegaly (Hahn 1997; Matsuda 1997, as cited above. The $GLB1^{-/-}$ mouse is therefore a representative model of the neurological features of infantile GM1 gangliosidosis, but not the systemic disease manifestations.

$GLB1^{-/-}$ mice were treated at one month of age, and observed until four months of age, when they would typically develop marked gait abnormalities associated with brain GM1 levels similar to those of infantile GM1 gangliosidosis patients with advanced disease (Matsuda 1997, as cited above). $GLB1^{-/-}$ mice were treated with a single ICV injection of $1.0\times10^{11}$ genome copies (GC) of AAVhu68.UbC.hGLB1 (n=15) or vehicle (n=15). A group of heterozygous ($GLB1^{-/-}$) mice treated with vehicle (n=15) served as normal controls. Serum was collected on the day of injection (Day 0) and on Days 10, 28, 60 and 90. Motor function was assessed using the CatWalk XT gait analysis system (Noldus) 90 days post treatment, after which animals were euthanized and tissues collected for histological and biochemical analysis.

Figure 3A:
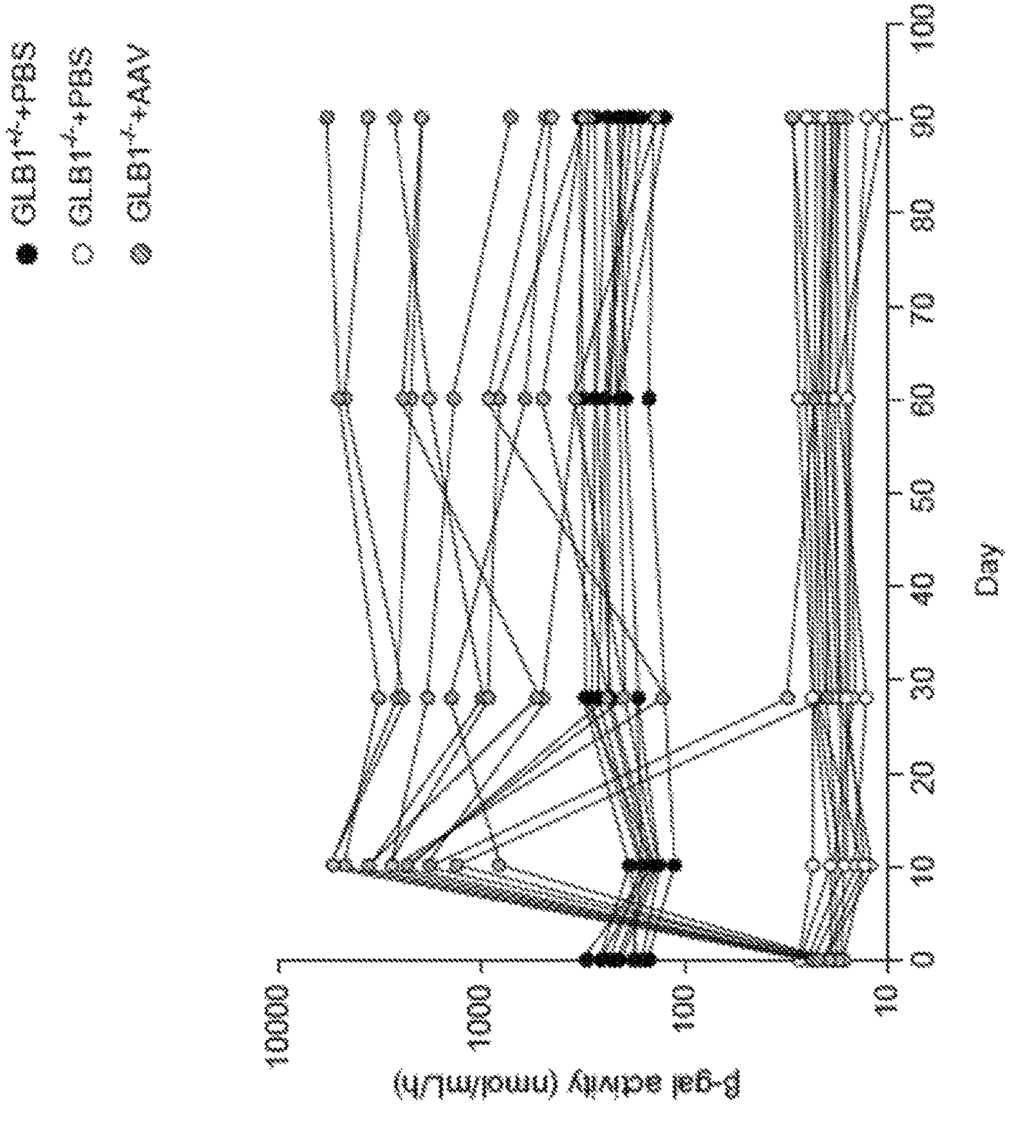

One AAV-treated mouse died during the ICV injection procedure. All other mice survived until the 90-day study endpoint. AAV delivery into the CSF has been shown to result in vector distribution in the peripheral blood and significant hepatic transduction. (Hinderer, C., et al. Intrathecal gene therapy corrects CNS pathology in a feline model of mucopolysaccharidosis I. Molecular therapy: the journal of the American Society of Gene Therapy 22, 2018-2027 (2014); Gray, S. J., Nagabhushan Kalburgi, S., McCown, T. J. & Jude Samulski, R. Global CNS gene delivery and evasion of anti-AAV-neutralizing antibodies by intrathecal AAV administration in non-human primates. Gene therapy 20, 450-459 (2013); Haurigot, V., et al. Whole body correction of mucopolysaccharidosis IIIA by intracerebrospinal fluid gene therapy. The Journal of clinical investigation (2013); Hinderer, C., et al. Widespread gene transfer in the central nervous system of cynomolgus macaques following delivery of AAV9 into the cisterna magna. Molecular therapy. Methods & clinical development 1, 14051 (2014); Hordeaux, J., et al. Toxicology Study of Intra-Cisterna Magna Adeno-Associated Virus 9 Expressing Human Alpha-L-Iduronidase in Rhesus Macaques. Molecular therapy. Methods & clinical development 10, 79-88 (2018)). $GLB1^{-/-}$ mice treated with AAVhu68.UbC.hGLB1 exhibited serum β-gal activity greater than that of heterozygous ($GLB1^{-/-}$) controls 10 days after vector administration (FIG. 3A). Serum antibodies against human j-gal were detectable in 5/15 mice treated with AAVhu68.UbC.hGLB1 by Day 90. Elevated serum β-gal activity persisted throughout the study for all but two mice, both of which developed antibodies against human β-gal (FIG. 6). Peripheral organs including the heart, lung, liver and spleen also exhibited elevated β-gal activity (FIGS. 3B-3E). Some animals that developed antibodies against the human transgene product had lower β-gal activity in peripheral organs.

CSF collected at the time of necropsy demonstrated β-gal activity exceeding that of heterozygous controls in $GLB1^{-/-}$ mice treated with AAVhu68.UbC.hGLB1 (FIG. 4B). β-gal activity in the brains of vector-treated mice was similar to heterozygous controls (FIG. 4A). Anti-β-gal antibodies did not appear to impact brain or CSF β-gal levels.

Correction of brain abnormalities was assessed using biochemical and histological assays. Lysosomal enzymes are frequently upregulated in the setting of lysosomal storage, an observation that has been confirmed in GM1 gangliosidosis patients (Van Hoof, F. & Hers, H. G. The abnormalities of lysosomal enzymes in mucopolysaccharidoses. European journal of biochemistry 7, 34-44 (1968)). Therefore, the activity of the lysosomal enzyme hexosaminidase (HEX) was measured in brain lysates. HEX activity was elevated in brain samples from vehicle-treated $GLB1^{-/-}$ mice and was normalized in vector-treated animals (FIG. 5).

Lysosomal storage lesions were evaluated by staining brain sections with filipin, a fluorescent molecule that binds to GM1 ganglioside, as well as immunostaining for the lysosomal-associated membrane 1 (protein LAMP1). Filipin also binds to unesterified cholesterol, though previous studies have demonstrated that filipin staining primarily reflects GM1 accumulation in $GLB1^{-/-}$ mice (Arthur, J. R., Heinecke, K. A. & Seyfried, T. N. Filipin recognizes both GM1 and cholesterol in GM1 gangliosidosis mouse brain. Journal of lipid research 52, 1345-1351 (2011)). Filipin staining revealed marked GM1 accumulation in neurons of the cortex, hippocampus and thalamus of vehicle-treated $GLB1^{-/-}$ mice which was normalized in mice treated with AAVhu68.UbC.hGLB1 (data not shown). LAMP1 immunohistochemistry demonstrated increased lysosomal membrane staining in the cortex and thalamus of $GLB1V^{-/-}$ mice, which was reduced in vector-treated mice (data not shown). Gliosis was assessed by staining for the astrocyte marker, glial fibrillary acidic protein (GFAP). Vector treated $GLB1^{-/-}$ mice exhibited markedly reduced astrogliosis in the thalamus compared to vehicle-treated controls (data not shown).

In order to evaluate neurological function in vector-treated $GLB1^{-/-}$ mice, gait analysis was performed at 4 months of age (3 months after vector or vehicle administration). Untreated $GLB1^{-/-}$ mice were previously noted to exhibit clinically apparent gait abnormalities by 3-4 months of age. Quantitative gait assessments performed using the CatWalk system on a cohort of untreated $GLB1^{-/-}$ mice and normal controls revealed a variety of abnormalities, including slower voluntary walking speed, differences in stride length, and the duration of some phases of the step cycle (FIGS. 7C and 7D). Due to the significantly slower walking speed of the $GLB1^{-/-}$ mice, interpretation of many of these apparent differences was complicated by the speed dependence of most gait parameters (FIGS. 8A and 8B) (Batka, R. J., et al. The need for speed in rodent locomotion analyses. Anatomical record (Hoboken, N.J.: 2007) 297, 1839-1864 (2014)). $GLB1^{-/-}$ mice also exhibited a consistent abnormality in the placement of the hind paws, which could be measured as an increased length of the hind paw prints (FIG. 7D). This abnormality was found to be independent of walking speed, consistent with previous reports (Batka, et al, as cited above), making it a useful gait signature to assess speed-independent gait dysfunction in $GLB1^{-/-}$ mice (FIGS. 8A and 8B). Tests conducted using the same cohort of mice on two consecutive days revealed that slower voluntary walking speed and increased hind print length are reproducible observations in untreated $GLB1^{-/-}$ mice (FIGS. 7A and 7B). Vehicle treated $GLB1^{-/-}$ mice exhibited similar gait abnormalities to those previously identified in untreated animals (FIGS. 7A-7G). Walking speed and print length were normalized in vector-treated $GLB1^{-/-}$ mice (FIGS. 7A-7G).

C. Discussion:

This study demonstrated decrease of neuronal storage lesions in $GLB1^{-/-}$ mice treated with an AAV vector at 4 weeks of age. This is one week after prominent brain storage lesions appear in this model (Hahn 1997, as cited herein). These results suggest that AAVhu68.hGLB1 administration into the CSF increases brain β-gal activity, reduces neuronal lysosomal storage lesions, and prevents neurological decline, and gene transfer may both prevent and reverse GM1 storage in the brain.

Example 4: Animal Models

A. Identification of the Minimum Effective Dose (MED) of AAVhu68.UbC.GLB1 in the $GLB1^{-/-}$ Mouse Model The impact of different doses of rAAVhu68.UbC.GLB1 was evaluated on CNS lesions and neurological signs in the $GLB1^{-/-}$ mouse model. Efficacy was assessed by serum enzyme activity, reduction of brain lesions, neurological signs measured by automated gait analysis (for example via CatWalk system) and a standardized neurological exam (for example, 9 point assessment of posture, motor function, sensation and reflexes) performed by a blinded reviewer, and survival. Safety analyses (including blood collection and analysis) were also performed. Four-week old GLB1$^{-/-}$ mice received one of 4 doses of rAAVhu68.UbC.GLB1 ($1.3\times10^{11}$ GC, $4.4\times10^{10}$ GC, $1.3\times10^{10}$ GC or $4.4\times10^{9}$ GC) or vehicle by ICV injection (n=24 per group). Heterozygous littermates treated with vehicle (n=24) served as normal controls.

Serum β-gal enzyme activity, gait analysis and neurological exam were performed on half of the animals for each group every 60 days while the body weights were measured at least every 30 days in an observation period of 120 days. Results are plotted as FIGS. 9A-9F and briefly described below.

Figure 9A:
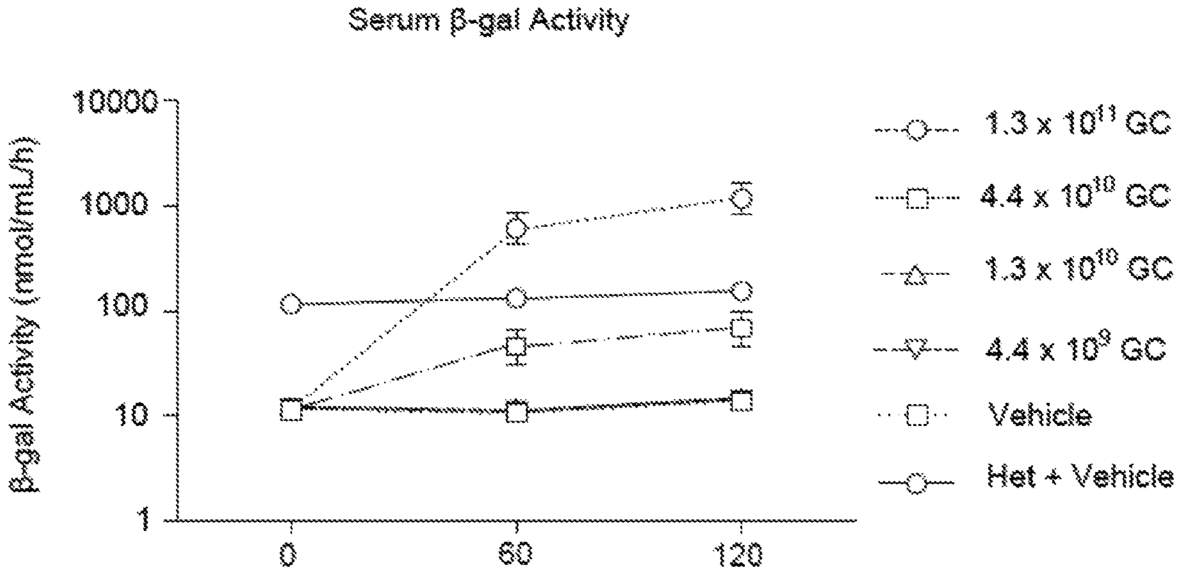
Figure 9B:
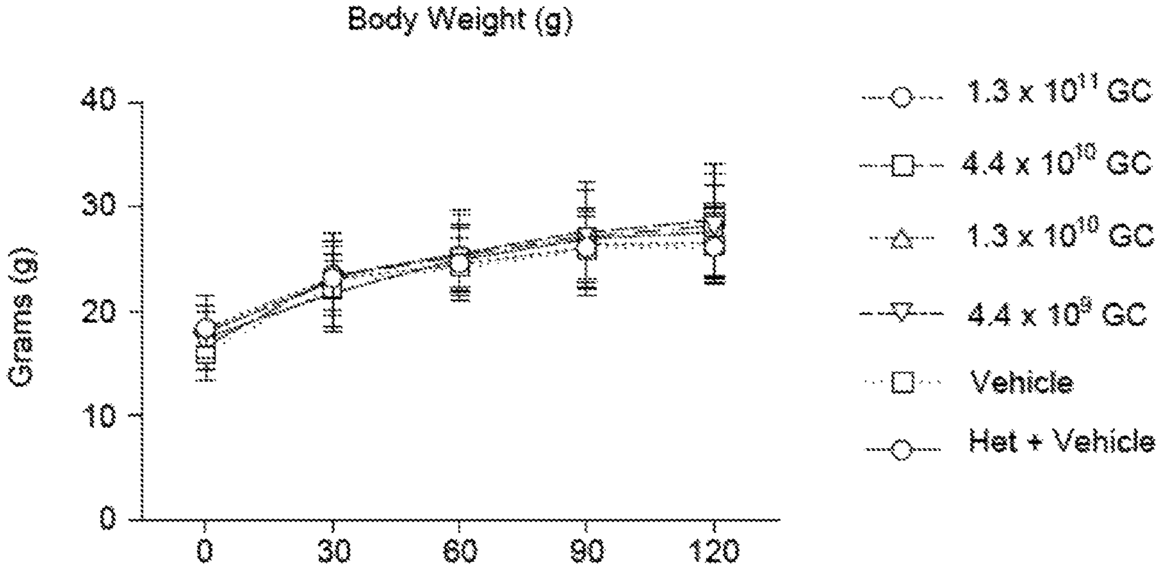

All treated mice appeared healthy, exhibiting normal weight gain. During the observation period, no significant differences in body weights among groups were detected (FIG. 9B).

Serum enzyme expression was consistent with the study discussed in Example 3. As shown in FIG. 9A, β-gal enzyme activity of the vehicle treated GLB1$^{-/-}$ mice (which served as a negative control) remained around 10 nmol/mL/hour while the positive control group (which are vehicle treated GLB1$^{-/-}$ mice) demonstrated an about 100 nmol/mL/h enzyme activity. Upon treatment with rAAVhu68.UbC.GLB1 at a dose of $4.4\times10^{10}$ GC per mouse, the β-gal enzyme activity increased significantly compared to the negative control on both Day 60 and Day 120. A higher dose of rAAVhu68.UbC.GLB1 at $1.3\times10^{11}$ GC per mouse resulted in a β-gal enzyme activity higher than the positive control on Day 60 with a further elevation on Day 120.

Figure 9C:
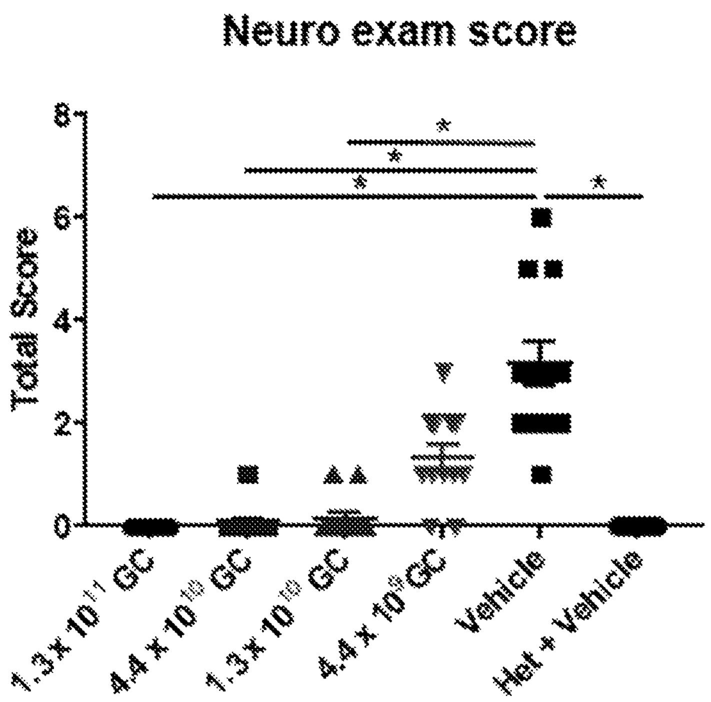
Figure 9D:
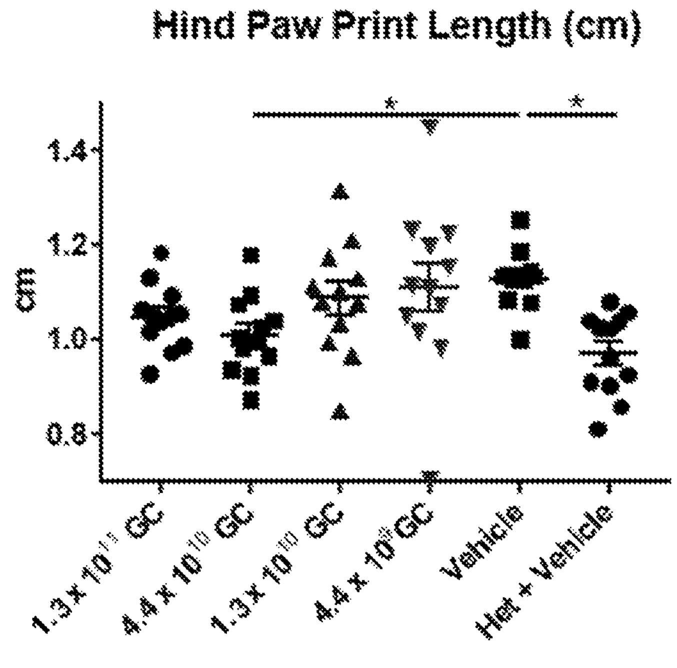
Figure 9E:
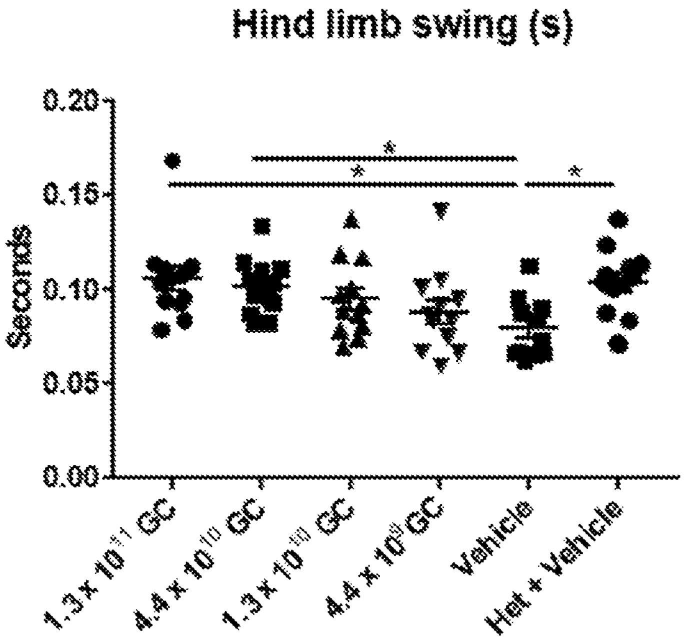
Figure 9F:
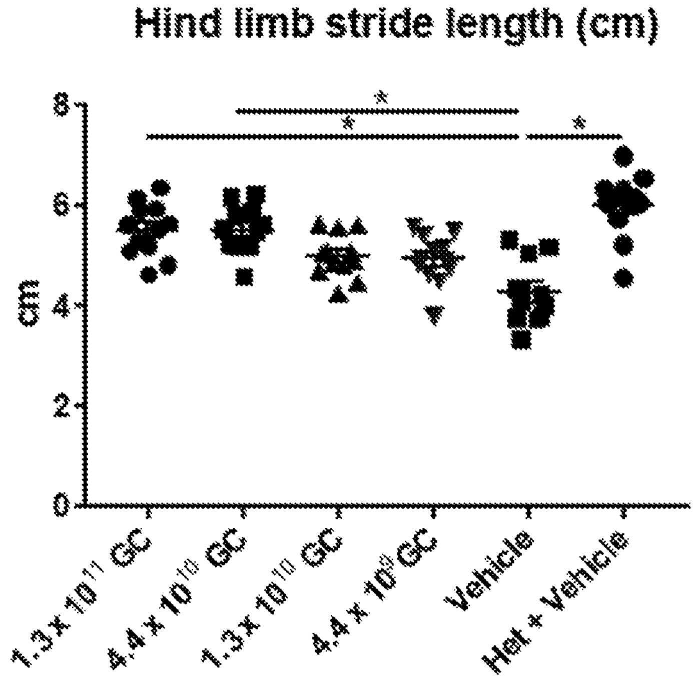

Gait phenotype of GM1 mouse was also consistent with the previous results shown in Example 3. Neurological exam score, hind paw print length, hind limb swing time, and hind limb stride length were acquired and the results are plotted in FIGS. 9C-9F. For all four plotted parameters, there is a significant statistical difference between the negative control and the positive control, indicating those parameters may serve as good indicators for evaluating efficacy. Compared to vehicle treated GLB1$^{-/-}$ mice, mice treated with $4.4\times10^{10}$ GC of rAAVhu68.UbC.GLB1 showed significant improvements in hind paw print length, hind limb swing time and hind limb stride length. A higher dose at $1.3\times10^{11}$ GC provided an increased swing time and longer stride length in hind limb, indicating successful corrections. Neurological exam is more sensitive compared to gait analysis. An dosage dependent amelioration shown by decreased neurological score with increased dose was observed as shown in FIG. 9C, while treatment with $1.3\times10^{10}$ GC of rAAVhu68.UbC.GLB1 displayed a statistical significance in the total score compared to that of the negative control. Evidence of phenotype correction was observed at doses as low as $1.3\times10^{10}$ GC per mouse.

The same set of parameters continues being collected in this animal cohort for at least another 150 days, when all untreated animals are expected to remain alive. Survival changes relative to untreated Glb1$^{-/-}$ mice are evaluated.

The first half of animals discussed in the above paragraph are sacrificed 270 days after treatment. The remaining half animals are sacrificed 150 days after treatment. Another 24 mice are served as a baseline necropsy control. Histological and biochemical comparisons are performed between treated and untreated animals for all sacrificed animals. After necropsy, brains are sectioned and stained for LAMP1 to evaluate lysosomal storage lesions, which are quantified using an automated imaging system. β-gal activity is measured in the brain, serum and peripheral organs. For safety analysis, blood is collected at necropsy for complete blood counts and serum chemistry panels, and the brain, spinal cord, heart, lungs, liver, spleen, kidneys and gonads are collected for evaluation of histopathology by a board certified veterinary pathologist. The lowest dose of rAAVhu68.UbC.GLB1 that achieves a significant reduction of brain storage lesions relative to vehicle-treated GLB1$^{-/-}$ mice are selected as the minimum effective dose (MED).

B. Toxicology Study in Nonhuman Primates (NHPs)

Rhesus monkeys were selected for toxicology studies because they best replicate the size and CNS anatomy of the patient population (infants 4-18 months of age) and can be treated using the clinical route of administration (ROA). Juvenile animals were selected to be representative of the pediatric trial population. In one embodiment, the juvenile rhesus monkeys are 15 to 20 months of age. The similarity in size, anatomy, and ROA resulting in representative vector distribution and transduction profiles, allow for accurate assessment of toxicity. In addition, more rigorous neurological assessments are performed in NHPs than in rodent models, allowing for more sensitive detection of CNS toxicity.

A 120 day GLP-compliant safety study is conducted in juvenile rhesus macaques to investigate the toxicology of AAVhu68.UbC.GLB1 following ICM administration. The 120-day evaluation period was selected as this allows sufficient time for a secreted transgene product to reach stable plateau levels following ICM AAV administration. The study design is outlined in Table below. Rhesus macaques receive one of three dose levels: $3.0\times10^{12}$ GC total, $1.0\times10^{13}$ GC total, or $3.0\times10^{13}$ GC total (n=6/dose) or vehicle (n=4). Dose levels were selected to be equivalent to those that are evaluated in the MED study when scaled by brain mass (assuming 0.4 g for mouse and 90 g for rhesus monkey). Baseline neurologic examinations, clinical pathology (cell counts with differentials, clinical chemistries, and coagulation panel), CSF chemistry and CSF cytology are performed. After AAVhu68.UbC.GLB1 or vehicle administration, the animals are monitored daily for signs of distress and abnormal behavior.

Blood and CSF clinical pathology assessments and neurologic examinations are performed on a weekly basis for 30 days following rAAVhu68.UbC.GLB1 or vehicle administration, and every 30 days thereafter. At baseline and at each 30-day timepoint thereafter, neutralizing antibodies to AAVhu68 and cytotoxic T lymphocyte (CTL) responses to AAVhu68 and the AAVhu68.UbC.GLB1 transgene product are assessed by an interferon gamma (IFN-γ) enzyme-linked immunospot (ELISpot) assay.

| Rhesus macaque Good Laboratory Practice (GLP) Toxicology Study | | | | |
|---|---|---|---|---|
| | Group Designation | | | |
| | 1 | 2 | 3 | 4 |
| Number of macaques | 4 | 6 | 6 | 6 |
| Sex/age | M + F/juvenile | M + F/juvenile | M + F/juvenile | M + F/juvenile |
| Test article | Vehicle | AAVhu68.UbC.GLB1 | AAVhu68.UbC.GLB1 | AAVhu68.UbC.GLB1 |
| Route of administration | ICM | ICM | ICM | ICM |
| Vector Dose (total dose) | N/A | $3.0 \times 10^{12}$ GC | $1.0 \times 10^{13}$ GC | $3.0 \times 10^{13}$ GC |
| Necropsy Day | 60 (3)<br>120 (3) | 60 (3)<br>120 (3) | 60 (3)<br>120 (3) | 60 (3)<br>120 (3) |

After administration of either rAAVhu68.UbC.GLB1 or vehicle, half of the animals are euthanized on Day 60 and half are euthanized on Day 120. Tissues are harvested for comprehensive microscopic histopathological examination. The histopathological examination focuses on central nervous system tissues (brain, spinal cord, and dorsal root ganglia) and the liver because these are the most heavily transduced tissues following ICM administration of AAVhu68 vectors. In addition, lymphocytes are harvested from the spleen and bone marrow to evaluate the presence of T cells reactive to both the capsid and transgene product in these organs at the time of necropsy.

Vector biodistribution is evaluated by quantitative PCR in tissue samples. Vector genomes are quantified in serum and CSF samples.

C. Sensory Neuron Toxicity in Nonclinical AAV Studies

Nonclinical studies evaluating systemic and intrathecal (IT) administration of AAV have consistently demonstrated efficient transduction of sensory neurons within dorsal root ganglia (DRG), and in some cases, evidence of toxicity involving these cells. Intrathecal administration could allow for sensory neuron transduction because their central axons are exposed to CSF, or the rAAV may directly reach the cell body since the DRG is exposed to the spinal CSF.

Minimal to mild asymptomatic degeneration of DRG sensory neurons is expected to appear in the AAVhu68.UbC.GLB1 GLP NHP toxicology study at all doses evaluated. Based on existing nonclinical and clinical data for other AAV programs, it is anticipated that sensory neuron findings do not translate to adverse events in humans, and therefore asymptomatic sensory neuron lesions are not used for determination of maximum tolerated dose (MTD) in nonclinical studies. However, the true risk of sensory neuron toxicity in humans is unknown. The current trial is designed to further improve on the safety profile of previous AAV clinical trials by using an ICM route of administration that requires lower doses of the AAVhu68.UbC.GLB1 than those typically administered systemically, and which appears to result in a lower degree of sensory neuron toxicity. This study employs detailed monitoring for sensory changes as well as nerve conduction studies to detect even subclinical DRG toxicity. Given the severity of infantile GM1 gangliosidosis, the risk-benefit profile for ICM administration of AAVhu68.UbC.GLB1 is expected to remain favorable despite the unknown risk of sensory neuron toxicity.

Example 5: A Phase 1/2 Open-Label, Multi-Center Dose Escalation Study to Assess the Safety and Tolerability of Single Doses of rAAVhu68.GLB1 Delivered into the Cisterna Magna (ICM) of Pediatric Subjects with Infantile GM1 Gangliosidosis Pediatric subjects between 1 month and 18 months of age with the infantile form of GM1 gangliosidosis are selected for the phase 1/2 study as they represent the population with the highest unmet need and the most devastating disease course characterized by rapid and predictable decline of both motor and cognitive impairment (James Utz et al., 2017, Infantile gangliosidoses: Mapping a timeline of clinical changes. *Molecular Genetics and Metabolism.* 121(2):170-179). Patients with infantile GM1 gangliosidosis typically have symptom onset with neurological manifestations before 6 months of age, with some patients presenting at birth with hypotonia, psychomotor delay or other disease manifestations (Caciotti et al., 2011, GM1 gangliosidosis and Morquio B disease: An update on genetic alterations and clinical findings. *Biochimica et Biophysica Acta (BBA)—Molecular Basis of Disease.* 1812(7):782-790). The majority of patients with infantile GM1 die within the first few years of life (median survival 19-46 months depending on the study and level of supportive care (Regier et al., 2016, MRI/MRS as a surrogate marker for clinical progression in GM1 gangliosidosis. *American Journal of Medical Genetics Part A.* 170(3):634-644; Regier et al., 2016, The GM1 and GM2 Gangliosidoses: Natural History and Progress toward Therapy. *Pediatric endocrinology reviews: PER.* 13 Suppl 1:663-673; and James Utz et al., 2017). Consequently these patients represent the population with potentially the most favorable risk/benefit profile. Additionally the predictable and rapid decline in these patients supports a robust study design and allows evaluation of functional outcomes within a reasonable follow-up period. For this group, treatment is expected to stabilize the underlying pathology, thereby stabilizing disease progression, prolonging survival, preventing loss of skills (such as acquired developmental milestones, neurocognitive and/or motor skills) and delay progression of neurocognitive and behavioral decline.

Nonclinical safety studies of the administration procedure conducted in adult nonhuman primates are most representative of the size and cisterna magna anatomy of infants 4 months of age or greater. However, given the rapid course of disease after onset of symptoms and the early age at symptom onset, treatment should occur as early as possible to maximize potential benefit of gene therapy. The lower age limit utilized here is 1 month of age at the time of enrolment to ensure that the treatment and, specifically, the ICM procedure can be safely performed. After careful review of imaging scans from infants as young as 1 or 2 weeks of age, an expert interventional radiologist at the University of Pennsylvania indicated that there is no specific anatomical concern with performing CT-guided ICM administration in a 1 month old infant, provided that the rationale for treatment is supported. As discussed above, patients with infantile (Type 1) GM1 have a rapid disease course with typical age of onset of seizures and other signs of advanced disease by 18 months of age (Jarnes Utz et al., 2017). Due to advanced neurological disease the upper age limit of 18 months has been selected to prevent enrolment of subjects who may have limited potential to benefit from AAVhu68.GLB1 beyond stabilization of disease at a low level of clinical function. Natural history studies indicate that patients with infantile GM1 gangliosidosis have lost most developmental milestones by 2 years of age.

As stated above given the rapid and devastating course of disease after onset of symptoms, treatment should occur as early as possible to maximize potential benefit of gene therapy. Data on sibling concordance suggest that the clinical course in sibling with infantile GM1 is similar in terms of time to onset and prevailing disease manifestations (Gururaj et al., 2005. Magnetic Resonance Imaging Findings and Novel Mutations in GM1 Gangliosidosis. *Journal of Child Neurology*. 20(1):57-60). Therefore, a presymptomatic infant with a confirmed genetic and biochemical diagnosis of GM1 gangliosidosis could be included in the study if they have an older affected sibling who had documented symptom onset (with hypotonia) on or before 6 months of age.

The study is a Phase 1/2, open-label, dose escalation study of AAVhu68.GLB1 to evaluate the safety, tolerability, and exploratory efficacy endpoints following a single dose of AAVhu68.GLB1 delivered into the cisterna magna (ICM) of pediatric subjection with the infantile form of GM1. This study enrolls up to 12 pediatric subjects with the infantile form of GM1 gangliosidosis (Type 1) and subjects receive a single dose of ICM-administered AAVhu68.GLB1. Subjects are followed for 2 years to assess safety, tolerability, pharmacodynamics and clinical outcomes, with additional long term follow up (LTFU) for a total of 5 years post-treatment to evaluate long term outcomes and durability of transgene expression and clinical responses. LTFU to 5 years post-treatment allows for evaluation of durability of transgene expression, and assessment of whether the treatment is effective in prolonging survival and stabilizing subject at a level of function superior to untreated patients in accordance with the draft FDA Guidance for Industry: Long Term Follow-Up After Administration of Human Gene Therapy Products (July 2018), European, Brazilian and other local regulations. Upon study completion, subjects may be invited to enroll in a patient registry to continue to be monitored for long term outcomes, including safety (monitoring for oncologic events), survival and clinical outcomes. Subsequent development of AAVhu68.GLB1 includes expansion into treatment of patients with milder later onset forms of the disease.

Two doses of rAAVhu68.GLB1 are evaluated with staggered, sequential dosing of subjects. The rAAVhu68.GLB1 dose levels are determined based on data from the murine MED study and GLP NHP toxicology study and consist of a low dose (administered to Cohort 1) and a high dose (administered Cohort 2). The high dose is based on the maximum tolerated dose (MTD) in NHP toxicology study scaled to an equivalent human dose. A safety margin is applied so that the high dose selected for human subjects is one third to half of the equivalent human dose. The low dose typically is 2-3 fold less than the selected high dose provided it is a dose that exceeds the equivalent scaled MED in animal studies. This would ensure that both dose levels have the potential to confer therapeutic benefit, with the understanding that if tolerated, the higher dose would be expected to be advantageous. The sequential evaluation of the low dose followed by the high dose enables the identification of the maximum tolerated dose (MTD) of the two doses tested. Finally, an expansion cohort (Cohort 3) receive the MTD of rAAVhu68.GLB1. The 6 subjects in Cohort 3 (MTD) are enrolled simultaneously without staggered dosing. Cohort 3 may receive combination treatment with haematopoietic stem cell transplantation (HSCT) and rAAVhu68.GLB1. If tolerated, the higher dose would be expected to be advantageous.

The primary focus of this study is to evaluate the safety and tolerability of rAAVhu68.GLB1. NHP studies of ICM AAVhu68 delivery have demonstrated minimal to mild asymptomatic degeneration of DRG sensory neurons in some animals, thus detailed examinations are performed to evaluate sensory nerve toxicity, and sensory nerve conduction studies are employed in this trial to monitor for subclinical sensory neuron lesions. Of note, sensory neuron function loss (due to potential dorsal root ganglia toxicity) is evaluated by sensory nerve conduction studies conducted at 30 days, 3 months, 6 months, 12 months, 18 months, 24 months and at yearly intervals thereafter. Given that sensory neuron lesions appear within 2-4 weeks after AAV administration in non-clinical NHP studies, the more frequent assessments through 3 months post-treatment would enable evaluation of similar events in humans, allowing for potential variability in the toxicity kinetics. The follow up throughout the study would allow evaluation of late effects should the time course be different in humans, or in case clinical sequelae are observed, to evaluate how long they persist and whether they improve, stay stable or worsen over time.

Pharmacodynamic and efficacy endpoints are also evaluated in this study, and were chosen for their potential to demonstrate meaningful functional and clinical outcomes in this population. Endpoints are measured at 30 days, 90 days, 6 months, 12 months, 18 months, 24 months and then yearly up to the 5 year follow-up period, except for those that require sedation and/or LP. During the long-term follow up phase, measurement frequency decreases to once every 12 months. These time points were selected to facilitate thorough assessment of the safety and tolerability of rAAVhu68.GLB1. The early time points and 6 month interval were also selected in consideration of the rapid rate of disease progression in untreated infantile GM1 patients. This approach allows for thorough evaluation of pharmacodynamics and clinical efficacy measures in treated subjects over a period of follow up for which untreated comparator data exist and during which untreated patients are expected to show significant decline.

The secondary and exploratory efficacy endpoints include survival, feeding tube independence, seizure incidence and frequency, quality of life as measured by PedsQL and neurocognitive and behavioral development. The Bayley Scales of Infant Development and Vineland Scales are used to quantify the effects of rAAVhu68.GLB1 on development of and changes in adaptive behaviors, cognition, language, motor function, and health-related quality of life. Each measure was used either in the GM1 disease population or in a related population and are further refined based on input from parents and families to select the measures that are most meaningful and impactful to them. In order to standardize assessments, the sites participating in the trial are trained in the administration of the various scales by an experienced neuropsychologist.

Given the severity of disease in the target population, subjects may have achieved motor skills by enrollment, developed and subsequently lost other motor milestones, or not yet shown signs of motor milestone development. Assessments tracks age-at-achievement and age-at-loss for all milestones. Motor milestone achievement is defined for six gross milestones based on the WHO criteria.

Given that subjects with infantile GM1 gangliosidosis can develop symptoms within the months of life, and acquisition of the first WHO motor milestone (sitting without support) typically does not manifest before 4 months of age (median: 5.9 months of age), this endpoint may lack sensitivity to evaluate the extent of therapeutic benefit, especially in subjects who had more overt symptoms at the time of treatment. For this reason, assessment of age-appropriate developmental milestones that can be applied to infants are also be included (Scharf et al., 2016, Developmental Milestones. Pediatr Rev. 37(1):25-37; quiz 38, 47). These data may be informative for summarizing retention, acquisition, or loss of developmental milestones over time relative to untreated children with infantile GM1 disease or the typical time of acquisition in neurotypical children.

As the disease progresses, children can develop seizures. The onset of seizure activity enables us to determine whether treatment with rAAVhu68.GLB1 can either prevent or delay onset of seizures or decrease the frequency of seizure events in this population. Parents are asked to keep seizure diaries, which tracks onset, frequency, length, and type of seizure. These entries are discussed with and interpreted by the clinician at each visit.

To assess the effect of rAAVhu68.GLB1 on the CNS manifestations of the disease volumetric changes are measured on MRI over time. The infantile phenotype of all gangliosidoses was shown to have a consistent pattern of macrocephaly and rapidly increasing intracranial MRI volume with both brain tissue volume (cerebral cortex and other smaller structures) and ventricular volume. Additionally, various smaller brain substructures including the corpus callosum, caudate and putamen as well as the cerebellar cortex generally decrease in size as the disease progresses (Regier et al., 2016, and Nestrasil et al., 2018, as cited herein). Treatment with rAAVhu68.GLB1 is expected to slow or cease the progression of CNS disease manifestations with evidence of stabilization in atrophy and volumetric changes. The exploratory endpoint assessing changes (normal/abnormal) in T1/T2 signal intensity in the thalamus and basal ganglia is based on reported evidence for changes in the thalamic structure in patients with GM1 and GM2 gangliosidosis (Kobayashi and Takashima, 1994, Thalamic hyperdensity on CT in infantile GM1-gangliosidosis. Brain and Development. 16(6):472-474).

Biomarkers for the trial include β-gal enzyme (GLB1) activity, which can be measured in CSF and serum, and brain MRI, which demonstrates consistent, rapid atrophy in infantile GM1 gangliosidosis (Regier et al., 2016b, as cited herein). Additional biomarkers are investigated in CSF and serum from collected samples.

A. Primary Objective:
- To assess the safety and tolerability of rAAVhu68.GLB1 through 2 years following administration of a single dose into the cisterna magna (ICM).

B. Secondary Objectives:
- To assess the pharmacodynamics and biological activity of rAAVhu68.GLB1 over 24 months following a single ICM dose, based on GLB1 activity in CSF and serum. This assessment may further include CSF GM1 concentration, and serum and urine keratan sulfate levels, hexosaminidase activity.
- To assess the impact of rAAVhu68.GLB1 on survival
- To assess the impact of rAAVhu68.GLB1 on the probability of feeding tube dependence at 24 months of age
- To assess Disease progression as assessed by age at achievement, age at loss, and percentage of children maintaining or acquiring age—appropriate developmental and motor milestones (as defined by World Health Organization [WHO] criteria)
- To assess the impact of rAAVhu68.GLB1 on neurocognitive development based on:
  - Change in age equivalent cognitive, gross motor, fine motor, receptive and expressive communication scores of the Bayley Scales of Infant and Toddler Development
  - Change in standard scores for each domain of the Vineland Adaptive Behavior Scales C. Exploratory Objectives:
- To further assess the efficacy of rAAVhu68.GLB1 through 24 months following a single ICM dose as measured by:
  - Age-at-onset and frequency of seizures as assessed by a seizure dairy
  - To assess the impact of rAAVhu68.GLB1 on pediatric quality of life by change in total score on the Pediatric Quality of Life Inventory- and the Pediatric Quality of Life Inventory Infant Scale (PedsQL and PedsQL-IS)
- To further assess the pharmacodynamic effects of rAAVhu68.GLB1 through 24 months following a single ICM dose, as measured by:
  - Changes in total brain volume, brain substructure volume, and lateral ventricle volume as measured by MRI
  - Changes in T1/T2 signal intensity in the thalamus and basal ganglia activity,
  - To evaluate the effect of rAAVhu68.GLB1 on liver and spleen volume.
  - To evaluate the effect of rAAVhu68.GLB1 on EEG, ECHO and visual evoked potentials (VEP).

D. Study Design:
- Multicenter, open-label, single-arm dose escalation study of rAAVhu68.GLB1 (Table below). Up to a total of 12 pediatric subjects with infantile GM1 gangliosidosis are enrolled into 2 dose cohorts, and receive a single dose of rAAVhu68.GLB1 administered by ICM injection. Safety and tolerability are assessed through 2 years, and all subjects are followed through 5 years post-administration of rAAVhu68.GLB1 for the long-term evaluation of safety and tolerability, pharmacodynamics (durability of transgene expression) and durability of clinical outcomes.

| | |
|---|---|
| Product Name: | AAVhu68.UbC.GLB1 |
| Gene Inserts: | Codon-optimized version of human GLB1 gene encoding beta-galactosidase (beta-gal or β-gal) |
| Control Element: | Regulatory element derived from human ubiquitin C (UbC) promoter |
| Other elements: | Chimeric intron (CI)- a hybrid intron consisting of a human beta-globin splice donor and immunoglobulin G (IgG) splice acceptor elements |

-continued

| | |
|---|---|
| | A polyadenylation (PolyA) signal derived from Simian Virus 40 (SV40) late genes |
| AAV Serotype: | Hu68 |

Potential subjects are screened from Days −35 to −1 prior to dosing to determine eligibility for the study. Those subjects who meet the inclusion/exclusion criteria are admitted to the hospital on the morning of Day 1 or per institutional practice. Subjects receive a single ICM dose of rAAVhu68.GLB1 on Day 1 and remain in the hospital for at least 24 h after dosing for observation. Subsequent assessments are performed 7, 14 and 30 days after dosing, then every 60 days for the first year and every 90 days for the second year. The safety and tolerability of rAAVhu68.GLB1 are monitored through assessment of adverse events (AEs) and serious adverse events (SAEs), vital signs, physical examinations, sensory nerve conduction studies, and laboratory assessments (chemistry, hematology, coagulation studies, CSF analysis). Immunogenicity of the AAV and transgene product are also assessed. Efficacy assessments include survival, measurements of cognitive, motor and social development, changes in visual function and EEG, changes in liver and spleen volume, and biomarkers in CSF, serum, and urine.

The study consists of the following three cohorts administered rAAVhu68.GLB1 as a single ICM injection:

Cohort 1 (Low Dose): Three eligible subjects (subjects #1 to #3) are enrolled and administered the low dose of rAAVhu68.GLB1 with a 4-week safety observation period between the first and second subject. If no safety review triggers (SRTs) are observed, all available safety data is evaluated by an independent safety board 4 weeks after the third subject in Cohort 1 is administered rAAVhu68.GLB1.

Cohort 2 (High Dose): If the decision is made to proceed, three eligible subjects (Subjects #4 to #6) are enrolled and administered the high dose of rAAVhu68.GLB1 with a 4-week safety observation period between the fourth and fifth subject. If no SRTs are observed, the independent safety board evaluates all available safety data, including safety data from subjects in Cohort 1, 4 weeks after the third subject Cohort 2 is administered rAAVhu68.GLB1.

Cohort 3 (MTD): Pending a positive recommendation by the safety board, up to 6 additional subjects are enrolled and administered a single ICM dose of rAAVhu68.GLB1 at the MTD. Dosing for subjects in this cohort is not staggered with a 4-week safety observation period between subjects, and a safety board review is required following dosing of the first three subjects in this cohort.

E. Inclusion Criteria:

1. >1 month of age and <18 months of age at enrollment
2. Documented biochemical and molecular diagnosis of GM1 gangliosidosis, based on identification of homozygous or compound heterozygous mutations or deletions in the GLB1 gene and beta-galactosidase enzyme activity below lower limit of normal
3. Documented symptom onset by 6 months of age, with hypotonia on exam or history elicited from parent/caregiver

OR

Be presymptomatic AND have a sibling with a confirmed diagnosis of infantile GM1 gangliosidosis disease who had symptom onset by 6 months of age F. Exclusion Criteria:

1. Any clinically significant neurocognitive deficit not attributable to GM1 gangliosidosis or a secondary cause that may in the opinion of the investigator confound interpretation of study results.
2. Any condition (e.g., history of any disease, evidence of any current disease, any finding upon physical examination, or any laboratory abnormality) that, in the opinion of the investigator, would put the subject at undue risk or would interfere with evaluation of the investigational product or interpretation of subject safety or study results.
3. Any acute illness requiring hospitalization within 30 days of enrollment.
4. Respiratory issues requiring treatment or hospitalization within 30 days of enrollment.
5. Any contraindication to ICM administration procedure, including contraindications to fluoroscopic imaging.
6. Any contraindication to MRI or lumbar puncture.
7. Enrollment in any other clinical study with an investigational product within 4 weeks prior to Screening or within 5 half-lives of the investigational product used in that clinical study, whichever is longer (Patients receiving miglustat off-label are eligible).

G. Route of Administration and Procedure rAAVhu68.GLB1 as a single dose is administered on Day 1 to subjects via CT-guided sub-occipital injection into the cisterna magna.

On Day 1 the appropriate concentration of rAAVhu68.GLB1 is prepared by the Investigational Pharmacy associated with the study. A syringe containing 5.6 mL of rAAVhu68.GLB1 at the appropriate concentration is delivered to the procedure room. The following personnel are present for study drug administration: interventionalist performing the procedure; anesthesiologist and respiratory technician(s); nurses and physician assistants; CT (or operating room) technicians; site research coordinator.

Prior to study drug administration, a lumbar puncture is performed to remove a predetermined volume of CSF and then to inject iodinated contrast intrathecally (IT) to aid in visualization of relevant anatomy of the cisterna magna. Intravenous (IV) contrast may be administered prior to or during needle insertion as an alternative to the intrathecal contrast. The decision to used IV or IT contrast is at the discretion of the interventionalist. The subject is anesthetized, intubated, and positioned on the procedure table. The injection site is prepared and draped using sterile technique. A spinal needle (22-25 G) is advanced into the cisterna magna under fluoroscopic guidance. A larger introducer needle may be used to assist with needle placement. After confirmation of needle placement, the extension set is attached to the spinal needle and allowed to fill with CSF. At the discretion of the interventionalist, a syringe containing contrast material may be connected to the extension set and a small amount injected to confirm needle placement in the cisterna magna. After the needle placement is confirmed by CT guidance+/−contrast injection, a syringe containing 5.6 mL of rAAVhu68.GLB1 is connected to the extension set. The syringe contents are slowly injected over 1-2 minutes, delivering a volume of 5.0 mL. The needle is slowly removed from the subject.

A single dose into the cisterna magna (ICM) of rAAVhu68.GLB1 is safe and tolerable through 2 years following administration.

A single dose into the cisterna magna (ICM) of rAAVhu68.GLB1 improves survival, reduces probability of feeding tube dependence at 24 months of age, and/or reduces Disease progression as assessed by age at achievement, age at loss, and percentage of children maintaining or acquiring age-appropriate developmental and motor milestones.

Treatment slows of loss of neurocognitive function.

All documents cited in this specification are incorporated herein by reference, as are U.S. Provisional Patent Application No. 62/739,811, filed Oct. 1, 2018, and US Provisional Patent Application No. 62/835,178, filed Apr. 17, 2019. Similarly, the Sequence Listing filed herewith, labelled "18-8537PCT_SequenceListing_ST25.txt", and the sequences and text therein are incorporated by reference. While the invention has been described with reference to particular embodiments, it will be appreciated that modifications can be made without departing from the spirit of the invention. Such modifications are intended to fall within the scope of the appended claims.

Sequence Listing Free Text

The following information is provided for sequences containing free text under numeric identifier <223>.

| SEQ ID NO: (containing free text) | Free text under <223> |
|---|---|
| 1 | <223> AAVhu68 vp1 capsid of Homo Sapiens origin<br><220><br><221> CDS<br><222> (1) . . . (2211) |
| 2 | <223> Synthetic Construct |
| 3 | <223> modified hu68vp1<br><220><br><221> MISC_FEATURE<br><222> (23) . . . (23)<br><223> Xaa may be W (Trp, tryptophan), or oxidated W.<br><220><br><221> MISC_FEATURE<br><222> (35) . . . (35)<br><223> Xaa may be Asn, or deamidated to Asp, isoAsp, or Asp/isoAsp<br><220><br><221> MISC_FEATURE<br><222> (57) . . . (57)<br><223> Xaa may be Asn, or deamidated to Asp, isoAsp, or Asp/isoAsp<br><220><br><221> MISC_FEATURE<br><222> (66) . . . (66)<br><223> Xaa may be Asn, or deamidated to Asp, isoAsp, or Asp/isoAsp<br><220><br><221> MISC_FEATURE<br><222> (94) . . . (94)<br><223> Xaa may be Asn, or deamidated to Asp, isoAsp, or Asp/isoAsp<br><220><br><221> MISC_FEATURE<br><222> (97) . . . (97)<br><223> Xaa may be D (asp, aspartic acid), or isomerized D.<br><220><br><221> MISC_FEATURE<br><222> (107) . . . (107)<br><223> Xaa may be D (asp, aspartic acid), or isomerized D.<br><220><br><221> misc_feature<br><222> (113) . . . (113) |

-continued

| SEQ ID NO: (containing free text) | Free text under <223> |
|---|---|
| | <223> Xaa can be any naturally occurring amino acid<br><220><br><221> MISC_FEATURE<br><222> (149) . . . (149)<br><223> Xaa may be S (Ser, serine), or Phosphorilated S<br><220><br><221> MISC_FEATURE<br><222> (149) . . . (149)<br><223> Xaa may be S (Ser, serine), or Phosphorylated S<br><220><br><221> MISC_FEATURE<br><222> (247) . . . (247)<br><223> Xaa may be W (Trp, tryptophan), or oxidated W (e.g., kynurenine).<br><220><br><221> MISC_FEATURE<br><222> (253) . . . (253)<br><223> Xaa may be Asn, or deamidated to Asp, isoAsp, or Asp/isoAsp<br><220><br><221> MISC_FEATURE<br><222> (259) . . . (259)<br><223> Xaa represents Q, or Q deamidated to glutamic acid<br>(alpha-glutamic acid), gamma-glutamic acid (Glu), or a blend of<br>alpha- and gamma-glutamic acid<br><220><br><221> MISC_FEATURE<br><222> (270) . . . (270)<br><223> Xaa may be Asn, or deamidated to Asp, isoAsp, or Asp/isoAsp<br><220><br><221> MISC_FEATURE<br><222> (297) . . . (297)<br><223> Xaa represents D (Asp, aspartic acid) or amindated D to N (Asn,<br>asparagine)<br><220><br><221> MISC_FEATURE<br><222> (304) . . . (304)<br><223> Xaa may be Asn, or deamidated to Asp, isoAsp, or Asp/isoAsp<br><220><br><221> MISC_FEATURE<br><222> (306) . . . (306)<br><223> Xaa may be W (Trp, tryptophan), or oxidated W (e.g., kynurenine).<br><220><br><221> MISC_FEATURE<br><222> (314) . . . (314)<br><223> Xaa may be Asn, or deamidated to Asp, isoAsp, or Asp/isoAsp<br><220><br><221> MISC_FEATURE<br><222> (319) . . . (319)<br><223> Xaa may be Asn, or deamidated to Asp, isoAsp, or Asp/isoAsp<br><220><br><221> MISC_FEATURE<br><222> (329) . . . (329)<br><223> Xaa may be Asn, or deamidated to Asp, isoAsp, or Asp/isoAsp<br><220><br><221> MISC_FEATURE<br><222> (332) . . . (332)<br><223> Xaa may be K (lys, lysine), or acetylated K<br><220><br><221> MISC_FEATURE<br><222> (336) . . . (336)<br><223> Xaa may be Asn, or deamidated to Asp, isoAsp, or Asp/isoAsp |

-continued

| SEQ ID NO: (containing free text) | Free text under <223> |
| --- | --- |
| | <220><br><221> MISC_FEATURE<br><222> (384) . . . (384)<br><223> Xaa may be D (asp, aspartic acid), or isomerized D. |
| | <220><br><221> MISC_FEATURE<br><222> (404) . . . (404)<br><223> Xaa may be M (Met, Methionine), or oxidated M. |
| | <220><br><221> MISC_FEATURE<br><222> (409) . . . (409)<br><223> Xaa may be Asn, or deamidated to Asp, isoAsp, or Asp/isoAsp |
| | <220><br><221> MISC_FEATURE<br><222> (436) . . . (436)<br><223> Xaa may be M (Met, Methionine), or oxidated M. |
| | <220><br><221> MISC_FEATURE<br><222> (452) . . . (452)<br><223> Xaa may be Asn, or deamidated to Asp, isoAsp, or Asp/isoAsp |
| | <220><br><221> MISC_FEATURE<br><222> (477) . . . (477)<br><223> Xaa may be Asn, or deamidated to Asp, isoAsp, or Asp/isoAsp |
| | <220><br><221> MISC_FEATURE<br><222> (499) . . . (499)<br><223> Xaa may be S (Ser, serine), or Phosphorylated S |
| | <220><br><221> MISC_FEATURE<br><222> (512) . . . (512)<br><223> Xaa may be Asn, or deamidated to Asp, isoAsp, or Asp/isoAsp |
| | <220><br><221> MISC_FEATURE<br><222> (515) . . . (515)<br><223> Xaa may be Asn, or deamidated to Asp, isoAsp, or Asp/isoAsp |
| | <220><br><221> MISC_FEATURE<br><222> (518) . . . (518)<br><223> Xaa may be M (Met, Methionine), or oxidated M. |
| | <220><br><221> MISC_FEATURE<br><222> (524) . . . (524)<br><223> Xaa may be M (Met, Methionine), or oxidated M. |
| | <220><br><221> MISC_FEATURE<br><222> (559) . . . (559)<br><223> Xaa may be M (Met, Methionine), or oxidated M. |
| | <220><br><221> MISC_FEATURE<br><222> (569) . . . (569)<br><223> Xaa may be T (Thr, threonine), or Phosphorylated T |
| | <220><br><221> MISC_FEATURE<br><222> (586) . . . (586)<br><223> Xaa may be S (Ser, serine), or Phosphorylated S |
| | <220><br><221> MISC_FEATURE<br><222> (599) . . . (599)<br><223> Xaa represents Q, or Q deamidated to glutamic acid (alpha-glutamic acid), gamma-glutamic acid (Glu), or a blend of alpha- and gamma-glutamic acid |
| | <220><br><221> MISC_FEATURE<br><222> (605) . . . (605)<br><223> Xaa may be M (Met, Methionine), or oxidated M. |
| | <220><br><221> MISC_FEATURE<br><222> (619) . . . (619)<br><223> Xaa may be W (Trp, tryptophan), or oxidated W (e.g., kynurenine). |
| | <220><br><221> MISC_FEATURE<br><222> (628) . . . (628)<br><223> Xaa may be Asn, or deamidated to Asp, isoAsp, or Asp/isoAsp |
| | <220><br><221> MISC_FEATURE<br><222> (640) . . . (640)<br><223> Xaa may be M (Met, Methionine), or oxidated M. |
| | <220><br><221> MISC_FEATURE<br><222> (651) . . . (651)<br><223> Xaa may be Asn, or deamidated to Asp, isoAsp, or Asp/isoAsp |
| | <220><br><221> MISC_FEATURE<br><222> (663) . . . (663)<br><223> Xaa may be Asn, or deamidated to Asp, isoAsp, or Asp/isoAsp |
| | <220><br><221> MISC_FEATURE<br><222> (666) . . . (666)<br><223> Xaa may be K (lys, lysine), or acetylated K |
| | <220><br><221> MISC_FEATURE<br><222> (689) . . . (689)<br><223> Xaa may be K (lys, lysine), or acetylated K |
| | <220><br><221> MISC_FEATURE<br><222> (693) . . . (693)<br><223> Xaa may be K (lys, lysine), or acetylated K |
| | <220><br><221> MISC_FEATURE<br><222> (695) . . . (695)<br><223> Xaa may be W (Trp, tryptophan), or oxidated W. |
| | <220><br><221> MISC_FEATURE<br><222> (709) . . . (709)<br><223> Xaa may be Asn, or deamidated to Asp, isoAsp, or Asp/isoAsp |
| | <220><br><221> MISC_FEATURE<br><222> (735) . . . (735)<br><223> Xaa may be Asn, or deamidated to Asp, isoAsp, or Asp/isoAsp |
| 6 | <223> Engineered coding sequence for human GLB1 |
| 7 | <223> Engineered coding sequence for human GLB1 |
| | <220><br><221> misc_feature<br><222> (6) . . . (6)<br><223> n is a, c, g, or t |
| | <220><br><221> misc_feature<br><222> (9) . . . (9)<br><223> n is a, c, g, or t |
| | <220><br><221> misc_feature<br><222> (15) . . . (15) |

-continued

| SEQ ID NO: (containing free text) | Free text under <223> |
|---|---|
| | <223> n is a, c, g, or t |
| | <220> |
| | <221> misc_feature |
| | <222> (18) . . . (18) |
| | <223> n is a, c, g, or t |
| | <220> |
| | <221> misc_feature |
| | <222> (21) . . . (21) |
| | <223> n is a, c, g, or t |
| | <220> |
| | <221> misc_feature |
| | <222> (27) . . . (27) |
| | <223> n is a, c, g, or t |
| | <220> |
| | <221> misc_feature |
| | <222> (30) . . . (30) |
| | <223> n is a, c, g, or t |
| | <220> |
| | <221> misc_feature |
| | <222> (33) . . . (33) |
| | <223> n is a, c, g, or t |
| | <220> |
| | <221> misc_feature |
| | <222> (36) . . . (36) |
| | <223> n is a, c, g, or t |
| | <220> |
| | <221> misc_feature |
| | <222> (39) . . . (39) |
| | <223> n is a, c, g, or t |
| | <220> |
| | <221> misc_feature |
| | <222> (42) . . . (42) |
| | <223> n is a, c, g, or t |
| | <220> |
| | <221> misc_feature |
| | <222> (45) . . . (45) |
| | <223> n is a, c, g, or t |
| | <220> |
| | <221> misc_feature |
| | <222> (48) . . . (48) |
| | <223> n is a, c, g, or t |
| | <220> |
| | <221> misc_feature |
| | <222> (51) . . . (51) |
| | <223> n is a, c, g, or t |
| | <220> |
| | <221> misc_feature |
| | <222> (54) . . . (54) |
| | <223> n is a, c, g, or t |
| | <220> |
| | <221> misc_feature |
| | <222> (57) . . . (57) |
| | <223> n is a, c, g, or t |
| | <220> |
| | <221> misc_feature |
| | <222> (60) . . . (60) |
| | <223> n is a, c, g, or t |
| | <220> |
| | <221> misc_feature |
| | <222> (63) . . . (63) |
| | <223> n is a, c, g, or t |
| | <220> |
| | <221> misc_feature |
| | <222> (66) . . . (66) |
| | <223> n is a, c, g, or t |
| | <220> |
| | <221> misc_feature |
| | <222> (69) . . . (69) |
| | <223> n is a, c, g, or t |
| | <220> |
| | <221> misc_feature |
| | <222> (72) . . . (72) |
| | <223> n is a, c, g, or t |
| | <220> |
| | <221> misc_feature |

-continued

| SEQ ID NO: (containing free text) | Free text under <223> |
|---|---|
| | <222> (75) . . . (75) |
| | <223> n is a, c, g, or t |
| | <220> |
| | <221> misc_feature |
| | <222> (81) . . . (81) |
| | <223> n is a, c, g, or t |
| | <220> |
| | <221> misc_feature |
| | <222> (84) . . . (84) |
| | <223> n is a, c, g, or t |
| | <220> |
| | <221> misc_feature |
| | <222> (90) . . . (90) |
| | <223> n is a, c, g, or t |
| | <220> |
| | <221> misc_feature |
| | <222> (111) . . . (111) |
| | <223> n is a, c, g, or t |
| | <220> |
| | <221> misc_feature |
| | <222> (114) . . . (114) |
| | <223> n is a, c, g, or t |
| | <220> |
| | <221> misc_feature |
| | <222> (120) . . . (120) |
| | <223> n is a, c, g, or t |
| | <220> |
| | <221> misc_feature |
| | <222> (126) . . . (126) |
| | <223> n is a, c, g, or t |
| | <220> |
| | <221> misc_feature |
| | <222> (135) . . . (135) |
| | <223> n is a, c, g, or t |
| | <220> |
| | <221> misc_feature |
| | <222> (141) . . . (141) |
| | <223> n is a, c, g, or t |
| | <220> |
| | <221> misc_feature |
| | <222> (147) . . . (147) |
| | <223> n is a, c, g, or t |
| | <220> |
| | <221> misc_feature |
| | <222> (156) . . . (156) |
| | <223> n is a, c, g, or t |
| | <220> |
| | <221> misc_feature |
| | <222> (159) . . . (159) |
| | <223> n is a, c, g, or t |
| | <220> |
| | <221> misc_feature |
| | <222> (162) . . . (162) |
| | <223> n is a, c, g, or t |
| | <220> |
| | <221> misc_feature |
| | <222> (174) . . . (174) |
| | <223> n is a, c, g, or t |
| | <220> |
| | <221> misc_feature |
| | <222> (177) . . . (177) |
| | <223> n is a, c, g, or t |
| | <220> |
| | <221> misc_feature |
| | <222> (180) . . . (180) |
| | <223> n is a, c, g, or t |
| | <220> |
| | <221> misc_feature |
| | <222> (183) . . . (183) |
| | <223> n is a, c, g, or t |
| | <220> |
| | <221> misc_feature |
| | <222> (186) . . . (186) |
| | <223> n is a, c, g, or t |
| | <220> |

-continued

| SEQ ID NO: (containing free text) | Free text under <223> |
|---|---|
| | <221> misc_feature<br><222> (204) . . . (204)<br><223> n is a, c, g, or t<br><220><br><221> misc_feature<br><222> (207) . . . (207)<br><223> n is a, c, g, or t<br><220><br><221> misc_feature<br><222> (210) . . . (210)<br><223> n is a, c, g, or t<br><220><br><221> misc_feature<br><222> (225) . . . (225)<br><223> n is a, c, g, or t<br><220><br><221> misc_feature<br><222> (228) . . . (228)<br><223> n is a, c, g, or t<br><220><br><221> misc_feature<br><222> (231) . . . (231)<br><223> n is a, c, g, or t<br><220><br><221> misc_feature<br><222> (237) . . . (237)<br><223> n is a, c, g, or t<br><220><br><221> misc_feature<br><222> (246) . . . (246)<br><223> n is a, c, g, or t<br><220><br><221> misc_feature<br><222> (252) . . . (252)<br><223> n is a, c, g, or t<br><220><br><221> misc_feature<br><222> (255) . . . (255)<br><223> n is a, c, g, or t<br><220><br><221> misc_feature<br><222> (273) . . . (273)<br><223> n is a, c, g, or t<br><220><br><221> misc_feature<br><222> (279) . . . (279)<br><223> n is a, c, g, or t<br><220><br><221> misc_feature<br><222> (282) . . . (282)<br><223> n is a, c, g, or t<br><220><br><221> misc_feature<br><222> (297) . . . (297)<br><223> n is a, c, g, or t<br><220><br><221> misc_feature<br><222> (312) . . . (312)<br><223> n is a, c, g, or t<br><220><br><221> misc_feature<br><222> (324) . . . (324)<br><223> n is a, c, g, or t<br><220><br><221> misc_feature<br><222> (327) . . . (327)<br><223> n is a, c, g, or t<br><220><br><221> misc_feature<br><222> (330) . . . (330)<br><223> n is a, c, g, or t<br><220><br><221> misc_feature<br><222> (333) . . . (333)<br><223> n is a, c, g, or t<br><220><br><221> misc_feature<br><222> (342) . . . (342)<br><223> n is a, c, g, or t<br><220><br><221> misc_feature<br><222> (345) . . . (345)<br><223> n is a, c, g, or t<br><220><br><221> misc_feature<br><222> (348) . . . (348)<br><223> n is a, c, g, or t<br><220><br><221> misc_feature<br><222> (351) . . . (351)<br><223> n is a, c, g, or t<br><220><br><221> misc_feature<br><222> (354) . . . (354)<br><223> n is a, c, g, or t<br><220><br><221> misc_feature<br><222> (360) . . . (360)<br><223> n is a, c, g, or t<br><220><br><221> misc_feature<br><222> (363) . . . (363)<br><223> n is a, c, g, or t<br><220><br><221> misc_feature<br><222> (366) . . . (366)<br><223> n is a, c, g, or t<br><220><br><221> misc_feature<br><222> (369) . . . (369)<br><223> n is a, c, g, or t<br><220><br><221> misc_feature<br><222> (372) . . . (372)<br><223> n is a, c, g, or t<br><220><br><221> misc_feature<br><222> (384) . . . (384)<br><223> n is a, c, g, or t<br><220><br><221> misc_feature<br><222> (399) . . . (399)<br><223> n is a, c, g, or t<br><220><br><221> misc_feature<br><222> (402) . . . (402)<br><223> n is a, c, g, or t<br><220><br><221> misc_feature<br><222> (405) . . . (405)<br><223> n is a, c, g, or t<br><220><br><221> misc_feature<br><222> (408) . . . (408)<br><223> n is a, c, g, or t<br><220><br><221> misc_feature<br><222> (411) . . . (411)<br><223> n is a, c, g, or t<br><220><br><221> misc_feature<br><222> (417) . . . (417)<br><223> n is a, c, g, or t<br><220><br><221> misc_feature<br><222> (420) . . . (420)<br><223> n is a, c, g, or t<br><220><br><221> misc_feature<br><222> (432) . . . (432) |

-continued

| SEQ ID NO: (containing free text) | Free text under <223> |
|---|---|
| | <223> n is a, c, g, or t<br><220><br><221> misc_feature<br><222> (438) . . . (438)<br><223> n is a, c, g, or t<br><220><br><221> misc_feature<br><222> (441) . . . (441)<br><223> n is a, c, g, or t<br><220><br><221> misc_feature<br><222> (444) . . . (444)<br><223> n is a, c, g, or t<br><220><br><221> misc_feature<br><222> (447) . . . (447)<br><223> n is a, c, g, or t<br><220><br><221> misc_feature<br><222> (450) . . . (450)<br><223> n is a, c, g, or t<br><220><br><221> misc_feature<br><222> (456) . . . (456)<br><223> n is a, c, g, or t<br><220><br><221> misc_feature<br><222> (465) . . . (465)<br><223> n is a, c, g, or t<br><220><br><221> misc_feature<br><222> (468) . . . (468)<br><223> n is a, c, g, or t<br><220><br><221> misc_feature<br><222> (471) . . . (471)<br><223> n is a, c, g, or t<br><220><br><221> misc_feature<br><222> (474) . . . (474)<br><223> n is a, c, g, or t<br><220><br><221> misc_feature<br><222> (486) . . . (486)<br><223> n is a, c, g, or t<br><220><br><221> misc_feature<br><222> (489) . . . (489)<br><223> n is a, c, g, or t<br><220><br><221> misc_feature<br><222> (492) . . . (492)<br><223> n is a, c, g, or t<br><220<br><221> misc_feature<br><222> (495) . . . (495)<br><223> n is a, c, g, or t<br><220<br><221> misc_feature<br><222> (498) . . . (498)<br><223> n is a, c, g, or t<br><220<br><221> misc_feature<br><222> (501) . . . (501)<br><223> n is a, c, g, or t<br><220<br><221> misc_feature<br><222> (513) . . . (513)<br><223> n is a, c, g, or t<br><220<br><221> misc_feature<br><222> (516) . . . (516)<br><223> n is a, c, g, or t<br><220<br><221> misc_feature |

-continued

| SEQ ID NO: (containing free text) | Free text under <223> |
|---|---|
| | <222> (519) . . . (519)<br><223> n is a, c, g, or t<br><220<br><221> misc_feature<br><222> (531) . . . (531)<br><223> n is a, c, g, or t<br><220><br><221> misc_feature<br><222> (534) . . . (534)<br><223> n is a, c, g, or t<br><220><br><221> misc_feature<br><222> (537) . . . (537)<br><223> n is a, c, g, or t<br><220><br><221> misc_feature<br><222> (540) . . . (540)<br><223> n is a, c, g, or t<br><220><br><221> misc_feature<br><222> (546) . . . (546)<br><223> n is a, c, g, or t<br><220><br><221> misc_feature<br><222> (549) . . . (549)<br><223> n is a, c, g, or t<br><220><br><221> misc_feature<br><222> (555) . . . (555)<br><223> n is a, c, g, or t<br><220><br><221> misc_feature<br><222> (570) . . . (570)<br><223> n is a, c, g, or t<br><220><br><221> misc_feature<br><222> (573) . . . (573)<br><223> n is a, c, g, or t<br><220><br><221> misc_feature<br><222> (582) . . . (582)<br><223> n is a, c, g, or t<br><220><br><221> misc_feature<br><222> (600) . . . (600)<br><223> n is a, c, g, or t<br><220><br><221> misc_feature<br><222> (603) . . . (603)<br><223> n is a, c, g, or t<br><220><br><221> misc_feature<br><222> (609) . . . (609)<br><223> n is a, c, g, or t<br><220><br><221> misc_feature<br><222> (618) . . . (618)<br><223> n is a, c, g, or t<br><220><br><221> misc_feature<br><222> (624) . . . (624)<br><223> n is a, c, g, or t<br><220><br><221> misc_feature<br><222> (633) . . . (633)<br><223> n is a, c, g, or t<br><220><br><221> misc_feature<br><222> (636) . . . (636)<br><223> n is a, c, g, or t<br><220><br><221> misc_feature<br><222> (645) . . . (645)<br><223> n is a, c, g, or t<br><220> |

| SEQ ID NO: (containing free text) | Free text under <223> |
|---|---|
| | <221> misc_feature<br><222> (648) . . . (648)<br><223> n is a, c, g, or t<br><220><br><221> misc_feature<br><222> (651) . . . (651)<br><223> n is a, c, g, or t<br><220><br><221> misc_feature<br><222> (657) . . . (657)<br><223> n is a, c, g, or t<br><220><br><221> misc_feature<br><222> (660) . . . (660)<br><223> n is a, c, g, or t<br><220><br><221> misc_feature<br><222> (666) . . . (666)<br><223> n is a, c, g, or t<br><220><br><221> misc_feature<br><222> (669) . . . (669)<br><223> n is a, c, g, or t<br><220><br><221> misc_feature<br><222> (678) . . . (678)<br><223> n is a, c, g, or t<br><220><br><221> misc_feature<br><222> (684) . . . (684)<br><223> n is a, c, g, or t<br><220><br><221> misc_feature<br><222> (693) . . . (693)<br><223> n is a, c, g, or t<br><220><br><221> misc_feature<br><222> (696) . . . (696)<br><223> n is a, c, g, or t<br><220><br><221> misc_feature<br><222> (699) . . . (699)<br><223> n is a, c, g, or t<br><220><br><221> misc_feature<br><222> (705) . . . (705)<br><223> n is a, c, g, or t<br><220><br><221> misc_feature<br><222> (708) . . . (708)<br><223> n is a, c, g, or t<br><220><br><221> misc_feature<br><222> (714) . . . (714)<br><223> n is a, c, g, or t<br><220><br><221> misc_feature<br><222> (717) . . . (717)<br><223> n is a, c, g, or t<br><220><br><221> misc_feature<br><222> (720) . . . (720)<br><223> n is a, c, g, or t<br><220><br><221> misc_feature<br><222> (729) . . . (729)<br><223> n is a, c, g, or t<br><220><br><221> misc_feature<br><222> (732) . . . (732)<br><223> n is a, c, g, or t<br><220><br><221> misc_feature<br><222> (735) . . . (735)<br><223> n is a, c, g, or t |

| SEQ ID NO: (containing free text) | Free text under <223> |
|---|---|
| | <220><br><221> misc_feature<br><222> (738) . . . (738)<br><223> n is a, c, g, or t<br><220><br><221> misc_feature<br><222> (747) . . . (747)<br><223> n is a, c, g, or t<br><220><br><221> misc_feature<br><222> (753) . . . (753)<br><223> n is a, c, g, or t<br><220><br><221> misc_feature<br><222> (759) . . . (759)<br><223> n is a, c, g, or t<br><220><br><221> misc_feature<br><222> (762) . . . (762)<br><223> n is a, c, g, or t<br><220><br><221> misc_feature<br><222> (768) . . . (768)<br><223> n is a, c, g, or t<br><220><br><221> misc_feature<br><222> (780) . . . (780)<br><223> n is a, c, g, or t<br><220><br><221> misc_feature<br><222> (786) . . . (786)<br><223> n is a, c, g, or t<br><220><br><221> misc_feature<br><222> (789) . . . (789)<br><223> n is a, c, g, or t<br><220><br><221> misc_feature<br><222> (792) . . . (792)<br><223> n is a, c, g, or t<br><220><br><221> misc_feature<br><222> (801) . . . (801)<br><223> n is a, c, g, or t<br><220><br><221> misc_feature<br><222> (813) . . . (813)<br><223> n is a, c, g, or t<br><220><br><221> misc_feature<br><222> (816) . . . (816)<br><223> n is a, c, g, or t<br><220><br><221> misc_feature<br><222> (822) . . . (822)<br><223> n is a, c, g, or t<br><220><br><221> misc_feature<br><222> (834) . . . (834)<br><223> n is a, c, g, or t<br><220><br><221> misc_feature<br><222> (840) . . . (840)<br><223> n is a, c, g, or t<br><220><br><221> misc_feature<br><222> (846) . . . (846)<br><223> n is a, c, g, or t<br><220><br><221> misc_feature<br><222> (849) . . . (849)<br><223> n is a, c, g, or t<br><220><br><221> misc_feature<br><222> (858) . . . (858) |

-continued

| SEQ ID NO: (containing free text) | Free text under <223> |
|---|---|
| | <223> n is a, c, g, or t |
| | <220> |
| | <221> misc_feature |
| | <222> (864) . . . (864) |
| | <223> n is a, c, g, or t |
| | <220> |
| | <221> misc_feature |
| | <222> (867) . . . (867) |
| | <223> n is a, c, g, or t |
| | <220> |
| | <221> misc_feature |
| | <222> (870) . . . (870) |
| | <223> n is a, c, g, or t |
| | <220> |
| | <221> misc_feature |
| | <222> (873) . . . (873) |
| | <223> n is a, c, g, or t |
| | <220> |
| | <221> misc_feature |
| | <222> (876) . . . (876) |
| | <223> n is a, c, g, or t |
| | <220> |
| | <221> misc_feature |
| | <222> (879) . . . (879) |
| | <223> n is a, c, g, or t |
| | <220> |
| | <221> misc_feature |
| | <222> (891) . . . (891) |
| | <223> n is a, c, g, or t |
| | <220> |
| | <221> misc_feature |
| | <222> (894) . . . (894) |
| | <223> n is a, c, g, or t |
| | <220> |
| | <221> misc_feature |
| | <222> (897) . . . (897) |
| | <223> n is a, c, g, or t |
| | <220> |
| | <221> misc_feature |
| | <222> (900) . . . (900) |
| | <223> n is a, c, g, or t |
| | <220> |
| | <221> misc_feature |
| | <222> (903) . . . (903) |
| | <223> n is a, c, g, or t |
| | <220> |
| | <221> misc_feature |
| | <222> (906) . . . (906) |
| | <223> n is a, c, g, or t |
| | <220> |
| | <221> misc_feature |
| | <222> (909) . . . (909) |
| | <223> n is a, c, g, or t |
| | <220> |
| | <221> misc_feature |
| | <222> (915) . . . (915) |
| | <223> n is a, c, g, or t |
| | <220> |
| | <221> misc_feature |
| | <222> (930) . . . (930) |
| | <223> n is a, c, g, or t |
| | <220> |
| | <221> misc_feature |
| | <222> (933) . . . (933) |
| | <223> n is a, c, g, or t |
| | <220> |
| | <221> misc_feature |
| | <222> (936) . . . (936) |
| | <223> n is a, c, g, or t |
| | <220> |
| | <221> misc_feature |
| | <222> (945) . . . (945) |
| | <223> n is a, c, g, or t |
| | <220> |
| | <221> misc_feature |

-continued

| SEQ ID NO: (containing free text) | Free text under <223> |
|---|---|
| | <222> (957) . . . (957) |
| | <223> n is a, c, g, or t |
| | <220> |
| | <221> misc_feature |
| | <222> (960) . . . (960) |
| | <223> n is a, c, g, or t |
| | <220> |
| | <221> misc_feature |
| | <222> (966) . . . (966) |
| | <223> n is a, c, g, or t |
| | <220> |
| | <221> misc_feature |
| | <222> (969) . . . (969) |
| | <223> n is a, c, g, or t |
| | <220> |
| | <221> misc_feature |
| | <222> (975) . . . (975) |
| | <223> n is a, c, g, or t |
| | <220> |
| | <221> misc_feature |
| | <222> (978) . . . (978) |
| | <223> n is a, c, g, or t |
| | <220> |
| | <221> misc_feature |
| | <222> (984) . . . (984) |
| | <223> n is a, c, g, or t |
| | <220> |
| | <221> misc_feature |
| | <222> (987) . . . (987) |
| | <223> n is a, c, g, or t |
| | <220> |
| | <221> misc_feature |
| | <222> (990) . . . (990) |
| | <223> n is a, c, g, or t |
| | <220> |
| | <221> misc_feature |
| | <222> (1005) . . . (1005) |
| | <223> n is a, c, g, or t |
| | <220> |
| | <221> misc_feature |
| | <222> (1008) . . . (1008) |
| | <223> n is a, c, g, or t |
| | <220> |
| | <221> misc_feature |
| | <222> (1011) . . . (1011) |
| | <223> n is a, c, g, or t |
| | <220> |
| | <221> misc_feature |
| | <222> (1014) . . . (1014) |
| | <223> n is a, c, g, or t |
| | <220> |
| | <221> misc_feature |
| | <222> (1020) . . . (1020) |
| | <223> n is a, c, g, or t |
| | <220> |
| | <221> misc_feature |
| | <222> (1023) . . . (1023) |
| | <223> n is a, c, g, or t |
| | <220> |
| | <221> misc_feature |
| | <222> (1029) . . . (1029) |
| | <223> n is a, c, g, or t |
| | <220> |
| | <221> misc_feature |
| | <222> (1032) . . . (1032) |
| | <223> n is a, c, g, or t |
| | <220> |
| | <221> misc_feature |
| | <222> (1047) . . . (1047) |
| | <223> n is a, c, g, or t |
| | <220> |
| | <221> misc_feature |
| | <222> (1050) . . . (1050) |
| | <223> n is a, c, g, or t |
| | <220> |

-continued

| SEQ ID NO: (containing free text) | Free text under <223> |
|---|---|
| | <221> misc_feature |
| | <222> (1053) . . . (1053) |
| | <223> n is a, c, g, or t |
| | <220> |
| | <221> misc_feature |
| | <222> (1080) . . . (1080) |
| | <223> n is a, c, g, or t |
| | <220> |
| | <221> misc_feature |
| | <222> (1083) . . . (1083) |
| | <223> n is a, c, g, or t |
| | <220> |
| | <221> misc_feature |
| | <222> (1089) . . . (1089) |
| | <223> n is a, c, g, or t |
| | <220> |
| | <221> misc_feature |
| | <222> (1092) . . . (1092) |
| | <223> n is a, c, g, or t |
| | <220> |
| | <221> misc_feature |
| | <222> (1098) . . . (1098) |
| | <223> n is a, c, g, or t |
| | <220> |
| | <221> misc_feature |
| | <222> (1101) . . . (1101) |
| | <223> n is a, c, g, or t |
| | <220> |
| | <221> misc_feature |
| | <222> (1104) . . . (1104) |
| | <223> n is a, c, g, or t |
| | <220> |
| | <221> misc_feature |
| | <222> (1107) . . . (1107) |
| | <223> n is a, c, g, or t |
| | <220> |
| | <221> misc_feature |
| | <222> (1110) . . . (1110) |
| | <223> n is a, c, g, or t |
| | <220> |
| | <221> misc_feature |
| | <222> (1119) . . . (1119) |
| | <223> n is a, c, g, or t |
| | <220> |
| | <221> misc_feature |
| | <222> (1125) . . . (1125) |
| | <223> n is a, c, g, or t |
| | <220> |
| | <221> misc_feature |
| | <222> (1131) . . . (1131) |
| | <223> n is a, c, g, or t |
| | <220> |
| | <221> misc_feature |
| | <222> (1134) . . . (1134) |
| | <223> n is a, c, g, or t |
| | <220> |
| | <221> misc_feature |
| | <222> (1137) . . . (1137) |
| | <223> n is a, c, g, or t |
| | <220> |
| | <221> misc_feature |
| | <222> (1146) . . . (1146) |
| | <223> n is a, c, g, or t |
| | <220> |
| | <221> misc_feature |
| | <222> (1152) . . . (1152) |
| | <223> n is a, c, g, or t |
| | <220> |
| | <221> misc_feature |
| | <222> (1155) . . . (1155) |
| | <223> n is a, c, g, or t |
| | <220> |
| | <221> misc_feature |
| | <222> (1158) . . . (1158) |
| | <223> n is a, c, g, or t |

-continued

| SEQ ID NO: (containing free text) | Free text under <223> |
|---|---|
| | <220> |
| | <221> misc_feature |
| | <222> (1161) . . . (1161) |
| | <223> n is a, c, g, or t |
| | <220> |
| | <221> misc_feature |
| | <222> (1164) . . . (1164) |
| | <223> n is a, c, g, or t |
| | <220> |
| | <221> misc_feature |
| | <222> (1167) . . . (1167) |
| | <223> n is a, c, g, or t |
| | <220> |
| | <221> misc_feature |
| | <222> (1176) . . . (1176) |
| | <223> n is a, c, g, or t |
| | <220> |
| | <221> misc_feature |
| | <222> (1182) . . . (1182) |
| | <223> n is a, c, g, or t |
| | <220> |
| | <221> misc_feature |
| | <222> (1185) . . . (1185) |
| | <223> n is a, c, g, or t |
| | <220> |
| | <221> misc_feature |
| | <222> (1188) . . . (1188) |
| | <223> n is a, c, g, or t |
| | <220> |
| | <221> misc_feature |
| | <222> (1191) . . . (1191) |
| | <223> n is a, c, g, or t |
| | <220> |
| | <221> misc_feature |
| | <222> (1200) . . . (1200) |
| | <223> n is a, c, g, or t |
| | <220> |
| | <221> misc_feature |
| | <222> (1203) . . . (1203) |
| | <223> n is a, c, g, or t |
| | <220> |
| | <221> misc_feature |
| | <222> (1209) . . . (1209) |
| | <223> n is a, c, g, or t |
| | <220> |
| | <221> misc_feature |
| | <222> (1212) . . . (1212) |
| | <223> n is a, c, g, or t |
| | <220> |
| | <221> misc_feature |
| | <222> (1215) . . . (1215) |
| | <223> n is a, c, g, or t |
| | <220> |
| | <221> misc_feature |
| | <222> (1227) . . . (1227) |
| | <223> n is a, c, g, or t |
| | <220> |
| | <221> misc_feature |
| | <222> (1242) . . . (1242) |
| | <223> n is a, c, g, or t |
| | <220> |
| | <221> misc_feature |
| | <222> (1248) . . . (1248) |
| | <223> n is a, c, g, or t |
| | <220> |
| | <221> misc_feature |
| | <222> (1251) . . . (1251) |
| | <223> n is a, c, g, or t |
| | <220> |
| | <221> misc_feature |
| | <222> (1257) . . . (1257) |
| | <223> n is a, c, g, or t |
| | <220 |
| | <221> misc_feature |
| | <222> (1260) . . . (1260) |

-continued

| SEQ ID NO: (containing free text) | Free text under <223> |
|---|---|
| | <223> n is a, c, g, or t |
| | <220 |
| | <221> misc_feature |
| | <222> (1263) . . . (1263) |
| | <223> n is a, c, g, or t |
| | <220 |
| | <221> misc_feature |
| | <222> (1266) . . . (1266) |
| | <223> n is a, c, g, or t |
| | <220 |
| | <221> misc_feature |
| | <222> (1269) . . . (1269) |
| | <223> n is a, c, g, or t |
| | <220 |
| | <221> misc_feature |
| | <222> (1281) . . . (1281) |
| | <223> n is a, c, g, or t |
| | <220 |
| | <221> misc_feature |
| | <222> (1287) . . . (1287) |
| | <223> n is a, c, g, or t |
| | <220 |
| | <221> misc_feature |
| | <222> (1290) . . . (1290) |
| | <223> n is a, c, g, or t |
| | <220> |
| | <221> misc_feature |
| | <222> (1293) . . . (1293) |
| | <223> n is a, c, g, or t |
| | <220> |
| | <221> misc_feature |
| | <222> (1296) . . . (1296) |
| | <223> n is a, c, g, or t |
| | <220> |
| | <221> misc_feature |
| | <222> (1299) . . . (1299) |
| | <223> n is a, c, g, or t |
| | <220> |
| | <221> misc_feature |
| | <222> (1302) . . . (1302) |
| | <223> n is a, c, g, or t |
| | <220> |
| | <221> misc_feature |
| | <222> (1305) . . . (1305) |
| | <223> n is a, c, g, or t |
| | <220> |
| | <221> misc_feature |
| | <222> (1308) . . . (1308) |
| | <223> n is a, c, g, or t |
| | <220> |
| | <221> misc_feature |
| | <222> (1314) . . . (1314) |
| | <223> n is a, c, g, or t |
| | <220> |
| | <221> misc_feature |
| | <222> (1317) . . . (1317) |
| | <223> n is a, c, g, or t |
| | <220> |
| | <221> misc_feature |
| | <222> (1326) . . . (1326) |
| | <223> n is a, c, g, or t |
| | <220> |
| | <221> misc_feature |
| | <222> (1329) . . . (1329) |
| | <223> n is a, c, g, or t |
| | <220> |
| | <221> misc_feature |
| | <222> (1335) . . . (1335) |
| | <223> n is a, c, g, or t |
| | <220> |
| | <221> misc_feature |
| | <222> (1338) . . . (1338) |
| | <223> n is a, c, g, or t |
| | <220> |
| | <221> misc_feature |
| | <222> (1341) . . . (1341) |
| | <223> n is a, c, g, or t |
| | <220> |
| | <221> misc_feature |
| | <222> (1347) . . . (1347) |
| | <223> n is a, c, g, or t |
| | <220> |
| | <221> misc_feature |
| | <222> (1353) . . . (1353) |
| | <223> n is a, c, g, or t |
| | <220> |
| | <221> misc_feature |
| | <222> (1359) . . . (1359) |
| | <223> n is a, c, g, or t |
| | <220> |
| | <221> misc_feature |
| | <222> (1362) . . . (1362) |
| | <223> n is a, c, g, or t |
| | <220> |
| | <221> misc_feature |
| | <222> (1365) . . . (1365) |
| | <223> n is a, c, g, or t |
| | <220> |
| | <221> misc_feature |
| | <222> (1371) . . . (1371) |
| | <223> n is a, c, g, or t |
| | <220> |
| | <221> misc_feature |
| | <222> (1380) . . . (1380) |
| | <223> n is a, c, g, or t |
| | <220> |
| | <221> misc_feature |
| | <222> (1386) . . . (1386) |
| | <223> n is a, c, g, or t |
| | <220> |
| | <221> misc_feature |
| | <222> (1389) . . . (1389) |
| | <223> n is a, c, g, or t |
| | <220> |
| | <221> misc_feature |
| | <222> (1398) . . . (1398) |
| | <223> n is a, c, g, or t |
| | <220> |
| | <221> misc_feature |
| | <222> (1401) . . . (1401) |
| | <223> n is a, c, g, or t |
| | <220> |
| | <221> misc_feature |
| | <222> (1407) . . . (1407) |
| | <223> n is a, c, g, or t |
| | <220> |
| | <221> misc_feature |
| | <222> (1410) . . . (1410) |
| | <223> n is a, c, g, or t |
| | <220> |
| | <221> misc_feature |
| | <222> (1413) . . . (1413) |
| | <223> n is a, c, g, or t |
| | <220 |
| | <221> misc_feature |
| | <222> (1416) . . . (1416) |
| | <223> n is a, c, g, or t |
| | <220 |
| | <221> misc_feature |
| | <222> (1419) . . . (1419) |
| | <223> n is a, c, g, or t |
| | <220 |
| | <221> misc_feature |
| | <222> (1425) . . . (1425) |
| | <223> n is a, c, g, or t |
| | <220 |
| | <221> misc_feature |
| | <222> (1428) . . . (1428) |
| | <223> n is a, c, g, or t |
| | <220 |

-continued

| SEQ ID NO: (containing free text) | Free text under <223> |
|---|---|
| | <221> misc_feature<br><222> (1431) . . . (1431)<br><223> n is a, c, g, or t<br><220<br><221> misc_feature<br><222> (1443) . . . (1443)<br><223> n is a, c, g, or t<br><220<br><221> misc_feature<br><222> (1446) . . . (1446)<br><223> n is a, c, g, or t<br><220><br><221> misc_feature<br><222> (1449) . . . (1449)<br><223> n is a, c, g, or t<br><220><br><221> misc_feature<br><222> (1458) . . . (1458)<br><223> n is a, c, g, or t<br><220><br><221> misc_feature<br><222> (1461) . . . (1461)<br><223> n is a, c, g, or t<br><220><br><221> misc_feature<br><222> (1482) . . . (1482)<br><223> n is a, c, g, or t<br><220><br><221> misc_feature<br><222> (1485) . . . (1485)<br><223> n is a, c, g, or t<br><220><br><221> misc_feature<br><222> (1488) . . . (1488)<br><223> n is a, c, g, or t<br><220><br><221> misc_feature<br><222> (1491) . . . (1491)<br><223> n is a, c, g, or t<br><220><br><221> misc_feature<br><222> (1497) . . . (1497)<br><223> n is a, c, g, or t<br><220><br><221> misc_feature<br><222> (1500) . . . (1500)<br><223> n is a, c, g, or t<br><220><br><221> misc_feature<br><222> (1503) . . . (1503)<br><223> n is a, c, g, or t<br><220><br><221> misc_feature<br><222> (1506) . . . (1506)<br><223> n is a, c, g, or t<br><220><br><221> misc_feature<br><222> (1509) . . . (1509)<br><223> n is a, c, g, or t<br><220><br><221> misc_feature<br><222> (1518) . . . (1518)<br><223> n is a, c, g, or t<br><220><br><221> misc_feature<br><222> (1521) . . . (1521)<br><223> n is a, c, g, or t<br><220><br><221> misc_feature<br><222> (1530) . . . (1530)<br><223> n is a, c, g, or t<br><220><br><221> misc_feature<br><222> (1539) . . . (1539)<br><223> n is a, c, g, or t |

-continued

| SEQ ID NO: (containing free text) | Free text under <223> |
|---|---|
| | <220><br><221> misc_feature<br><222> (1542) . . . (1542)<br><223> n is a, c, g, or t<br><220><br><221> misc_feature<br><222> (1548) . . . (1548)<br><223> n is a, c, g, or t<br><220><br><221> misc_feature<br><222> (1557) . . . (1557)<br><223> n is a, c, g, or t<br><220><br><221> misc_feature<br><222> (1560) . . . (1560)<br><223> n is a, c, g, or t<br><220><br><221> misc_feature<br><222> (1563) . . . (1563)<br><223> n is a, c, g, or t<br><220><br><221> misc_feature<br><222> (1566) . . . (1566)<br><223> n is a, c, g, or t<br><220><br><221> misc_feature<br><222> (1572) . . . (1572)<br><223> n is a, c, g, or t<br><220><br><221> misc_feature<br><222> (1575) . . . (1575)<br><223> n is a, c, g, or t<br><220><br><221> misc_feature<br><222> (1578) . . . (1578)<br><223> n is a, c, g, or t<br><220><br><221> misc_feature<br><222> (1584) . . . (1584)<br><223> n is a, c, g, or t<br><220><br><221> misc_feature<br><222> (1590) . . . (1590)<br><223> n is a, c, g, or t<br><220><br><221> misc_feature<br><222> (1596) . . . (1596)<br><223> n is a, c, g, or t<br><220><br><221> misc_feature<br><222> (1599) . . . (1599)<br><223> n is a, c, g, or t<br><220><br><221> misc_feature<br><222> (1614) . . . (1614)<br><223> n is a, c, g, or t<br><220><br><221> misc_feature<br><222> (1620) . . . (1620)<br><223> n is a, c, g, or t<br><220><br><221> misc_feature<br><222> (1629) . . . (1629)<br><223> n is a, c, g, or t<br><220><br><221> misc_feature<br><222> (1632) . . . (1632)<br><223> n is a, c, g, or t<br><220><br><221> misc_feature<br><222> (1641) . . . (1641)<br><223> n is a, c, g, or t<br><220><br><221> misc_feature<br><222> (1644) . . . (1644) |

| SEQ ID NO: (containing free text) | Free text under <223> |
|---|---|
| | <223> n is a, c, g, or t |
| | <220> |
| | <221> misc_feature |
| | <222> (1647) . . . (1647) |
| | <223> n is a, c, g, or t |
| | <220> |
| | <221> misc_feature |
| | <222> (1650) . . . (1650) |
| | <223> n is a, c, g, or t |
| | <220> |
| | <221> misc_feature |
| | <222> (1662) . . . (1662) |
| | <223> n is a, c, g, or t |
| | <220> |
| | <221> misc_feature |
| | <222> (1671) . . . (1671) |
| | <223> n is a, c, g, or t |
| | <220> |
| | <221> misc_feature |
| | <222> (1677) . . . (1677) |
| | <223> n is a, c, g, or t |
| | <220> |
| | <221> misc_feature |
| | <222> (1680) . . . (1680) |
| | <223> n is a, c, g, or t |
| | <220> |
| | <221> misc_feature |
| | <222> (1683) . . . (1683) |
| | <223> n is a, c, g, or t |
| | <220> |
| | <221> misc_feature |
| | <222> (1689) . . . (1689) |
| | <223> n is a, c, g, or t |
| | <220> |
| | <221> misc_feature |
| | <222> (1695) . . . (1695) |
| | <223> n is a, c, g, or t |
| | <220> |
| | <221> misc_feature |
| | <222> (1698) . . . (1698) |
| | <223> n is a, c, g, or t |
| | <220> |
| | <221> misc_feature |
| | <222> (1707) . . . (1707) |
| | <223> n is a, c, g, or t |
| | <220> |
| | <221> misc_feature |
| | <222> (1722) . . . (1722) |
| | <223> n is a, c, g, or t |
| | <220> |
| | <221> misc_feature |
| | <222> (1725) . . . (1725) |
| | <223> n is a, c, g, or t |
| | <220> |
| | <221> misc_feature |
| | <222> (1731) . . . (1731) |
| | <223> n is a, c, g, or t |
| | <220> |
| | <221> misc_feature |
| | <222> (1737) . . . (1737) |
| | <223> n is a, c, g, or t |
| | <220> |
| | <221> misc_feature |
| | <222> (1743) . . . (1743) |
| | <223> n is a, c, g, or t |
| | <220> |
| | <221> misc_feature |
| | <222> (1755) . . . (1755) |
| | <223> n is a, c, g, or t |
| | <220> |
| | <221> misc_feature |
| | <222> (1764) . . . (1764) |
| | <223> n is a, c, g, or t |
| | <220> |
| | <221> misc_feature |
| | <222> (1767) . . . (1767) |
| | <223> n is a, c, g, or t |
| | <220> |
| | <221> misc_feature |
| | <222> (1770) . . . (1770) |
| | <223> n is a, c, g, or t |
| | <220> |
| | <221> misc_feature |
| | <222> (1779) . . . (1779) |
| | <223> n is a, c, g, or t |
| | <220> |
| | <221> misc_feature |
| | <222> (1782) . . . (1782) |
| | <223> n is a, c, g, or t |
| | <220> |
| | <221> misc_feature |
| | <222> (1785) . . . (1785) |
| | <223> n is a, c, g, or t |
| | <220> |
| | <221> misc_feature |
| | <222> (1788) . . . (1788) |
| | <223> n is a, c, g, or t |
| | <220> |
| | <221> misc_feature |
| | <222> (1791) . . . (1791) |
| | <223> n is a, c, g, or t |
| | <220> |
| | <221> misc_feature |
| | <222> (1797) . . . (1797) |
| | <223> n is a, c, g, or t |
| | <220 |
| | <221> misc_feature |
| | <222> (1800) . . . (1800) |
| | <223> n is a, c, g, or t |
| | <220 |
| | <221> misc_feature |
| | <222> (1803) . . . (1803) |
| | <223> n is a, c, g, or t |
| | <220 |
| | <221> misc_feature |
| | <222> (1809) . . . (1809) |
| | <223> n is a, c, g, or t |
| | <220 |
| | <221> misc_feature |
| | <222> (1812) . . . (1812) |
| | <223> n is a, c, g, or t |
| | <220 |
| | <221> misc_feature |
| | <222> (1824) . . . (1824) |
| | <223> n is a, c, g, or t |
| | <220 |
| | <221> misc_feature |
| | <222> (1830) . . . (1830) |
| | <223> n is a, c, g, or t |
| | <220 |
| | <221> misc_feature |
| | <222> (1833) . . . (1833) |
| | <223> n is a, c, g, or t |
| | <220> |
| | <221> misc_feature |
| | <222> (1836) . . . (1836) |
| | <223> n is a, c, g, or t |
| | <220> |
| | <221> misc_feature |
| | <222> (1839) . . . (1839) |
| | <223> n is a, c, g, or t |
| | <220> |
| | <221> misc_feature |
| | <222> (1845) . . . (1845) |
| | <223> n is a, c, g, or t |
| | <220> |
| | <221> misc_feature |
| | <222> (1851) . . . (1851) |
| | <223> n is a, c, g, or t |
| | <220> |

-continued

| SEQ ID NO: (containing free text) | Free text under <223> |
|---|---|
| | <221> misc_feature<br><222> (1854) . . . (1854)<br><223> n is a, c, g, or t<br><220><br><221> misc_feature<br><222> (1857) . . . (1857)<br><223> n is a, c, g, or t<br><220><br><221> misc_feature<br><222> (1863) . . . (1863)<br><223> n is a, c, g, or t<br><220><br><221> misc_feature<br><222> (1872) . . . (1872)<br><223> n is a, c, g, or t<br><220><br><221> misc_feature<br><222> (1875) . . . (1875)<br><223> n is a, c, g, or t<br><220><br><221> misc_feature<br><222> (1881) . . . (1881)<br><223> n is a, c, g, or t<br><220><br><221> misc_feature<br><222> (1884) . . . (1884)<br><223> n is a, c, g, or t<br><220><br><221> misc_feature<br><222> (1893) . . . (1893)<br><223> n is a, c, g, or t<br><220><br><221> misc_feature<br><222> (1899) . . . (1899)<br><223> n is a, c, g, or t<br><220><br><221> misc_feature<br><222> (1905) . . . (1905)<br><223> n is a, c, g, or t<br><220><br><221> misc_feature<br><222> (1908) . . . (1908)<br><223> n is a, c, g, or t<br><220><br><221> misc_feature<br><222> (1911) . . . (1911)<br><223> n is a, c, g, or t<br><220><br><221> misc_feature<br><222> (1917) . . . (1917)<br><223> n is a, c, g, or t<br><220><br><221> misc_feature<br><222> (1923) . . . (1923)<br><223> n is a, c, g, or t<br><220><br><221> misc_feature<br><222> (1926) . . . (1926)<br><223> n is a, c, g, or t<br><220><br><221> misc_feature<br><222> (1929) . . . (1929)<br><223> n is a, c, g, or t<br><220><br><221> misc_feature<br><222> (1935) . . . (1935)<br><223> n is a, c, g, or t<br><220><br><221> misc_feature<br><222> (1938) . . . (1938)<br><223> n is a, c, g, or t<br><220><br><221> misc_feature<br><222> (1941) . . . (1941)<br><223> n is a, c, g, or t<br><220><br><221> misc_feature<br><222> (1944) . . . (1944)<br><223> n is a, c, g, or t<br><220><br><221> misc_feature<br><222> (1947) . . . (1947)<br><223> n is a, c, g, or t<br><220><br><221> misc_feature<br><222> (1959) . . . (1959)<br><223> n is a, c, g, or t<br><220><br><221> misc_feature<br><222> (1962) . . . (1962)<br><223> n is a, c, g, or t<br><220><br><221> misc_feature<br><222> (1968) . . . (1968)<br><223> n is a, c, g, or t<br><220><br><221> misc_feature<br><222> (1971) . . . (1971)<br><223> n is a, c, g, or t<br><220><br><221> misc_feature<br><222> (1980) . . . (1980)<br><223> n is a, c, g, or t<br><220><br><221> misc_feature<br><222> (1983) . . . (1983)<br><223> n is a, c, g, or t<br><220><br><221> misc_feature<br><222> (1989) . . . (1989)<br><223> n is a, c, g, or t<br><220><br><221> misc_feature<br><222> (1992) . . . (1992)<br><223> n is a, c, g, or t<br><220><br><221> misc_feature<br><222> (1995) . . . (1995)<br><223> n is a, c, g, or t<br><220><br><221> misc_feature<br><222> (1998) . . . (1998)<br><223> n is a, c, g, or t<br><220><br><221> misc_feature<br><222> (2016) . . . (2016)<br><223> n is a, c, g, or t<br><220><br><221> misc_feature<br><222> (2022) . . . (2022)<br><223> n is a, c, g, or t<br><220><br><221> misc_feature<br><222> (2031) . . . (2031)<br><223> n is a, c, g, or t |
| 8 | <223> Engineered coding sequence for human GLB1 |
| 10 | <223> chicken beta actin promoter with a cytomegalovirus enhancer (CB7) |
| 11 | <223> human elongation initiation factor 1 alpha promoter (EF1a) |
| 12 | <223> UbC.GLB1.SV40 vector genome |
| 13 | <223> EF1a.GLB1.SV40 vector genome |
| 14 | <223> UbC.GLB1.SV40 - 2 |
| 15 | <223> UbC.GLB1.SV40 - 3 |
| 16 | <223> Vector genome CB7.CI.GLB1.RBG<br><220><br><221> repeat_region<br><222> (1) . . . (130)<br><223> 5" ITR from AAV2 |

-continued

| SEQ ID NO: (containing free text) | Free text under <223> |
|---|---|
| | <220><br><221> repeat_region<br><222> (4232) . . . (4362)<br><223> 5" ITR from AAV2 |
| 17 | <223> chicken beta-actin intron |
| 18 | <223> CB promoter |
| 19 | <223> CMV Immediate early Promoter |
| 20 | <223> Encoded AAV9 vp1 amino acid sequence |
| 21 | <223> Encoded AAVhu31 vp1 amino acid sequence |
| 22 | <223> Encoded AAVhu32 vp1 amino acid sequence |
| 23 | <223> AAV9 vp1 coding sequence |
| 24 | <223> AAVhu31 vp1 coding sequence |
| 25 | <223> AAVhu32 vp1 coding sequence |

The invention claimed is:

1. An adeno-associated virus (AAV) having an AAVhu68 capsid and a vector genome comprising a β-galactosidase 1 (GLB1) gene encoding human β-galactosidase operably linked to regulatory sequences, wherein the GLB1 gene comprises SEQ ID NO: 8 or a sequence at least 95% identical to SEQ ID NO: 8 that encodes human β-galactosidase comprising amino acids 1 to 677 of SEQ ID NO: 4.

2. The AAV according to claim 1, wherein the vector genome comprises:

(i) a 5' AAV inverted terminal repeat (ITR);

(ii) the human UbC promoter;

(iii) a chimeric intron;

(iv) the GLB1 gene encoding human β-galactosidase;

(v) an SV40 poly A; and (vi) a 3' AAV ITR.

3. The AAV according to claim 2, wherein the UbC promoter comprises SEQ ID NO: 9.

4. The AAV according to claim 1, wherein vector genome comprises SEQ ID NO: 12 or a sequence at least 95% identical to SEQ ID NO: 12.

5. An aqueous pharmaceutical composition comprising a formulation buffer and the AAV according to claim 1.

6. The aqueous pharmaceutical composition according to claim 5, wherein the composition is at a pH in the range of 7.5 to 7.8.

7. The aqueous pharmaceutical composition according to claim 5, wherein the composition is at a pH in the range of 6.2 to 7.7.

8. An aqueous pharmaceutical composition comprising an aqueous formulation buffer and the AAV according to claim 7.

9. The aqueous pharmaceutical composition according to claim 5, wherein the composition is at a pH in the range of about 7.

10. The aqueous pharmaceutical composition according to claim 5, wherein the formulation buffer comprises:

an artificial cerebrospinal fluid comprising buffered saline and one or more of sodium, calcium, magnesium, potassium, or mixtures thereof; and a surfactant.

11. The aqueous pharmaceutical composition according to claim 10, wherein the surfactant is present at 0.0005% w/w to about 0.001% w/w of the aqueous pharmaceutical composition.

12. The AAV according to claim 1, wherein the GLB1 gene comprises a sequence at least 99% identical to SEQ ID NO: 8.

13. The AAV according to claim 1, wherein the UbC promoter comprises SEQ ID NO: 9.

14. An adeno-associated virus (AAV) having an AAVhu68 capsid and a vector genome comprising a β-galactosidase 1 (GLB1) gene encoding human β-galactosidase operably linked to regulatory sequences which comprise a human ubiquitin C (UbC) promoter, wherein the GLB1 gene comprises SEQ ID NO: 8 or a sequence at least 99% identical to SEQ ID NO: 8 that encodes human β-galactosidase comprising amino acids 1 to 677 of SEQ ID NO: 4.

15. The AAV according to claim 14, wherein the UbC promoter comprises SEQ ID NO: 9.

16. The AAV according to claim 14, wherein the vector genome comprises:

(i) a 5' AAV inverted terminal repeat (ITR);

(ii) the human UbC promoter;

(iii) a chimeric intron;

(iv) the GLB1 gene encoding human β-galactosidase;

(v) an SV40 poly A; and (vi) a 3' AAV ITR.

17. The AAV according to claim 16, wherein the chimeric intron comprises SEQ ID NO: 17.

* * * * *